(12) United States Patent
Costantino et al.

(10) Patent No.: US 9,173,954 B2
(45) Date of Patent: Nov. 3, 2015

(54) POLYSACCHARIDE IMMUNOGENS CONJUGATED TO E. COLI CARRIER PROTEINS

(75) Inventors: Paolo Costantino, Colle Val d'Elsa (IT); Francesco Berti, Colle Val D'Elsa (IT); Francesca Micoli, Florence (IT); Anna Kabanova, Bellinzona (CH); Laura Serino, Monticiano (IT); Maria Rosaria Romano, Pontodero (IT); Marta Tontini, Lora Cluffenna (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 13/520,338

(22) PCT Filed: Dec. 30, 2010

(86) PCT No.: PCT/IB2010/003484
§ 371 (c)(1),
(2), (4) Date: Jul. 26, 2012

(87) PCT Pub. No.: WO2011/080595
PCT Pub. Date: Jul. 7, 2011

(65) Prior Publication Data
US 2012/0308600 A1    Dec. 6, 2012

Related U.S. Application Data

(60) Provisional application No. 61/291,262, filed on Dec. 30, 2009.

(51) Int. Cl.
| | | |
|---|---|---|
| *A61K 47/48* | (2006.01) | |
| *A61K 39/108* | (2006.01) | |
| *A61K 39/00* | (2006.01) | |
| *A61K 39/39* | (2006.01) | |

(52) U.S. Cl.
CPC ......... *A61K 47/4833* (2013.01); *A61K 39/0002* (2013.01); *A61K 39/0258* (2013.01); *A61K 39/39* (2013.01); *A61K 2039/6068* (2013.01)

(58) Field of Classification Search
USPC .................. 424/9.1, 9.2, 178.1, 184.1, 185.1, 424/234.1, 257.1
See application file for complete search history.

(56) References Cited

U.S. PATENT DOCUMENTS

| | | | | |
|---|---|---|---|---|
| 4,356,170 A | * | 10/1982 | Jennings et al. | ........... 424/194.1 |
| 4,727,136 A | | 2/1988 | Jennings et al. | |
| 6,858,211 B1 | | 2/2005 | Szu et al. | |

FOREIGN PATENT DOCUMENTS

| | | | |
|---|---|---|---|
| WO | 92/16232 A1 | | 10/1992 |
| WO | WO-92/16232 | | 10/1992 |
| WO | 02/058737 A2 | | 8/2002 |
| WO | WO-02/058737 | | 8/2002 |
| WO | 2005/037320 A2 | | 4/2005 |
| WO | WO-2005/037320 | | 4/2005 |
| WO | WO2006/089264 | * | 4/2006 |
| WO | 2006/091517 A2 | | 8/2006 |
| WO | WO-2006/089264 | | 8/2006 |
| WO | WO-2006/091517 | | 8/2006 |
| WO | WO-2009/104092 | | 8/2009 |
| WO | WO2009/104092 | * | 8/2009 |

OTHER PUBLICATIONS

International Search Report mailed on May 21, 2012, for PCT Application No. PCT/IB2010/003484 filed on Dec. 30, 2010, 7 pages.
International Search Report & Written Opinion received for PCT Patent Application No. PCT/IB2010/003484, mailed on May 21, 2012, 17 pages.
International Preliminary Report on Patentability received for PCT Patent Application No. PCT/IB2010/003484, mailed on Jul. 12, 2012, 12 pages.

* cited by examiner

*Primary Examiner* — Rodney P Swartz
(74) *Attorney, Agent, or Firm* — Morrison & Foerster LLP

(57) ABSTRACT

*E. coli* proteins have been identified that are useful as carrier proteins to improve a response to a polysaccharide immunogen conjugated to such protein. In particular, AcfD precursor protein (orf3526 polypeptide), Flu antigen 43 protein (orf1364 polypeptide), and Sel1 repeat-containing protein (upec-5211 polypeptide) have been shown to be effective. Additionally, these *E. coli* proteins can enhance the immune response to glucans, particularly fungal glucans.

13 Claims, 3 Drawing Sheets

POLYSACCHARIDE IMMUNOGENS CONJUGATED TO E. COLI CARRIER PROTEINS

CROSS REFERENCE TO RELATED APPLICATIONS

This application is a U.S. National Phase patent application of PCT/IB2010/003484, filed Dec. 30, 2010, which claims priority to U.S. provisional patent application Ser. No. 61/291,262 filed Dec. 30, 2009, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002111200SeqListing.txt, date recorded: Jul. 2, 2012, size: 426 KB).

TECHNICAL FIELD

This invention relates to immunization using polysaccharide immunogens conjugated to E. coli carrier polypeptides. Of particular interest is use of such compositions as vaccines against bacterial and fungal infections and diseases.

BACKGROUND ART

Carrier proteins are used to improve the immune response to polysaccharide immunogens. Such carrier proteins can be particularly advantageous in the induction of an immune response in the very young and are therefore found in a number of pediatric vaccines. The recommended pediatric immunization schedule includes a significant number of vaccines including hepatitis B vaccine at birth; starting at six weeks, all of diphtheria/tetanus/pertussis (DTaP), rotavirus, H. influenzae type b (Hib) conjugate, inactivated poliovirus and pneumococcal conjugates; starting at six months, inactivated influenza vaccines; starting at 12 months, measles/mumps/rubella (MMR), varicella, and hepatitis A; and after two years, meningococcal conjugate. Among this list, the following are polysaccharide conjugates: Hib conjugate (e.g., HbOC—a diphtheria $CRM_{197}$ conjugate); pneumococcal conjugates (e.g., Prevnar—a diphtheria $CRM_{197}$ conjugate and Synflorix—a protein carrier derived from non-typeable Haemophilus influenzae strains); and meningococcal conjugate (e.g., Menactra—a diphtheria $CRM_{197}$ conjugate).

Adding new vaccines to the current pediatric immunization schedule can encounter two potential problems that must be addressed. First, the issue of carrier-induced epitopic suppression (or "carrier suppression", as it is generally known) must be addressed, particularly suppression arising from carrier priming. "Carrier suppression" is the phenomenon whereby pre-immunization of an animal with a carrier protein prevents it from later eliciting an immune response against a new antigenic epitope that is presented on that carrier (Herzenberg et al. (1980) Nature 285: 664-667).

As reported in Schutze et al. (1985) J Immunol 135:2319-2322, where several vaccine antigens contain the same protein component (being used as an immunogen and/or as a carrier protein in a conjugate) then there is the potential for interference between those antigens. Schutze et al. observed that the immune response against an antigen that was conjugated to a tetanus toxoid (Tt) carrier was suppressed by pre-existing immunity against Tt.

Dagan et al. observed that a combination of DTP vaccines with a Hib conjugate vaccine was adversely affected where the carrier for the Hib conjugate was the same as the tetanus antigen from the DTP vaccine ((1998) Infect Immun 66:2093-2098). Dagan et al. concluded that this "carrier suppression" phenomenon, arising from interference by a common protein carrier, should be taken into account when introducing vaccines that include multiple conjugates.

In contrast to Schutze et al. and Dagan et al., Barington et al. reported that priming with tetanus toxoid had no negative impact on the immune response against a subsequently-administered Hib-Tt conjugate, but suppression was seen in patients with maternally acquired anti-Tt antibodies ((1994) Infect Immun 62:9-14). Di John et al., however, observed an "epitopic suppression" effect for a Tt-based peptide conjugate in patients having existing anti-Tt antibodies resulting from tetanus vaccination ((1989) Lancet 2(8677):1415-8).

Granoff et al. suggested that a conjugate having $CRM_{197}$ (a detoxified mutant of diphtheria toxin) as the carrier may be ineffective in children that had not previously received diphtheria toxin as part of a vaccine (e.g., as part of a DTP or DT vaccine) ((1993) Vaccine Suppl 1: 546-51). This work was further developed in Granoff et al. (1994) JAMA 272:1116-1121, where a carrier priming effect by D-T immunization was seen to persist for subsequent immunization with Hib conjugates.

In Barington et al. (1993) Infect Immun 61:432-438, the authors found that pre-immunization with a diphtheria or tetanus toxoid carrier protein reduced the increase in anti-Hib antibody levels after a subsequent immunization with the Hib capsular saccharide conjugated to those carriers, with IgG1 and IgG2 being equally affected. Responses to the carrier portions of the conjugates were also suppressed. Furthermore, a more general non-epitope-specific suppression was seen, as pre-immunization with one conjugate was seen to affect immune responses against both the carrier and saccharide portions of a second conjugate that was administered four weeks later.

Thus, given the confusion over the impact of "carrier suppression," having additional carrier proteins available for conjugation will be beneficial to reduce such adverse interactions.

Second, given the already crowded immunization schedule, addition of new vaccines to the immunization schedule will become increasingly difficult due to possible adverse interactions, but also due simply to the number of separate injections required. Thus, being able to combine vaccines into a single injection such as the DTaP or MMR vaccines is advantageous. Having additional carrier proteins that can enhance an immune response to a polysaccharide immunogen as well as induce an immune response to itself will be beneficial as it can allow combination of vaccines against different pathogens into a single injectable composition.

It is an object of the invention to provide further and/or better carrier polypeptides for conjugation to polysaccharide immunogens. It is also an object of the invention to provide carrier polypeptides for conjugation to polysaccharide immunogens where the carrier polypeptides can be used in immunization against pathogenic E. coli strains, and more particularly against intestinal pathotypes (e.g. EAEC, EIEC, EPEC and ETEC strains) as well as ExPEC pathotypes. It is also an object of the invention to provide conjugates with such further and/or better carrier polypeptides where the polysaccharide immunogen is a glucan polysaccharide, which in some embodiments can be used in immunization against fungal pathogens.

SUMMARY

Accordingly, one aspect of the invention provides a glucan polysaccharide conjugate comprising a glucan polysaccharide conjugated to a carrier polypeptide selected from the group consisting of an *E. coli* AcfD precursor protein (orf3526 polypeptide), an *E. coli* Flu antigen 43 protein (orf1364 polypeptide), and an *Escherichia* Sel1 repeat-containing protein (upec-5211 polypeptide). When the carrier polypeptide is the *E. coli* AcfD precursor protein (orf3526 polypeptide), the carrier polypeptide may: (a) have the amino acid sequence of SEQ ID NO 50; (b) have an amino acid sequence having from 1 to 10 single amino acid alterations compared to SEQ ID NO: 50; (c) have at least 85%, at least 90%, at least 95%, at least 97%, at least 98%, or at least 99% sequence identity to SEQ ID NO: 50; (d) comprise a fragment of at least 10, at least 12, at least 14, at least 16, at least 18, at least 20, at least 25, at least 30, at least 40, at least 50, at least 75, at least 100, at least 125, or at least 150 consecutive amino acids from SEQ ID NO: 50; and/or (e) when aligned with SEQ ID NO: 50 using a pairwise alignment algorithm, each moving window of x amino acids from N terminus to C terminus has at least x·y identical aligned amino acids, where x is 30 and y is 0.75. When the carrier polypeptide is the *E. coli* Flu antigen 43 protein (orf1364 polypeptide), the carrier polypeptide may: (a) have the amino acid sequence of SEQ ID NO 44; (b) have an amino acid sequence having from 1 to 10 single amino acid alterations compared to SEQ ID NO: 44; (c) have at least 85%, at least 90%, at least 95%, at least 97%, at least 98%, or at least 99% sequence identity to SEQ ID NO: 44; (d) comprise a fragment of at least 10, at least 12, at least 14, at least 16, at least 18, at least 20, at least 25, at least 30, at least 40, at least 50, at least 75, at least 100, at least 125, or at least 150 consecutive amino acids from SEQ ID NO: 44; and/or (e) when aligned with SEQ ID NO: 44 using a pairwise alignment algorithm, each moving window of x amino acids from N terminus to C terminus has at least x·y identical aligned amino acids, where x is 30 and y is 0.75. When the carrier polypeptide is the *Escherichia* Sel1 repeat-containing protein (upec-5211 polypeptide), the carrier polypeptide may: (a) have the amino acid sequence of SEQ ID NO 48; (b) have an amino acid sequence having from 1 to 10 single amino acid alterations compared to SEQ ID NO: 48; (c) have at least 85%, at least 90%, at least 95%, at least 97%, at least 98%, or at least 99% sequence identity to SEQ ID NO: 48; (d) comprise a fragment of at least 10, at least 12, at least 14, at least 16, at least 18, at least 20, at least 25, at least 30, at least 40, at least 50, at least 75, at least 100, at least 125, or at least 150 consecutive amino acids from SEQ ID NO: 48; and/or (e) when aligned with SEQ ID NO: 48 using a pairwise alignment algorithm, each moving window of x amino acids from N terminus to C terminus has at least x·y identical aligned amino acids, where x is 30 and y is 0.75. In certain embodiments which may be combined with any of the preceding embodiments, the glucan polysaccharide contains β-1,3-linkages and/or β-1,6-linkages. In certain embodiments which may be combined with any of the preceding embodiments, the glucan polysaccharide is a single molecular species. In certain embodiments which may be combined with any of the preceding embodiments, the glucan polysaccharide is conjugated to the carrier protein directly or is conjugated to the carrier protein via a linker. In certain embodiments which may be combined with any of the preceding embodiments, the glucan polysaccharide has a molecular weight of less than 100 kDa (e.g. less than 80, 70, 60, 50, 40, 30, 25, 20, or 15 kDa). In certain embodiments which may be combined with any of the preceding embodiments, the glucan polysaccharide has 60 or fewer (e.g., 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4) glucose monosaccharide units. In certain embodiments which may be combined with any of the preceding embodiments, the glucan polysaccharide is β-1,3 glucan polysaccharide with some β-1,6 branching. In certain embodiments where the polysaccharide is a β-1,3 glucan polysaccharide with some β-1,6 branching, the glucan polysaccharide is a laminarin. In certain embodiments which may be combined with any of the preceding embodiments, the glucan polysaccharide comprises both β-1,3-linked glucose residues and β-1,6-linked glucose residues, with a ratio of β1,3 linked glucose residues to β-1,6-linked residues of at least 8:1 and/or there are one or more sequences of at least five adjacent non-terminal residues linked to other residues only by β-1,3 linkages. In certain embodiments which may be combined with any of the preceding embodiments, the glucan polysaccharide comprises both β-1,3-linked glucose residues and β-1,6-linked glucose residues, with a ratio of β-1,3 linked glucose residues to β-1,6-linked residues of at least 8:1. In certain embodiments which may be combined with any of the preceding embodiments excluding those which have β-1,6-linked residues, the glucan polysaccharide has exclusively β-1,3 linkages. In certain embodiments which may be combined with any of the preceding embodiments, the glucan polysaccharide is a curdlan. In certain embodiments which may be combined with any of the preceding embodiments, the glucan polysaccharide conjugate further comprises an adjuvant.

Another aspect of the invention provides vaccine components comprising the glucan polysaccharide conjugate according to the preceding aspect in any of its embodiments.

Still another aspect of the invention provides vaccines comprising the vaccine component of the preceding aspect. In certain embodiments, the vaccine further comprises an adjuvant. In certain embodiments that may be combined with the preceding embodiment, the vaccine further comprises an additional vaccine component selected from: a *Neisseria meningitidis* antigen, a *Streptococcus pneumoniae* antigen, a *Streptococcus pyogenes* antigen, a *Moraxella catarrhalis* antigen, a *Bordetella pertussis* antigen, a *Staphylococcus aureus* antigen, a *Staphylococcus epidermidis* antigen, a *Clostridium tetani* antigen, a *Cornynebacterium diphtheriae* antigen, a *Haemophilus influenzae* type B (Hib) antigen, a *Pseudomonas aeruginosa* antigen, a *Legionella pneumophila* antigen, a *Streptococcus agalactiae* antigen, a *Neiserria gonorrhoeae* antigen, a *Chlamydia trachomatis* antigen, a *Treponema pallidum* antigen, a *Haemophilus ducreyi* antigen, an *Enterococcus faecalis* antigen, an *Enterococcus faecium* antigen, a *Helicobacter pylori* antigen, a *Staphylococcus saprophyticus* antigen, a *Yersinia enterocolitica* antigen, an additional *E. coli* antigen, a *Bacillus anthracis* antigen, a *Yersinia pestis* antigen, a *Mycobacterium tuberculosis* antigen, a *Rickettsia* antigen, a *Listeria monocytogenes* antigen, a *Chlamydia pneumoniae* antigen, a *Vibrio cholerae* antigen, a *Salmonella typhi* antigen, a *Borrelia burgdorferi* antigen, a *Porphyromonas gingivalis* antigen, a *Shigella* antigen and a *Klebsiella* antigen. In certain preferred embodiments that may be combined with the preceding embodiment, the vaccine further comprises an additional vaccine component selected from a bacteria associated with nosocomial infections, which can include: a *Staphylococcus aureus* antigen, a

*Candida albicans* antigen, a *Clostridium difficile* antigen, or a *Pseudomonas aeruginosa* antigen.

Yet another aspect of the invention provides methods of inducing an enhanced immune response in a mammalian subject to a glucan polysaccharide comprising administering to the mammalian subject of the glucan polysaccharide conjugate according to the preceding aspect in any of its embodiments, the vaccine component according to the preceding aspect, or the vaccine according to the preceding aspect in any of its embodiments.

Another aspect of the invention provides uses of the glucan polysaccharide conjugate according to the preceding aspect in any of its embodiments, the vaccine component according to the preceding aspect, or the vaccine according to the preceding aspect in any of its embodiments to induce an enhanced immune response in a mammalian subject to the polysaccharide.

Still another aspect of the invention provides polysaccharide conjugates comprising a polysaccharide conjugated to a carrier polypeptide selected from the group consisting of an *E. coli* AcfD precursor protein (orf3526 polypeptide), an *E. coli* Flu antigen 43 protein (orf1364 polypeptide), and an *Escherichia* Sel1 repeat-containing protein (upec-5211 polypeptide). In embodiments where the carrier polypeptide is the *E. coli* AcfD precursor protein (orf3526 polypeptide), the carrier polypeptide may comprise a mutation reducing the toxicity and/or a deletion improving purification as compared to the *E. coli* AcfD precursor protein (orf3526 polypeptide) of SEQ ID NO: 39. In another embodiment which may be combined with the preceding embodiments where the carrier polypeptide is the *E. coli* AcfD precursor protein (orf3526 polypeptide) with a mutation reducing the toxicity, the mutation may be selected from a deletion of all or a portion of the zincin metalloprotease domain and a point mutation in zincin metalloprotease domain which reduces the protease activity. In another embodiment which may be combined with the preceding embodiments where the carrier polypeptide is the *E. coli* AcfD precursor protein (orf3526 polypeptide) with a mutation reducing the toxicity, the point mutation is a mutation of a zinc binding residue or a mutation of a catalytic residue, which in some cases may be amino acid number 1305 based upon alignment with SEQ ID NO: 39. In another embodiment which may be combined with the preceding embodiments where the carrier polypeptide is the *E. coli* AcfD precursor protein (orf3526 polypeptide) with a mutation reducing the toxicity, the carrier polypeptide does not comprise at least the last 100 C-terminal amino acids of the *E. coli* AcfD (orf3526) protein, at least the last 200 C-terminal amino acids of the *E. coli* AcfD (orf3526) protein, at least the last 300 C-terminal amino acids of the *E. coli* AcfD (orf3526) protein, at least the last 400 C-terminal amino acids of the *E. coli* AcfD (orf3526) protein, at least the last 500 C-terminal amino acids of the *E. coli* AcfD (orf3526) protein, at least the last 600 C-terminal amino acids of the *E. coli* AcfD (orf3526) protein, at least the last 700 C-terminal amino acids of the *E. coli* AcfD (orf3526) protein, at least the last 750 C-terminal amino acids of the *E. coli* AcfD (orf3526) protein, or at least the last 758 C-terminal amino acids of the *E. coli* AcfD (orf3526) protein or does not comprise at least the first 100 N-terminal amino acids of the *E. coli* AcfD (orf3526) protein, at least the first 200 N-terminal amino acids of the *E. coli* AcfD (orf3526) protein, at least the first 300 N-terminal amino acids of the *E. coli* AcfD (orf3526) protein, at least the first 400 N-terminal amino acids of the *E. coli* AcfD (orf3526) protein, at least the first 500 N-terminal amino acids of the *E. coli* AcfD (orf3526) protein, at least the first 600 N-terminal amino acids of the *E. coli* AcfD (orf3526) protein, at least the first 700 N-terminal amino acids of the *E. coli* AcfD (orf3526) protein, at least the first 750 N-terminal amino acids of the *E. coli* AcfD (orf3526) protein, or at least the first 760 N-terminal amino acids of the *E. coli* AcfD (orf3526) protein. In another embodiment which may be combined with the preceding embodiments where the carrier polypeptide is the *E. coli* AcfD precursor protein (orf3526 polypeptide), the carrier polypeptide does not comprise at least the last 100 C-terminal amino acids of the *E. coli* AcfD (orf3526) protein, at least the last 125 C-terminal amino acids of the *E. coli* AcfD (orf3526) protein, at least the last 150 C-terminal amino acids of the *E. coli* AcfD (orf3526) protein, at least the last 175 C-terminal amino acids of the *E. coli* AcfD (orf3526) protein, at least the last 200 C-terminal amino acids of the *E. coli* AcfD (orf3526) protein, at least the last 210 C-terminal amino acids of the *E. coli* AcfD (orf3526) protein, or at least the last 217 C-terminal amino acids of the *E. coli* AcfD (orf3526) protein and optionally do not comprise at least the first 10 N-terminal amino acids of the *E. coli* AcfD (orf3526) protein, at least the first 20 N-terminal amino acids of the *E. coli* AcfD (orf3526) protein, at least the first 30 N-terminal amino acids of the *E. coli* AcfD (orf3526) protein, or at least the first 33 N-terminal amino acids of the *E. coli* AcfD (orf3526) protein. In another embodiment which may be combined with the preceding embodiments where the carrier polypeptide is the *E. coli* AcfD precursor protein (orf3526 polypeptide), the carrier polypeptide may: (a) have the amino acid sequence of SEQ ID NOs 26-40; (b) have an amino acid sequence having from 1 to 10 single amino acid alterations compared to SEQ ID NO: 26-40; (c) have at least 85%, at least 90%, at least 95%, at least 97%, at least 98%, or at least 99% sequence identity to SEQ ID NOs 26-40; (d) comprise a fragment of at least 10, at least 12, at least 14, at least 16, at least 18, at least 20, at least 25, at least 30, at least 40, at least 50, at least 75, at least 100, at least 125, or at least 150 consecutive amino acids from SEQ ID NOs 26-40; and/or (e) when aligned with any of SEQ ID NOs: 26-40 using a pairwise alignment algorithm, each moving window of x amino acids from N terminus to C terminus has at least x·y identical aligned amino acids, where x is 30 and y is 0.75. In another embodiment which may be combined with the preceding embodiments where the carrier polypeptide is the *E. coli* AcfD precursor protein (orf3526 polypeptide), the carrier polypeptide further contains a deletion relative to the *E. coli* AcfD (orf3526) protein which increases solubility of the carrier polypeptide as compared to the *E. coli* AcfD (orf3526) protein. In another embodiment which may be combined with the preceding embodiments where the carrier polypeptide is the *E. coli* AcfD precursor protein (orf3526 polypeptide) with a deletion which increases the solubility, the deletion is removal of substantially all of the N-terminal amino acids up to the gly-ser region, removal of all or a part of the N-terminal proline-rich repeat, or both. In another embodiment which may be combined with the preceding embodiments where the carrier polypeptide is the *E. coli* AcfD precursor protein (orf3526 polypeptide) with a deletion which increases the solubility, the deletion is removal of at least the first 10 N-terminal amino acids as compared to the *E. coli* AcfD (orf3526) protein, at least the first 20 N-terminal amino acids as compared to the *E. coli* AcfD (orf3526) protein, at least the first 30 N-terminal amino acids as compared to the *E. coli* AcfD (orf3526) protein, at least the first 33 N-terminal amino acids as compared to the *E. coli* AcfD (orf3526) protein, at least the first 40 N-terminal amino acids as compared to the *E. coli* AcfD (orf3526) protein, at least the first 50 N-terminal amino acids as compared to the *E. coli* AcfD (orf3526) protein, at least the first 60 N-terminal amino acids as compared to the *E. coli* AcfD (orf3526) protein, at least the first 70 N-terminal amino acids as compared to the *E. coli* AcfD (orf3526) protein, at least the first 80 N-terminal amino acids as compared to the *E. coli* AcfD (orf3526) protein, at least the first 90 N-terminal amino acids as compared to the *E. coli* AcfD (orf3526) protein, or at least the first 94 N-terminal amino acids as compared to the *E. coli* AcfD (orf3526) protein. In embodiments where the carrier polypeptide is the *E. coli* Flu antigen 43 protein (orf1364 polypeptide), the carrier polypeptide may be a fragment of the *E. coli* Flu antigen 43 protein (orf1364 polypeptide) wherein the fragment contains a deletion relative to the full length *E. coli* Flu antigen 43 protein (orf1364 polypeptide) which deletion increases solubility of the fragment as compared to the full length protein. In certain embodiments where the carrier polypeptide is the *E. coli* Flu antigen 43 protein (orf1364 polypeptide) has a deletion which increases the solubility, the deletion comprises the carboxyl-terminal β-barrel domain or the carrier polypeptide corresponds to the amino acid sequence of SEQ ID NO:44. In another embodiment which may be combined with the preceding embodiments where the carrier polypeptide is the *E. coli* Flu antigen 43 protein (orf1364 polypeptide) has a deletion which increases the solubility, the fragment comprises less than 950 amino acids, less than 900 amino acids, less than 850 amino acids, less than 800 amino acids, less than 750 amino acids, less than 700 amino acids, less than 650 amino acids, less than 600 amino acids, less than 550 amino acids, less than 500 amino acids, less than 450 amino acids, less than 440 amino acids, or less than 430 amino acids of the flu antigen 43 (orf1364) protein. In another embodiment which may be combined with the preceding embodiments where the carrier polypeptide is the *E. coli* Flu antigen 43 protein (orf1364 polypeptide), the carrier polypeptide may: (a) have the amino acid sequence of SEQ ID NOs 1-22; (b) have an amino acid sequence having from 1 to 10 single amino acid alterations compared to SEQ ID NOs 1-22; (c) have at least 85%, at least 90%, at least 95%, at least 97%, at least 98%, or at least 99% sequence identity to SEQ ID NOs 1-22; (d) comprise a fragment of at least 10, at least 12, at least 14, at least 16, at least 18, at least 20, at least 25, at least 30, at least 40, at least 50, at least 75, at least 100, at least 125, or at least 150 consecutive amino acids from SEQ ID NOs 1-22; and/or (e) when aligned with any of SEQ ID NOs 1-22 using a pairwise alignment algorithm, each moving window of x amino acids from N terminus to C terminus has at least x·y identical aligned amino acids, where x is 30 and y is 0.75. In another embodiment which may be combined with the preceding embodiments where the carrier polypeptide is the *E. coli* Flu antigen 43 protein (orf1364 polypeptide), the fragment does not comprise at least the first 10 N-terminal amino acids as compared to the *E. coli* Flu antigen 43 protein (orf1364 polypeptide), at least the first 20 N-terminal amino acids as compared to the *E. coli* Flu antigen 43 protein (orf1364 polypeptide), at least the first 30 N-terminal amino acids as compared to *E. coli* Flu antigen 43 protein (orf1364 polypeptide), at least the first 40 N-terminal amino acids as compared to *E. coli* Flu antigen 43 protein (orf1364 polypeptide), at least the first 50 N-terminal amino acids as compared to *E. coli* Flu antigen 43 protein (orf1364 polypeptide), or at least the first 52 N-terminal amino acids as compared to the *E. coli* AcfD (orf3526) protein, and/or the fragment does not comprise at least the last 50 C-terminal amino acids as compared to the *E. coli* Flu antigen 43 protein (orf1364 polypeptide), at least the last 100 C-terminal amino acids as compared to the *E. coli* Flu antigen 43 protein (orf1364 polypeptide), at least the last 150 C-terminal amino acids as compared to the *E. coli* Flu antigen 43 protein (orf1364 polypeptide), at least the last 200 C-terminal amino acids as compared to the *E. coli* Flu antigen 43 protein (orf1364 polypeptide), at least the last 250 C-terminal amino acids as compared to the *E. coli* Flu antigen 43 protein (orf1364 polypeptide), at least the last 300 C-terminal amino acids as compared to the *E. coli* Flu antigen 43 protein (orf1364 polypeptide), at least the last 325 C-terminal amino acids as compared to the *E. coli* Flu antigen 43 protein (orf1364 polypeptide), or at least the last 328 C-terminal amino acids as compared to the *E. coli* Flu antigen 43 protein (orf1364 polypeptide). In embodiments where the carrier polypeptide is the *Escherichia* Sel1 repeat-containing protein (upec-5211 polypeptide), the carrier polypeptide may: (a) have the amino acid sequence of SEQ ID NOs 23-25; (b) have an amino acid sequence having from 1 to 10 single amino acid alterations compared to SEQ ID NOs 23-25; (c) have at least 85%, at least 90%, at least 95%, at least 97%, at least 98%, or at least 99% sequence identity to SEQ ID NOs 23-25; (d) comprise a fragment of at least 10, at least 12, at least 14, at least 16, at least 18, at least 20, at least 25, at least 30, at least 40, at least 50, at least 75, at least 100, at least 125, or at least 150 consecutive amino acids from SEQ ID NOs 23-25; and/or when aligned with any of SEQ ID NOs: 23-25 using a pairwise alignment algorithm, each moving window of x amino acids from N terminus to C terminus has at least x·y identical aligned amino acids, where x is 30 and y is 0.75. In certain embodiments which may be combined with any of the preceding embodiments, the polysaccharide may be: (a) a glucan, (b) a capsular saccharide from at least one of serogroups A, C, W135 and Y of *Neisseria meningitidis*, (c) a saccharide antigen from *Streptococcus pneumoniae*, (d) a capsular polysaccharide from *Staphylococcus aureus*, (e) a *Haemophilus influenzae* B polysaccharide, (f) a saccharide antigen from *Streptococcus agalactiae*, (g) a lipopolysaccharide from *Vibrio cholerae*, or (h) a capsular polysaccharide from *Salmonella typhi*. In certain embodiments which may be combined with any of the preceding embodiments, the polysaccharide has a molecular weight of less than 100 kDa (e.g. less than 80, 70, 60, 50, 40, 30, 25, 20, or 15 kDa). In certain embodiments which may be combined with any of the preceding embodiments, the polysaccharide has 60 or fewer (e.g., 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4) monosaccharide units. In certain embodiments which may be combined with any of the preceding embodiments, the polysaccharide may be directly or indirectly conjugated to the carrier protein. In certain embodiments which may be combined with any of the preceding embodiments, the polysaccharide conjugate further comprises an adjuvant.

Another aspect of the invention provides vaccine components comprising the polysaccharide conjugate according to the preceding aspect in any of its embodiments.

Still another aspect of the invention provides vaccines comprising the vaccine component of the preceding aspect. In certain embodiments, the vaccine further comprises an adjuvant. In certain embodiments that may be combined with the preceding embodiment, the vaccine further comprises an additional vaccine component selected from: a *Neisseria meningitidis* antigen, a *Streptococcus pneumoniae* antigen, a *Streptococcus pyogenes* antigen, a *Moraxella catarrhalis* antigen, a *Bordetella pertussis* antigen, a *Staphylococcus aureus* antigen, a *Staphylococcus epidermidis* antigen, a *Clostridium tetani* antigen, a *Corynebacterium diphtheriae* antigen, a *Haemophilus influenzae* type B (Hib) antigen, a *Pseudomonas aeruginosa* antigen, a *Legionella pneumophila* antigen, a *Streptococcus agalactiae* antigen, a *Neiserria gonorrhoeae* antigen, a *Chlamydia trachomatis* antigen, a *Tre-*

*ponema pallidum* antigen, a *Haemophilus ducreyi* antigen, an *Enterococcus faecalis* antigen, an *Enterococcus faecium* antigen, a *Helicobacter pylori* antigen, a *Staphylococcus saprophyticus* antigen, a *Yersinia enterocolitica* antigen, an additional *E. coli* antigen, a *Bacillus anthracis* antigen, a *Yersinia pestis* antigen, a *Mycobacterium tuberculosis* antigen, a *Rickettsia* antigen, a *Listeria monocytogenes* antigen, a *Chlamydia pneumoniae* antigen, a *Vibrio cholerae* antigen, a *Salmonella typhi* antigen, a *Borrelia burgdorferi* antigen, a *Porphyromonas gingivalis* antigen, *Shigella* antigen and a *Klebsiella* antigen. In certain preferred embodiments that may be combined with the preceding embodiment, the vaccine further comprises an additional vaccine component selected from a bacteria associated with nosocomial infections, which can include: a *Staphylococcus aureus* antigen, a *Candida albicans* antigen, a *Clostridium difficile* antigen, or a *Pseudomonas aeruginosa* antigen.

Yet another aspect of the invention provides methods of inducing an enhanced immune response in a mammalian subject to a polysaccharide comprising administering to the mammalian subject of the polysaccharide conjugate according to the preceding aspect in any of its embodiments, the vaccine component according to the preceding aspect, or the vaccine according to the preceding aspect in any of its embodiments.

Another aspect of the invention provides uses of the polysaccharide conjugate according to the preceding aspect in any of its embodiments, the vaccine component according to the preceding aspect, or the vaccine according to the preceding aspect in any of its embodiments to induce an enhanced immune response in a mammalian subject to the polysaccharide.

DETAILED DESCRIPTION

Pure polysaccharides are often poor immunogens and therefore need to be conjugated to a carrier polypeptide. Even where a polysaccharide has sufficient immunogenicity, conjugation to a carrier protein can enhance the immunogenicity so that less polysaccharide need be delivered. Furthermore, for protective efficacy in the very young, conjugation to a carrier polypeptides is often required. The use of conjugation to carrier proteins in order to enhance the immunogenicity of carbohydrate antigens is well known (see, e.g., Lindberg (1999) *Vaccine* 17 Suppl 2:S28-36, Buttery & Moxon (2000) *J R Coll Physicians Lond* 34: 163-8, Ahmad & Chapnick (1999) *Infect Dis an North Am* 13: 113-33, vii, Goldblatt (1998) *J. Med. Microbiol.* 47:563-567, EP-B-0477508, U.S. Pat. No. 5,306,492, WO98/42721, Dick et al. in *Conjugate Vaccines* (eds. Cruse et al.) Karger, Basel, 1989, Vol. 10, 48-114, Hermanson *Bioconjugate Techniques*, Academic Press, San Diego Calif. (1996), etc.); and is used in particular for pediatric vaccines (Ramsay et al. (2001) *Lancet* 357(9251):195-6). The inventors have surprisingly found that three *E. coli* antigens can act as carrier polypeptides: accessory colonization factor D (AcfD) precursor protein (orf3526 polypeptide), Flu antigen 43 protein (orf1364 polypeptide), and Sel1 repeat-containing protein (upec-5211 polypeptide).

An aspect of the invention therefore provides a polysaccharide conjugate comprising a polysaccharide conjugated to a carrier protein and optionally, an adjuvant (as defined below).

The carrier polypeptide may be covalently conjugated to the polysaccharide directly or via a linker. Any suitable conjugation reaction can be used, with any suitable linker where necessary.

Attachment of the polysaccharide to the carrier polypeptide is preferably via a —$NH_2$ group, e.g., through the side chain(s) of a lysine residue(s) or arginine residue(s) in the carrier polypeptide. Where the polysaccharide has a free aldehyde group, this group can react with an amine in the carrier polypeptide to form a conjugate by reductive amination. Attachment to the carrier may also be via a —SH group, e.g., through the side chain(s) of a cysteine residue(s) in the carrier polypeptide. Alternatively the polysaccharide may be attached to the carrier protein via a linker molecule.

The polysaccharide will typically be activated or functionalized prior to conjugation. Activation may involve, for example, cyanylating reagents such as CDAP (1-cyano-4-dimethylamino pyridinium tetrafluoroborate). Other suitable techniques use carbodiimides, hydrazides, active esters, norborane, p-nitrobenzoic acid, N-hydroxysuccinimide, S-NHS, EDC, TSTU (see, e.g., the introduction to WO98/42721).

Direct linkages to the carrier polypeptide may comprise oxidation of the polysaccharide followed by reductive amination with the carrier polypeptide, as described in, for example, U.S. Pat. No. 4,761,283 and U.S. Pat. No. 4,356,170.

Linkages via a linker group may be made using any known procedure, for example, the procedures described in U.S. Pat. No. 4,882,317 and U.S. Pat. No. 4,695,624. Typically, the linker is attached via an anomeric carbon of the poylsaccharide. A preferred type of linkage is an adipic acid linker, which may be formed by coupling a free —NH2 group (e.g., introduced to a polysaccharide by amination) with adipic acid (using, for example, diimide activation), and then coupling a protein to the resulting saccharide-adipic acid intermediate (see, e.g., EP-B-0477508, *Mol. Immunol*, (1985) 22, 907-919, and EP-A-0208375). A similar preferred type of linkage is a glutaric acid linker, which may be formed by coupling a free —NH group with glutaric acid in the same way. Adipid and glutaric acid linkers may also be formed by direct coupling to the polysaccharide, i.e., without prior introduction of a free group, e.g., a free —NH group, to the polysaccharide, followed by coupling a protein to the resulting saccharide-adipic/glutaric acid intermediate. Another preferred type of linkage is a carbonyl linker, which may be formed by reaction of a free hydroxyl group of a modified polysaccharide with CDI (Bethell G. S. et al. (1979) *J Biol Chem* 254, 2572-4 and Hearn M. T. W. (1981) *J. Chromatogr* 218, 509-18); followed by reaction with a protein to form a carbamate linkage. Other linkers include β-propionamido (WO00/10599), nitrophenyl-ethylamine (Geyer et al. (1979) *Med Microbiol Immunol* 165, 171-288), haloacyl halides (U.S. Pat. No. 4,057,685), glycosidic linkages (U.S. Pat. Nos. 4,673,574; 4,761,283; and 4,808,700), 6-aminocaproic acid (U.S. Pat. No. 4,459,286), N-succinimidyl-3-(2-pyridyldithio)-propionate (SPDP) (U.S. Pat. No. 5,204,098), adipic acid dihydrazide (ADH) (U.S. Pat. No. 4,965,338), C4 to C12 moieties (U.S. Pat. No. 4,663,160), etc. Carbodiimide condensation can also be used (WO2007/000343).

A bifunctional linker may be used to provide a first group for coupling to an amine group in the polysaccharide (e.g., introduced to the polysaccharide by amination) and a second group for coupling to the carrier (typically for coupling to an amine in the carrier). Alternatively, the first group is capable of direct coupling to the polysaccharide, i.e., without prior introduction of a group, e.g., an amine group, to the polysaccharide.

In some embodiments, the first group in the bifunctional linker is thus able to react with an amine group (—NH2) on the polysaccharide. This reaction will typically involve an electrophilic substitution of the amine's hydrogen. In other embodiments, the first group in the bifunctional linker is able to react directly with the polysaccharide. In both sets of embodiments, the second group in the bifunctional linker is typically able to react with an amine group on the carrier polypeptide. This reaction will again typically involve an electrophilic substitution of the amine.

Where the reactions with both the polysaccharide and the carrier protein involve amines then it is preferred to use a bifunctional linker. For example, a homobifunctional linker of the formula X-L-X, may be used where: the two X groups are the same as each other and can react with the amines; and where L is a linking moiety in the linker. Similarly, a heterobifunctional linker of the formula X-L-X may be used, where: the two X groups are different and can react with the amines; and where L is a linking moiety in the linker. A preferred X group is N-oxysuccinimide. L preferably has formula $L'-L^2-L'$, where L' is carbonyl. Preferred $L^2$ groups are straight chain alkyls with 1 to 10 carbon atoms (e.g., $C_1, C_2, C_3, C_4, C_5, C_6, C_7, C_8, C_9, C_{10}$) e.g. —$(CH_2)_4$— or —$(CH_2)_3$—.

Other X groups for use in the bifunctional linkers described in the preceding paragraph are those which form esters when combined with HO-L-OH, such as norborane, p-nitrobenzoic acid, and sulfo-N— hydroxysuccinimide.

Further bifunctional linkers for use with the invention include acryloyl halides (e.g., chloride) and haloacylhalides.

The linker will generally be added in molar excess to polysaccharide during coupling to the polysaccharide.

Conjugates may have excess carrier (w/w) or excess polysaccharide (w/w), e.g., in the ratio range of 1:5 to 5:1. Conjugates with excess carrier protein are typical, e.g., in the range 0.2:1 to 0.9:1, or equal weights. The conjugate may include small amounts of free (i.e., unconjugated) carrier. When a given carrier protein is present in both free and conjugated form in a composition of the invention, the unconjugated form is preferably no more than 5% of the total amount of the carrier protein in the composition as a whole, and more preferably present at less than 2% (by weight).

The composition may also comprise free carrier protein as immunogen (WO96/40242).

After conjugation, free and conjugated polysaccharides can be separated. There are many suitable methods, e.g., hydrophobic chromatography, tangential ultrafiltration, diafiltration, etc. (see also Lei et al. (2000) *Dev Biol* (Basel) 103:259-264 and WO00/38711). Tangential flow ultrafiltration is preferred.

The polysaccharide moiety in the conjugate is preferably a low molecular weight polysaccharide, as defined below (see section on glucans). Oligosaccharides will typically be sized prior to conjugation.

The protein-polysaccharide conjugate is preferably soluble in water and/or in a physiological buffer.

For some polysaccharides, the immunogenicity may be improved if there is a spacer between the polysaccharide and the carrier protein. In this context, a "spacer" is a moiety that is longer than a single covalent bond. This spacer may be a linker, as described above. Alternatively, it may be a moiety covalently bonded between the polysaccharide and a linker. Typically, the moiety will be covalently bonded to the polysaccharide prior to coupling to the linker or carrier. For example, the spacer may be moiety Y, wherein Y comprises a straight chain alkyl with 1 to 10 carbon atoms (e.g., $C_1, C_2, C_3, C_4, C_5, C_6, C_7, C_8, C_9, C_{10}$), typically 1 to 6 carbon atoms (e.g., $C_1, C_2, C_3, C_4, C_5, C_6$). The inventors have found that a straight chain alkyl with 6 carbon atoms (i.e., —$(CH_2)_6$) is particularly suitable, and may provide greater immunogenicity than shorter chains (e.g., —$(CH_2)_2$). Typically, Y is attached to the anomeric carbon of the polysaccharide, usually via an —O— linkage. However, Y may be linked to other parts of the polysaccharide and/or via other linkages. The other end of Y is bonded to the linker by any suitable linkage. Typically, Y terminates with an amine group to facilitate linkage to a bifunctional linker as described above. In these embodiments, Y is therefore bonded to the linker by an —NH— linkage. Accordingly, a conjugate with the following structure is specifically envisaged for use in the present invention: wherein n+2 is in the range of 2-60, e.g., between 10-50 or between 2-40. Preferably, n+2 is in the range of 25-30 or 11-19, e.g., β-17. The inventors have found that n+2=15 is suitable. Y is as described above.

In one aspect, the invention provides a method for making a polysaccharide conjugated to a carrier protein, wherein the step of conjugation is carried out in a phosphate buffer with >10 mM phosphate; and to a conjugate obtained by this method. The inventors have found that sodium phosphate is a suitable form of phosphate for the buffer. The pH of the buffer may be adjusted to between 7.0-7.5, particularly 7.2. The step of conjugation is typically carried out in a phosphate buffer with between 20-200 mM phosphate, e.g., 50-150 mM. In particular, the inventors have found that a phosphate buffer with 90-110 mM, e.g., about 100 mM, phosphate is suitable. The step of conjugation is usually carried out at room temperature. Similarly, the step of conjugation is usually carried out at room pressure. Typically, the polysaccharide is attached to a linker as described above prior to the step of conjugation. In particular, the polysaccharide may be attached to a bifunctional linker as described above. The free end of the linker may comprise a group to facilitate conjugation to the carrier protein. For example, the inventors have found that the free end of the linker may comprise an ester group, e.g., an N-hydroxysuccinimide ester group.

The polysaccharide conjugates disclosed herein can further include a pharmaceutically acceptable carrier.

The polysaccharide conjugates disclosed herein can further include an adjuvant. The adjuvant can comprise one or more of the adjuvants described below.

The polysaccharide conjugates may also be used in methods for raising an immune response in a mammal (or avian), comprising administering to the mammal (or avian) a composition of the invention.

Polysaccharide Immunogens

Any polysaccharide capable of inducing an immune response in a mammal or avian (either alone or conjugated to a carrier protein) may be used in the polysaccharide conjugates as disclosed herein (i.e., a polysaccharide immunogen). Preferably, the polysaccharide is capably of inducing an immune response against a pathogen of interest. The polysaccharide may be branched or linear.

Low molecular weight polysaccharides may be used, particularly those with a molecular weight of less than 100 kDa (e.g., less than 80, 70, 60, 50, 40, 30, 25, 20, or 15 kDa). It is also possible to use oligosaccharides containing, for example, 60 or fewer (e.g., 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4) monosaccharide units. Within this range, oligosaccharides with between 10 and 50 or between 20 and 40 monosaccharide units are preferred.

Exemplary polysaccharide immunogens are detailed below.

Glucan Polysaccharides:

Glucans are glucose-containing polysaccharides found in, among other pathogens, fungal cell walls. The β-glucans include one or more α-linkages between glucose subunits, whereas β-glucans include one or more β-linkages between glucose subunits. The glucan used in accordance with the invention includes β linkages, and may contain only β linkages (i.e., no α linkages).

The glucan may comprise one or more β-1,3-linkages and/or one or more β-1,6-linkages. It may also comprise one or more β-1,2-linkages and/or β-1,4-linkages, but normally its only β linkages will be β-1,3-linkages and/or β-1,6-linkages.

The glucan may be branched or linear.

Full-length native β-glucans are insoluble and have a molecular weight in the megadalton range. It is preferred to use soluble glucans in immunogenic compositions of the invention. Solubilization may be achieved by fragmenting long insoluble glucans. This may be achieved by hydrolysis or, more conveniently, by digestion with a glucanase (e.g., with a β-1,3-glucanase or a β-1,6-glucanase). As an alternative, short glucans can be prepared synthetically by joining monosaccharide building blocks.

Low molecular weight glucans are preferred, particularly those with a molecular weight of less than 100 kDa (e.g., less than 80, 70, 60, 50, 40, 30, 25, 20, or 15 kDa). It is also possible to use oligosaccharides containing, for example, 60 or fewer (e.g., 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4) glucose monosaccharide units. Within this range, oligosaccharides with between 10 and 50 or between 20 and 40 monosaccharide units are preferred.

The glucan may be a fungal glucan. A "fungal glucan" will generally be obtained from a fungus but, where a particular glucan structure is found in both fungi and non-fungi (e.g., in bacteria, lower plants or algae) then the non-fungal organism may be used as an alternative source. Thus the glucan may be derived from the cell wall of a *Candida*, such as *C. albicans*, or from *Coccidioides immitis*, *Trichophyton verrucosum*, *Blastomyces dermatidis*, *Cryptococcus neoformans*, *Histoplasma capsulatum*, *Saccharomyces cerevisiae*, *Paracoccidioides brasiliensis*, or *Pythiumn insidiosum*. Exemplary sources of fungal β-glucans may be found in WO2009/077854.

In some embodiments, the glucan is a β-1,3 glucan with some β-1,6 branching, as seen in, for example, laminarins. Laminarins are found in brown algae and seaweeds. The β(1-3):β(1-6) ratios of laminarins vary between different sources, for example, the ratio is as low as 3:2 in *Eisenia bicyclis* laminarin, but as high as 7:1 in *Laminaria digititata* laminarin (Pang et al. (2005) *Biosci Biotechnol Biochem* 69:553-8). Thus the glucan used with the invention may have a β(1-3):β(1-6) ratio of between 1.5:1 and 7.5:1 (e.g., about 2:1, 3:1, 4:1, 5:1, 6:1 or 7:1). Optionally, the glucan may have a terminal mannitol subunit, e.g., a 1,1-α-linked mannitol residue (Read et al. (1996) *Carbohydr Res.* 281:187-201). The glucan may also comprise mannose subunits.

In other embodiments, the glucan has exclusively or mainly β-1,3 linkages, as seen in curdlan. The inventors have found that these glucans may be more immunogenic than glucans comprising other linkages, particularly glucans comprising β-1,3 linkages and a greater proportion of β-1,6 linkages. Thus the glucan may be made solely of β-1,3-linked glucose residues (e.g., linear β-D-glucopyranoses with exclusively 1,3 linkages). Optionally, though, the glucan may include monosaccharide residues that are not β-1,3-linked glucose residues, e.g., it may include β-1,6-linked glucose residues. The ratio of β-1,3-linked glucose residues to these other residues should be at least 8:1 (e.g. >9:1, >10:1, >11:1, >12:1, >13:1, >14:1, >15:1, >16:1, >17:1, >18:1, >19:1, >20:1, >25:1, >30:1, >35:1, >40:1, >45:1, >50:1, >75:1, >100:1, etc.) and/or there are one or more (e.g. >1, >2, >3, >4, >5, >6, >7, >8, >9, >10, >11, >12, etc.) sequences of at least five (e.g. >5, >6, >7, >8, >9, >10, >11, >12, >13, >14, >15, >16, >17, >18, >19, >20, >30, >40, >50, >60, etc.) adjacent non-terminal residues linked to other residues only by β-1,3 linkages. By "non-terminal" it is meant that the residue is not present at a free end of the glucan. In some embodiments, the adjacent non-terminal residues may not include any residues conjugated to a carrier molecule, linker or other spacer as described below. The inventors have found that the presence of five adjacent non-terminal residues linked to other residues only by β-1,3 linkages may provide a protective antibody response, e.g., against *C. albicans*.

In further embodiments, a composition may include two different glucans, e.g., a first glucan having a β(1-3): β(1-6) ratio of between 1.5:1 and 7.5:1, and a second glucan having exclusively or mainly β-1,3 linkages. For instance a composition may include both a laminarin glucan and a curdlan glucan.

Exemplary methods of preparing β-glucans may be found in WO2009/077854.

Laminarin and curdlan are typically found in nature as high molecular weight polymers e.g. with a molecular weight of at least 100 kDa. They are often insoluble in aqueous media. In their natural forms, therefore, they are not well suited to immunization. Thus the invention may use a shorter glucan, e.g., those containing 60 or fewer glucose monosaccharide units (e.g. 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4). A glucan having a number of glucose residues in the range of 2-60 may be used, for example, between 10-50 or between 20-40 glucose units. A glucan with 25-30 glucose residues is particularly useful. Suitable glucans may be formed e.g. by acid hydrolysis of a natural glucan, or by enzymatic digestion, e.g., with a glucanase, such as a β-1,3-glucanase. A glucan with 11-19, e.g., β-19 and particularly 15 or 17, glucose monosaccharide units is also useful. In particular, glucans with the following structures (A) or (B) are specifically envisaged for use in the present invention:

(A)

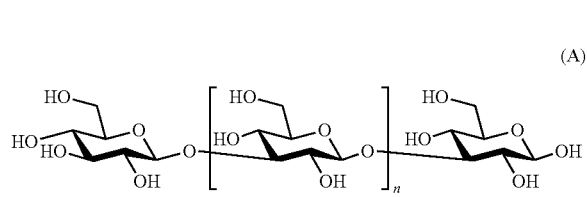

wherein n+2 is in the range of 2-60, e.g., between 10-50 or between 2-40. Preferably, n+2 is in the range of 25-30 or 11-19, e.g., β-17. The inventors have found that n+2=15 is suitable.

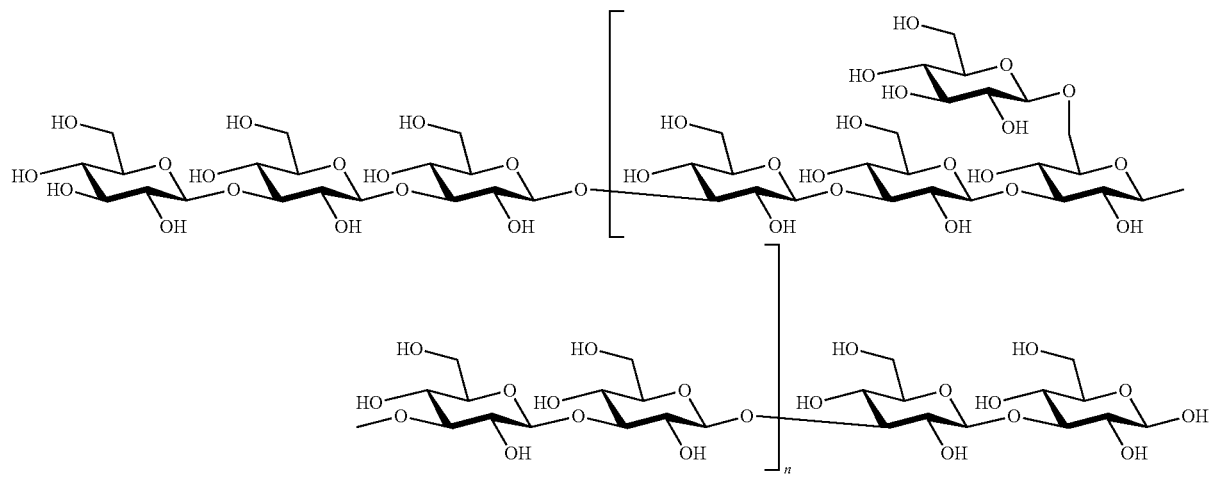

(B)

wherein n is in the range of 0-9, e.g., between 1-7 or between 2-6. Preferably, n is in the range of 3-4 or 1-3. The inventors have found that n=2 is suitable.

The glucan (as defined above) is preferably a single molecular species. In this embodiment, all of the glucan molecules are identical in terms of sequence. Accordingly, all of the glucan molecules are identical in terms of their structural properties, including molecular weight, etc. Typically, this form of glucan is obtained by chemical synthesis, e.g., using the methods described above.

For example, Jamois et al. (2005) *Glycobiology* 15(4):393-407, describes the synthesis of a single β-1,3 linked species. Alternatively, in other embodiments, the glucan may be obtained from a natural glucan, e.g., a glucan from *L. digitata, Agrobacterium* or *Euglena* as described above, with the glucan being purified until the required single molecular species is obtained. Natural glucans that have been purified in this way are commercially available. A glucan that is a single molecular species may be identified by measuring the polydispersity (Mw/Mn) of the glucan sample. This parameter can conveniently be measured by SEC-MALLS, for example as described in Bardotti et al. (2008) *Vaccine* 26:2284-96. Suitable glucans for use in this embodiment of the invention have a polydispersity of about 1, e.g., 1.01 or less.

The solubility of natural glucans, such as curdlan, can be increased by introducing ionic groups (e.g., by sulfation, particularly at O-6 in curdlan). Such modifications may be used with the invention, but are ideally avoided as they may alter the glucan's antigenicity.

When glucans are isolated from natural sources, they may be isolated in combination with contaminants. For example, the inventors have found that glucans may be contaminated with phlorotannin, which is identifiable by ultraviolet-visible (UV/VIS) spectroscopy. This problem is particularly common when the glucan is isolated from a brown alga or seaweed. For example, the UV spectrum of a commercially-available laminarin extracted from *Laminaria digitata* includes an absorption peak resulting from the presence of phlorotannin contamination. Similarly, glucans extracted from *Artie laminarialis, Saccorhiza dermatodea* and *Alaria esculenta* have UV spectra that include an absorption peak resulting from phlorotannin contamination.

The presence of phlorotannin in a sample of glucan may affect the biological properties of the glucan. Accordingly, it may be desirable to remove phlorotannin from the sample, especially when the glucan is for medical use numerous aspects of the present invention. Exemplary methods of removing phlorotannins from β-glucans may be found in WO2009/077854.

*N. meningitidis:*

In certain embodiments, the conjugate compositions may include capsular saccharides from at least two of serogroups A, C, W135 and Y of *Neisseria meningitidis*. In other embodiments, such compositions further comprise an antigen from one or more of the following: (a) *N. meningitidis*; (b) *Haemophilus influenzae* type B; *Staphylococcus aureus*, groups A and B *streptococcus*, pathogenic *E. coli*, and/or (c) *Streptococcus pneumoniae*.

In certain embodiments the conjugate compositions include capsular polysaccharides from serogroups C, W135 & Y of *N. meningitidis*. In certain embodiments the conjugate compositions include capsular polysaccharides from serogroups A, C, W135 & Y of *N. meningitidis*. In certain embodiments the conjugate compositions include capsular polysaccharides from *H. influenzae* type B and serogroups C, W135 & Y of *N. meningitidis*. In certain embodiments the conjugate compositions include capsular polysaccharides from *H. influenzae* type B and serogroups A, C, W135 & Y of *N. meningitidis*. In certain embodiments the conjugate compositions include capsular polysaccharides from *S. pneumoniae* and serogroups C, W135 & Y of *N. meningitidis*. In certain embodiments the conjugate compositions include capsular polysaccharides from *S. pneumoniae* and serogroups A, C, W135 & Y of *N. meningitidis*. In certain embodiments the conjugate compositions include capsular polysaccharides from *H. influenzae* type B, *S. pneumoniae* and serogroups C, W135 & Y of *N. meningitidis*. In certain embodiments the conjugate compositions include capsular polysaccharides from *H. influenzae* type B, *S. pneumoniae* and serogroups A, C, W135 & Y of *N. meningitidis*.

*Streptococcus pneumoniae:*

*Streptococcus pneumoniae* polysaccharide conjugates may include a saccharide (including a polysaccharide or an oligosaccharide) and optionally one or more proteins from *Streptococcus pneumoniae*. Saccharide antigens maybe selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Optional protein antigens may be selected from a protein identified in WO98/18931, WO98/18930, U.S. Pat. No. 6,699,703, U.S. Pat. No. 6,800,744, WO97/43303, and WO97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, SpIO1, Sp130, Sp125 or Sp133.

*Staphylococcus aureus:*

*Staphylococcus aureus* polysaccharide conjugates may include *S. aureus* type 5, 8 and 336 capsular polysaccharides and fragments thereof and optionally protein antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). Exemplary depolymerization methods of generating fragments of *S. aureus* capsular polysaccharides may be found in U.S. Ser. No. 61/247,518, titled "Conjugation of *Staphylococcus Aureus* Type 5 and Type 8 Capsular Polysaccharides," filed Sep. 30, 2009, from page 5, line 6 through page 6, line 23, which is hereby incorporated by reference for its teaching of such depolymerization techniques.

*Haemophilus influenzae* B (Hib):

Hib polysaccharide conjugates may include Hib saccharide antigens.

*Streptococcus agalactiae* (Group B *Streptococcus*):

Group B *Streptococcus* polysaccharide conjugates may include saccharide antigens derived from serotypes Ia, Ib, Ia/c, II, III, IV, V, VI, VII and VIII as identified in WO04/041157 and optionally one or more protein antigens including, without limitation as identified in WO02/34771, WO03/093306, WO04/041157, or WO05/002619 (including by way of example proteins GBS 80, GBS104, GBS 276 and GBS 322).

*Vibrio cholerae:*

*V. cholerae* polysaccharide conjugates may include LPS, particularly lipopolysaccharides of *Vibrio cholerae* II, O1 Inaba O-specific polysaccharides.

*Salmonella typhi* (Typhoid Fever):

Polysaccharide conjugates may include capsular polysaccharides such as Vi.

Carrier Polypeptides

A number of promising antigens from *E. coli* were tested for their efficacy as carrier polypeptides. One such antigen is annotated as Bacterial Ig-like domain (group 1) protein (also as 'orf405', SEQ IDs 809 & 810 in reference 1), which is also known as: 'orf284' from *E. coli* NMEC strain IHE3034, 'c0415' from *E. coli* strain CFT073 and ecp_0367 from *E. coli* strain 536. Yet another such antigen is annotated as Flu antigen 43 protein (also as 'orf1364', SEQ IDs 2727 & 2728 in reference 1), which is also known as: 'orf1109' from *E. coli* NMEC strain IHE3034, 'c1273' from *E. coli* strain CFT073 and ecp_3009 from *E. coli* strain 536. Yet another such antigen is annotated as accessory colonization factor D (AcfD) precursor protein (also as 'orf3526', SEQ IDs 7051 & 7052 in reference 1), which is also known as: 'ECP_3050' from *E. coli* UPEC strain 536, 'yghJ' from *E. coli* commensal strain W3110, 'EcE24377A_3432' from *E. coli* ETEC strain E24377A, and 'EcHS_A3142' from *E. coli* commensal strain HS. Yet another such antigen is annotated as Fimbrial protein (also as 'orf3613', SEQ IDs 7225 & 7226 in reference 1), which is also known as: 'orf3431' from *E. coli* NMEC strain IHE3034 and 'c3791' from *E. coli* strain CFT073. Still another such antigen is annotated as Sel1 repeat-containing protein (also as 'upec-5211', disclosed in reference 2 SEQ ID 577) is also known as: 'c5321' from CFT073; 'ECED1_5081' from ED1a and 'EFER_4303' from *E. fergusonii* ATCC 35469. In particular, AcfD precursor (orf3526), Flu antigen 43 protein (orf1364), and Sel1 repeat-containing protein (upec-5211) were all demonstrated to be conjugatable, soluble as conjugates and effective in enhancing the immune response to the conjugated polysaccharide.

Carrier polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). For instance, a polypeptide of the invention may have a lipidated N-terminal cysteine.

Carrier polypeptides used with the invention can be prepared by various means (e.g. recombinant expression, purification from cell culture, chemical synthesis, etc.). Recombinantly-expressed proteins are preferred.

Carrier polypeptides used with the invention are preferably provided in purified or substantially purified form, i.e., substantially free from other polypeptides (e.g. free from naturally-occurring polypeptides), particularly from other *E. coli* or host cell polypeptides, and are generally at least about 50% pure (by weight), and usually at least about 90% pure, i.e., less than about 50%, and more preferably less than about 10% (e.g., 5%) of a composition is made up of other expressed polypeptides. Thus the antigens in the compositions are separated from the whole organism with which the molecule is expressed. For the avoidance of doubt, when a purified or substantially carrier protein conjugated to a polysaccharide is used as a component of a vaccine, the carrier protein is still "purified" or "substantially purified" despite the presence of other protein antigens and cellular components (e.g., other polysaccharides, outer membrane vesicles, etc.).

The carrier polypeptides used with the invention are preferably *E. coli* polypeptides. Such polypeptides may be further selected from NMEC, APEC, UPEC, EAEC, EIEC, EPEC and ETEC *E. coli* polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. Polypeptides can occur as single chains or associated chains.

The invention also includes carrier polypeptides comprising a sequence —P-Q- or -Q-P—, wherein: —P— is an amino acid sequence as defined above and -Q- is not a sequence as defined above i.e. the invention provides fusion proteins. Where the N-terminus codon of —P— is not ATG, but this codon is not present at the N-terminus of a polypeptide, it will be translated as the standard amino acid for that codon rather than as a Met. Where this codon is at the N-terminus of a polypeptide, however, it will be translated as Met. Examples of -Q- moieties include, but are not limited to, histidine tags (i.e., $His_n$ where n=3, 4, 5, 6, 7, 8, 9, 10 or more), a maltose-binding protein, or glutathione-5-transferase (GST).

The invention also includes oligomeric proteins comprising a carrier polypeptide of the invention. The oligomer may be a dimer, a trimer, a tetramer, etc. The oligomer may be a homo-oligomer or a hetero-oligomer. Polypeptides in the oligomer may be covalently or non-covalently associated.

Comparison of the immune response raised in a subject by the carrier polypeptide with the immune response raised by the full length protein may be carried out use by any means available to one of skill in the art. One simple method as used in the examples below involves immunization of a model subject such as mouse and then challenge with a lethal dose of *E. coli*. For proper comparison, one of skill in the art would naturally select the same adjuvant such as Freund's complete adjuvant. In such a test the carrier polypeptide fragments of the present invention will raise a substantially similar immune response in a subject (i.e., will provide substantially the same protection against the lethal challenge) if, for example, the polypeptide provides at least 70% of the protection provided by the full length protein, at least 80% of the protection provided by the full length protein, at least 85% of the protection provided by the full length protein, at least 90% of the protection provided by the full length protein, at least 95% of the protection provided by the full length protein, at least 97% of the protection provided by the full length protein, at least 98% of the protection provided by the full length protein, or at least 99% of the protection provided by the full length protein.

The invention also provides a process for producing a polypeptide of the invention, comprising the step of culturing a host cell transformed with nucleic acid of the invention under conditions which induce polypeptide expression. The polypeptide may then be purified, e.g., from culture supernatants.

The invention provides an *E. coli* cell, containing a plasmid that encodes a carrier polypeptide of the invention. The chromosome of the *E. coli* cell may include a homolog of the carrier polypeptide, or such a homolog may be absent, but in both cases the polypeptide of the invention can be expressed from the plasmid. The plasmid may include a gene encoding a marker, etc. These and other details of suitable plasmids are given below.

Although expression of the carrier polypeptides of the invention may take place in an *E. coli* strain, the invention will usually use a heterologous host for expression. The heterologous host may be prokaryotic (e.g., a bacterium) or eukaryotic. Suitable hosts include, but are not limited to, *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

The invention provides a process for producing a carrier polypeptide of the invention, comprising the step of synthesising at least part of the polypeptide by chemical means.

Any and all of the foregoing proteins, polypeptides, hybrid polypeptides, epitopes and immunogenic fragments may be in any one of a number of forms including, without limitation, recombinant, isolated or substantially purified (from materials co-existing with such proteins, polypeptides, hybrid polypeptides, epitopes and immunogenic fragments in their natural state).

Orf1364 Polypeptide

Flu antigen 43 protein is referred to herein as 'orf1364.' 'orf1364' polypeptide from *E. coli* NMEC is disclosed in reference 1 (SEQ IDs 2727 & 2728) is also known as: 'orf1109' from *E. coli* NMEC strain IHE3034, 'c1273' from CFT073 and ecp_3009 from 536.

When used according to the present invention, orf1364 polypeptide may take various forms. Preferred orf1364 sequences have 50% or more identity (e.g., 60%, 65%, 70%, 75%, 80%, 85%, 87.5%, 90%, 91%, 92%, 93%, 94%, 95%, 96%, 97%, 98%, 99%, 99.5% or more) to SEQ ID NOs 1-22. This includes variants (e.g., allelic variants, homologs, orthologs, paralogs, mutants etc. Alternatively, the orf1364 sequences when aligned with any of SEQ ID NOs 1-22 using a pairwise alignment algorithm, each moving window of x amino acids from N terminus to C terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer.

The preferred pairwise alignment algorithm is the Needleman-Wunsch global alignment algorithm (3), using default parameters (e.g., with Gap opening penalty=10.0, and with Gap extension penalty=0.5, using the EBLOSUM62 scoring matrix). This algorithm is conveniently implemented in the needle tool in the EMBOSS package (4).

Orf1364 polypeptide sequences may have 1, 2, 3, 4, 5, 6, 7, 8, 9 or 10 (or more) single amino acid alterations (deletions, insertions, substitutions), which may be at separate locations or may be contiguous, as compared to SEQ ID NOs 1-22.

Orf1364 polypeptide sequences may, compared to any one of SEQ ID NOs 1-22, include one or more (e.g., 1, 2, 3, 4, 5, 6, 7, 8, 9, 10, etc.) amino acid substitutions, such as conservative substitutions (i.e., substitutions of one amino acid with another which has a related side chain). Genetically encoded amino acids are generally divided into four families: (1) acidic, i.e., aspartate, glutamate; (2) basic, i.e., lysine, arginine, histidine; (3) non-polar, i.e., alanine, valine, leucine, isoleucine, proline, phenylalanine, methionine, tryptophan; and (4) uncharged polar, i.e., glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity.

Orf1364 polypeptide sequences may include one or more (e.g. 1, 2, 3, 4, 5, 6, 7, 8, 9, etc.) single amino acid deletions relative to any one of SEQ ID NOs 1-22. Similarly, a polypeptides may include one or more (e.g. 1, 2, 3, 4, 5, 6, 7, 8, 9, 10, etc.) insertions (e.g., each of 1, 2, 3, 4 or 5 amino acids) relative to any one of SEQ ID NOs 1-22.

Other preferred orf1364 sequences comprise at least n consecutive amino acids from SEQ ID NOs 1-22, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope or immunogenic fragment from orf1364. Other preferred fragments lack one or more amino acids (e.g. 1, 2, 3, 4, 5, 6, 7, 8, 9, 10, 15, 20, 25, 30, 35, 40, 45, 50, 52 or more) from the C-terminus and/or the N-terminus of SEQ ID NOs 1-22. An exemplary fragment is indicated by # under the alignment below. The exemplary fragment may comprise less than 950 amino acids, less than 900 amino acids, less than 850 amino acids, less than 800 amino acids, less than 750 amino acids, less than 700 amino acids, less than 650 amino acids, less than 600 amino acids, less than 550 amino acids, less than 500 amino acids, less than 450 amino acids, less than 440 amino acids, or less than 430 amino acids of the flu antigen 43 (orf1364) protein. Further, the exemplary fragment may not comprise at least the first 10 N-terminal amino acids as compared to the *E. coli* Flu antigen 43 protein (orf1364 polypeptide), at least the first 20 N-terminal amino acids as compared to the *E. coli* Flu antigen 43 protein (orf1364 polypeptide), at least the first 30 N-terminal amino acids as compared to *E. coli* Flu antigen 43 protein (orf1364 polypeptide), at least the first 40 N-terminal amino acids as compared to *E. coli* Flu antigen 43 protein (orf1364 polypeptide), at least the first 50 N-terminal amino acids as compared to *E. coli* Flu antigen 43 protein (orf1364 polypeptide), or at least the first 52 N-terminal amino acids as compared to the *E. coli* AcfD (orf3526) protein. Finally, the exemplary fragment may not comprise at least the last 50 C-terminal amino acids as compared to the *E. coli* Flu antigen 43 protein (orf1364 polypeptide), at least the last 100 C-terminal amino acids as compared to the *E. coli* Flu antigen 43 protein (orf1364 polypeptide), at least the last 150 C-terminal amino acids as compared to the *E. coli* Flu antigen 43 protein (orf1364 polypeptide), at least the last 200 C-terminal amino acids as compared to the *E. coli* Flu antigen 43 protein (orf1364 polypeptide), at least the last 250 C-terminal amino acids as compared to the *E. coli* Flu antigen 43 protein (orf1364 polypeptide), at least the last 300 C-terminal amino acids as compared to the *E. coli* Flu antigen 43 protein (orf1364 polypeptide), at least the last 325 C-terminal amino acids as compared to the *E. coli* Flu antigen 43 protein (orf1364 polypeptide), or at least the last 328 C-terminal amino acids as compared to the *E. coli* Flu antigen 43 protein (orf1364 polypeptide).

```
                                                                    (SEQ ID NO: 1)
        Strain E110019

(SEQ ID NO: 2)
        Group A: strain Sakai, EDL933, EC508, EC869, EC4024, EC4042, EC4045, EC4076, EC4113, EC4115, EC4196, EC4206, EC4401, EC4486, EC4501 and TW14588

(SEQ ID NO: 3)
        strain B171

(SEQ ID NO: 4)
        strain E22

(SEQ ID NO: 5)
        strain B171

(SEQ ID NO: 6)
        strain B171

(SEQ ID NO: 7)
        strain E24377A and O42

(SEQ ID NO: 8)
        strain E24377A (SEQ ID NO: 9)
        Group B: strain UTI89, RS218 and IHE3034

(SEQ ID NO: 10)
        strain E110019

(SEQ ID NO: 11)
        strain E22

(SEQ ID NO: 12)
        strain H10407

(SEQ ID NO: 13)
        strain F11 and 536

(SEQ ID NO: 14)
        strain SECEC (SEQ ID NO: 15)
        strain H10407

(SEQ ID NO: 16)
        strain W3110 and DH10B (SEQ ID NO: 17)
        strain MG1655

(SEQ ID NO: 18)
        strain O42

(SEQ ID NO: 19)
        strain B7A (SEQ ID NO: 20)
```

-continued strain CFT073

(SEQ ID NO: 21)

strain O42

(SEQ ID NO: 22)

strain CFT073

```
                           1                                                      50
strain E110019             MKRHLNTSYR LVWNHITGTL VVASELARSR GKRAGVAVAL SLAAVTSVPA
Group A                    MKRHLNTSYR LVWNHITGTL VVASELARSR GKRAGVAVAL SLAAVTSVPA
strain B171                MKRHLNTSYR LVWNHITGTL VVASELARSR GKRAGVAVAL SLAAVTSVPA
strain E22                 MKRHLNTSYR LVWNHITGTL VVASELARSR GKRAGVAVAL SLAAVTSVPA
strain B171                MKRHLNTSYR LVWNHITGTL VVASELARSR GKRTGVAVAL SLAAVTSVPV
strain B171                MKRHLNTSYR LVWNHITGTL VVASELARSR GKRTGVAVAL SLAAVTSVPV
strain E24377A and O42     MKRHLNTSYR LVWNHITGTL VVASELARSR GKRTGVAVAL SLAAVTSVPV
strain E24377A             MKRHLNTSYR LVWNHITGTL VVASELARSR GKRAGVAIAL SLAAVTSVPA
Group B                    MKRHLNTSYR LVWNHITGTL VVASELARSR GKGAGVAVAL SLAAVTSVPA
strain E110019             MKRHLNTSYR LVWNHITGTL VVASELARSR GKRTGVAVAL SLAAVTSVPV
strain E22                 MKRHLNTSYR LVWNHITGTL VVASELARSR GKRAGVAVAL SLAAVTSVPA
strain H10407              MKRHLNTSYR LVWNHITGTL VVASELARSR GKRAGVAIAL SLAAVTSVPA
strain F11 and 536         MKRHLNTSYR LVWNHITGTL VVASELARSR GKRAGVAVAL SLAAVTSVPA
strain SECEC               MKRHLNTSYR LVWNHITGTL VVASELARSR GKRAGVAVAL SLAAVTPVPA
strain H10407              MKRHLNTSYR LVWNHITGTL VVASELARSR GKRTGVAVAL SLATATSVPA
strain W3110 and DH10B     MKRHLNTCYR LVWNHMTGAF VVASELARAR GKRGGVAVAL SLAAVTSLPV
strain MG1655              MKRHLNTCYR LVWNHMTGAF VVASELARAR GKRGGVAVAL SLAAVTSLPV
strain O42                 MKRHLNTCYR LVWNHITGAF VVASELARAR GKRGGVAVAL SLAAVTSLPV
strain B7A                 MKRHLNTSYR LVWNHITGTL VVASELARSR GKRAGVAVAL SLAAVTSVPA
strain CFT073              MKRHLNTSYR LVWNHITGAF VVASELARAR GKRAGVAVAL SLAAATSLPA
strain O42                 MKRHLNTCYR LVWNHITGAF VVASELARAR GKRGGVAVAL SLAAVTSLPV
strain CFT073              MKRHLNTCYR LVWNHITGAF VVASELARAR GKRGGVAVAL SLAAVTPLPV
Consensus                  MKRHLNT-YR LVWNH-TG-- VVASELAR-R GK--GVA-AL SLA--T--P-

51                                                     100
strain E110019             LAADKVVQAG ETVNDGTLTN HDNQIVFGTA NGMTISTGLE LGPDSEENTG
Group A                    LAADKVVQAG ETVNDGTLTN HDNQIVFGTA NGMTISTGLE LGPDSEENTG
strain B171                LAADTVVQAG ETVNGGTLTN HDNQIVLGTA NGMTISTGLE LGPDSEENTG
strain E22                 LAADTVVQAG ETVNGGTLTN HDNQIVLGTA NGMTISTGLE LGPDSEENTG
strain B171                LAADTVVQAG ETVSGGTLTN HDNQIVLGTA NGMTISTGLE YGPDNEANTG
strain B171                LAADTVVQAG ETVSGGTLTN HDNQIVLGTA NGMTISTGLE YGPDNEANTG
strain E24377A and O42     LAADTVVQAG ETVSGGTLTN HDNQIVFGTA NGMTISTGLE YGPDNEANTG
strain E24377A             LAADTVVQAG ETVNDGTLTN HDNQIVLGTA NGMTISTGLE YGPDNEANTG
Group B                    LAADTVVQAG ETVNGGTLTN HDNQIVLGTA NGMTISTGLE YGPDNEANTG
strain E110019             LAADTVVQAG ETVSGGTLTN HDNQIVFGTA NGMTISTGLE YGPDNEANTG
strain E22                 LAADTVVQAG ETVSGGTLVN HDNQIVFGTA NGMTISTGLE YGPDNEANTG
strain H10407              LAADTVVQAG ETVSGGTLTN HDNQIVFGTA NGMTISSGLE YGPDNEANTG
strain F11 and 536         LAADTVVQAG ETVNGGTLTN HDNQIVLGTA NGMTISTGLE YGPDNEANTG
strain SECEC               LAADTVVEAG ETVNGGTLTN HDNQIVFGTT NGMTISTGLE YGTDNEANTG
strain H10407              LAADSVVQAG ETVSGGTLEN HDNQIVFGTT NGITISTGLE YGPDNEANTG
strain W3110 and DH10B     LAADIVVHPG ETVNGGTLAN HDNQIVFGTT NGMTISTGLE YGPDNEANTG
strain MG1655              LAADIVVHPG ETVNGGTLAN HDNQIVFGTT NGMTISTGLE YGPDNEANTG
strain O42                 LAADIVVHPG ETVNGGTLAN HDNQIVFGTT NGMTISTGLE YGPDNEANTG
strain B7A                 LAADKVVQAG ETVNDGTLTN HDNQIVLGTA NGMTISTGLE YGPDNEANTG
strain CFT073              LAADSVVPAG ETVNGGTLIN HDRQFVSGTA DGMTVSTGLE LGADSDNNTG
strain O42                 LAADIVVHPG ETVNGGTLVN HDNQFVSGTA DGVTVSTGLE LGPDSDDNTG
strain CFT073              LSADIVVHPG ETVNGGTLVN HDNQFVSGTA NGVTVSTGLE LGPDSDENTG
Consensus                  L-AD-VV--G ETV--GTL-N HD-Q-V-GT- -G-T-S-GLE -G-D---NTG
                           ######## ########## ########## ########## ##########

101                                                    150
strain E110019             GQWIQNGGIA GNTTVTTNGR QVVLEGGTAS DTVIRDGGGQ SLNGLAVNTT
Group A                    GQWIQNGGIA GNTTVTTNGR QVVLEGGTAS DTVIRDGGGQ SLNGLAVNTT
strain B171                GQWIQNGGIA GNTTVTTNGR QVVLEGGTAS DTVIRDGGGQ SLNGLAVNTT
strain E22                 GQWIQNGGIA GNTTVTTNGR QVVLEGGTAS DTVIRDGGGQ SLNGLAVNTT
strain B171                GQWIQNGGIA NNTTVTGGGL QRVNAGGSVS DTVISAGGGQ SLQGQAVNTT
strain B171                GQWIQNGGIA NNTTVTGGGL QRVNAGGSVS DTVISAGGGQ SLQGQAVNTT
strain E24377A and O42     GQWIQNGGIA NNTTVTGGGL QRVNAGGSVS DTVISAGGGQ SLQGQAVNTT
strain E24377A             GQWIQNGGIA NNTTVTGGGL QRVNAGGSVS DTVISAGGGQ SLQGQAVNTT
Group B                    GQWIQNGGIA NNTTVTGGGL QRVNAGGSVS DTVISAGGGQ SLQGQAVNTT
strain E110019             GQWIQNGGIA NNTTVTGGGL QRVNAGGSVS DTVISAGGGQ SLQGQAVNTT
strain E22                 GQWIQNGGTA NNTTVTGGGL QRVNTGGSVS DTVISAGGGQ SLQGQAVNTT
strain H10407              GQWIQNGGIA NNTTVTGGGL QRVNAGGSVS DTVISAGGGQ SLQGQAVNTT
strain F11 and 536         GQWIQNGGIA NNTTVTGGGL QRVNAGGSVS DTVISAGGGQ SLQGQAVNTT
strain SECEC               GQWVQDGGTA SNTTISSGGL QFVGAGGKAT DTIINEGGGQ SLKGLALNTT
strain H10407              GQWVQDGGTA SNTTISSGGL QFVGAGGKAT DTIINEGGGQ SLKGLALNTT
strain W3110 and DH10B     GQWVQDGGTA NKTTVTSGGL QRVNPGGSVS DTVISAGGGQ SLQGRAVNTT
strain MG1655              GQWVQDGGTA NKTTVTSGGL QRVNPGGSVS DTVISAGGGQ SLQGRAVNTT
strain O42                 GQWVQDGGTA NKTTVTSGGL QRVNPGGSVS DTVISAGGGQ SLQGRAVNTT
strain B7A                 GQWIQNGGIA NNTTVTGGGL QRVNAGGSVS DTVISAGGGQ SLQGQAVNTT
strain CFT073              GQQIARGGTA RNTRVTANGL QDVMAGGSTS DTVISTGGGQ NLRGKASGTV
```

-continued

```
strain O42              GQQIARGGTA RNTTVTANGL QDVMAGGSAT DTVISAGGGQ NLRGQAYGTV
strain CFT073           GQWIKAGGTG RNTTVTANGR QIVQAGGTAS DTVIRDGGGQ SLNGLAVNTT
Consensus               GQ----GG-- --T-----G- Q-V--GG--- DT-I--GGGQ -L-G-A--T-
                        ########## ########## ########## ########## ##########

151                                                  200
strain E110019          LNNRGEQWVH EGGVATGTII NRDGYQSVKS GGLATGTIIN TGAEGGPDSD
Group A                 LNNRGEQWVH EGGVATGTII NRDGYQSVKS GGLATGTIIN TGAEGGPDSD
strain B171             LNNRGEQWVH EGGVATGTII NRDGYQSVKS GGLATGTIIN TGAEGGPDSD
strain E22              LNNRGEQWVH EGGVATGTII NRDGYQSVKS GGLATGTIIN TGAEGGPDSD
strain B171             LNG.GEQWVH EGGIATGTVI NEKGWQAVKS GAMATDTVVN TGAEGGPDAE
strain B171             LNG.GEQWVH EGGIATGTVI NEKGWQAVKS GAMATDTVVN TGAEGGPDAE
strain E24377A and O42  LNG.GEQWVH EGGIATGTVI NEKGWQAVKS GAMATDTVVN TGAEGGPDAE
strain E24377A          LNG.GEQWVH EGGIATGTVI NEKGWQAVKS GAMATDTVVN TGAEGGPDAE
Group B                 LNG.GEQWVH EGGIATGTVI NEKGWQAVKS GAMATDTVVN TGAEGGPDAE
strain E110019          LNG.GEQWVH EGGIATVTVI NEKGWQAVKS GAMATDTVVN TGAEGGPDAD
strain E22              LNG.GEQWVH EGGIATGTVI NEKGWQAIKS GAVATDTVVN TGAEGGPDAE
strain H10407           LNG.GEQWVH EGGIATGTVI NEKGWQAVKS GAMATDTVVN TGAEGGPDAE
strain F11 and 536      LNG.GEQWVH EGGIATGTVI NEKGWQAVKS GAMATDTVVN TGAEGGPDAE
strain SECEC            LNG.GEQWMH EGAIATGTVI NDKGWQVVKP GAVATDTVVN TGAEGGPDAE
strain H10407           LNG.GEQWMH EGAIATGTVI NDKGWQVVKP GAVATDTVVN TGAEGGPDAE
strain W3110 and DH10B  L.NGGEQWMH EGAIATGTVI NDKGWQVVKP GTVATDTVVN TGAEGGPDAE
strain MG1655           L.NGGEQWMH EGAIATGTVI NDKGWQVVKP GTVATDTVVN TGAEGGPDAE
strain O42              L.NGGEQWMH EGAIATGTVI NDKGWQVVKP GTVATDTVVN TGAEGGPDAE
strain B7A              L.NGGEQWVH EGGIATGTVI NEKGWQAIKS GAVATDTVVN TGAEGGPDAE
strain CFT073           L.NGGDQWTH AGGRASGTVI NQDGYQTIKH GGLVTGTIIN TGAEGGPDSE
strain O42              L.NGGEQWMH AGGSASGTVI NQDGYQTIKH GGQATGTIVN TGAEGGPESE
strain CFT073           LDNRGEQWVH GGGKAAGTII NQDGYQTIKH GGLATGTIVN TGAEGGPESE
Consensus               L---G-QW-H -G--A--T-I N--G-Q--K- G---T-T--N TGAEGGP---
                        ########## ########## ########## ########## ##########

201                                                  250
strain E110019          NSYTGQKVQG TAESTTINKN GRQIILFSGL ARDTLIYAGG DQSVHGRALN
Group A                 NSYTGQKVQG TAESTTINKN GRQIILFSGL ARDTLIYAGG DQSVHGRALN
strain B171             NSYTGQKVQG TAESTTINKN GRQIILFSGI ARDTLIYAGG DQSVHGRALN
strain E22              NSYTGQKVQG TAESTTINKN GRQIILFSGI ARDTLIYAGG DQSVHGRALN
strain B171             NGDTGQFVRG NAVRTTINKN GRQIVAAEGT ANTTVVYAGG DQTVHGHALD
strain B171             NGDTGQFVRG NAVRTTINKN GRQIVAAEGT ANTTVVYAGG DQTVHGHALD
strain E24377A and O42  NGDTGQFVRG NAVRTTINEN GRQIVAAEGT ANTTVVYAGG DQTVHGHALD
strain E24377A          NGDTGQFVRG NAVRTTINKN GRQIVAAEGT ANTTVVYAGG DQTVHGHALD
Group B                 NGDTGQTVYG DAVRTTINKN GRQIVAAEGT ANTTVVYAGG DQTVHGHALD
strain E110019          NGDTGQFVRG NAVRTTINKN GRQIVAVEGT ANTTVVYAGG DQTVHGHALD
strain E22              NGDTGQTVYG DAVRTTINKN GRQIVAAEGT ANTTVVYAGG DQTVHGHALD
strain H10407           NGDTGQFVRG NAVRTTINKN GRQIVAAEGT ANTTVVYAGG DQTVHGHALD
strain F11 and 536      NGDTGQFVRG NAVRTTINEN GRQIVAAEGT ANTTVVYAGG DQTVHGYALD
strain SECEC            NGDTGQFVRG NAVRTTINKN GRQIVTVEGT ANTTVVYAGG DQTVHGHALD
strain H10407           NADTGQFVRG DAVRTTINKN GRQIVVATGV ANTTVVYAGG DQTVHGYALD
strain W3110 and DH10B  NGDTGQFVRG DAVRTTINKN GRQIVRAEGT ANTTVVYAGG DQTVHGHALD
strain MG1655           NGDTGQFVRG DAVRTTINKN GRQIVRAEGT ANTTVVYAGG DQTVHGHALD
strain O42              NGDTGQFVRG DAVRTTINKN GRQIVRAEGT ANTTVVYAGG DQTVHGHALD
strain B7A              NGDTGQTVYG DAVRTTINKN GRQIVAAEGT ANTTVVYAGG DQTVHGHALD
strain CFT073           NVSTGQMVGG IAESTTINKN GRQVIWSSGI ARDTLIYTGG DQTVHGEAHN
strain O42              NVSSGQMVGG TAESTTINKN GRQVIWSSGM ARDTLIYAGG DQTVHGEAHN
strain CFT073           NVSSGQMVGG TAESTTINKN GRQVIWSSGM ARDTLIYAGG DQTVHGEAHN
Consensus               N---GQ-V-G -A--TTIN-N GRQ-----G- A--T--Y-GG DQ-VHG-A--
                        ########## ########## ########## ########## ##########

251                                                  300
strain E110019          TTLNGGYQYV HRDGLALNTV INEGGWQVVK AGGAAGNTTI NQNGELRVHA
Group A                 TTLNGGYQYV HRDGLALNTV INEGGWQVVK AGGAAGNTTI NQNGELRVHA
strain B171             TTLNGGYQYV HKDGLALNTV INEGGWQVVK AGGAVGNTTI NQNGELRVHA
strain E22              TTLNGGYQYV HKDGLALNTV INEGGWQVVK AGGAVGNTTI NQNGELRVHA
strain B171             TTLNGGYQYV HNGGTASGTV VNSDGWQIIK EGGLADFTTV NQKGKLQVNA
strain B171             TTLNGGYQYV HNGGTASGTV VNSDGWQIIK EGGLADFTTV NQKGKLQVNA
strain E24377A and O42  TTLNGGYQYV HNGGTASDTV VNSDGWQIVK EGGLADFTTV NQKGKLQVNA
strain E24377A          TTLNGGYQYV HNGGTASGTV VNSDGWQIIK EGGLADFTTV NQKGKLQVNA
Group B                 TTLNGGYQYV HNGGTASDTV VNSDGWQIIK EGGLADFTTV NQKGKLQVNA
strain E110019          TTLNGGYQYV HNGGTASDTV VNSDGWQIVK EGGLADFTTV NQKGKLQVNA
strain E22              TTLNGGYQYV HNGGTASGTV VNSDGWQIIK EGGLADFTTV NQKGKLQVNA
strain H10407           TTLNGGYQYV HNGGTASGTV VNSDGWQIIK EGGLADFTTV NQKGKLQVNA
strain F11 and 536      TTLNGGNQYV HNGGTASGTV VNSDGWQIVK EGGLADFTIV NQKGKLQVNA
strain SECEC            TTLNGGYQYV HNGGTTSDTV VNSDGWQIIK EGGLADFTTV NQKGKLQVNA
strain H10407           TTLNGGNQYV HNGGTASDTV VNSDGWQIIK EGGLADFTTV NQKGKLQVNA
strain W3110 and DH10B  TTLNGGYQYV HNGGTASDTV VNSDGWQIVK NGGVAGNTTV NQKGRLQVDA
strain MG1655           TTLNGGYQYV HNGGTASDTV VNSDGWQIVK NGGVAGNTTV NQKGRLQVDA
strain O42              TTLNGGYQYV HNGGTASDTV VNSDGWQIVK NGGVAGNTTV NQKGRLQVDA
strain B7A              TTLNGGYQYV HNGGTASGTV VNSDGWQIVK NGGVAGNTTV NQKGRLQVDA
strain CFT073           TRLEGGNQYV HKYGLALNTV INEGGWQVVK AGGTAGNTTI NQNGELRVHA
```

```
                                                                                              27                                                               28
                                                                              -continued
                     strain O42                   TRLEGGNQYV HKYGLALNTV INEGGWQVIK EGGTTAHTTI NQKGKLQVNA
                     strain CFT073                TRLEGGNQYV HNGGTATETL INRDGWQVIK EGGTAAHTTI NQKGKLQVNA
                     Consensus                    T-L-GG-QYV H--G----T- -N--GWQ--K -GG----T-- NQ-G-L-V-A
                                                  ########## ########## ########## ########## ##########

301                                                      350
                     strain E110019               GGEATAVTQN TGGALVTSTA ATVIGTNRLG NFTVENGKAD GVVLESGGRL
                     Group A                      GGEATAVTQN TGGALVTSTA ATVIGTNRLG NFTVENGKAD GVVLESGGRL
                     strain B171                  GGEATAVTQN TGGALVTSTA ATVTGANRLG HFSVGNGMAD NVVLENGGRL
                     strain E22                   GGEATAVTQN TGGALVTSTA ATVTGANRLG HFSVGNGMAD NVVLENGGRL
                     strain B171                  GGTATHVTLK QGGALVTSTA ATVLGSNRLG NFTVENGKAD GVVLESGGRL
                     strain B171                  GGTATHVTLK QGGALVTSTA ATVLGSNRLG NFTVENGKAD GVVLESGGRL
                     strain E24377A and O42       GGTATNVTLK QGGALVTSTA ATVTGSNRLG NFTVENGNAD GVVLESGGRL
                     strain E24377A               GGTATNVTLK QGGALVTSTA ATVTGSNRLG NFTVENGKAD GVVLESGGRL
                     Group B                      GGTATNVTLT QGGALVTSTA ATVTGSNRLG NFTVENGNAD GVVLESGGRL
                     strain E110019               GGTATNVTLK QGGALVTSTA ATVTGSNRLG NFTVENGNAD GVVLESGGRL
                     strain E22                   GGTATNVTLK QGGALVTSTA ATVLGSNRLG NFTVENGKAD GVVLESGGRL
                     strain H10407                GGTATHVTLK QGGALVTSTA ATVLGSNRLG NFTVENGKAD GVVLESGGRL
                     strain F11 and 536           GGTATNVTLK QGGALVTSTA ATVTGSNRLG NFTVENGNAD GVVLESGGRL
                     strain SECEC                 GGTATNVTLK QGGALVTSTA ATVTGSNRLG NFAVENGKAD GVVLESGGRL
                     strain H10407                GGTATNVTLK QGGALVTSTA ATVLGSNRLG NFTVENGKAD GVVLESGGRL
                     strain W3110 and DH10B       GGTATNVTLK QGGALVTSTA ATVTGINRLG AFSVVEGKAD NVVLENGGRL
                     strain MG1655                GGTATNVTLK QGGALVTSTA ATVTGINRLG AFSVVEGKAD NVVLENGGRL
                     strain O42                   GGTATNVTLK QGGALVTSTA ATVTGINRLG AFSVVEGKAD NVVLENGGRL
                     strain B7A                   GGTATNVTLK QGGALVTSTA ATVTGINRLG AFSVVEGKAD NVVLENGGRL
                     strain CFT073                GGEASDVTQN TGGALVTSTA ATVTGTNRLG AFSVVEGKAD NVVLENGGRL
                     strain O42                   GGKASDVTQN TGGALVTSTA ATVTGTNRLG AFSVLAGKAD NVVLENGGRL
                     strain CFT073                GGKASDVTQN TGGALVTSTA ATVTGTNRLG AFSVVAGKAD NVVLENGGRL
                     Consensus                    GG-A--VT-- -GGALVTSTA ATV-G-NRLG -F-V--G-AD -VVLE-GGRL
                                                  ########## ########## ########## ########## ##########

351                                                      400
                     strain E110019               DVLESHSAQN TLVDDGGTLA VSAGGKATSV TITSGGALIA DSGATVEGTN
                     Group A                      DVLESHSAQN TLVDDGGTLA VSAGGKATSV TITSGGALIA DSGATVEGTN
                     strain B171                  DVLEGHSAQN TLVDDGGTLA VSAGGKATDV TMTSGGALIA DSGATVEGTN
                     strain E22                   DVLEGHSAQN TLVDDGGTLA VSAGGKATDV TMTSGGALIA DSGATVEGTN
                     strain B171                  DVLEGHSAQK TRVDDGGTLA VSAGGKATDV TMTSGSALIA DSGATVEGTN
                     strain B171                  DVLEGHSAQK TRVDDGGTLA VSAGGKATDV TMTSGSALIA DSGATVEGTN
                     strain E24377A and O42       DVLEGHSAWK TLVDDGGTLA VSAGGKATDV TMTSGSALIA DSGATVEGTN
                     strain E24377A               DVLEGHSAWK TLVDDGGTLA VSAGGKATDV TMTSGGALIA DSGATVEGTN
                     Group B                      DVLEGHSAWK TLVDDGGTLA VSAGGKATDV TMTSGGALIA DSGATVEGTN
                     strain E110019               DVLEGHSAWK TRVDDGGTLA VSAGGKATGV TMTSGGALIA DSGATVEGTN
                     strain E22                   DVLEGHSAWK TLVDDGGTLA VSAGGKATGV TMTSGGALIA DSGATVEGTN
                     strain H10407                DVLEGHSAQK TRVDDGGTLA VSAGGKATGV TMTSGGALIA DSGATVEGTN
                     strain F11 and 536           DVLEGHSAWK TLVDDGGTLA VSAGGKATDV TMTSGGALIA DSGATVEGTN
                     strain SECEC                 DVLEGHSAQK TRVDDGGTLA VSAGGKATGV TMTSGGALIA DSGATVEGTN
                     strain H10407                DVLEGHSAWK TLVDDGGILA VSAGGKATDV TMTSGGALIA DSGATVEGTN
                     strain W3110 and DH10B       DVLTGHTATN TRVDDGGTLD VRNGGTATTV SMGNGGVLLA DSGAAVSGTR
                     strain MG1655                DVLTGHTATN TRVDDGGTLD VRNGGTATTV SMGNGGVLLA DSGAAVSGTR
                     strain O42                   DVLTGHTATN TRVDDGGTLD VRNGGTATTV SMGNGGVLLA DSGAAVSGTR
                     strain B7A                   DVLTGHTATN TRVDDGGTLD VRNGGTATTV SMGNGGVLLA DSGAAVSGTR
                     strain CFT073                DVLSGHTATR TLVDDGGTLD VRNGGTATAV SMGNGGVLLA DSGAAVSGTR
                     strain O42                   DVLSGHTATN TRVDDGGTLD VRNGGAATTV SMGNGGVLLA DSGAAVSGTR
                     strain CFT073                DVLSGHTATN TRVDDGGTLD IRNGGAATTV SMGNGGVLLA DSGAAVSGTR
                     Consensus                    DVL--H-A-- T-VDDGG-L- ---GG-AT-V ----G--L-A DSGA-V-GT-
                                                  ########## ########## ########## ########## ##########

401                                                      450
                     strain E110019               ASGK.FSIDG TSGQASGLLL ENGGSFTVNA GGQAGNTTVG HRGTLTLAAG
                     Group A                      ASGK.FSIDG TSGQASGLLL ENGGSFTVNA GGQAGNTTVG HRGTLTLAAG
                     strain B171                  ASGK.FSIDG ISGQASGLLL ENGGSFTVNA GGQAGNTTVG HRGTLTLAAG
                     strain E22                   ASGK.FSIDG ISGQASGLLL ENGGSFTVNA GGQAGNTTVG HRGTLTLAAG
                     strain B171                  ASGK.FSIDG ISGQASGLLL ENGGSFTVNA GGLASNTTVG HRGTLTLAAG
                     strain B171                  ASGK.FSIDG TSGQASGLLL ENGGSFTVNA GGLASNTTVG HRGTLTLAAG
                     strain E24377A and O42       ASGK.FSIDG TSGQASGLLL ENGGSFTVNA GGLASNTTVG HRGTLTLAAG
                     strain E24377A               ASGK.FSIDG TSGQASGLLL ENGGSFTVNA GGLASNTTVG HRGTLTLAAG
                     Group B                      ASGK.FSIDG ISGQASGLLL ENGGSFTVNA GGLASNTTVG HRGTLTLAAG
                     strain E110019               ASGK.FSIDG ISGQASGLLL ENGGSFTVNA GGQASNTTVG HRGTLMLAAG
                     strain E22                   ASGK.FSIDG ISGQASGLLL ENGGSFTVNA GGQASNTTVG HRGTLMLAAG
                     strain H10407                ASGK.FSIDG TSGQASGLLL ENGGSFTVNA GGQASNTTVG HRGTLMLAAG
                     strain F11 and 536           ASGK.FSIDG ISGQASGLLL ENGGSFTVNA GGQAGNTTVG HRGTLTLAAG
                     strain SECEC                 ASGK.FSIDG ISGQASGLLL ENGGSFTVNA GGQAGNTTVG HRGTLTLAAG
                     strain H10407                ASGK.FSIDG ISGQASGLLL ENGGSFTVNA GGQAGNTTVG HRGTLTLAAG
                     strain W3110 and DH10B       SDGKAFSIGG ..GQADALML EKGSSFTLNA GDTATDTTV. .NGGLFTARG
                     strain MG1655                SDGKAFSIGG ..GQADALML EKGSSFTLNA GDTATDTTV. .NGGLFTARG
                     strain O42                   SDGKAFSIGG ..GQADALML EKGSSFTLNA GDTATDTTV. .NGGLFTARG
                     strain B7A                   SDGKAFSIGG ..GQADALML EKGSSFTLNA GDTATDTTV. .NGGLFTARG
                     strain CFT073                SDGTAFRIGG ..GQADALML EKGSSFTLNA GDTATDTTV. .NGGLFTARG
```

```
                            -continued
strain O42                  SDGTAFRIGG ..GQADALML EKGSSFTLNA GDTATDTTV. .NGGLFTARG
strain CFT073               SDGKAFSIGG ..GQADALML EKGSSFTLNA GDTATDTTV. .NGGLFTARG
Consensus                   --G--F-I-G --GQA--L-L E-G-SFT-NA G--A--TTV- --G-L--A-G
                            ########## ########## ########## ########## ##########

451                                                500
strain E110019              GSLSGRTQLS KGASMVLNGD VVST...... GDIV...... ..........
Group A                     GSLSGRTQLS KGASMVLNGD VVST...... GDIV...... ..........
strain B171                 GSLSGRTQLS KGASMVLNGD VVST...... GDIV...... ..........
strain E22                  GSLSGRTQLS KGASMVLNGD VVST...... GDIV...... ..........
strain B171                 GSLSGRTQLS KGASMVLNGD VVST...... GDIV...... ..........
strain B171                 GSLSGRTQLS KGASMVLNGD VVST...... GDIV...... ..........
strain E24377A and O42      GSLSGRTQLS KGASMVLNGD VVST...... GDIV...... ..........
strain E24377A              GSLSGRTQLS KGASMVLNGD VVST...... GDIV...... ..........
Group B                     GSLSGRTQLS KGASMVLNGD VVST...... GDIV...... ..........
strain E110019              GSLSGRTQLS KGASMVLNGD VVST...... GDIV...... ..........
strain E22                  GSLSGRTQLS KGASMVLNGD VVST...... GDIV...... ..........
strain H10407               GSLSGRTQLS KGASMVLNGD VVST...... GDIV...... ..........
strain F11 and 536          GSLSGRTQLS KGASMVLNGD VVST...... GDIV...... ..........
strain SECEC                GSLSGRTQLS KGASMVLNGD VVST...... GDIV...... ..........
strain H10407               GSLSGRTQLS KGASMVLNGD VVST...... GDIV...... ..........
strain W3110 and DH10B      GTLAGTTTLN NGAILTLSGK TVNNDTLTIR EGDALLQGGS LTGNGSVEKS
strain MG1655               GTLAGTTTLN NGAILTLSGK TVNNDTLTIR EGDALLQGGS LTGNGSVEKS
strain O42                  GTLAGTTTLN NGAILTLSGK TVNNDTLTIR EGDALLQGGS LTGNGSVEKS
strain B7A                  GTLAGTTTLN NGAILTLSGK TVNNDTLTIR EGDALLQGGS LTGNGSVEKS
strain CFT073               GSLAGTTTLN NGATFTLAGK TVNNDTLTIR EGDALLQGGA LTGNGSVEKS
strain O42                  GSLAGTTTLN NGATLTLSGK TVNNDTLTIR EGDALLQGGA LTGNGRVEKS
strain CFT073               GTLAGTTTLN NGAILTLSGK TVNNDTLTIR EGDALLQGGA LTGNGSVEKS
Consensus                   G-L-G-T-L- -GA---L-G- -V GD
                            ###########################

501                                                550
strain E110019              NAGEIRFDNQ T.TPNAA.LS R.AVAKSNSP VTFH...... ...KLTTT..
Group A                     NAGEIRFDNQ T.TPNAA.LS R.AVAKGDSP VTFH...... ...KLTTT..
strain B171                 NAGEIRFDNQ T.TQDAV.LS R.AVAKGDSP VTFH...... ...KLTTN..
strain E22                  NAGEIRFDNQ T.TQDAV.LS R.AVAKGDSP VTFH...... ...KLTTN..
strain B171                 NAGEIRFDNQ T.TQDAV.LS R.AVAKGDSP VTFH...... ...KLTTS..
strain B171                 NAGEIRFDNQ T.TQDAV.LS R.AVAKGDSP VTFH...... ...KLTTS..
strain E24377A and O42      NAGEIRFDNQ T.TPDAA.LS R.AVAKGDSP VTFH...... ...KLTTS..
strain E24377A              NAGEIRFDNQ T.TPDAA.LS R.AVAKGDSP VTFH...... ...KLTTS..
Group B                     NAGEIRFDNQ T.TPDAA.LS R.AVAKGDSP VTFH...... ...KLTTS..
strain E110019              NAGEIYFDNQ T.TPDAV.LS R.AVAKGNAP VTFH...... ...KLTTS..
strain E22                  NAGEIYFDNQ T.TPDAV.LS R.AVAKGNAP VTFH...... ...KLTTS..
strain H10407               NAGEIHFDNQ T.TQDAV.LS R.AVAKSNSP VTFH...... ...KLTTT..
strain F11 and 536          NAGEIHFDNQ T.TPDAA.LS R.AVAKGDSP VTFH...... ...KLTTS..
strain SECEC                NAGEIRFDNQ T.TQDAV.LS R.AVAKGDAP VTFH...... ...KLTTS..
strain H10407               NAGEIRFDNQ T.TQDAV.LS R.AVAKSNSP VTFH...... ...KLTTT..
strain W3110 and DH10B      GSGTLTVSNT TLTQKAVNLN EGTLTLNDST VTTDVIAQRG TALKLTGSTV
strain MG1655               GSGTLTVSNT TLTQKAVNLN EGTLTLNDST VTTDVIAQRG TALKLTGSTV
strain O42                  GSGTLTVSNT TLTQKAVNLN EGTLTLNDST VTTDVIAQRG TALKLTGSTV
strain B7A                  GSGTLTVSNT TLTQKAVNLN EGTLTLNDST VTTDVIAQRG TALKLTGSTV
strain CFT073               GSGTLTVSNT TLTQKAVNLN EGTLTLNDST VTTDIIAHRG TALKLTGSTV
strain O42                  GSGTLTVSNT TLTQKTVNLN EGTLTLNDST VTTDVIAQRG TALKLTGSTV
strain CFT073               GSGTLTVSNT TLTQKAVNLN EGTLTLNDST VTTDVIAQRG TALKLTGSTV
Consensus                   --G-----N- T-T-----L- ---------- VT-------- ---KLT----
                            ########## ########## ########## ####       #####

551                                                600
strain E110019              .......... .......... .......... .......... ..........
Group A                     .......... .......... .......... .......... ..........
strain B171                 .......... .......... .......... .......... ..........
strain E22                  .......... .......... .......... .......... ..........
strain B171                 .......... .......... .......... .......... ..........
strain B171                 .......... .......... .......... .......... ..........
strain E24377A and O42      .......... .......... .......... .......... ..........
strain E24377A              .......... .......... .......... .......... ..........
Group B                     .......... .......... .......... .......... ..........
strain E110019              .......... .......... .......... .......... ..........
strain E22                  .......... .......... .......... .......... ..........
strain H10407               .......... .......... .......... .......... ..........
strain F11 and 536          .......... .......... .......... .......... ..........
strain SECEC                .......... .......... .......... .......... ..........
strain H10407               .......... .......... .......... .......... ..........
strain W3110 and DH10B      LNGAIDPTNV TLASGATWNI PDNATVQSVV DDLSHAGQIH FTSTRTGKFV
strain MG1655               LNGAIDPTNV TLASGATWNI PDNATVQSVV DDLSHAGQIH FTSTRTGKFV
strain O42                  LNGAIDPTNV TLASGATWNI PDNATVQSVV DDLSHAGQIH FTSTRTGKFV
strain B7A                  LNGAIDPTNV TLASGATWNI PDNATVQSVV DDLSHAGQIH FTSTRTGKFV
strain CFT073               LNGAIDPTNV TLTSGATWNI PDNATVQSVV DDLSHAGQIH FTSARTGKFV
strain O42                  LNGAIDPTNV TLTSGATWNI PDNATVQSVV DDLSHAGQIH FTSTRTGKFV
strain CFT073               LNGAIDPTNV TLASDATWNI PDNATVQSVV DDLSHAGQIH FTSRTGTFV
```

```
                          -continued
Consensus                 ---------- ---------- ---------- ---------- ----------

601                                                 650
strain E110019            .......NLT GQGGTINMRV RLD.GSNASD QLVINGGQAT GKTWLAFTNV
Group A                   .......NLT GQGGTINMRV RLD.GSNASD QLVINGGQAT GKTWLAFTNV
strain B171               .......NLT GQGGTINMRV RLD.GSNASD QLVINGGQAT GKTWLAFTNV
strain E22                .......NLT GQGGTINMRV RLD.GSNASD QLVINGGQAT GKTWLAFTNV
strain B171               .......NLT GQGGTINMRV RLD.GSNTSD QLVINGGQAT GKTWLAFTNV
strain B171               .......NLT GQGGTINMRV RLD.GSNTSD QLVINGGQAT GKTWLAFTNV
strain E24377A and O42    .......NLT GQGGTINMRV RLD.GSNTSD QLVINGGQAT GKTWLAFTNV
strain E24377A            .......NLT GQGGTINMRV RLD.GSNTSD QLVINGGQAT GKTWLAFTNV
Group B                   .......NLT GQGGTINMRV RLD.GSNASD QLVINGGQAT GKTWLAFTNV
strain E110019            .......NLT GQGGTINMRV RLD.GSNASD QLVINGGQAT GKTWLAFTNV
strain E22                .......NLT GQGGTINMRV RLD.GSNTSD QLVINGGQAT GKTWLAFTNV
strain H10407             .......NLT GQGGTINMRV SLD.GSNASD QLVINGGQAT GKTWLAFTNV
strain F11 and 536        .......NLT GQGGTINMRV RLD.GSNTSD QLVINGGQAT GKTWLAFTNV
strain SECEC              .......NLT GQGGTINMRV RLD.GSNASD QLVINGGQAT GKTWLAFTNV
strain H10407             .......NLT GQGGTINMRV SLD.GSNASD QLVINGGQAT GKTWLAFTNV
strain W3110 and DH10B    PATLKVKNLN GQNGTISLRV RPDMAQNNAD RLVIDGGRAT GKTILNLVNA
strain MG1655             PATLKVKNLN GQNGTISLRV RPDMAQNNAD RLVIDGGRAT GKTILNLVNA
strain O42                PATLKVKNLN GQNGTISLRV RPDMAQNNAD RLVIDGGRAT GKTILNLVNA
strain B7A                PATLKVKNLN GQNGTISLRV RPDMAQNNAD RLVIDGGRAT GKTILNLVNA
strain CFT073             PTTLQVKNLN GQNGTISLRV RPDMAQNNAD RLVIDGGRAT GKTILNLVNA
strain O42                PATLQVKNLN GQNGTISLRV RPDMAQNNAD RLVIDGGRAT GKTILNLVNA
strain CFT073             PATLKVKNLN GQNGTISLRV RPDMAQNNAD RLVIDGGRAT GKTILNLVNA
Consensus                 -------NL- GQ-GTI--RV --D---N--D -LVI-GG-AT GKT-L---N-
                          ### ########## ########## ########## ##########

651                                                 700
strain E110019            GNSNLGVATT GQGIRVVDAQ NGATTEEGAF ALSRPLQAGA FNYTLNRDSD
Group A                   GNSNLGVATT GQGIRVVDAQ NGATTEEGAF ALSRPLQAGA FNYTLNRDSD
strain B171               GNSNLGVATS GQGIRVVDAQ NGATTEESAF ALSRPLHAGA FNYTLNRDSD
strain E22                GNSNLGVATS GQGIRVVDAQ NGATTEEGAF ALSRPLQAGA FNYTLNRDSD
strain B171               GNSNLGVATS GQGIRVVDAQ NGATTEEGAF ALSRPLQAGA FNYTLNRDSD
strain B171               GNSNLGVATS GQGIRVVDAQ NGATTEEGAF ALSRPLQAGA FNYTLNRDSD
strain E24377A and O42    GNSNLGVATS GQGIRVVDAQ NGATTEEGAF ALSRPLQAGA FNYTLNRDSD
strain E24377A            GNSNLGVATS GQGIRVVDAQ NGATTEEGAF ALSRPLQAGA FNYTLNRDSD
Group B                   GNSNLGVATS GQGIRVVDAQ NGATTEEGAF ALSRPLQAGA FNYTLNRDSD
strain E110019            GNSNLGVATT GQGIRVVDAQ NGATTEEGVF ALSRPLQAGA FNYTLNRDSD
strain E22                GNSNLGVATS GQGIRVVDAQ NGATTEEGAF ALSRPLQAGA FNYTLNRDSD
strain H10407             GNSNLGVATS GQGIRVVDAQ NGATTEEGAF ALSRPLQAGA FNYTLNRDSD
strain F11 and 536        GNSNLGVATT GQGIRVVDAQ NGATTEEGAF ALSRPLQAGA FNYTLNRDSD
strain SECEC              GNSNLGVATS GQGIRVVDAQ NGATTEEGAF ALSRPLQAGA FNYTLNRDSD
strain H10407             GNSNLGVATS GQGIRVVDAQ NGATTEEGAF ALSRPLQAGA FNYTLNRDSD
strain W3110 and DH10B    GNSASGLATS GKGIQVVEAI NGATTEEGAF VQGNRLQAGA FNYSLNRDSD
strain MG1655             GNSASGLATS GKGIQVVEAI NGATTEEGAF VQGNRLQAGA FNYSLNRDSD
strain O42                GNSASGLATS GKGIQVVEAI NGATTEEGAF VQGNRLQAGA FNYSLNRDSD
strain B7A                GNSASGLATS GKGIQVVEAI NGATTEEGAF IQGNKLQAGA FNYSLNRDSD
strain CFT073             GNSGTGLATT GKGIQVVEAI NGATTEEGAF VQGNMLQAGA FNYTLNRDSD
strain O42                GNSGTGLATT GKGIQVVEAI NGATTEEGAF VQGNMLQAGA FNYTLNRDSD
strain CFT073             GNSASGLATS GKGIQVVEAI NGATTEEGAF VQGNRLQAGA FNYSLNRDSD
Consensus                 GNS--G-AT- G-GI-VV-A- NGATTEE--F -----L-AGA FNY-LNRDSD
                          ########## ########## ########## ########## ##########

701                                                 750
strain E110019            EDWYLRSENA YRAEVPLYTS MLTQAMDYDR ILAGSRSHQT GVNGENNSVR
Group A                   EDWYLRSENA YRAEVPLYTS MLTQAMDYDR ILAGSRSHQT GVNGENNSVR
strain B171               EDWYLRSENA YRAEVPLYAS MLTQAMDYDR ILAGSRSHQT GVNGENNSVR
strain E22                EDWYLRSENA YRAEVPLYAS MLTQAMDYDR ILAGSRSHQS GVSGENNSVR
strain B171               EDWYLRSENA YRAEVPLYAS MLTQAMDYDR ILAGSRSHQT GVNGENNSVR
strain B171               EDWYLRSENA YRAEVPLYAS MLTQAMDYDR ILAGSRSHQT GVNGENNSVR
strain E24377A and O42    EDWYLRSENA YRAEVPLYTS MLTQAMDYDR ILAGSRSHQT GVNGENNSVR
strain E24377A            EDWYLRSENA YRAEVPLYAS MLTQAMDYDR ILAGSRSHQT GVSGENNSVR
Group B                   EDWYLRSENA YRAEVPLYAS MLTQAMDYDR ILAGSRSHQS GVSGENNSVR
strain E110019            EDWYLRSENA YRAEVPLYTS MLTQAMDYDR ILAGSRSHQT GVNGENNSVR
strain E22                EDWYLRSENA YRAEVPLYAS MLTQAMDYDR ILAGSRSHQS GVSGENNSVR
strain H10407             EDWYLRSENA YRAEVPLYTS MLTQAMDYDR ILAGSRSHQT GVNGENNSVR
strain F11 and 536        EDWYLRSENA YRAEVPLYAS MLTQAMDYDR ILAGSRSHQT GVNGENNSFR
strain SECEC              EDWYLRSENA YRAEVPLYAS MLTQAMDYDR ILAGSRSHQT GVNGENNSVR
strain H10407             EDWYLRSENA YRAEVPLYTS MLTQAMDYDR ILAGSRSHQT GVNGENNSVR
strain W3110 and DH10B    ESWYLRSENA YRAEVPLYAS MLTQAMDYDR IVAGSRSHQT GVNGENNSVR
strain MG1655             ESWYLRSENA YRAEVPLYAS MLTQAMDYDR IVAGSRSHQT GVNGENNSVR
strain O42                ESWYLRSENA YRAEVPLYAS MLTQAMDYDR ILAGSRSHQT GVSGENNSVR
strain B7A                ESWYLRSENA YRAEVPLYAS MLTQAMDYDR ILAGSRSHQT GVNGENNSVR
strain CFT073             ESWYLRSEER YRAEVPLYAS MLTQAMDYDR ILAGSRSHQT GVNGENNSVR
```

-continued

```
                                        751                                               800
strain E110019             LSIQGGHLGH DNNGGIARGA TPESSGSYGF VRLEGDLLRT EVAGMSLTTG
Group A                    LSIQGGHLGH DNNGGIARGA TPESSGSYGF VRLEGDLLRT EVAGMSLTTG
strain B171                LSIQGGHLGH DNNGGIARGA TPESSGSYGL VRLEGDLLRT EVAGMSLTTG
strain E22                 LSIQGGHLGH DNNGGIARGA TPESNGSYGF VRLEGDLLRT EVAGMSLTTG
strain B171                LSIQGGHLGH DNNGGIARGA TPESNGSYGF VRLEGDLLRT EVAGMSLTTG
strain B171                LSIQGGHLGH DNNGGIARGA TPESSGSYGF VRLEGDLLRT EVAGMSLTTG
strain E24377A and O42     LSIQGGHLGH DNNGGIARGA TPESSGSYGF VRLEGDLLRT EVAGMSLTTG
strain E24377A             LSIQGGHLGH DNNGGIARGA TPESSGSYGF VRLEGDLLRT EVAGMSLTTG
Group B                    LSIQGGHLGH DNNGGIARGA TPESNGSYGF VRLEGDLLRT EVAGMSLTTG
strain E110019             LSIQGGHLGH DNNGGIARGA TPESSGSYGF VRLEGDLLRT EVAGMSLTTG
strain E22                 LSIQGGHLGH DNNGGIARGA TPESNGSYGF VRLEGDLLRT EVAGMSLTTG
strain H10407              LSIQGGHLGH DNNGGIARGA TPESSGSYGF VRLEGDLLRT EVAGMSLTTG
strain F11 and 536         LSIQGGHLGH VNNGGIARGA TPESSGSYGL VRLEGDLLRT EVAGMSLTTG
strain SECEC               LSIQGGHLGH DNNGGIARGA TPESSGSYGF VRLESDLLRT EVAGMSVTAG
strain H10407              LSIQGGHLGH DNNGGIARGA TPESSGSYGF VRLEGDLLRT EVAGMSVTAG
strain W3110 and DH10B     LSIQGGHLGH DNNGGIARGA TPESSGSYGF VRLEGDLMRT EVAGMSVTAG
strain MG1655              LSIQGGHLGH DNNGGIARGA TPESSGSYGF VRLEGDLMRT EVAGMSVTAG
strain O42                 LSIQGGHLGH DNNGGIARGA TPESSGSYGF VRLEGDLLRT EVAGMSLTTG
strain B7A                 LSIQGGHLGH DNNGGIARGA TPESSGSYGF VRLEGDLLRT EVAGMSVTAG
strain CFT073              LSIQGGHLGH DNNGGIARGA TPESSGSYGF VRLEGDLLRT EVAGMSLTTG
strain O42                 LSIQGGHLGH DNNGGIARGA TPESSGSYGF VRLEGDLLRT EVAGMSLTTG
strain CFT073              LSIQGGHLGH DNNGGIARGA TPESSGSYGF VRLEGDLLRT DVAGMSVTAG
Consensus                  LSIQGGHLGH -NNGGIARGA TPES-GSYG- VRLE-DL-RT -VAGMS-T-G 801                                               850
strain E110019             VYGAAGHSSV DVKDDDGSRA GTVRDDAGSL GGYLNLVHTS SGLWADIVAQ
Group A                    VYGAAGHSSV DVKDDDGSRA GTVRDDAGSL GGYLNLVHTS SGLWADIVAQ
strain B171                VYGAAGHSSV DVKDDDGSRA GTVRDDAGSL GGYLNLTHTS SGLWADIVAQ
strain E22                 VYGAAGHSSV DVKNDDGSRA GTVRDDAGSL GGYLNLVHTS SGLWADIVAQ
strain B171                VYGAAGHSSV DVKDDDGSRA GTVRDDAGSL GGYLNLTHTS SGLWADIVAQ
strain B171                VYGAAGHSSV DVKDDDGSRA GTVRDDAGSL GGYLNLTHTS SGLWADIVAQ
strain E24377A and O42     VHGAAGHSSV DVKDDDGSRA GTVRDDAGSL GGYLNLVHTS SGLWADIVAQ
strain E24377A             VYGAAGHSSV DVKDDDGSRA GTARDDAGSL GGYLNLVHTS SGLWADIVAQ
Group B                    VYGAAGHSSV DVKDDDGSRA GTVRDDAGSL GGYLHLVHTS SGLWADIVAQ
strain E110019             VYGAAGHSSV DVKDDDGSRA GTVRDDAGSL GGYLNLVHTS SGLWADIVAQ
strain E22                 VYGAAGHSSV DVKDDDGSRA GTVRDDAGSL GGYLNLTHTS SGLWADIVAQ
strain H10407              VYGAAGHSSV DVKDDDGSRA GTVRDDAGSL GGYLNLVHTS SGLWADIVAQ
strain F11 and 536         VYGAAGHSSV DVKDDDGSRA GTVRDDAGSL GGYLNLVHTS SGLWADIVAQ
strain SECEC               VYSAAGHSSV DVKDDDGSRA GTVRDDAGSL GGYLNLVHTS SGLWADIMAQ
strain H10407              VYGAAGHSSV DVKDDDGSRA GTVRDDAGSL GGYLNLVHTS SGLWADIVAQ
strain W3110 and DH10B     VYGAAGHSSV DVKDDDGSRA GTVRDDAGSL GGYLNLVHTS SGLWADIVAQ
strain MG1655              VYGAAGHSSV DVKDDDGSRA GTVRDDAGCL GGYLNLVHTS SGLWADIVAQ
strain O42                 VYGAAGHSSV DVKDDDGSRA GTVRDDAGSL GGYLNLTHTS SGLWADIVAQ
strain B7A                 VYGAAGHSSV DVKDDDGSRA GTVRDDAGSL GGYLNLIHNA SGLWADIVAQ
strain CFT073              VYGAAGHSSV DVKDDDGSRA GTVRDDAGSL GGYMNLTHTS SGLWADIVAQ
strain O42                 VYGAAGHSSV DVKDDDGSRA GTVRDDAGSL GGYMNLTHTS SGLWADIVAQ
strain CFT073              IYGAAGHSSV DVKDDDGSRA GTVRDDAGSL GGYMNLTHTS SGLWADIVAQ
Consensus                  ---AAGHSSV DVK-DDGSRA GT-RDDAG-L GGY--L-H-- SGLWADI-AQ 851                                               900
strain E110019             GTRHSMKASS DNNDFRARGW GWLGSLETGL PFSITDNLML EPQLQYTWQG
Group A                    GTRHSMKASS DNNDFRARGW GWLGSLETGL PFSITDNLML EPQLQYTWQG
strain B171                GTRHSMKASS DNNDFRARGW GWLGSLETGL PFSITDNLML EPQLQYTWQG
strain E22                 GTRHSMKASS DNNDFRARGW GWLGSLETGL PFSITDNLML EPQLQYTWQG
strain B171                GTRHSMKASS DNNDFRARGW GWLGSLETGL PFSITDNVML EPQLQYTWQG
strain B171                GTRHSMKASS DNNDFRARGW GWLGSLETGL PFSITDNLML EPQLQYTWQG
strain E24377A and O42     GTRHSMKASS DNNDFRARGW GWLGSLETGL PFSITDNLML EPQLQYTWQG
strain E24377A             GTRHSMKASS DNNDFRARGW GWLGSLETGL PFSITDNLML EPQLQYTWQG
Group B                    GTRHSMKASS DNNDFRARGW GWLGSLETGL PFSITDNLML EPQLQYTWQG
strain E110019             GTRHSMKASS DNNDFRARGW GWLGSLETGL PFSITDNLML EPQLQYTWQG
strain E22                 GTRHSMKASS DNNDFRARGW GWLGSLETGL PFSITDNLML EPQLQYTWQG
strain H10407              GTRHSMKASS DNNDFRARGW GWLGSLETGL PFSITDNLML EPQLHYTWQG
strain F11 and 536         GTRHSMKASS DNNDFRARGW GWLGSLETGL PFSITDNLML EPQLQYTWQG
strain SECEC               GTRHSMKASS DNNDFRARGW GWLGSLETGL PFSITDNLML EPQLQYTWQG
strain H10407              GTRHSMKAST DNNDFRARGW GWLGSLETGL PFSITDNLML EPQLQYTWQG
strain W3110 and DH10B     GTRHSMKASS DNNDFRARGW GWLGSLETGL PFSITDNLML EPQLQYTWQG
strain MG1655              GTRHSMKASS DNNDFRARGW GWLGSLETGL PFSITDNLML EPQLQYTWQG
strain O42                 GTRHSMKASS DNNDFRARGW GWLGSLETGL PFSITDNLML EPQLHYTWQG
strain B7A                 GTRHSMKASS DNNDFRVRGW GWLGSLETGL PFSITDNLML EPQLQYTWQG
strain CFT073              GTRHSMKASS DNNDFRARGR GWLGSLETGL PFSITDNLML EPRLQYTWQG
```

Above section (beginning of page):

```
strain O42                 ESWYLRSEER YRAEVPLYAS MLTQAMDYDR ILAGSRSHQT GVNGENNSVR
strain CFT073              ESWYLRSENA YRAEVPLYAS MLTQAMDYDR ILAGSRSHQT GVNGENNSVR
Consensus                  E-WYLRSE-- YRAEVPLY-S MLTQAMDYDR I-AGSRSHQt GVnGENNS-R
                           ########## ######
```

-continued

```
strain O42                 GTRHSMKASS GNNDFRARGW GWLGSLETGL PFSITDNLML EPRLQYTWQG
strain CFT073              GTRHSMKASS GNNDFRARGR GWLGSLETGL PFSITDNLML EPRLQYTWQG
Consensus                  GT-HSMKAS- -NNDFR-RG- GWLGSLETGL PFSITDN-ML EP-L-YTWQG 901                                                    950
strain E110019             LSLDDGQDNA GYVKFGHGSA QHVRAGFRLG SHNDMTFGEG TSSRDTLRDS
Group A                    LSLDDGQDNA GYVKFGHGSA QHVRAGFRLG SHNDMTFGEG TSSRDTLRDS
strain B171                LSLDDGQDNA GYVKFGHGSA QHVRAGFRLG SHNDMTFGEG TSSRDTLRDS
strain E22                 LSLDDGQDNA GYVKFGHGSA QHVRAGFRLG SHNDMSFGEG TSSRDTLRDS
strain B171                LSLDDGQDNA GYVKFGHGSA QHVRAGFRLG SHNDMSFGEG TSSRDTLRDS
strain B171                LSLDDGQDNA GYVKFGHGSA QHVRAGFRLG SHNDMSFGEG TSSRDTLRDS
strain E24377A and O42     LSLDDGQDNA GYVKFGHGSA QHVRAGFRLG SHNDMSFGEG TSSRDTLRDS
strain E24377A             LSLDDGQDNA GYVKFGHGSA QHVRAGFRLG SHNDMNFGKG TSSRDTLRDS
Group B                    LSLDDGQDNA GYVKFGHGSA QHVRAGFRLG SHNDMNFGKG TSSRDTLHDS
strain E110019             LSLDDGQDNA GYVKFGHGST QHVRAGFRLG SHNDMTFGEG TSSRDTLRDS
strain E22                 LSLDDGQDNA GYVKFGHGSA QHVRAGFRLG SHNDMSFGEG TSSRDTLRDS
strain H10407              LSLDDGQDNA GYVKFGHGSA QHVRAGFRLG SHNDMTFGEG TSSRDTLRDS
strain F11 and 536         LSLDDGQDNA GYVKFGHGSA QHVRAGFRLG SHNDMNFGKG TSSRDTLRDS
strain SECEC               LSLDDGQDNA GYVKFGHGSA QHMRAGFRLG SHNDMTFGEG TSSRDTLRDS
strain H10407              LSLDDGKDNA GYVKFGHGSA QHVRAGFRLG SHNDMTFGEG TSSRAPLRDS
strain W3110 and DH10B     LSLDDGKDNA GYVKFGHGSA QHVRAGFRLG SHNDMTFGEG TSSRAPLRDS
strain MG1655              LSLDDGQDNA GYVKFGHGSA QHVRAGFRLG SHNDMTFGEG TSSRAPLRDS
strain O42                 LSLDDGQDNA GYVKFGHGSA QHVRAGFRLG SHNDMTFGEG TSSRDTLRDS
strain B7A                 LSLDDGQDNA SYVKFGHGSA QHVRAGFRLG SHHDMNFGKG TSSRDTLRGS
strain CFT073              LSLDDGKDNA GYVKFGHGSA QHVRAGFRLG SHNDMTFGEG TSSRAPLRDS
strain O42                 LSLDDGQDNA GYVKFGHGSA QHVRAGFRLG SHNDMTFGEG TSSRAPLRDS
strain CFT073              LSLDDGKDNA GYVKFGHGSA QHVRAGFRLG SHNDMTFGEG TSSRAPLRDS
Consensus                  LSLDDG-DNA -YVKFGHGS- QH-RAGFRLG SH-DM-FG-G TSSR--L--S 951                                                    1000
strain E110019             AKHSVSELPV NWWVQPSVIR TFSSRGDMSM GTAAAGSNMT FSPSRNGTSL
Group A                    AKHSVSELPV NWWVQPSVIR TFSSRGDMSM GTAAAGSNMT FSPSRNGTSL
strain B171                AKHSVSELPV NWWVQPSVIR TVSSRGDMSM GTAAAGSNMT FSPSRNGTSL
strain E22                 AKHRVRELPV NWWVQPSVIR TVSSRGDMSM GTAAAGSNMT FSPSRNGTSL
strain B171                AKHRVRELPV NWWVQPSVIR TFSSRGDMSM GTAAAGSNMT FSPSRNGTSL
strain B171                AKHRVRELPV NWWVQPSVIR TFSSRGDMSM GTAAAGSNMT FSPSRNGTSL
strain E24377A and O42     AKHRVRELPV NWWVQPSVIR TFSSRGDMSM GTAAAGSNMT FSPSRNGTSL
strain E24377A             AKHSVRELPV NWWVQPSVIR TFSSRGDMSM GTAAAGSNMT FSPSRNGTSL
Group B                    AKHSVRELPV NWWVQPSVIR TFSSRGDMSM GTAAAGSNMT FSPSRNGTSL
strain E110019             AKHRVRELPV NWWVQPSVIR TFSSRGDMSM GTAAAGSNMT FSPSRNGTSL
strain E22                 AKHRVRELPV NWWVQPSVIR TFSSRGDMSM GTAAAGSNMT FSPSRNGTSL
strain H10407              TKHGVSELPV NWWVQPSVIR TFSSRGDMSM GTAAAGSNMT FSPSRNGTSL
strain F11 and 536         AKHRVRELPV NWWVQPSVIR TFSSRGDMSM GTAAAGSNMT FSPSQNGTTL
strain SECEC               AKHRVRELPV NWWVQPSVIR TFSSRGDMSM GTAAAGSNMT FSPSQNGTSL
strain H10407              AKHSMRELPV NWWVQPSVIR TFSSRGDMSM GTAAAGSNMT FSPSRNGTSL
strain W3110 and DH10B     AKHSVSELPV NWWVQPSVIR TFSSRGDMRV GTSTAGSGMT FSPSQNGTSL
strain MG1655              AKHSVSELPV NWWVQPSVIR TFSSRGDMRV GTSTAGSGMT FSPSQNGTSL
strain O42                 TKHGVSELPV NWWVQPSVIR TFSSRGDMSM GTAAAGSNMT FSPSQNGTSL
strain B7A                 AKHSVRELPV NWWVQPSVIR TFSSRGDMSM GTAAAGSNMT FSPSQNGTSL
strain CFT073              AKHSVRELPV NWWVQPSVIR TFSSRGDMRV GTSTAGSGMT FSPSQNGTSL
strain O42                 AKHSVRELPV NWWVQPSVIR TFSSRGDMRV GTSTAGSGMT FSPSQNGTSL
strain CFT073              AKHSVRELPV NWWVQPSVIR TFSSRGDMRV GTSTAGSGMT FSPSQNGTSL
Consensus                  -KH---ELPV NWWVQPSVIR T-SSRGDM-- GT--AGS-MT FSPS-NGT-L 1001                                              1044
strain E110019             DLQAGLEARI RENITLGVQA GYAHSVSGSS AEGYNGQATL NMTF
Group A                    DLQAGLEARI RENITLGVQA GYAHSVSGSS AEGYNGQATL NMTF
strain B171                DLQAGLEARV RENITLGVQA GYAHSVSGSS AEGYNGQATL NMTF
strain E22                 DLQAGLEARV RENITLGVQA GYAHSVSGSS AEGYNGQATL NMTF
strain B171                DLQAGLEARV RENITLGVQA GYAHSVSGSS AEGYNGQATL NVTF
strain B171                DLQAGLEARV RENITLGVQA GYAHSVSGSS AEGYNGQATL NVTF
strain E24377A and O42     DLQAGLEARV RENITLGVQA GYAHSVSGSS AEGYNGQATL NVTF
strain E24377A             DLQAGLEARV RENITLGVQA GYAHSVSGSS AEGYNGQATL NVTF
Group B                    DLQAGLEARV RENITLGVQA GYAHSVSGSS AEGYNGQATL NVTF
strain E110019             DLQAGLEARV RENITLGVQA GYAHSVSGSS AEGYNGQATL NVTF
strain E22                 DLQAGLEARV RENITLGVQA GYAHSVSGSS AEGYNGQATL NVTF
strain H10407              DLQAGLEARV RENITLGVQA GYAHSVSGNS AEGYNGQATL NVTF
strain F11 and 536         DLQAGLEARV RENITLGVQA GYAHSVSGSS AEGYNGQATL NVTF
strain SECEC               DLQAGLEARV RENITLGVQA GYAHSVIGSS AEGYNGQATL NVTF
strain H10407              DLQAGLEARV RENITLGVQA GYAHSVSGSS AEGYNGQATL NVTF
strain W3110 and DH10B     DLQAGLEARV RENITLGVQA GYAHSVSGSS AEGYNGQATL NVTF
strain MG1655              DLQAGLEARV RENITLGVQA GYAHSVSGSS AEGYNGQATL NVTF
strain O42                 DLQAGLEARV RENITLGVQA GYVHSVSGSS AEGYNGQATL NVTF
strain B7A                 DLQAGLEARV RENITLGVQA GYAHSINGSS AEGYNSQATL NVTF
strain CFT073              DLQAGLEARV RENITLGVQA GYAHSVSGSS AEGYNGQATL NVTF
strain O42                 DLQAGLEARV RENITLGVQA GYAHSVSGSS AEGYNSQATL NVTF
strain CFT073              DLQAGLEARV RENITLGVQA GYAHSVSGSS AEGYNGQATL NVTF
Consensus                  DLQAGLEAR- RENITLGVQA GY-HS--G-S AEGYN-QATL N-TF
```

Upec-5211 Polypeptide

Sel1 repeat-containing protein is referred to herein as 'upec-5211.' 'upec-5211' polypeptide from *E. coli* is also known as: 'c5321' from CFT073; 'ECED1_5081' from ED1a and 'EFER_4303' from *E. fergusonii* ATCC 35469.

When used according to the present invention, upec-5211 polypeptide may take various forms. Preferred upec-5211 sequences have 50% or more identity (e.g., 60%, 65%, 70%, 75%, 80%, 85%, 87.5%, 90%, 91%, 92%, 93%, 94%, 95%, 96%, 97%, 98%, 99%, 99.5% or more) to SEQ ID NOs 23-25. This includes variants (e.g., allelic variants, homologs, orthologs, paralogs, mutants etc).

Alternatively, the upec-5211 sequences when aligned with any of SEQ ID NOs 23-25 using a pairwise alignment algorithm, each moving window of x amino acids from N terminus to C terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer.

The preferred pairwise alignment algorithm is the Needleman-Wunsch global alignment algorithm (3), using default parameters (e.g., with Gap opening penalty=10.0, and with Gap extension penalty=0.5, using the EBLOSUM62 scoring matrix). This algorithm is conveniently implemented in the needle tool in the EMBOSS package (4).

Upec-5211 polypeptide sequences may have 1, 2, 3, 4, 5, 6, 7, 8, 9 or 10 (or more) single amino acid alterations (deletions, insertions, substitutions), which may be at separate locations or may be contiguous, as compared to SEQ ID NOs 23-25.

Upec-5211 polypeptide sequences may, compared to any one of SEQ ID NOs 23-25, include one or more (e.g., 1, 2, 3, 4, 5, 6, 7, 8, 9, 10, etc.) amino acid substitutions, such as conservative substitutions (i.e., substitutions of one amino acid with another which has a related side chain). Genetically encoded amino acids are generally divided into four families: (1) acidic, i.e., aspartate, glutamate; (2) basic, i.e., lysine, arginine, histidine; (3) non-polar, i.e., alanine, valine, leucine, isoleucine, proline, phenylalanine, methionine, tryptophan; and (4) uncharged polar, i.e., glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity.

Upec-5211 polypeptide sequences may include one or more (e.g. 1, 2, 3, 4, 5, 6, 7, 8, 9, etc.) single amino acid deletions relative to any one of SEQ ID NOs 23-25. Similarly, a polypeptides may include one or more (e.g. 1, 2, 3, 4, 5, 6, 7, 8, 9, 10, etc.) insertions (e.g., each of 1, 2, 3, 4 or 5 amino acids) relative to any one of SEQ ID NOs 23-25.

Other preferred upec-5211 sequences comprise at least n consecutive amino acids from SEQ ID NOs 23-25, wherein n is 7 or more (eg. 8, 10, 12, 14, 16, 18, 20, 25, 30, 35, 40, 50, 60, 70, 80, 90, 100, 150, 200, 250 or more). Preferred fragments comprise an epitope or immunogenic fragment from upec-5211. Other preferred fragments lack one or more amino acids (e.g. 1, 2, 3, 4, 5, 6, 7, 8, 9, 10, 15, 20, 25 or more) from the C-terminus and/or the N-terminus of SEQ ID NOs 23-25.

```
                                                                    (SEQ ID NO: 23)
Strains CFT073 and 83972

(SEQ ID NO: 24)
Strain ED1a (SEQ ID NO: 25)
Escherichia fergusonii ATCC 35469 strain CFT073 and 83972 MKKSLLAVML TGLFALVSLP ALGNVNLEQL KQKAESGEAK AQLELGYRYF
strain ED1a             MKKSLLAVML TGLFALVSLP ALGNVNLEQL KQKAESGEAK AQLELGYRYF
E. fergusonii           MKKSLLAALL TGLFALVSLP ALGNVNFEQL KQKAERGEAK AQLELGYRYF
Consensus               MKKSLLA +L TGLFALVSLP ALGNVN EQL KQKAE GEAK AQLELGYRYF
                        ########## ########## ########## ########## ########## strain CFT073 and 83972 QGNETTKDLT QAMDWFRRAA EQGYTPAEYV LGLRYMNGEG VPQDYAQAVI
strain ED1a             QGNETTKDLT LAMDWFRRAA EQGYTPAEYV LGLRYMNGEG VPQDYAQAVI
E. fergusonii           QGNETTKDLT QAIDWFRRAA EQGYTPAEFV LGLRYMNGEG VPKDYAQAVI
Consensus               QGNETTKDLT  A+DWFRRAA EQGYTPAE+V LGLRYMNGEG VP+DYAQAVI
                        ########## ########## ########## ########## ########## strain CFT073 and 83972 WYKKAALKGL PQAQQNLGVM YHEGNGVKVD KAESVKWFRL AAEQGRDSGQ
strain ED1a             WYKKAALKGL PQAQQNLGVM YHEGNGVKVD KAESVKWFRL AAEQGRDSGQ
E. fergusonii           WYKKAALKGL PQAQQNLGVM YHDGKGVKID KAESVKWFRL AAEQGRDSGQ
Consensus               WYKKAALKGL PQAQQNLGVM YH+G GVK+D KAESVKWFRL AAEQGRDSGQ
                        ########## ########## ########## ########## ########## strain CFT073 and 83972 QSMGDAYFEG DGVTRDYVMA REWYSKAAEQ GNVWSCNQLG YMYSRGLGVE
strain ED1a             QSMGDAYFEG DGVTRDYVMA REWYSKAAEQ GNVWSCNQLG YMYSRGLGVE
E. fergusonii           QSMGDAYFEG DGVTRDYVMA REWYSKAAEQ GNVWSCNQLG YIYSKGLGVE
Consensus               QSMGDAYFEG DGVTRDYVMA REWYSKAAEQ GNVWSCNQLG Y+YS+GLGVE
                        ########## ########## ########## ########## ########## strain CFT073 and 83972 RNDAISAQWY RKSATSGDEL GQLHLADMYY FGIGVTQDYT QSRVLFSQSA
strain ED1a             RNDAISAQWY RKSATSGDEL GQLHLADMYY FGIGVTQDYT QSRVLFSQSA
E. fergusonii           KNDAISAQWY RKSATSGDEL GQLHLADMYY FGIGVTQDYT QSRILFTQSA
Consensus               +NDAISAQWY RKSATSGDEL GQLHLADMYY FGIGVTQDYT QSR+LF+QSA
                        ########## ########## ########## ########## ##########
```

```
strain CFT073 and 83972   EQGNSIAQFR LGYILEQGLA GAKEPLKALE WYRKSAEQGN SDGQYYLAHL
strain ED1a               EQGNSIAQFR LGYILEQGLA GAKEPLKALE WYRKSAEQGN SDGQYYLAHL
E. fergusonii             EQGNAIAQYR LGYILEEGLA GAKEPLKALE WYRKSAEQGN AIGQYYLAEI
Consensus                 EQGN+IAQ+R LGYILE+GLA GAKEPLKALE WYRKSAEQGN + GQYYLA +
                          ########## ########## ########## ########## ########## strain CFT073 and 83972   YDKGAEGVAK NREQAISWYT KSAEQGDATA QANLGAIYFR LGSEEEHKKA
strain ED1a               YDKGAEGVAK NREQAISWYT KSAEQGDATA QANLGAIYFR LGSEEEHKKA
E. fergusonii             YIRRAEGIPY NREQAIYWYT KSAEQGDTDA QVNLGALLYR HGSEEEQRRA
Consensus                 Y + AEG+   NREQAI WYT KSAEQGD  A Q NLGA+ +R GSEEE ++A
                          ########## ########## ########## ########## ########## strain CFT073 and 83972   VEWFRKAAAK GEKAAQFNLG NALLQGKGVK KDEQQAAIWM RKAAEQGLSA
strain ED1a               VEWFRKAAAK GEKAAQFNLG NALLQGKGVK KDEQQAAIWM RKAAEQGLSA
E. fergusonii             VDWYRKAAEE GVAMAQFNLG NALLQGKGVK KDEQQAAIWM RKAAEQGFSS
Consensus                 V+W+RKAA + G    AQFNLG NALLQGKGVK KDEQQAAIWM RKAAEQG S+
                          ########## ########## ########## ########## ########## strain CFT073 and 83972   AQVQLGEIYY YGLGVERDYV QAWAWFDTAS TNDMNLFGTE NRNITEKKLT
strain ED1a               AQVQLGEIYY YGLGVERDYV QAWAWFDTAS TNDMNLFGTE NRNITEKKLT
E. fergusonii             AQVQLGEIYY YGLGVERDYV QAWAWFDTAS TNDMNLFGTE NRNITEKKLT
Consensus                 AQVQLGEIYY YGLGVERDYV QAWAWFDTAS TNDMNLFGTE NRNITEKKLT
                          ########## ########## ########## ########## ########## strain CFT073 and 83972   AKQLQQAELL SQQYIEKYAP EAWARMQKLK AQSAVKTGNK
strain ED1a               TKQLQQAELL SQQYIEKYAT EAWARMQKLK AQSAVKTGNK
E. fergusonii             AKQLQQAELL SQQYIEKYAP EAWARMQKLN ARSTVTTGNK
Consensus                  KQLQQAELL SQQYIEKYA  EAWARMQKL  A+S V TGNK
                          ########## ########## ########## ##########
```

Orf3526 Polypeptide

The accessory colonization factor D (AcfD) precursor protein is referred to herein as 'orf3526.' 'orf3526' polypeptide from E. coli NMEC is disclosed in reference 1 (SEQ ID NOs: 7051 & 7052) is also known as: 'ECP_3050' from E. coli UPEC strain 536, 'yghJ' from E. coli commensal strain W3110, 'EcE24377A_3432' from E. coli ETEC strain E24377A, and 'EcHS_A3142' from E. coli commensal strain HS.

When used according to the present invention, orf3526 polypeptide may take various forms. Preferred orf3526 sequences have 50% or more identity (e.g., 60%, 65%, 70%, 75%, 80%, 85%, 87.5%, 90%, 91%, 92%, 93%, 94%, 95%, 96%, 97%, 98%, 99%, 99.5% or more) to SEQ ID NOs 26-40. This includes variants (e.g., allelic variants, homologs, orthologs, paralogs, mutants etc).

Alternatively, the orf3526 sequences when aligned with any of SEQ ID NOs 26-40 using a pairwise alignment algorithm, each moving window of x amino acids from N terminus to C terminus (such that for an alignment that extends to p amino acids, where p>x, there are p−X+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer.

The preferred pairwise alignment algorithm is the Needleman-Wunsch global alignment algorithm (3), using default parameters (e.g., with Gap opening penalty=10.0, and with Gap extension penalty=0.5, using the EBLOSUM62 scoring matrix). This algorithm is conveniently implemented in the needle tool in the EMBOSS package (4).

Orf3526 polypeptide sequences may have 1, 2, 3, 4, 5, 6, 7, 8, 9 or 10 (or more) single amino acid alterations (deletions, insertions, substitutions), which may be at separate locations or may be contiguous, as compared to SEQ ID NOs 26-40.

Orf3526 polypeptide sequences may, compared to any one of SEQ ID NOs 26-40, include one or more (e.g., 1, 2, 3, 4, 5, 6, 7, 8, 9, 10, etc.) amino acid substitutions, such as conservative substitutions (i.e., substitutions of one amino acid with another which has a related side chain). Genetically encoded amino acids are generally divided into four families: (1) acidic, i.e., aspartate, glutamate; (2) basic, i.e., lysine, arginine, histidine; (3) non-polar, i.e., alanine, valine, leucine, isoleucine, proline, phenylalanine, methionine, tryptophan; and (4) uncharged polar, i.e., glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity.

Orf3526 polypeptide sequences may include one or more (e.g. 1, 2, 3, 4, 5, 6, 7, 8, 9, etc.) single amino acid deletions relative to any one of SEQ ID NOs 26-40. Similarly, a polypeptides may include one or more (e.g. 1, 2, 3, 4, 5, 6, 7, 8, 9, 10, etc.) insertions (e.g., each of 1, 2, 3, 4 or 5 amino acids) relative to any one of SEQ ID NOs 26-40.

Other preferred orf3526 sequences comprise at least n consecutive amino acids from SEQ ID NOs 26-40, wherein n is 7 or more (e.g. 8, 10, 12, 14, 16, 18, 20, 25, 30, 35, 40, 50, 60, 70, 80, 90, 100, 150, 200, 250 or more). Preferred fragments comprise an epitope or immunogenic fragment from orf3526. Other preferred fragments lack one or more amino acids (e.g., 1, 2, 3, 4, 5, 6, 7, 8, 9, 10, 15, 20, 25 or more) from the C-terminus and/or the N-terminus of SEQ ID NOs 26-40. The extent of the gly-ser region is indicated by "G" under the alignment below. The extent of the N-terminal proline-rich repeat is indicated by "P" under the alignment below. Three preferred fragments denoted orf3526A, orf3526B, and orf3526C are denoted by 'A', 'B' or 'C', respectively below the alignment.

EAEC strain 101-1 (GI: 83587587) (SEQ ID NO: 26)

UPEC strain 536 (GI: 110643204) (SEQ ID NO: 27)

EAEC strain O42 (SEQ ID NO: 28)

EPEC strain E2348/69 (SEQ ID NO: 29)

EIEC strain 53638 (GI: 75515237) (SEQ ID NO: 30)

Commensal strain W3110 (GI: 89109748) (SEQ ID NO: 31)

ETEC strain B7A (GI: 75227618) (SEQ ID NO: 32)

EPEC strain E22 (GI: 75259912) (SEQ ID NO: 33)

ETEC strain E24377A (GI: 157156747) (SEQ ID NO: 34)

ETEC strain H10407 (SEQ ID NO: 35)

EPEC strain E110019 (GI: 75239450) (SEQ ID NO: 36)

commensal strain HS (GI: 157162442) (SEQ ID NO: 37)

antibiotic-resistant strain SECEC (SEQ ID NO: 38)

NMEC strain IHE3034 (SEQ ID NO: 39)

UPEC strain F11 (GI: 75241179) (SEQ ID NO: 40)

```
               |          |          |          |          |          |
strain 101-1   MNKKFKYKKS LLAAILSATL LAGCDGGGSG SSSDTPPVDS GTGSLPEVKP DPTPNPEPTP
strain 536     MNKKFKYKKS LLAAILSATL LAGCDGGGSG SSSDTPPVDS GTGSLPEVKP DPTPNPEPTP
strain O42     MNKKFKYKKS LLAAILSATL LAGCDGGGSG SSSDTPPVDS GTGSLPEVKP DPTPNPEPTP
str E2348/69   MNKKFKYKKS LLAAILSATL LAGCDGGGSG PSSDTPPVDS GTGSLPEVKP DPTPNPEPTP
strain 53638   MNKKFKYKKS LLAAILSATL LAGCDGGGSG SSSDTPPVDS GTGSLPEVKP DPTPNPEPTP
strain W3110   MNKKFKYKKS LLAAILSATL LAGCDGGGSG SSSDTPPVDS GTGSLPEVKP DPTPNPEPTP
strain B7A     MNKKFKYKKS LLAAILSATL LAGCDGGGSG SSSDTPPVDS GTGSLPEVKP DPTPNPEPTP
strain E22     MNKKFKYKKS LLAAILSATL LAGCDGGGSG SSSDTPPVDS GTGSLPEVKP DPTPNPEPTP
str E24377A    MNKKFKYKKS LLAAILSATL LAGCDGGGSG SSSDTPPVDS GTGSLPEVKP DPTPNPEPTP
str H10407     MNKKFKYKKS LLAAILSATL LAGCDGGGSG SSSDTPPVDS GTGSLPEVKP DPTPNPEPTP
str E110019    MNKKFKYKKS LLAAILSATL LAGCDGGGSG SSSDTPPVDS GTGSLPEVKP DPTPNPEPTP
strain HS      MNKKFKYKKS LLAAILSATL LAGCDGGGSG SSSDTPPVDS GTGSLPEVKP DPTPNPEPTP
strain SECEC   MNKKFKYKKS LLAAILSATL LAGCDGGGSG SSSDTPPVDS GTGSLPEVKP DPTPNPEPTP
str IHE3034    MNKKFKYKKS LLAAILSATL LAGCDGGGSG SSSDTPSVDS GSGTLPEVKP DPTPTPEPTP
strain F11     MNKKFKYKKS LLAAILSATL LAGCDGGGSG SSSDTPSVDS GSGTLPEVKP DPTPTPEPTP
Consensus      MNKKFKYKKS LLAAILSATL LAGCDGGGSG SSSDTPPVDS GTGSLPEVKP DPTPNPEPTP
N-TERM REG     GGGGGGGGGG GGGGGGGGGG GGGGGGGGGG GGGPPPPPPP PPPPPPPPPP PPPPPPPPPP
               ########## ########## ########## ########## ########## ##########
                                                AAAAAAA AAAAAAAAAA AAAAAAAAAA AAAAAAAAAA
                                                        CCCCCCC CCCCCCCCCC CCCCCCCCCC

|          |          |          |          |          |
strain 101-1   EPTPDPEPTP EPTPDP--EP TPEPEPEPVP TKTGYLTLGG SQRITG-ATC NGESSDGFTF
strain 536     EPTPDPEPTP EPTPDP--EP TPEPEPEPVP TKTGYLTLGG SQRITG-ATC NGESSDGFTF
strain O42     EPTPDPEPTP EPTPDP--EP TPEPEPEPVP TKTGYLTLGG SQRITG-ATC NGESSDGFTF
str E2348/69   EPTPDPEPTP EPTPDP--EP TPEPEPEPVP TKTGYLTLGG SQRITG-ATC NGESSDGFTF
strain 53638   EPTPDPEPTP EPIPDP--EP TPEPEPEPVP TKTGYLTLGG SQRVTG-ATC NGESSDGFTF
strain W3110   EPTPDPEPTP EPIPDP--EP TPEPEPEPVP TKTGYLTLGG SQRVTG-ATC NGESSDGFTF
strain B7A     EPTPDPEPTP EPTPDP--EP TPEPEPEPVP TKTGYLTLGG SLRVTGDITC NDESSDGFTF
strain E22     EPTPDPEPTP EPTPDP--EP TPEPEPEPVP TKTGYLTLGG SLRVTGDITC NDESSDGFTF
str E24377A    EPTPDPEPTP EPTPDP--EP TPEPEPEPVP TKTGYLTLGG SLRVTGDITC NDESSDGFTF
str H10407     EPTPDPEPTP EPIPDP--EP TPEPEPEPVP TKTGYLTLGG SQRVTG-ATC NGESSDGFTF
str E110019    EPTPDPEPTP EPTPDP--EP TPEPEPEPVP TKTGYLTLGG SLRVTGDITC NDESSDGFTF
strain HS      EPTPDPEPTP EPIPDP--EP TPEPEPEPVP TKTGYLTLGG SQRVTG-ATC NGESSDGFTF
strain SECEC   EPTPDPEPTP EPIPDP--EP TPEPEPEPVP TKTGYLTLGG SQRVTG-ATC NGESSDGFTF
```

-continued

```
str IHE3034    EPTPDPEPTP DPTPDP--EP TPEPEPEPVP TKTGYLTLGG SQRVTG-ATC NGESSDGFTF
strain F11     EPTPDPEPTP DPTPDPDPEP TPEPEPEPVP TKTGYLTLGG SQRVTG-ATC NGESSDGFTF
Consensus      EPTPDPEPTP EPTPDPDPEP TPEPEPEPVP TKTGYLTLGG SQRVTGDATC NGESSDGFTF
N-TERM REG     PPPPPPPPPP PPPPPPPPPP PPPPPPPPPP P
               ########## ########## ########## ########## ########## ##########
               AAAAAAAAAA AAAAAAAAAA AAAAAAAAAA AAAAAAAAAA AAAAAAAAAA AAAAAAAAAA
               CCCCCCCCCC CCCCCCCCCC CCCCCCCCCC CCCCCCCCCC CCCCCCCCCC CCCCCCCCCC

|          |          |          |          |          |
strain 101-1   TPGDKVTCVA GNNTTIATFD TQSEAARSLR AVEKVSFSLE DAQELAASDD KKSNAVSLVT
strain 536     TPGDKVTCVA GNNTTIATFD TQSEAARSLR AVEKVSFSLE DAQELAASDD KKSNAVSLVT
strain O42     TPGDKVTCVA GNNTTIATFD TQSEAARSLR AVEKVSFSLE DAQELAASDD KKSNAVSLVT
str E2348/69   TPGDKVTCVA GNNTTIATFD TQSEAARSLR AVEKVSFSLE DAQELAASDD KKSNAVSLVT
strain 53638   KPGEDVTCVA G-NTTIATFN TQSEAARSLR AVEKVSFSLE DAQELAGSDD KKSNAVSLVT
strain W3110   KPGEDVTCVA G-NTTIATFN TQSEAARSLR AVEKVSFSLE DAQELAGSDD KKSNAVSLVT
strain B7A     TPGDKVTCVA GNNTTIATFD TQSEAARSLR AVEKVSFSLE DAQELAGSDN KKSNALSLVT
strain E22     TPGDKVTCVA GNNTTIATFD TQSEAARSLR AVEKVSFSLE DAQELAGSDN KKSNALSLVT
str E24377A    TPGDKVTCVA GNNTTIATFD TQSEAARSLR AVEKVSFSLE DAQELAGSDN KKSNALSLVT
str H10407     KPGEDVTCVA G-NTTIATFN TQSEAARSLR AVEKVSFSLE DAQELAGSDD KKSNAVSLVT
str E110019    TPGDKVTCVA GNNTTIATFD TQSEAARSLR AVEKVSFSLE DAQELAGSDN KKSNALSLVT
strain HS      KPGEDVTCVA G-NTTIATFN TQSEAARSLR AVEKVSFSLE DAQELAGSDD KKSNAVSLVT
strain SECEC   KPGEDVTCVA G-NTTIATFN TQSEAARSLR AVEKVSFSLE DAQELAGSDD KKSNAVSLVT
str IHE3034    TPGNTVSCVV G-STTIATFN TQSEAARSLR AVDKVSFSLE DAQELANSEN KKTNAISLVT
strain F11     TPGNTVSCVV G-STTIATFN TQSEAARSLR AVDKVSFSLE DAQELANSEN KKTNAISLVT
Consensus      TPGDKVTCVA GNNTTIATFD TQSEAARSLR AVEKVSFSLE DAQELAGSDD KKSNAVSLVT
               ########## ########## ########## ########## ########## ##########
               AAAAAAAAAA AAAAAAAAAA AAAAAAAAAA AAAAAAAAAA AAAAAAAAAA AAAAAAAAAA
               CCCCCCCCCC CCCCCCCCCC CCCCCCCCCC CCCCCCCCCC CCCCCCCCCC CCCCCCCCCC

|          |          |          |          |          |
strain 101-1   SSNSCPANTE QVCLTFSSVI ESKRFDSLYK QIDLAPEEFK KLVNEEVENN AATDKAPSTH
strain 536     SSNSCPADTE QVCLTFSSVI ESKRFDSLYK QIDLAPEEFK KLVNEEVENN AATDKAPSTH
strain O42     SSNSCPANTE QVCLTFSSVI ESKRFDSLYK QIDLAPEEFK KLVNEEVENN AATDKAPSTH
str E2348/69   SSNSCPADTE QVCLTFSSVI ESKRFDSLYK QIDLAPEEFK KLVNEEVENN AATDKAPSTH
strain 53638   SSNSCPANTE QVCLTFSSVI ESKRFDSLYK QIDLAPEEFK KLVNEEVENN AATDKAPSTH
strain W3110   SSNSCPANTE QVCLTFSSVI ESKRFDSLYK QIDLAPEEFK KLVNEEVENN AATDKAPSTH
strain B7A     SMNSCPANTE QVCLEFSSVI ESKRFDSLYK QIDLAPEEFK KLVNEEVENN AATDKAPSTH
strain E22     SMNSCPANTE QVCLEFSSVI ESKRFDSLYK QIDLAPEEFK KLVNEEVENN AATDKAPSTH
str E24377A    SMNSCPANTE QVCLTFSSVI ESKRFDSLYK QIDLAPEEFK KLVNEEVENN AATDKAPSTH
str H10407     SSNSCPANTE QVCLTFSSVI ESKRFDSLYK QIDLAPEEFK KLVNEEVENN AATDKAPSTH
str E110019    SMNSCPANTE QVCLEFSSVI ESKRFDSLYK QIDLAPEEFK KLVNEEVENN AATDKAPSTH
strain HS      SSNSCPANTE QVCLTFSSVI ESKRFDSLYK QIDLAPEEFK KLVNEEVENN AATDKAPSTH
strain SECEC   SSNSCPANTE QVCLTFSSVI ESKRFDSLYK QIDLAPEEFK KLVNEEVENN AATDKAPSTH
str IHE3034    SSDSCPADAE QLCLTFSSVV DRARFEKLYK QIDLATDNFS KLVNEEVENN AATDKAPSTH
strain F11     SSDSCPADAE QLCLTFSSVV DRARFEKLYK QIDLATDNFS KLVNEEVENN AATDKAPSTH
Consensus      SSNSCPANTE QVCLTFSSVI ESKRFDSLYK QIDLAPEEFK KLVNEEVENN AATDKAPSTH
               ########## ########## ########## ########## ########## ##########
               AAAAAAAAAA AAAAAAAAAA AAAAAAAAAA AAAAAAAAAA AAAAAAAAAA AAAAAAAAAA
               CCCCCCCCCC CCCCCCCCCC CCCCCCCCCC CCCCCCCCCC CCCCCCCCCC CCCCCCCCCC

|          |          |          |          |          |
strain 101-1   TSPVVPVTTP GTKPDLNASF VSANAEQFYQ YQPTEIILSE GRLVDSMGNG VVGVNYYTSS
strain 536     TSPVVPVTTP GTKPDLNASF VSANAEQFYQ YQPTEIILSE GRLVDSMGNG VVGVNYYTSS
strain O42     TSPVVPVTTP GTKPDLNASF VSANAEQFYQ YQPTEIILSE GRLVDSMGNG VVGVNYYTSS
str E2348/69   TSPVVPVTTP GTKPDLNASF VSANAEQFYQ YQPTEIILSE GRLVDSQGYG VAGVNYYTNS
strain 53638   TSPVVPVTTP GTKPDLNASF VSANAEQFYQ YQPTEIILSE GRLVDSQGYG VAGVNYYTNS
strain W3110   TSPVVPVTTP GTKPDLNASF VSANAEQFYQ YQPTEIILSE GRLVDSQGYG VAGVNYYTNS
strain B7A     TSPVVPVTTP GTKPDLNASF VSANAEQFYQ YQPSEIILSE GRLVDSQGYG VAGVNYYTNS
strain E22     TSPVVPVTTP GTKPDLNASF VSANAEQFYQ YQPTEIILSE GRLVDSQGYG VAGVNYYTNS
str E24377A    TSPVVPATTP GTKPDLNASF VSANAEQFYQ YQPTEIILSE GRLVDSQGDG VVGVNYYTNS
str H10407     TSPVVPVTTP GTKPDLNASF VSANAEQFYQ YQPTEIILSE GRLVDSQGYG VAGVNYYTNS
str E110019    TSPVVPVTTP GTKPDLNASF VSANAEQFYQ YQPSEIILSE GRLVDSQGYG VAGVNYYTNS
strain HS      TSPVVPVTTP GTKPDLNASF VSANAEQFYQ YQPTEIILSE GRLVDSQGYG VAGVNYYTNS
strain SECEC   TSPVVPVTTP GTKPDLNASF VSANAEQFYQ YQPTEIILSE GRLVDSQGYG VAGVNYYTNS
str IHE3034    TSTVVPVTTE GTKPDLNASF VSANAEQFYQ YQPTEIILSE GQLVDSLGNG VAGVDYYTNS
strain F11     TSTVVPVTTE GTKPDLNASF VSANAEQFYQ YQPTEIILSE GQLVDSLGNG VAGVDYYTNS
Consensus      TSPVVPVTTP GTKPDLNASF VSANAEQFYQ YQPTEIILSE GRLVDSQGYG VAGVNYYTNS
               ########## ########## ########## ########## ########## ##########
               AAAAAAAAAA AAAAAAAAAA AAAAAAAAAA AAAAAAAAAA AAAAAAAAAA AAAAAAAAAA
               CCCCCCCCCC CCCCCCCCCC CCCCCCCCCC CCCCCCCCCC CCCCCCCCCC CCCCCCCCCC

|          |          |          |          |          |
strain 101-1   GRGVTGENGK FNFSWGETIS FGIDTFELGS VRGNKSTIAL TELGDEVRGA NIDQLIHRYS
strain 536     GRGVTGENGK FNFSWGETIS FGIDTFELGS VRGNKSTIAL TELGDEVRGA NIDQLIHRYS
strain O42     GRGVTGENGK FNFSWGETIS FGIDTFELGS VRGNKSTIAL TELGDEVRGA NIDQLIHRYS
str E2348/69   GRGVTGENGE FSFSWGETIS FGIDTFELGS VRGNKSTIAL TELGDEVRGA NIDQLIHRYS
strain 53638   GRGVTGENGE FSFSWGETIS FGIDTFELGS VRGNKSTIAL TELGDEVRGA NIDQLIHRYS
strain W3110   GRGVTGENGE FSFSWGETIS FGIDTFELGS VRGNKSTIAL TELGDEVRGA NIDQLIHRYS
strain B7A     GRGVTGENGE FSFSWGETIS FGIDTFELGS VRGNKSTIAL TELGDEVRGA NIDQLIHRYS
strain E22     GRGVTGENGE FSFSWGETIS FGIDTFELGS VRGNKSTIAL TELGDEVRGA NIDQLIHRYS
str E24377A    GRGVTGENGE FSFSWGETIS FGIDTFELGS VRGNKSTIAL TELGDEVRGA NIDQLIHRYS
```

```
                       -continued
str H10407      GRGVTGENGE FSFSWGEAIS FGIDTFELGS VRGNKSTIAL TELGDEVRGA NIDQLIHRYS
str E110019     GRGVTGENGE FSFSWGETIS FGIDTFELGS VRGNKSTIAL TELGDEVRGA NIDQLIHRYS
strain HS       GRGVTGENGE FSFSWGETIS FGIDTFELGS VRGNKSTIAL TELGDEVRGA NIDQLIHRYS
strain SECEC    GRGVTGENGE FSFSWGETIS FGIDTFELGS VRGNKSTIAL TELGDEVRGA NIDQLIHRYS
str IHE3034     GRGVTGENGE FSFSWGETIS FGIDTFELGS VRGNKSTIAL TELGDEVRGA NIDQLIHRYS
strain F11      GRGVTDENGK FSFSWGETIS FGIDTFELGS VRGNKSTIAL TELGDEVRGA NIDQLIHRYS
Consensus       GRGVTGENGE FSFSWGETIS FGIDTFELGS VRGNKSTIAL TELGDEVRGA NIDQLIHRYS
                ########## ########## ########## ########## ########## ##########
                AAAAAAAAAA AAAAAAAAAA AAAAAAAAAA AAAAAAAAAA AAAAAAAAAA AAAAAAAAAA
                CCCCCCCCCC CCCCCCCCCC CCCCCCCCCC CCCCCCCCCC CCCCCCCCCC CCCCCCCCCC

|          |          |          |          |          |
strain 101-1    QAGKNDEREV PDVVRKVFAE YPNVINEIIN LSLSNGEALS EGDQTFERTN EFLEQFESGQ
strain 536      QAGKNDEREV PDVVRKVFAE YPNVINEIIN LSLSNGEALS EGDQTFERTN EFLEQFESGQ
strain O42      QAGKNDEREV PDVVRKVFAA YPNVINEIIN LSLSNGEALS EGDQTFERTN EFLEQFESGQ
str E2348/69    TTGQNNTRVV PDDVRKVFAE YPNVINEIIN LSLSNGATLD EGDQNVVLPN EFIEQFKTGQ
strain 53638    TTGQNNTRVV PDDVRKVFAE YPNVINEIIN LSLSNGATLG EGEQVVNLPN EFIEQFNTGQ
strain W3110    TTGQNNTRVV PDDVRKVFAE YPNVINEIIN LSLSNGATLG EGEQVVNLPN EFIEQFNTGQ
strain B7A      TTGQNNTRVV PDDVRKVFAE YPNVINEIIN LSLSNGATLD EGEQVVNLPN EFIEQFKTGQ
strain E22      TTGQNNTRVV PDDVRKVFAE YPNVINEIIN LSLSNGATLD EGEQVVNLPN EFIEQFKTGQ
str E24377A     KAGQNHTRVV PDEVRKVFAE YPNVINEIIN LSLSNGATLG EGEQVVNLPN EFIEQFKTGQ
str H10407      TTGQNNTRVV PDDVRKVFAE YPNVINEIIN LSLSNGATLG EGEQVVNLPN EFIEQFNTGQ
str E110019     TTGQNNTRVV PDDVRKVFAE YPNVINEIIN LSLSNGATLG EGEQVVNLPN EFIEQFKTGQ
strain HS       TTGQNNTRVV PDDVRKVFAE YPNVINEIIN LSLSNGATLG EGEQVVNLPN EFIEQFNTGQ
strain SECEC    TTGQNNTRVV PEDVRKVFAE YPNVINEIIN LSLSNGATLG EGEQVVNLPN EFIEQFNTGQ
str IHE3034     TTGQNNTRVV PDDVRKVFAE YPNVINEIIN LSLSNGATLG EGDQNVVLPN EFIEQFKTGQ
strain F11      TTGQNNTRVV PDDVRKVFAE YPNVINEIIN LSLSNGATLD EGDQNVVLPN EFIEQFKTGQ
Consensus       TTGQNNTRVV PDDVRKVFAE YPNVINEIIN LSLSNGATLG EGEQVVNLPN EFIEQFKTGQ
                ########## ########## ########## ########## ########## ##########
                AAAAAAAAAA AAAAAAAAAA AAAAAAAAAA AAAAAAAAAA AAAAAAAAAA AAAAAAAAAA
                CCCCCCCCCC CCCCCCCCCC CCCCCCCCCC CCCCCCCCCC CCCCCCCCCC CCCCCCCCCC

|          |          |          |          |          |
strain 101-1    AKEIDTAICD SLGGCNSQRW FSLTARNVNE GQIQGVINKL WGVDKDYKSV TKFHVFHDST
strain 536      AKEIDTAICD SLGGCNSQRW FSLTARNVNE GQIQGVINKL WGVDTNYKSV SKFHVFHDST
strain O42      AKEIDTAICD SLGGCNSQRW FSLTARNVNE GQIQGVINKL WGVDKDYKSV TKFHVFHDST
str E2348/69    AKEIDTAICA KTDGCNEARW FSLTTRNVND GQIQGVINKL WGVDKDYKSV TKFHVFHDST
strain 53638    AKEIDTAICA KTDGCNEARW FSLTTRNVND GQIQGVINKL WGVDTNYKSV SKFHVFHDST
strain W3110    AKEIDTAICA KTDGCNEARW FSLTTRNVND GQIQGVINKL WGVDTNYKSV SKFHVFHDST
strain B7A      AKEIDTAICA KTDGCNEARW FSLTTRNVND GQIQGVINKL WGVDTNYKSV SKFHVFHDST
strain E22      AKEIDTAICA KTDGCNEARW FSLTTRNVND GQIQGVINKL WGVDTNYKSV SKFHVFHDST
str E24377A     AKEIDTAICA KTDGCNEARW FSLTTRNVND GKIQGVINKL WGVDTNYKSV SKFHVFHDST
str H10407      AKEIDTAICA KTDGCNEARW FSLTTRNVND GQIQGVINKL WGVDTNYKSV SKFHVFHDST
str E110019     AKEIDTAICA KTDGCNEARW FSLTTRNVND GQIQGVINKL WGVDTNYKSV SKFHVFHDST
strain HS       AKEIDTAICA KTDGCNEARW FSLTTRNVND GQIQGVINKL WGVDTNYKSV SKFHVFHDST
strain SECEC    AKEIDTAICA KTDGCNEARW FSLTTRNVND GQIQGVINKL WGVDTNYKSV SKFHVFHDST
str IHE3034     AKEIDTAICA KTDGCNEARW FSLTTRNVND GQIQGVINKL WGVDTNYQSV SKFHVFHDST
strain F11      AKEIDTAICA KTNGCNEARW FSLTTRNVND GQIQGVINKL WGVDTNYQSV SKFHVFHDST
Consensus       AKEIDTAICA KTDGCNEARW FSLTTRNVND GQIQGVINKL WGVDTNYKSV SKFHVFHDST
                ########## ########## ########## ########## ########## ##########
                AAAAAAAAAA AAAAAAAAAA AAAAAAAAAA AAAAAAAAAA AAAAAAAAAA AAAAAAAAAA
                CCCCCCCCCC CCCCCCCCCC CCCCCCCCCC CCCCCCCCCC CCCCCCCCCC CCCCCCCCCC

|          |          |          |          |          |
strain 101-1     NFYGSTGNAR GQAVVNISNA APPILMARND KNYWLAFGEK RAWDKNELAY ITEAPSLVEP
strain 536       NFYGSTGNAR GQAVVNISNA APPILMARND KNYWLAFGEK RAWDKNELAY ITEAPSLVEP
strain O42       NFYGSTGNAR GQAVVNISNA APPILMARND KNYWLAFGEK RAWDKNELAY ITEAPSLVEP
str E2348/69     NFYGSTGNAR GQAVVNISNA APPILMARND KNYWLAFGEK RAWDKNELAY ITEAPSIVQP
strain 53638     NFYGSTGNAR GQAVVNISNA APPILMARND KNYWLAFGEK RAWDKNELAY ITEAPSLVEP
strain W3110     NFYGSTGNAR GQAVVNISNA APPILMARND KNYWLAFGEK RAWDKNELAY ITEAPSLVEP
strain B7A       NFYGSTGNAR GQAVVNISNA APPILMARND KNYWLAFGEK RAWDKNELAY ITEAPSLVEP
strain E22       NFYGSTGNAR GQAVVNISNA APPILMARND KNYWLAFGEK RAWDKNELAY ITEAPSLVEP
str E24377A      NFYGSTGNAR GQAVVNISNA APPILMARND KNYWLAFGEK RAWDKNELAY ITEAPSIVRP
str H10407       NFYGSTGNAR GQAVVNISNA APPILMARND KNYWLAFGEK RAWDKNELAY ITEAPSIVRP
str E110019      NFYGSTGNAR GQAVVNISNA APPILMARND KNYWLAFGEK RAWDKNDLAY ITEAPSIVRP
strain HS        NFYGSTGNAR GQAVVNISNA APPILMARND KNYWLAFGEK RAWDKNELAY ITEAPSIVRP
strain SECEC     NFYGSTGNAR GQAVVNISNA APPILMARND KNYWLAFGEK RAWDKNELAY ITEAPSIVRP
str IHE3034      NFYGSTGNAR GQAVVNISNS APPILMARND KNYWLAFGEK RAWDKNELAY ITEAPSIVRP
strain F11       NFYGSTGNAR GQAVVNISNA APPILMARND KNYWLAFGEK RAWDKNELAY ITEAPSIVQP
Consensus        NFYGSTGNAR GQAVVNISNA APPILMARND KNYWLAFGEK RAWDKNELAY ITEAPSIVEP
                 ########## ########## ########## ########## ########## ##########
                 AAAAAAAAAA AAAAAAAAAA AAAAAAAAAA AAAAAAAAAA AAAAAAAAAA AAAAAAAAAA
                 CCCCCCCCCC CCCCCCCCCC CCCCCCCCCC CCCCCCCCCC CCCCCCCCCC CCCCCCCCCC

|          |          |          |          |          |
strain 101-1     ENVTRDTATF NLPFISLGQV GEGKLMVIGN PHYNSILRCP NGYSWEGGVD KNGQCTRNSD
strain 536       ENVTRDTATF NLPFISLGQV GEGKLMVIGN PHYNSILRCP NGYSWEGGVD KNGQCTRNSD
strain O42       ENVTRDTATF NLPFISLGQV GEGKLMVIGN PHYNSILRCP NGYSWEGGVD KNGQCTRNSD
str E2348/69     ENVTRDTATF NLPFISLGQV GEGKLMVIGN PHYNSILRCP NGYSWNGGVN KDGQCTLSGD
strain 53638     ENVTRDTATF NLPFISLGQV GEGKLMVIGN PHYNSILRCP NGYSWNGGVN KDGQCTLNSD
strain W3110     ENVTRDTATF NLPFISLGQV GEGKLMVIGN PHYNSILRCP NGYSWNGGVN KDGQCTLNSD
```

```
                      -continued
strain B7A     ENVTRDTATF NLPFISLGQV GEGKLMVIGN PHYNSILRCP NGYSWNGGVN KDGQCTLNSD
strain E22     ENVTRDTATF NLPFISLGQV GEGKLMVIGN PHYNSILRCP NGYSWNGGVN KDGQCTLNSD
str E24377A    ENVTRDTATF NLPFISLGQV GDGKLMVIGN PHYNSILRCP NGYSWNGGVN KDGQCTLNSD
str H10407     ENVTRETASF NLPFISLGQV GDGKLMVIGN PHYNSILRCP NGYSWNGGVN KDGQCTLNSD
str E110019    ENVTRETATF NLPFISLGQV GDGKLMVIGN PHYNSILRCP NGYSWNGGVN KDGQCTLNSD
strain HS      ENVTRETATF NLPFISLGQV GDGKLMVIGN PHYNSILRCP NGYSWNGGVN KDGQCTLNSD
strain SECEC   ENVTRETATF NLPFISLGQV GDGKLMVIGN PHYNSILRCP NGYSWNGGVN KDGQCTLNSD
str IHE3034    ENVTRDTATF NLPFISLGQV GEGKLMVIGN PHYNSILRCP NGYSWGGGVN SKGECTLSGD
strain F11     ENVTRDTATF NLPFISLGQV GDGKLMVIGN PHYNSILRCP NGYSWGGGVN SKGECTLSGD
Consensus      ENVTRDTATF NLPFISLGQV GEGKLMVIGN PHYNSILRCP NGYSWNGGVN KDGQCTLNSD
               ########## ########## ########## ########## ########## ##########
               AAAAAAAAAA AAAAAAAAAA AAAAAAAAAA AAAAAAAAAA AAAAAAAAAA AAAAAAAAAA
               CCCCCCCCCC CCCCCCCCCC CCCCCCCCCC CCCCCCCCCC CCCCCCCCCC CCCCCCCCCC

|          |          |          |          |          |
strain 101-1   SNDMKHFMQNV LRYLSDDKW TPDAKASMTV GTNLDTVYFK RHGQVTGNSA EFGFHPDFAG
strain 536     SNDMKHFMQNV LRYLSDDKW TPDAKASMTV GTNLDTVYFK RHGQVTGNSA EFGFHPDFAG
strain O42     SNDMKHFMQNV LRYLSNDKW TPDAKASMTV GTNLDTVYFK RHGQVTGNSA EFGFHPDFAG
str E2348/69   SDDMKHFMQNV LRYLSDDKW TPDAKASMTV GTNLDTVYFK RHGQVTGNSA EFGFHPDFAG
strain 53638   SDDMKHFMQNV LRYLSDDKW TPDAKASMTV GTNLDTVYFK RHGQVTGNSA AFDFHPDFAG
strain W3110   PDDMKNFMENV LRYLSDDKW KPDAKASMTV GTNLDTVYFK RHGQVTGNSA AFDFHPDFAG
strain B7A     PDDMKNFMENV LRYLSDDKW TPDAKASMTV GTNLDTVYFK RHGQVTGNSA AFDFHPDFAG
strain E22     PDDMKNFMENV LRYLSDDKW TPDAKASMTV GTNLDTVYFK RHGQVTGNSA AFDFHPDFAG
str E24377A    PDDMKNFMENV LRYLSDDKW TPDAKASMTV GTNLDTVYFK RHGQVTGNSA AFDFHPDFAG
str H10407     PDDMKNFMENV LRYLSNDRW LPDAKSSMTV GTNLETVYFK KHGQVLGNSA PFAFHKDFTG
str E110019    PDDMKNFMENV LRYLSNDRW LPDAKSSMTV GTNLDTVYFK KHGQVTGNSA PFAFHKDFTG
strain HS      PDDMKNFMENV LRYLSNDRW LPDAKSNMTV GTNLDTVYFK KHGQVTGNSA AFGFHPDFAG
strain SECEC   PDDMKNFMENV LRYLSNDRW LPDAKSNMTV GTNLDTVYFK KHGQVTGNSA AFGFHPDFAG
str IHE3034    SDDMKHFMQNV LRYLSNDIW QPNTKSIMTV GTNLENVYFK KAGQVLGNSA PFAFHEDFTG
strain F11     SDDMKHFMQNV LRYLSDDIW QPNTKSIMTV GTNLENVYFK KAGQVLGNSA PFAFHPDFAG
Consensus      PDDMKNFMENV LRYLSDDKW TPDAKASMTV GTNLDTVYFK RHGQVTGNSA AFGFHPDFAG
               ########## ########## ########## ########## ########## ##########
               AAAAAAAAAA AAAAAAAAAA AAAAAAAAAA AAAAAAAAAA AAAAAAAAAA AAAAAAAAAA
               CCCCCCCCCC CCCCCCCCCC CCCCCCCCCC CCCCCCCCCC CCCCCCCCCC CCCCCCCCCC

|          |          |          |          |          |
strain 101-1   ISVEHLSSYG DLDPQEMPLL ILNGFEYVTQ VGNDPYAIPL RADTSKPKLT QQDVTDLIAY
strain 536     ISVEHLSSYG DLDPQEMPLL ILNGFEYVTQ VGNDPYAIPL RADTSKPKLT QQDVTDLIAY
strain O42     ISVEHLSSYG DLDPQKMPLL ILNGFEYVTQ VGGDPYAVPL RADTSKPKLS QQDVTDLIAY
str E2348/69   ISVEHLSSYG DLDPQEMPLL ILNGFEYVTQ VGNDPYAIPL RADTSKPKLT QQDVTDLIAY
strain 53638   ISVEHLSSYG DLDPQEMPLL ILNGFEYVTQ VGNDPYAIPL RADTSKPKLT QQDVTDLIAY
strain W3110   ISVEHLSSYG DLDPQEMPLL ILNGFEYVTQ VGNDPYAIPL RADTSKPKLT QQDVTDLIAY
strain B7A     ISVEHLSSYG DLDPQEMPLL ILNGFEYVTQ VGNDPYAIPL RADTSKPKLT QQDVTDLIAY
strain E22     ISVEHLSSYG DLDPQEMPLL ILNGFEYVTQ VGNDPYAIPL RADTSKPKLT QQDVTDLIAY
str E24377A    ISVEHLSSYG DLDPQEMPLL ILNGFEYVTQ VGNDPYAIPL RADTSKPKLT QQDVTDLIAY
str H10407     ITVKPMTSYG NLNPDEVPLL ILNGFEYVTQ WGSDPYSIPL RADTSKPKLT QQDVTDLIAY
str E110019    ITVKPMTSYG NLNPDEVPLL ILNGFEYVTQ WGSDPYSIPL RADTSKPKLT QQDVTDLIAY
strain HS      ISVEHLSSYG DLDPQEMPLL ILNGFEYVTQ VGNDPYAIPL RADTSKPKLT QQDVTDLIAY
strain SECEC   ISVEHLSSYG DLDPQEMPLL ILNGFEYVTQ VGNDPYAIPL RADTSKPKLT QQDVTDLIAY
str IHE3034    ITVKQLTSYG DLNPEEIPLL ILNGFEYVTQ WSGDPYAVPL RADTSKPKLT QQDVTDLIAY
strain F11     ITVKQLTSYG DLNPEEIPLL ILNGFEYVTQ WSGDPYAVPL RADTSKPKLT QQDVTDLIAY
Consensus      ISVEHLSSYG DLDPQEMPLL ILNGFEYVTQ VGNDPYAIPL RADTSKPKLT QQDVTDLIAY
               ########## ########## ########## ########## ########## ##########
               AAAAAAAAAA AAAAAAAAAA AAAAAAAAAA AAAAAAAAAA AAAAAAAAAA AAAAAAAAAA
               CCCCCCCCCC CCCCCCCCCC CCCCCCCCCC CCCCCCCCCC CCCCCCCCCC CCCCCCCCCC

|          |          |          |          |          |
strain 101-1   LNKGGSVLIM ENVMSNLKEE SASGFVRLLD AAGLSMALNK SVVNNDPQGY PNRVRQQRAT
strain 536     LNKGGSVLIM ENVMSNLKEE SASGFVRLLD AAGLSMALNK SVVNNDPQGY PNRVRQQRAT
strain O42     LNKGGSVLIM ENVMSNLKEE SASGFVRLLD AAGLSMALNK SVVNNDPQGY PDRVRQRRAT
str E2348/69   LNKGGSVLIM ENVMSNLKEE SASGFVRLLD AAGLSMALNK SVVNTDPQGY PNRVRQQREK
strain 53638   LNKGGSVLIM ENVMSNLKEE SASGFVRLLD AAGLSMALNK SVVNNDPQGY PNRVRQQRAT
strain W3110   LNKGGSVLIM ENVMSNLKEE SASGFVRLLD AAGLSMALNK SVVNNDPQGY PNRVRQQRAT
strain B7A     LNKGGSVLIM ENVMSNLKEE SASGFVRLLD AAGLSMALNK SVVNNDPQGY PNRVRQQRAT
strain E22     LNKGGSVLIM ENVMSNLKEE SASGFVRLLD AAGLSMALNK SVVNNDPQGY PNRVRQQRAT
str E24377A    LNKGGSVLIM ENVMSNLKEE SASGFVRLLD AAGLSMALNK SVVNNDPQGY PNRVRQRRST
str H10407     MNKGGSVLIM ENVMSNLKEE SASGFVRLLD AAGLSMALNK SVVNNDPQGY PDRVRQRRST
str E110019    MNKGGSVLIM ENVMSNLKEE SASGFVRLLD AAGLSMALNK SVVNNDPQGY PDRVRQRRST
strain HS      MNKGGSVLIM ENVMSNLKEE SASGFVRLLD AAGLSMALNK SVVNNDPQGY PDRVRQRRST
strain SECEC   MNKGGSVLIM ENVMSNLKEE SASGFVRLLD AAGLSMALNK SVVNNDPQGY PDRVRQRRST
str IHE3034    LNKGGSVLIM ENVMSNLKEE SASSFVRLLD AAGLSMALNK SVVNNDPQGY PDRVRQRRAT
strain F11     LNKGGSVLIM ENVMSNLKEE SASSFVRLLD AAGLSMALNK SVVNNDPQGY PDRVRQREK
Consensus      LNKGGSVLIM ENVMSNLKEE SASGFVRLLD AAGLSMALNK SVVNNDPQGY PNRVRQQRAT
               ########## ########## ########## ########## ########## ##########
               AAAAAAAAAA AAAAAAAAAA AAAAAAAAAA AAAAAAAAAA AAAA
                                                                BBBBB BBBBBBBBBB
               CCCCCCCCCC CCCCCCCCCC CCCCCCCCCC CCCCCCCCCC CCCCCCCCCC CCCCCCCCCC

|          |          |          |          |          |
strain 101-1   GIWVYERYPA VDGALP-YTI DSKTGEVKWK YQVENKPDDK PKLEVASWLE DVDGKQETRY
strain 536     GIWVYERYPA VDGALP-YTI DSKTGEVKWK YQVENKPDDK PKLEVASWLE DVDGKQETRY
```

-continued

```
strain 101-1    GIWVYERYPV VEGELP-YTI DSKTGKVTWK YQIDNKPDKK PKLEVASWQE EVDGKQVTQF
strain 536      GIWVYERYPA VDSAQPPYTI DPDTGKVTWK YQEEGKPDDK PKLEVASWQE DVDGKQVTRY
strain O42      GIWVYERYPA VDGALP-YTI DSKTGEVKWK YQVENKPDDK PKLEVASWLE DVDGKQETRY
str E2348/69    GIWVYERYPA VDGALP-YTI DSKTGEVKWK YQVENKPDDK PKLEVASWLE DVDGKQETRY
strain 53638    GIWVYERYPA VDGALP-YTI DSKTGEVKWK YQVENKPDDK PKLEVASWLE DVDGKQETRY
strain W3110    GIWVYERYPA VDGALP-YTI DSKTGEVKWK YQVENKPDDK PKLEVASWLE DVDGKQETRY
strain B7A      GIWVYERYPA VDGALP-YTI DSKTGEVKWK YQVENKPDDK PKLEVASWLE DVDGKQETRY
strain E22      GIWVYERYPA VDGKPP-YTI DDTTKEVIWK YQQENKPDDK PKLEVASWQE EVEGKQVTQF
str E24377A     GIWVYERYPA VDGKPP-YTI DDTTKEVIWK YQQENKPDDK PKLEVASWQE EVEGKQVTQF
str H10407      GIWVYERYPA VDGKPP-YTI DDTTKEVIWK YQQENKPDDK PKLEVASWQE EVEGKQVTQF
str E110019     GIWVYERYPA VDGKPP-YTI DDTTKEVIWK YQQENKPDDK PKLEVASWQE EVEGKQVTQF
strain HS       GIWVYERYPA VDGKPP-YTI DDTTKEVIWK YQQENKPDDK PKLEVASWQE EVEGKQVTQF
strain SECEC    GIWVYERYPA VDGKPP-YTI DDTTKEVIWK YQQENKPDDK PKLEVASWQE EVEGKQVTQF
str IHE3034     GIWVYERYPA ADGAQPPYTI DPNTGKVTWK YQQDNKPDDK PKLEVASWQE EVEGKQVTRY
strain F11      GIWVYERYPF VDG-KPPYTI DETTKEVIWK YQQDNKPDDK PKLEVASWLE DVDGKQVKRY
Consensus       GIWVYERYPA VDGALPPYTI DSKTGEV?WK YQQENKPDDK PKLEVASWQE DVDGKQVTRY
                ########## ########## ########## ########## ########## ##########
                BBBBBBBBBB BBBBBBBBBB BBBBBBBBBB BBBBBBBBBB BBBBBBBBBB BBBBBBBBBB
                CCCCCCCCCC CCCCCCCCCC CCCCCCCCCC CCCCCCCCCC CCCCCCCCCC CCCCCCCCCC

|          |          |          |          |          |
strain 101-1    AFIDEADHKT EDSLKAAKAK IFEKFPGLKE CKDPTYHYEV NCLEYRPGTG VPVTGGMYVP
strain 536      AFIDEADHKT EDSLKAAKAK IFEKFPGLKE CKDPTYHYEV NCLEYRPGTG VPVTGGMYVP
strain O42      AFIDEADHKT TESLDAAKKK ILEKFKGLEE CKDSTYHYEI NCLEYRPGTN VPATGGMYVP
str E2348/69    AFIDEAEHST EESLEAAKAK IFEKFPGLQE CKDSTYHYEI NCLERRPGTD VPVTGGMYVP
strain 53638    AFIDEADHKT EDSLKAAKEK IFAAFPGLKE CTNPAYHYEV NCLEYRPGTG VPVTGGMYVP
strain W3110    AFIDEADHKT EDSLKAAKEK IFAAFPGLKE CTNPAYHYEV NCLEYRPGTG VPVTGGMYVP
strain B7A      AFIDEADHKT EDSLKAAKEK IFAAFPGLKE CTNPAYHYEV NCLEYRPGTG VPVTGGMYVP
strain E22      AFIDEADHKT EDSLKAAKEK IFAAFPGLKE CTNPAYHYEV NCLEYRPGTG VPVTGGMYVP
str E24377A     AFIDEADHKT PESLAAAKQR ILDAFPGLEV CKDSDYHYEV NCLEYRPGTD VPVTGGMYVP
str H10407      AFIDEADHKT PESLAAAKQR ILDAFPGLEV CKDSDYHYEV NCLEYRPGTD VPVTGGMYVP
str E110019     AFIDEADHKT PESLAAAKQR ILDAFPGLEV CKDSDYHYEV NCLEYRPGSG VPVTGGMYVP
strain HS       AFIDEADHKT PESLAAAKKR ILDAFPGLEE CKDSDYHYEV NCLEYRPGTG VPVTGGMYVP
strain SECEC    AFIDEADHKT PESLAAAKKR ILDAFPGLEE CKDSDYHYEV NCLEYRPGTG VPVTGGMYVP
str IHE3034     AFIDEAEYTT EESLEAAKAK IFEKFPGLQE CKDSTYHYEI NCLERRPGTD VPVTGGMYVP
strain F11      AFIDEAEHET NESLEAAKAK IIKAFPGLEE CKDPTYHYEV NCLEYRPGTN VPVTGGMYVP
Consensus       AFIDEADHKT EESLKAAKAK IF?AFPGLEE CKDSTYHYEV NCLEYRPGTG VPVTGGMYVP
                ########## ########## ########## ########## ########## ##########
                BBBBBBBBBB BBBBBBBBBB BBBBBBBBBB BBBBBBBBBB BBBBBBBBBB BBBBBBBBBB
                CCCCCCCCCC CCCCCCCCCC CCCCCCCCCC CCCCCCCCCC CCCCCCCCCC CCCCCCCCCC

|          |          |          |          |          |
strain 101-1    QYTQLSLNAD TAKAMVQAAD LGTNIQRLYQ HELYFRTNGR KGERLSSVDL ERLYQNMSVW
strain 536      QYTQLSLNAD TAKAMVQAAD LGTNIQRLYQ HELYFRTNGR KGERLSSVDL ERLYQNMSVW
strain O42      RYTQLNLSAD TAKAMVQAAD LGTNIQRLYQ HELYFRTNGR KGERLSSVDL ERLYQNMSVW
str E2348/69    RYTQLNLDAD TAKAMVQAAD LGTNIQRLYQ HELYFRTNGR KGERLSSVDL ERLYQNMSVW
strain 53638    QYTQLSLNAD TAKAMVQAAD LGTNIQRLYQ HELYFRTNGR KGERLSSVDL ERLYQNMSVW
strain W3110    QYTQLSLNAD TAKAMVQAAD LGTNIQRLYQ HELYFRTNGR KGERLSSVDL ERLYQNMSVW
strain B7A      QYTQLSLNAD TAKAMVQAAD LGTNIQRLYQ HELYFRTNGR KGERLSCVDL ERLYQNMSVW
strain E22      QYTQLSLNAD TAKAMVQAAD LGTNIQRLYQ HELYFRTNGR KGERLSSVDL ERLYQNMSVW
str E24377A     QYTQLDLSAD TAKAMLQAAD LGTNIQRLYQ HELYFRTNGR QGERLNSVDL ERLYQNMSVW
str H10407      QYTQLDLSAD TAKAMLQAAD LGTNIQRLYQ HELYFRTNGR QGERLNSVDL ERLYQNMSVW
str E110019     QYTQLDLGAD TAKAMLQAAD LGTNIQRLYQ HELYFRTNGR QGERLNSVDL ERLYQNMSVW
strain HS       QYTQLSLNAD TAKAMVQAAD LGTNIQRLYQ HELYFRTNGR KGERLSSVDL ERLYQNMSVW
strain SECEC    QYTQLSLNAD TAKAMVQAAD LGTNIQRLYQ HELYFRTNGR KGERLSSVDL ERLYQNMSVW
str IHE3034     RYTQLNLDAD TAKAMVQAAD LGTNIQRLYQ HELYFRTKGS GERLNSVDL ERLYQNMSVW
strain F11      RYTQLNLSAD TAKAMVQAAD LGTNIQRLYQ HELYFRTNGR KGERLSSVDL ERLYQNMSVW
Consensus       QYTQLSLNAD TAKAMVQAAD LGTNIQRLYQ HELYFRTNGR KGERLSSVDL ERLYQNMSVW
                ########## ########## ########## ########## ########## ##########
                BBBBBBBBBB BBBBBBBBBB BBBBBBBBBB BBBBBBBBBB BBBBBBBBBB BBBBBBBBBB
                CCCCCCCCCC CCCCCCCCCC CCCCCCCCCC CCCCCCCCCC CCCCCCCCCC CCCCCCCCCC

|          |          |          |          |          |
strain 101-1    LWNKIEYRYE NDKDDELGFK TFTEFLNCYA NDAYTGGTQC SDELKKSLVD NNMIYGEKSV
strain 536      LWNKIEYRYE NDKDDELGFK TFTEFLNCYA NDAYTGGTQC SDELKKSLVD NNMIYGEKSV
strain O42      LWNEIEYSYD SSKEDELGFK TFTEFLNCYA NDAYTGGTQC SDELKKSLVD NNMIYGEKSV
str E2348/69    LWNKIEYRYE NDKDDELGFK TFTEFLNCYA NNAYSEGTQC SADLKKSLVD NNMIYGDGSS
strain 53638    LWNDTSYRYE EGKNDELGFK TFTEFLNCYA NDAYAGGTKC SADLKKSLVD NNMIYGDGSS
strain W3110    LWNDTSYRYE EGKNDELGFK TFTEFLNCYA NDAYAGGTKC SADLKKSLVD NNMIYGDGSS
strain B7A      LWNDTSYRYE EGKNDELGFK TFTEFLNCYA NDAYAGGTKC SADLKKSLVD NNMIYGDGSS
strain E22      LWNDTSYRYE EGKNDELGFK TFTEFLNCYA NDAYAGGTKC SADLKKSLVD NNMIYGDGSS
str E24377A     LWNETKYRYE EGKEDELGFK TFTEFLNCYT NNAYVG-TQC SAELKKSLID NKMIYGEESS
str H10407      LWNETKYRYE EGKEDELGFK TFTEFLNCYT NNAYVG-TQC SAELKKSLID NKMIYGEESS
str E110019     LWNETKYRYE EGKEDELGFK TFTEFLNCYT NNAYVG-TQC SAELKKSLID NKMIYGEESS
strain HS       LWNKIEYRYE NDKDDELGFK TFTEFLNCYA NNAYDGGTQC SAELKQSLID NKMIYGE-GS
strain SECEC    LWNKIEYRYE NDKDDELGFK TFTEFLNCYA NNAYDGGTQC SAELKQSLID NKMIYGE-GS
str IHE3034     LWNDTKYRYE EGKEDELGFK TFTEFLNCYA NDAYAGGTKC SADLKKSLVD NNMIYGDGSS
strain F11      LWNEIEYSYD SSKEDELGFK TFTEFLNCYA NDAYTKGTLC SAELKQSLID NKMIYGEGS-
```

```
Consensus      LWN3TEYRYE EGKEDELGFK TFTEFLNCYA NDAYAGGTQC SAELKKSLVD NNMIYGEGSS
               ########## ########## ########## ########## ########## ##########
               BBBBBBBBBB BBBBBBBBBB BBBBBBBBBB BBBBBBBBBB BBBBBBBBBB BBBBBBBBBB
               CCCCCCCCCC CCCCCCCCCC CCCCCCCCCC CCCCCCCCCC CCCCCCCCCC CCCCCCCCCC

|          |          |          |          |          |
strain 101-1   NKAGMMNPSY PLNYMEKPLT RLMLGRSWWD LNIKVDVEKY PGAVSAEGEK VTETISLYSN
strain 536     NKAGMMNPSY PLNYMEKPLT RLMLGRSWWD LNIKVDVEKY PGAVSAEGEK VTETISLYSN
strain O42     NKAGMMNPSY PLNYMEKPLT RLMLGRSWWD LNIKVDVEKY PGAVSEEGQE VTESISLYSN
str E2348/69   -KAGMMNPSY PLNYMEKPLT RLMLGRSWWD LNIKVDVEKY PGAVSAEGEK VTETISLYSN
strain 53638   -KAGMMNPSY PLNYMEKPLT RLMLGRSWWD LNIKVDVEKY PGAVSEEGQN VTETISLYSN
strain W3110   -KAGMMNPSY PLNYMEKPLT RLMLGRSWWD LNIKVDVEKY PGAVSEEGQN VTETISLYSN
strain B7A     -KAGMMNPSY PLNYMEKPLT RLMLGRSWWD LNIKVDVEKY PGAVSEEGQN VTETISLYSN
strain E22     -KAGMMNPSY PLNYMEKPLT RLMLGRSWWD LNIKVDVEKY PGAVSEEGQN VTETISLYSN
str E24377A    -KAGMMNPSY PLNYMEKPLT RLMLGRSWWD LNIKVDVEKY PGVVNTNGET VTQNINLYSA
str H10407     -KAGMMNPSY PLNYMEKPLT RLMLGRSWWD LNIKVDVEKY PGVVNTNGET VTQNINLYSA
str E110019    -KAGMMNPSY PLNYMEKPLT RLMLGRSWWD LNIKVDVEKY PGAVSEEGQN VTETISLYSN
strain HS      -KAGMMNPSY PLNYMEKPLT RLMLGRSWWD LNIKVDVEKY PGAVSAEGEE VTETINLYSN
strain SECEC   -KAGMMNPSY PLNYMEKPLT RLMLGRSWWD LNIKVDVEKY PGAVSAEGEE VTETINLYSN
str IHE3034    -KAGMMNPSY PLNYMEKPLT RLMLGRSWWD LNIKVDVEKY PGSVSAKGES VTENISLYSN
strain F11     -KAGMMNPSY PLNYMEKPLT RLMLGRSWWD LNIKVDVEKY PGAVSVGGEE VTETISLYSN
Consensus      NKAGMMNPSY PLNYMEKPLT RLMLGRSWWD LNIKVDVEKY PGAVS2EGEN VTETISLYSN
               ########## ########## ########## ########## ########## ##########
               BBBBBBBBBB BBBBBBBBBB BBBBBBBBBB BBBBBBBBBB BBBBBBBBBB BBBBBBBBBB
               CCCCCCCCCC CCCCCCCCCC CCCCCCCCCC CCCCCCCCCC CCCCCCCCCC CCCCCCCCCC

|          |          |          |          |          |
strain 101-1   PTKWFAGNMQ STGLWAPAQK EVTIES-
               SASV PVTVTVALAD DLTGREKHEV ALNRPPKVTK....
strain 536     PTKWFAGNMQ STGLWAPAQK EVTIESTASV AVTVTVALAD DLTGREKHEV ALNRPPKVTK
strain O42     PTKWFAGNMQ STGLWAPAQK EVTIKSNADV PVTVTVALAD DLTGREKHEV ALNRPPKVTK
str E2348/69   PTKWFAGNMQ STGLWAPAQQ EVTIESTASV PVTVTVALAD DLTGREKHEV ALNRPPKVTK
strain 53638   PTKWFAGNMQ STGLWAPAQK EVTIKSNANV PVTVTVALAD DLTGREKHEV ALNRPPRVTK
strain W3110   PTKWFAGNMQ STGLWAPAQK EVTIKSNANV PVTVTVALAD DLTGREKHEV ALNRPPRVTK
strain B7A     PTKWFAGNMQ STGLWAPAQK EVTIKSNANV PVTVTVALAD DLTGREKHEV ALNRPPRVTK
strain E22     PTKWFAGNMQ STGLWAPAQK EVTIKSNANV PVTVTVALAD DLTGREKHEV ALNRPPRVTK
str E24377A    PTKWFAGNMQ STGLWAPAQQ EVSIESKATV PVTVTVALAD DLTGREKHEV SLNRPPRVTK
str H10407     PTKWFAGNMQ STGLWAPAQQ EVSIESKSTV PVTVTVALAD DLTGREKHEV SLNRPPRVTK
str E110019    PTKWFAGNMQ STGLWAPAQK EVTIKSNANV PVTVTVALAD DLTGREKHEV ALNRPPRVTK
strain HS      PTKWFAGNMQ STGLWAPAQQ EVSIKSNAKV PVTVTVALAD DLTGREKHEV ALNRPPRVTK
strain SECEC   PTKWFAGNMQ STGLWAPAQQ EVSIKSNAKV PVTVTVALAD DLTGREKHEV ALNRPPRVTK
str IHE3034    PTKWFAGNMQ STGLWAPAQK DVTIKSSASV PVTVTVALAD DLTGREKHEV ALNRPPRVTK
strain F11     PTKWFAGNMQ STGLWAPAQK EVTIKSNANV PVTVTVALAD DLTGREKHEV ALNRPPRVTK
Consensus      PTKWFAGNMQ STGLWAPAQK EVTIKSNANV PVTVTVALAD DLTGREKHEV ALNRPPRVTK
               ########## ########## ########## ########## ########## ##########
               BBBBBBBBBB BBBBBBBBBB BBBBBBBBBB BBBBBBBBBB BBBBBBBBBB BBBBBBBBBB
               CCCCCCCCCC CCCCCCCCCC CCCCCCCCCC CCCCCCCCCC CCCCCCCCCC CCCCCCCCCC

|          |          |          |          |          |
strain 101-1   TYELKANGEV KFTVPYGGLI YIKGNSPQN- ESAEFTFTGV VKAPFYKDGA WKNALNSPAP
strain 536     TYELKANGEV KFTVPYGGLI YIKGNSPQN- ESAEFTFTGV VKAPFYKDGA WKNALNSPAP
strain O42     TYELKANGEV KFTVPYGGLI YIKGNSKENN KSASFTFTGV VKAPFYKNGA WKNALNSPAP
str E2348/69   TYDLKANDKV TFKVPYGGLI YIKGNSPKN- ESAEFTFTGV VKAPFYKDGE WKNALNSPAP
strain 53638   TYSLDASGTV KFKVPYGGLI YIKGNSSTN- ESASFTFTGV VKAPFYKDGA WKNDLNSPAP
strain W3110   TYSLDASGTV KFKVPYGGLI YIKGNSSTN- ESASFTFTGV VKAPFYKDGA WKNDLNSPAP
strain B7A     TYSLDASGTV KFKVPYGGLI YIKGNSSTN- ESASFTFTGV VKAPFYKDGA WKNDLNSPAP
strain E22     TYSLDASGTV KFKVPYGGLI YIKGNSSTN- ESASFTFTGV VKAPFYKDGA WKNDLNSPAP
str E24377A    TYDLKANDKV TFKVPYGGLI YIKGDSKEV- QSADFTFTGV VKAPFYKDGK WQHDLNSPAP
str H10407     TYDLKANDKV TFKVPYGGLI YIKGDSKEV- QSADFTFTGV VKAPFYKDGK WQHDLNSPAP
str E110019    TYSLDASGTV KFKVPYGGLI YIKGNSSTN- ESASFTFTGV VKAPFYKDGA WKNDLNSPAP
strain HS      TYSLDASGTV KFKVPYGGLI YIKSDSKEE- KSANFTFTGV VKAPFYKDGK WKNDLKSPAP
strain SECEC   TYSLDASGTV KFKVPYGGLI YIKSDSKEE- KSANFTFTGV VKAPFYKDGK WKNDLKSPAP
str IHE3034    TYTLEANGEV TFKVPYGGLI YIKGDSKDD- VSANFTFTGV VKAPFYKDGE WKNDLDSPAP
strain F11     TYSLDASGTV KFKVPYGGLI YIKGNSSTN- ESASFTFTGV VKAPFYKDGA WKNDLNSPAP
Consensus      TYSLDASGTV KFKVPYGGLI YIKGNS2TNN ESASFTFTGV VKAPFYKDGA WKNDLNSPAP
               ########## ########## ########## ########## ########## ##########
               BBBBBBBBBB BBBBBBBBBB BBBBBBBBBB BBBBBBBBBB BBBBBBBBBB BBBBBBBBBB
               CCCCCCCCCC CCCCCCCCCC CCCCCCCCCC CCCCCCCCCC CCCCCCCCCC CCCCCCCCCC

|          |          |          |          |          |
strain 101-1   LGELESDAFV YTTPKKNLEA S---NFTGGV AEFAKDLDTF ASSMNDFYGR NDEDGKHRMF
strain 536     LGELESDAFV YTTPKKNLEA S---NYKGGQ EQFAEELDTF ASSMNDFYGR NDEDGKHRMF
strain O42     LGELESDAFV YTTPKKNLEA S---NFTGGV AEFAKDLDTF ASSMNDFYGR NDEDGKHRMF
str E2348/69   LGELESDSFV YTAPKNNLNA SNYSNYTDGV AEFAKELDTF ASSMNDFYGR DGESGNHRMF
strain 53638   LGELESDAFV YTTPKKNLNA S---NYTGGL EQFANDLDTF ASSMNDFHGR DSEDGKHRMF
strain W3110   LGELESDAFV YTTPKKNLNA S---NYTGGL EQFANDLDTF ASSMNDFYGR DSEDGKHRMF
strain B7A     LGELESDAFV YTTPKKNLNA S---NYTGGL EQFANDLDTF ASSMNDFYGR DSEDGKHRMF
strain E22     LGELESDAFV YTTPKKNLNA S---NYTGGL EQFANDLDTF ASSMNDFYGR DETSGKHRMF
str E24377A    LGELESASFV YTTPKKNLNA S---NYTGGL EQFANDLDTF ASSMNDFYGR DSEDGKHRMF
str H10407     LGELESASFV YTTPKKNLNA S---NYTGGL EQFANDLDTF ASSMNDFYGR DSEDGKHRMF
str E110019    LGELESDAFV YTTPKKNLNA S---NYTGGL EQFANDLDTF ASSMNDFYGR DSESGKHRMF
```

-continued

```
strain HS      LGELESASFV YTTPKKNLEA S---NYKGGL KQFAEDLDTF ASSMNDFYGR DGESGKHRMF
strain SECEC   LGELESASFV YTTPKKNLEA S---NYKGGL KQFAEDLDTF ASSMNDFYGR DGESGKHRMF
str IHE3034    LGELESASFV YTTPKKNLEA S---NFTGGV AEFAKDLDTF ASSMNDFYGR NDEDGKHRMF
strain F11     LGELESASFV YTTPKKNLNA S---NYTGGL DQFAKDLDTF ASSMNDFYGR NDEDGKHRMF
Consensus      LGELESDAFV YTTPKKNLNA SNYSNYTGGL EQFANDLDTF ASSMNDFYGR DSEDGKHRMF
               ########## ########## ########## ########## ########## ##########
               BBBBBBBBBB BBBBBBBBBB BBBBBBBBBB BBBBBBBBBB BBBBBBBBBB BBBBBBBBBB
               CCCCCCCCCC CCCCCCCCCC CCCCCCCCCC CCCCCCCCCC CCCCCCCCCC CCCCCCCCCC

|          |          |          |          |          |
strain 101-1   TYKNLTGHKH RFTNDVQISI GDAHSGYPVM NSSFSTNSTT LPTTPLNDWL IWHEVGHNAA
strain 536     TYKNLTGHKH RFTNDVQISI GDAHSGYPVM NSSFSTNSTT LPTTPLNDWL IWHEAGHNAA
strain 042     TYKNLTGHKH RFTNDVQISI GDAHSGYPVM NSSFSTNSTT LPTTPLNDWL IWHEVGHNAA
str E2348/69   TYKALTGHKH RFANDVQISI GDAHSGYPVM NSSFSTNSTT LPTTPLNDWL IWHEVGHNAA
strain 53638   TYKNLPGHKH RFTNDVQISI GDAHSGYPVM NSSFSPNSTT LPTTPLNDWL IWHEVGHNAA
strain W3110   TYKNLPGHKH RFTNDVQISI GDAHSGYPVM NSSFSPNSTT LPTTPLNDWL IWHEVGHNAA
strain B7A     TYKNLPGHKH RFANDVQISI GDAHSGYPVM NSSFSPNSTT LPTTPLNDWL IWHEVGHNAA
strain E22     TYKNLTGHKH RFANDVQISI GDAHSGYPVM NSSFSTNSTT LPTTPLNDWL IWHEVGHNAA
str E24377A    TYKNLPGHKH RFANDVQISI GDAHSGYPVM NSSFSPNSTT LPTTPLNDWL IWHEVGHNAA
str H10407     TYKNLPGHKH RFANDVQISI GDAHSGYPVM NSSFSPNSTT LPTTPLNDWL IWHEVGHNAA
str E110019    TYKNLTGHKH RFANDVQISI GDAHSGYPVM NSSFSPNSTT LPTTPLNDWL IWHEVGHNAA
strain HS      TYEALTGHKH RFTNDVQISI GDAHSGYPVM NSSFSPNSTT LPTTPLNDWL IWHEVGHNAA
strain SECEC   TYEALTGHKH RFTNDVQISI GDAHSGYPVM NSSFSPNSTT LPTTPLNDWL IWHEVGHNAA
str IHE3034    TYKNLTGHKH RFTNDVQISI GDAHSGYPVM NSSFSTNSTT LPTTPLNDWL IWHEVGHNAA
strain F11     TYKNLTGHKH RFTNDVQISI GDAHSGYPVM NSSFSTNSTT LPTTPLNDWL IWHEVGHNAA
Consensus      TYKNLTGHKH RFTNDVQISI GDAHSGYPVM NSSFSPNSTT LPTTPLNDWL IWHEVGHNAA
               ########## ########## ########## ########## ########## ##########
               BBBBBBBBBB BBBBBBBBBB BBBBBBBBBB BBBBBBBBBB BBBBBBBBBB BBBBBBBBBB
               CCCCCCCCCC CCCCCCCCCC CCCCCCCCCC CCCCCCCCCC CCCCCCCCCC CC

|          |          |          |          |          |
strain 101-1   ETPLTVPGAT EVANNVLALY MQDRYLGKMN RVADDITVAP EYLEESNGQA WARGGAGDRL
strain 536     ETPLTVPGAT EVANNVLALY MQDRYLGKMN RVADDITVAP EYLEESNNQA WARGGAGDRL
strain 042     ETPLTVPGAT EVANNVLALY MQDRYLGKMN RVADDITVAP EYLEESNNQA WARGGAGDRL
str E2348/69   ETPLNVPGAT EVANNVLALY MQDRYLGKMN RVADDITVAP EYLDESNGQA WARGGAGDRL
strain 53638   ETPLTVPGAT EVANNVLALY MQDRYLGKMN RVADDITVAP EYLEESNNQA WARGGAGDRL
strain W3110   ETPLTVPGAT EVANNVLALY MQDRYLGKMN RVADDITVAP EYLEESNNQA WARGGAGDRL
strain B7A     ETPLTVPGAT EVANNVLALY MQDRYLGKMN RVADDITVAP EYLEESNGQA WARGGAGDRL
strain E22     ETPLTVPGAT EVANNVLALY MQDRYLGKMN RVADDITVAP EYLEESNGQA WARGGAGDRL
str E24377A    ETPLTVPGAT EVANNVLALY MQDRYLGKMN RVADDITVAP EYLEESNGQA WARGGAGDRL
str H10407     ETPLTVPGAT EVANNVLALY MQDRYLGKMN RVADDITVAP EYLEESNGQA WARGGAGDRL
str E110019    ETPLTVPGAT EVANNVLALY MQDRYLGKMN RVADDITVAP EYLEESNGQA WARGGAGDRL
strain HS      ETPLTVPGAT EVANNVLALY MQDRYLGKMN RVADDITVAP EYLEESNGQA WARGGAGDRL
strain SECEC   ETPLTVPGAT EVANNVLALY MQDRYLGKMN RVADDITVAP EYLEESNGQA WARGGAGDRL
str IHE3034    ETPLNVPGAT EVANNVLALY MQDRYLGKMN RVADDITVAP EYLDESNGQA WARGGAGDRL
strain F11     ETPLNVPGAT EVANNVLALY MQDRYLGKMN RVADDITVAP EYLDESNGQA WARGGAGDRL
Consensus      ETPLTVPGAT EVANNVLALY MQDRYLGKMN RVADDITVAP EYLEESNGQA WARGGAGDRL
               ########## ########## ########## ########## ########## ##########
               BBBBBBBBBB BBBBBBBBBB BBBBBBBBBB BBBBBBBBBB BBBBBBBBBB BBBBBBBBBB

|          |          |          |          |          |
strain 101-1   LMYAQLKEWA EKNFDIKQWY PEGD-LPKFY SDREGMKGWN LFQLMHRKAR GDEVGKTKFG
strain 536     LMYAQLKEWA EKNFDITKWY PEGN-LPKFY SEREGMKGWN LFQLMHRKAR GDEVGKTKFG
strain 042     LMYAQLKEWA EKNFDIKKWY PDGTPLPEFY SEREGMKGWN LFQLMHRKAR GDEVSNDKFG
str E2348/69   LMYAQLKEWA EENFDIKQWY PDGE-LPKFY SDRKGMKGWN LFQLMHRKAR GDDVSNDKFG
strain 53638   LMYAQLKEWA EKNFDIKKWY PDGTPLPEFY SEREGMKGWN LFQLMHRKAR GDEVSNDKFG
strain W3110   LMYAQLKEWA EKNFDIKKWY PDGTPLPEFY SEREGMKGWN LFQLMHRKAR GDEVSNDKFG
strain B7A     LMYAQLKEWA EKNFDIKKWY PDGTPLPEFY SEREGMKGWN LFQLMHRKAR GDEVSNDKFG
strain E22     LMYAQLKEWA EKNFDIKKWY PEGE-LPKFF SDREGMKGWN LFQLMHRKAR GDDVGDKTFG
str E24377A    LMYAQLKEWA EKNFDIKKWY PDGTPLPEFY SEREGMKGWN LFQLMHRKAR GDEVSNDKFG
str H10407     LMYAQLKEWA EKNFDIKKWY PDGTPLPEFY SEREGMKGWN LFQLMHRKAR GDEVSNDKFG
str E110019    LMYAQLKEWA EKNFDIKKWY PEGE-LPKFF SDREGMKGWN LFQLMHRKAR GDDVGNKTFG
strain HS      LMYAQLKEWA EKNFDIKQWY PEGS-LPAFY SEREGMKGWN LFQLMHRKAR GDDVGNDKFG
strain SECEC   LMYAQLKEWA EKNFDIKQWY PEGS-LPAFY SEREGMKGWN LFQLMHRKAR GDDVGNDKFG
str IHE3034    LMYAQLKEWA EENFDIKQWY PDGE-LPKFY SDRKGMKGWN LFQLMHRKAR GDDVGNSTFG
strain F11     LMYAQLKEWA EKNFDITKWY PDGK-LPAFY SEREGMKGWN LFQLMHRKAR GDDVGNSTFG
Consensus      LMYAQLKEWA EKNFDIKKWY PDGTPLP2FY SEREGMKGWN LFQLMHRKAR GDEVGNDKFG
               ########## ########## ########## ########## ########## ##########
               BBBBBBBBBB BBBBBBBBBB BBBBBBBBBB BBBBBBBBBB BBBBBBBBBB BBBBBBBBBB

|          |          |          |          |          |
strain 101-1   ERNYCAESNG NAADKLMLCA SWVAQTDLSE FFKKWNPGAN AYQLPGASEM NFEGGVSQSA
strain 536     ERNYCAESNG NAADTLMLCA SWVAQTDLSA FFKKWNPGAN AYQLPGASEM NFEGGVSQSA
strain 042     GRNYCAESNG NTADTLMLCA SWVAQTDLSE FFKKWNPGAN AYQLPGATEM SFEGGVSQSA
str E2348/69   GRNYCAESNG NAADTLMLCA SWVAQADLSE FFKKWNPGAN AYQLPGASEM SFEGGVSQSA
strain 53638   GKNYCAESNG NAADTLMLCA SWVAQTDLSE FFKKWNPGAN AYQLPGASEM SFEGGVSQSA
strain W3110   GKNYCAESNG NAADTLMLCA SWVAQTDLSE FFKKWNPGAN AYQLPGASEM SFEGGVSQSA
strain B7A     GKNYCAESNG NAADTLMLCA SWVAQTDLSE FFKKWNPGAN AYQLPGASEM SFEGGVSQSA
strain E22     GKNYCAESNG NAADTLMLCA SWVAQTDLSA FFKKWNPGAN AYQLPGATEM SFEGGVSQSA
str E24377A    GKNYCAESNG NAADTLMLCA SWVAQTDLSE FFKKWNPGAN AYQLPGASEM SFEGGVSQSA
str H10407     GKNYCAESNG NAADTLMLCA SWVAQTDLSE FFKKWNPGAN AYQLPGASEM SFEGGVSQSA
```

```
                    -continued
str E110019    GKNYCAESNG NAADSLMLCA SWVAQTDLSA FFKKWNPGAN AYQLPGATEM SFEGGVSQSA
strain HS      NRNYCAESNG NAADTLMLCA SWVAQTDLSA FFKKWNPGAN AYQLPGATEM SFEGGVSQSA
strain SECEC   NRNYCAESNG NAADTLMLCA SWVAQTDLSA FFKKWNPGAN AYQLPGATEM SFEGGVSQSA
str IHE3034    GKNYCAESNG NAADTLMLCA SWVAQADLSE FFKKWNPGAS AYQLPGATEM SFQGGVSSSA
strain F11     GKNYCAESNG NAADTLMLCA SWVAQTDLSE FFKKWNPGAN AYQLPGAAEM SFEGGVSSSA
Consensus      GKNYCAESNG NAADTLMLCA SWVAQTDLSE FFKKWNPGAN AYQLPGASEM SFEGGVSQSA
               ########## ########## ########## ########## ########## ##########
               BBBBBBBBBB BBBBBBBBBB BBBBBBBBBB BBBBBBBBBB BBBBBBBBBB BBBBBBBBBB

|         |          |          |         |          |
strain 101-1   YETLAALNLP KPQQGPETIN QVTEHKMSAE
strain 536     YETLAALNLP KPQQGPETIN KVTEYSMPAE
strain 042     YNTLASLDLP KPKQGPETIN KVTEYSMPAE
str E2348/69   YNTLAAMHLS KPEKGPETIN KVTEYSMPAE
strain 53638   YNTLASLDLP KPEQGPETIN QVTEHKMSAE
strain W3110   YNTLASLDLP KPEQGPETIN QVTEHKMSAE
strain B7A     YNTLASLKLP KPEQGPETIN KVTEHKMSVE
strain E22     YSTLASLKLP KPEQGPETIN KVTEHKMSLE
str E24377A    YNTLASLKLP KPEQGPETIN KVTEHKMSVE
str H10407     YNTLASLDLP KPEQGPETIN QVTEHKMSAE
str E110019    YSTLASLKLP KPEQGPETIN KVTEHKMSLE
strain HS      YNTLASLDLP KPKQGPETIN KVTEYSMPAE
strain SECEC   YNTLASLDLP KPEQGPETIN QVTEHKMSAE
str IHE3034    YSTLASLKLP KPEKGPETIN KVTEHKMSAE
strain F11     YSTLASLNLP KPEKGPETIN KVTEHKMSAE
Consensus      YNTLASLDLP KPEQGPETIN KVTEHKMSAE
               ########## ########## ##########
               BBBBBBBBBB BBBBBBBBBB BBBBBBBBBB
```

In certain embodiments, the carrier polypeptide comprising an *E. coli* AcfD (orf3526) polypeptide will have a mutation relative to the *E. coli* AcfD (orf3526) protein which decreases the toxicity of the carrier polypeptide as compared to the *E. coli* AcfD (orf3526) protein.

Exemplary mutations that decrease the toxicity include a deletion of all or a portion of the zincin metalloprotease domain and a point mutation in zincin metalloprotease domain which reduces the protease activity. In certain cases, the point mutation is a mutation of a zinc binding residue or a mutation of a catalytic residue. A preferred point mutation is substitution of amino acid number 1305 based upon alignment with SEQ ID NO: 39.

Exemplary deletions such as for orf3526A include removal of at least the last 100 C-terminal amino acids of the *E. coli* AcfD (orf3526) protein, at least the last 200 C-terminal amino acids of the *E. coli* AcfD (orf3526) protein, at least the last 300 C-terminal amino acids of the *E. coli* AcfD (orf3526) protein, at least the last 400 C-terminal amino acids of the *E. coli* AcfD (orf3526) protein, at least the last 500 C-terminal amino acids of the *E. coli* AcfD (orf3526) protein, at least the last 600 C-terminal amino acids of the *E. coli* AcfD (orf3526) protein, at least the last 700 C-terminal amino acids of the *E. coli* AcfD (orf3526) protein, at least the last 750 C-terminal amino acids of the *E. coli* AcfD (orf3526) protein, or at least the last 758 C-terminal amino acids of the *E. coli* AcfD (orf3526) protein or such as for orf3526B does not comprise at least the first 100 N-terminal amino acids of the *E. coli* AcfD (orf3526) protein, at least the first 200 N-terminal amino acids of the *E. coli* AcfD (orf3526) protein, at least the first 300 N-terminal amino acids of the *E. coli* AcfD (orf3526) protein, at least the first 400 N-terminal amino acids of the *E. coli* AcfD (orf3526) protein, at least the first 500 N-terminal amino acids of the *E. coli* AcfD (orf3526) protein, at least the first 600 N-terminal amino acids of the *E. coli* AcfD (orf3526) protein, at least the first 700 N-terminal amino acids of the *E. coli* AcfD (orf3526) protein, at least the first 750 N-terminal amino acids of the *E. coli* AcfD (orf3526) protein, or at least the first 760 N-terminal amino acids of the *E. coli* AcfD (orf3526) protein.

Exemplary fragments such as orf3526C do not comprise at least the last 100 C-terminal amino acids of the *E. coli* AcfD (orf3526) protein, at least the last 125 C-terminal amino acids of the *E. coli* AcfD (orf3526) protein, at least the last 150 C-terminal amino acids of the *E. coli* AcfD (orf3526) protein, at least the last 175 C-terminal amino acids of the *E. coli* AcfD (orf3526) protein, at least the last 200 C-terminal amino acids of the *E. coli* AcfD (orf3526) protein, at least the last 210 C-terminal amino acids of the *E. coli* AcfD (orf3526) protein, or at least the last 217 C-terminal amino acids of the *E. coli* AcfD (orf3526) protein and optionally do not comprise at least the first 10 N-terminal amino acids of the *E. coli* AcfD (orf3526) protein, at least the first 20 N-terminal amino acids of the *E. coli* AcfD (orf3526) protein, at least the first 30 N-terminal amino acids of the *E. coli* AcfD (orf3526) protein, or at least the first 33 N-terminal amino acids of the *E. coli* AcfD (orf3526) protein.

The foregoing carrier polypeptides may further contain a deletion relative to the *E. coli* AcfD (orf3526) protein which increases solubility of the carrier polypeptide as compared to the full length *E. coli* AcfD (orf3526) protein while the carrier polypeptide still raises a substantially similar immune response to the conjugated polysaccharide in a subject as the full length *E. coli* AcfD (orf3526) protein.

Exemplary deletions that increase the solubility include removal of substantially all of the N-terminal amino acids up to the gly-ser region, removal of all or a part of the N-terminal proline-rich repeat, or both. Furthermore, the deletion may include the removal of at least the first 20 N-terminal amino acids as compared to the *E. coli* AcfD (orf3526) protein, at least the first 20 N-terminal amino acids as compared to the *E. coli* AcfD (orf3526) protein, at least the first 30 N-terminal amino acids as compared to the *E. coli* AcfD (orf3526) protein, at least the first 33 N-terminal amino acids as compared to the *E. coli* AcfD (orf3526) protein, at least the first 40 N-terminal amino acids as compared to the *E. coli* AcfD (orf3526) protein, at least the first 50 N-terminal amino acids as compared to the *E. coli* AcfD (orf3526) protein, at least the first 60 N-terminal amino acids as compared to the *E. coli* AcfD (orf3526) protein, at least the first 70 N-terminal amino acids as compared to the *E. coli* AcfD (orf3526) protein, at least the first 80 N-terminal amino acids as compared to the *E. coli* AcfD (orf3526) protein, at least the first 90 N-terminal amino acids as compared to the *E. coli* AcfD (orf3526) protein, or at least the first 94 N-terminal amino acids as compared to the *E. coli* AcfD (orf3526) protein.

In addition to improving the solubility and lowering the toxicity, the deletions are easier to purify after expression in commensal *E. coli* strains that have an endogenous AcfD (orf3526) protein.

Immunogenic Compositions and Medicaments

Polysaccharide conjugates of the invention are useful as active ingredients (immunogens) in immunogenic compositions, and such compositions may be useful as vaccines. Vaccines according to the invention may either be prophylactic (i.e. to prevent infection) or therapeutic (i.e. to treat infection), but will typically be prophylactic.

Immunogenic compositions will be pharmaceutically acceptable. They will usually include components in addition to the antigens e.g. they typically include one or more pharmaceutical carrier(s), excipient(s) and/or adjuvant(s). A thorough discussion of carriers and excipients is available in ref. 129. Thorough discussions of vaccine adjuvants are available in refs. 5 and 6.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilized during manufacture and are reconstituted into an aqueous form at the time of use. Thus a composition of the invention may be dried, such as a lyophilized formulation.

The composition may include preservatives such as thiomersal or 2-phenoxyethanol. It is preferred, however, that the vaccine should be substantially free from (i.e. less than 5 µg/ml) mercurial material e.g. thiomersal-free. Vaccines containing no mercury are more preferred. Preservative-free vaccines are particularly preferred.

To improve thermal stability, a composition may include a temperature protective agent.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunization, or may include material for multiple immunizations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention may also comprise one or more immunoregulatory agents. Preferably, one or more of the immunoregulatory agents include one or more adjuvants. The adjuvants may include a TH1 adjuvant and/or a TH2 adjuvant, further discussed below.

Adjuvants which may be used in compositions of the invention include, but are not limited to:

A. Mineral-Containing Compositions

Mineral containing compositions suitable for use as adjuvants in the invention include mineral salts, such as aluminum salts and calcium salts (or mixtures thereof). Calcium salts include calcium phosphate (e.g. the "CAP" particles disclosed in ref. 7). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt (8).

The adjuvants known as aluminum hydroxide and aluminum phosphate may be used. These names are conventional, but are used for convenience only, as neither is a precise description of the actual chemical compound which is present (e.g. see chapter 9 of reference 5). The invention can use any of the "hydroxide" or "phosphate" adjuvants that are in general use as adjuvants. The adjuvants known as "aluminum hydroxide" are typically aluminum oxyhydroxide salts, which are usually at least partially crystalline. The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminum hydroxide adjuvants. The pI of aluminum hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminum hydroxide adjuvants.

Aluminum phosphate adjuvants generally have a $PO_4$/Al molar ratio between 0.3 and 1.2, preferably between 0.8 and 1.2, and more preferably 0.95±0.1. The aluminum phosphate will generally be amorphous, particularly for hydroxyphosphate salts. A typical adjuvant is amorphous aluminum hydroxyphosphate with $PO_4$/Al molar ratio between 0.84 and 0.92, included at 0.6 mg $Al^{3+}$/ml. The aluminum phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg $Al^{+++}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5 e.g. about 5.7.

Suspensions of aluminum salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminum hydroxide and an aluminum phosphate. In this case there may be more aluminum phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

B. Oil Emulsions

Oil emulsion compositions suitable for use as adjuvants in the invention include squalene-water emulsions, such as MF59™ (Chapter 10 of ref. 5; see also ref. 9) (5% Squalene, 0.5% TWEEN 80™, and 0.5% SPAN 85™, formulated into submicron particles using a microfluidizer). Complete Freund's adjuvant (CFA) and incomplete Freund's adjuvant (IFA) may also be used.

Various oil-in-water emulsion adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (SPAN 85™) and sorbitan monolaurate. Non-ionic surfactants are preferred. Preferred surfactants for including in the emulsion are TWEEN 80™ (polyoxyethylene sorbitan monooleate), SPAN 85™ (sorbitan trioleate), lecithin and Triton X-100.

Mixtures of surfactants can be used e.g. TWEEN 80™/SPAN 85™ mixtures. A combination of a polyoxyethylene sorbitan ester such as polyoxyethylene sorbitan monooleate (TWEEN 80™) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as TWEEN 80™) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of ≤1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

A submicron emulsion of squalene, TWEEN 80™, and SPAN 85™. The composition of the emulsion by volume can be about 5% squalene, about 0.5% polysorbate 80 and about 0.5% SPAN 85™. In weight terms, these ratios become 4.3% squalene, 0.5% polysorbate 80 and 0.48% SPAN 85™. This adjuvant is known as 'MF59™' (10-12), as described in more detail in Chapter 10 of ref. 13 and chapter 12 of ref. 14. The MF59™ emulsion advantageously includes citrate ions e.g. 10 mM sodium citrate buffer.

An emulsion of squalene, a tocopherol, and TWEEN 80™. The emulsion may include phosphate buffered saline. It may also include SPAN 85™ (e.g. at 1%) and/or lecithin. These emulsions may have from 2 to 10% squalene, from 2 to 10% tocopherol and from 0.3 to 3% TWEEN 80™, and the weight ratio of squalene:tocopherol is preferably <1 as this provides a more stable emulsion. Squalene and TWEEN 80™ may be present volume ratio of about 5:2. One such emulsion can be made by dissolving TWEEN 80™ in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("PLURONIC™ L$^{121}$"). The emulsion can be formulated in phosphate buffered saline, pH 7.4. This emulsion is a useful delivery vehicle for muramyl dipeptides, and has been used with threonyl-MDP in the "SAF-1" adjuvant (15) (0.05-1% Thr-MDP, 5% squalane, 2.5% PLURONIC™ L121 and 0.2% polysorbate 80). It can also be used without the Thr-MDP, as in the "AF" adjuvant (16) (5% squalane, 1.25% PLURONIC™ L$^{121}$ and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'SPAN 80™'). The emulsion is preferably thermoreversible and/or has at least 90% of the oil droplets (by volume) with a size less than 200 nm (17). The emulsion may also include one or more of: alditol; a cryoprotective agent (e.g. a sugar, such as dodecylmaltoside and/or sucrose); and/or an alkylpolyglycoside. Such emulsions may be lyophilized.

An emulsion of squalene, poloxamer 105 and Abil-Care (18). The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 19, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, TWEEN 80™ or SPAN 80™). Additives may be included, such as QuilA saponin, cholesterol, a saponin-lipophile conjugate (such as GPI-0100, described in reference 20, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles (21).

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) (22).

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) (22).

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Where a composition includes a tocopherol, any of the α, β, γ, ε, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group (23). They also have antioxidant properties that may help to stabilize the emulsions (24). A preferred α-tocopherol is DL-α-tocopherol, and the preferred salt of this tocopherol is the succinate. The succinate salt has been found to cooperate with TNF-related ligands in vivo.

C. Saponin Formulations (Chapter 22 of Ref. 5)

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaparilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 25. Saponin formulations may also comprise a sterol, such as cholesterol (26).

Combinations of saponins and cholesterols can be used to form unique particles called immunostimulating complexs (ISCOMs) (chapter 23 of ref. 5). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 26-28. Optionally, the ISCOMS may be devoid of additional detergent (29).

A review of the development of saponin based adjuvants can be found in refs. 30 & 31.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 32-37. Virosomes are discussed further in, for example, ref. 38

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 39. Such "small particles" of 3dMPL are small enough to be sterile filtered through a 0.22 μm membrane (39). Other non-toxic LPS derivatives include monophosphoryl lipid A mimics, such as aminoalkyl glucosaminide phosphate derivatives e.g. RC-529 (40,41).

Lipid A derivatives include derivatives of lipid A from *Escherichia coli* such as OM-174. OM-174 is described for example in refs. 42 & 43.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 44, 45 and 46 disclose possible analog substitutions e.g. replacement of guanosine with 2'-deoxy-7-deazaguanosine. The adjuvant effect of CpG oligonucleotides is further discussed in refs. 47-52.

The CpG sequence may be directed to TLR9, such as the motif GTCGTT or TTCGTT (53). The CpG sequence may be specific for inducing a Th1 immune response, such as a CpG-A ODN, or it may be more specific for inducing a B cell response, such a CpG-B ODN. CpG-A and CpG-B ODNs are discussed in refs. 54-56. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 53 & 57-59.

A useful CpG adjuvant is CpG7909, also known as ProMune™ (Coley Pharmaceutical Group, Inc.). Another is CpG1826. As an alternative, or in addition, to using CpG sequences, TpG sequences can be used (60), and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref. 60), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 60), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC-31™ (61). Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 51). The polycationic polymer may be a peptide comprising 11-mer amino acid sequence KLKLLLLLKLK (SEQ ID NO: 52).

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 62 and as parenteral adjuvants in ref. 63. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 64-71. A useful CT mutant is or CT-E29H (72). Numerical reference for amino acid substitutions is preferably based on the alignments of the A and B subunits of ADP-ribosylating toxins set forth in ref. 73, specifically incorporated herein by reference in its entirety solely for the purpose of the alignment and amino acid numbering therein.

F. Human Immunomodulators

Human immunomodulators suitable for use as adjuvants in the invention include cytokines, such as interleukins (e.g. IL-1, IL-2, IL-4, IL-5, IL-6, IL-7, IL-12 (74), etc.) (75), interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres (76) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (77).

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 5)

Examples of liposome formulations suitable for use as adjuvants are described in refs. 78-80.

J. Polyoxyethylene Ether and Polyoxyethylene Ester Formulations

Adjuvants suitable for use in the invention include polyoxyethylene ethers and polyoxyethylene esters (81). Such formulations further include polyoxyethylene sorbitan ester surfactants in combination with an octoxynol (82) as well as polyoxyethylene alkyl ethers or ester surfactants in combination with at least one additional non-ionic surfactant such as an octoxynol (83). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Phosphazenes

A phosphazene, such as poly(di(carboxylatophenoxy) phosphazene) ("PCPP") as described, for example, in references 84 and 85, may be used.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquimod ("R-837") (86,87), Resiquimod ("R-848") (88), and their analogs; and salts thereof (e.g. the hydrochloride salts). Further details about immunostimulatory imidazoquinolines can be found in references 89 to 93.

N. Substituted Ureas

Substituted ureas useful as adjuvants include compounds of formula I, II or III, or salts thereof:

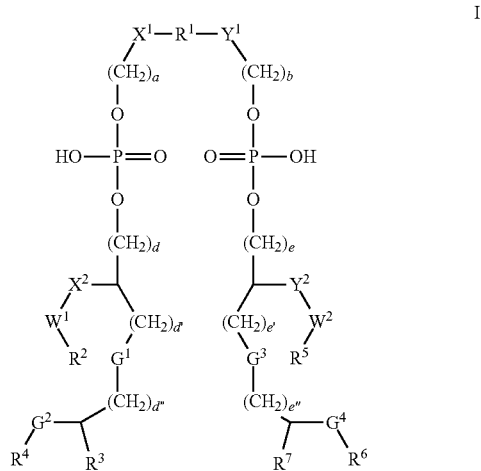

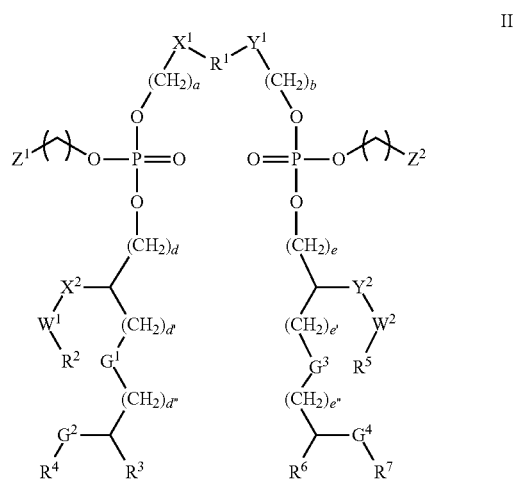

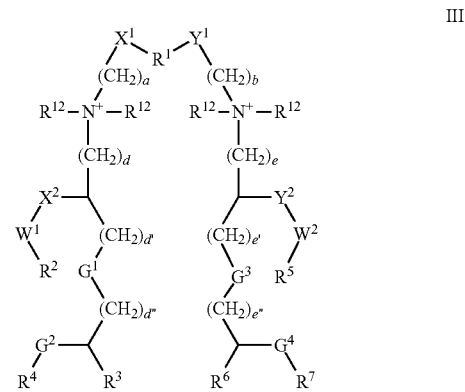

as defined in reference 94, such as 'ER 803058', 'ER 803732', 'ER 804053', ER 804058', 'ER 804059', 'ER 804442', 'ER 804680', 'ER 804764', ER 803022 or 'ER 804057' e.g.:

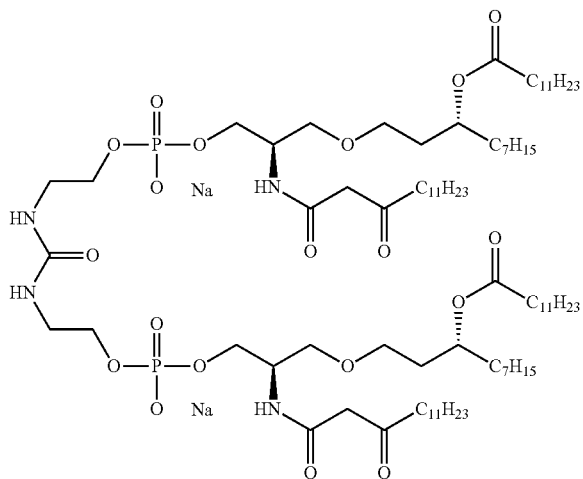

ER804057

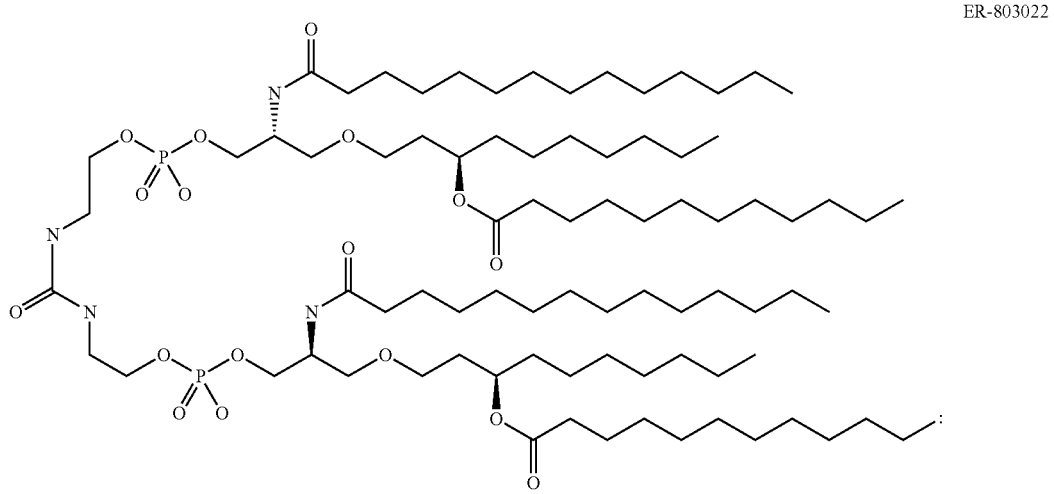

ER-803022

O. Further Adjuvants

Further adjuvants that may be used with the invention include:

An aminoalkyl glucosaminide phosphate derivative, such as RC-529 (95,96).

A thiosemicarbazone compound, such as those disclosed in reference 97. Methods of formulating, manufacturing, and screening for active compounds are also described in reference 97. The thiosemicarbazones are particularly effective in the stimulation of human peripheral blood mononuclear cells for the production of cytokines, such as TNF-α.

A tryptanthrin compound, such as those disclosed in reference 98. Methods of formulating, manufacturing, and screening for active compounds are also described in reference 98. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

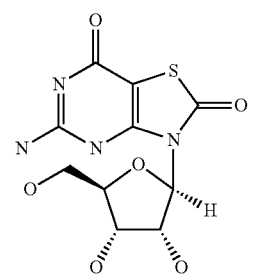 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 99 to 101Loxoribine (7-allyl-8-oxoguanosine) (102).

Compounds disclosed in reference 103, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (104,105), Hydrapthalamide compounds, Benzophenone compounds, Isoxazole compounds, Sterol compounds, Quinazilinone compounds, Pyrrole compounds (106), Anthraquinone compounds, Quinoxaline compounds, Triazine compounds, Pyrazalopyrimidine compounds, and Benzazole compounds (107).

Compounds containing lipids linked to a phosphate-containing acyclic backbone, such as the TLR4 antagonist E5564 (108,109):

A polyoxidonium polymer (110,111) or other N-oxidized polyethylene-piperazine derivative.

Methyl inosine 5'-monophosphate ("MIMP") (112).

A polyhydroxlated pyrrolizidine compound (113), such as one having formula:

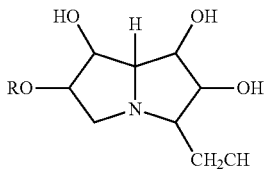

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide (114-121) (e.g. α-galactosylceramide), phytosphingosine-containing α-glycosylceramides, OCH, KRN7000 ((2S,3S,4R)-1-O-(α-D-galactopyranosyl)-2-(N-hexacosanoylamino)-1,3,4-octadecanetriol), CRONY-101, 3"-O-sulfo-galactosylceramide, etc.

A gamma inulin (122) or derivative thereof, such as algammulin.

derivative (e.g. 3dMPL)+a cholesterol; (4) a saponin (e.g. QS21)+3dMPL+IL-12 (optionally +a sterol) (125); (5) combinations of 3dMPL with, for example, QS21 and/or oil-in-water emulsions (126); (6) SAF, containing 10% squalane, 0.4% TWEEN 80™, 5% PLURONIC™-block polymer L121, and thr-MDP, either microfluidized into a submicron emulsion or vortexed to generate a larger particle size emulsion. (7) Ribi adjuvant system (RAS), (Ribi Immunochem) containing 2% squalene, 0.2% TWEEN 80™, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 5.

The use of an aluminum hydroxide and/or aluminum phosphate adjuvant is particularly preferred, and antigens are generally adsorbed to these salts. Calcium phosphate is another preferred adjuvant. Other preferred adjuvant combinations include combinations of Th1 and Th2 adjuvants such as CpG & alum or resiquimod & alum. A combination of aluminum phosphate and 3dMPL may be used.

The compositions of the invention may elicit both a cell mediated immune response as well as a humoral immune response. This immune response will preferably induce long lasting (e.g. neutralizing) antibodies and a cell mediated immunity that can quickly respond upon exposure to the pathogen immunized against.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognize or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells,

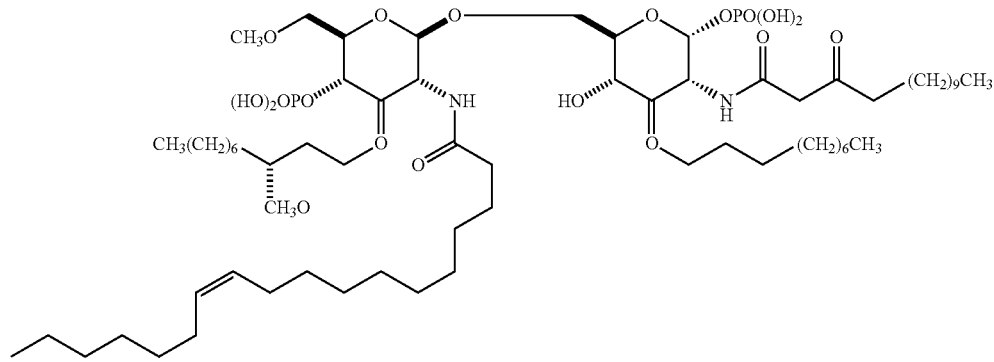

Adjuvant Combinations

The invention may also comprise combinations of aspects of one or more of the adjuvants identified above. For example, the following adjuvant compositions may be used in the invention: (1) a saponin and an oil-in-water emulsion (123); (2) a saponin (e.g. QS21)+a non-toxic LPS derivative (e.g. 3dMPL) (124); (3) a saponin (e.g. QS21)+a non-toxic LPS macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-13. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of: an increase in one or more of the cytokines associated with a TH2 immune response (such as IL-4, IL-5, IL-6 and IL-10), an increase in the production of IgG1, an increase in the production of IgE, an increase in the production of IgA and an increase in the production of memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminum salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Pharmaceutical Compositions

One aspect of the invention includes pharmaceutical compositions comprising (a) a polysaccharide conjugate as disclosed herein, (b) a pharmaceutically acceptable carrier, and optionally (c) an adjuvant as described in the preceding section.

The compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilized composition or a spray-freeze dried composition). The composition may be prepared for topical administration e.g. as an ointment, cream or powder. The composition may be prepared for oral administration e.g. as a tablet or capsule, as a spray, or as a syrup (optionally flavored). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilized antigens.

Where a composition is to be prepared extemporaneously prior to use (e.g. where a component is presented in lyophilized form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s) (e.g., the polysaccharide and/or the carrier protein), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

Methods of Treatment, and Administration of the Vaccine

The invention also provides a method for raising an immune response in a mammal comprising the step of administering an effective amount of a composition of the invention. The immune response is preferably protective and preferably involves antibodies and/or cell-mediated immunity. The method may raise a booster response.

The invention also provides a polypeptide of the invention for use as a medicament e.g. for use in raising an immune response in a mammal.

The invention also provides the use of a polypeptide of the invention in the manufacture of a medicament for raising an immune response in a mammal.

The invention also provides a delivery device pre-filled with an immunogenic composition of the invention.

Because glucans (and β-glucans in particular) are an essential and principal polysaccharide constituent of almost all pathogenic fungi, particularly those involved in infections in immunocompromised subjects, and also in bacterial pathogens and protozoa, anti-glucan immunity may have efficacy against a broad range of pathogens and diseases. For example, anti-glucan serum raised after immunization with *S. cerevisiae* is cross-reactive with *C. albicans*. Broad spectrum immunity is particularly useful because, for these human infectious fungal agents, chemotherapy is scanty, antifungal drug resistance is emerging and the need for preventative and therapeutic vaccines is increasingly recognized.

Therefore, where the polysaccharide immunogen of the polysaccharide conjugates disclosed herein are glucans, the uses and methods of the glucan polysaccharide conjugates disclosed herein are particularly useful for treating/protecting against infections of: *Candida* species, such as *C. albicans; Cryptococcus* species, such as *C. neoformans; Enterococcus* species, such as *E. faecalis; Streptococcus* species, such as *S. pneumoniae, S. mutans, S. agalactiae* and *S. pyogenes; Leishmania* species, such as *L. major; Acanthamoeba* species, such as *A. castellani; Aspergillus* species, such as *A. fumigatus* and *A. flavus; Pneumocystis* species, such as *P. carinii; Mycobacterium* species, such as *M. tuberculosis; Pseudomonas* species, such as *P. aeruginosa; Staphylococcus* species, such as *S. aureus; Salmonella* species, such as *S. typhimurium; Coccidioides* species such as *C. immitis; Trichophyton* species such as *T. verrucosum; Blastomyces* species such as *B. dermatidis; Histoplasma* species such as *H. capsulatum; Paracoccidioides* species such as *P. brasiliensis; Pythium* species such as *P. insidiosum*; and *Escherichia* species, such as *E. coli*.

The uses and methods are particularly useful for preventing/treating diseases including, but not limited to: candidiasis (including hepatosplenic candidiasis, invasive candidiasis, chronic mucocutaneous candidiasis and disseminated candidiasis); candidemia; aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, cystic fibrosis, typhoid fever, gastroenteritis and hemolytic-uremic syndrome. Anti-*C. albicans* activity is particularly useful for treating infections in AIDS patients.

Efficacy of immunization can be tested by monitoring immune responses against β-glucan (e.g., anti-β-glucan antibodies) after administration of the composition. Efficacy of therapeutic treatment can be tested by monitoring microbial infection after administration of the composition of the invention.

By raising an immune response in the mammal by these uses and methods, the mammal can be protected against infection by the pathogen from which the polysaccharide immunogen is derived (or mimics) as well as from *E. coli* infection owing to the *E. coli* carrier protein, including ExPEC and non-ExPEC strains. The invention is particularly useful for providing broad protection against pathogenic *E. coli*, including intestinal pathotypes such as EPEC, EAEC, EIEC, ETEC and DAEC pathotypes. Thus the mammal may be protected against diseases including, but not limited to peritonitis, pyelonephritis, cystitis, endocarditis, prostatitis, urinary tract infections (UTIs), meningitis (particularly neonatal meningitis), sepsis (or SIRS), dehydration, pneumonia, diarrhea (infantile, travellers', acute, persistent, etc.), bacillary dysentery, hemolytic uremic syndrome (HUS), pericarditis, bacteriuria, etc.

The mammal is preferably a human, but may be, e.g., a cow, a pig, a cat or a dog, as *E. coli* disease is also problematic in these species. While the specification refers to mammals and mammalian subjects, the polysaccharide conjugates disclosed herein are also useful for avian species such as chicken and duck and therefore wherever mammal or mammalian is recited herein, avian can also be included. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

One way of checking efficacy of therapeutic treatment involves monitoring *E. coli* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Typically, antigen-specific serum antibody responses are determined post-immunization but pre-challenge whereas antigen-specific mucosal antibody responses are determined post-immunization and post-challenge.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of vaccine compositions can also be determined in vivo by challenging animal models of *E. coli* infection, e.g., guinea pigs or mice, with the vaccine compositions. A murine model of ExPEC and lethal sepsis is described in reference 127. A cotton rat model is disclosed in ref. 128.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal or transcutaneous, intranasal, ocular, aural, pulmonary or other mucosal administration. Novel direct delivery forms can also include transgenic expression of the polypeptides disclosed herein in foods, e.g., transgenic expression in a potato.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunization schedule and/or in a booster immunization schedule. In a multiple dose schedule the various doses may be given by the same or different routes e.g. a parenteral prime and mucosal boost, a mucosal prime and parenteral boost, etc.

Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines of the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalized patients, healthcare workers, armed service and military personnel, pregnant women, the chronically ill, or immunodeficient patients. The vaccines are not suitable solely for these groups, however, and may be used more generally in a population.

Vaccines of the invention are particularly useful for patients who are expecting a surgical operation, or other hospital in-patients. They are also useful in patients who will be catheterized. They are also useful in adolescent females (e.g. aged 11-18) and in patients with chronic urinary tract infections.

Vaccines of the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C—W135-Y vaccine), a respiratory syncytial virus vaccine, etc.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 129-136, etc.

The term "comprising" encompasses "including" as well as "consisting" e.g. a composition "comprising" X may consist exclusively of X or may include something additional e.g. X+Y.

The term "about" in relation to a numerical value x means, for example, x±10%.

"GI" numbering is used herein. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 137. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 138.

One of skill in the art would understand that "isolated" means altered "by the hand of man" from its natural state, i.e., if it occurs in nature, it has been changed or removed from its original environment, or both. For example, a polynucleotide or a polypeptide naturally present in a living organism is not "isolated" when in such living organism, but the same polynucleotide or polypeptide separated from the coexisting materials of its natural state is "isolated," as the term is used in this disclosure. Further, a polynucleotide or polypeptide that is introduced into an organism by transformation, genetic manipulation or by any other recombinant method would be understood to be "isolated" even if it is still present in said organism, which organism may be living or non-living, except where such transformation, genetic manipulation or other recombinant method produces an organism that is otherwise indistinguishable from the naturally occurring organism.

BRIEF DESCRIPTION OF SEQUENCE LISTING

Figure 1:
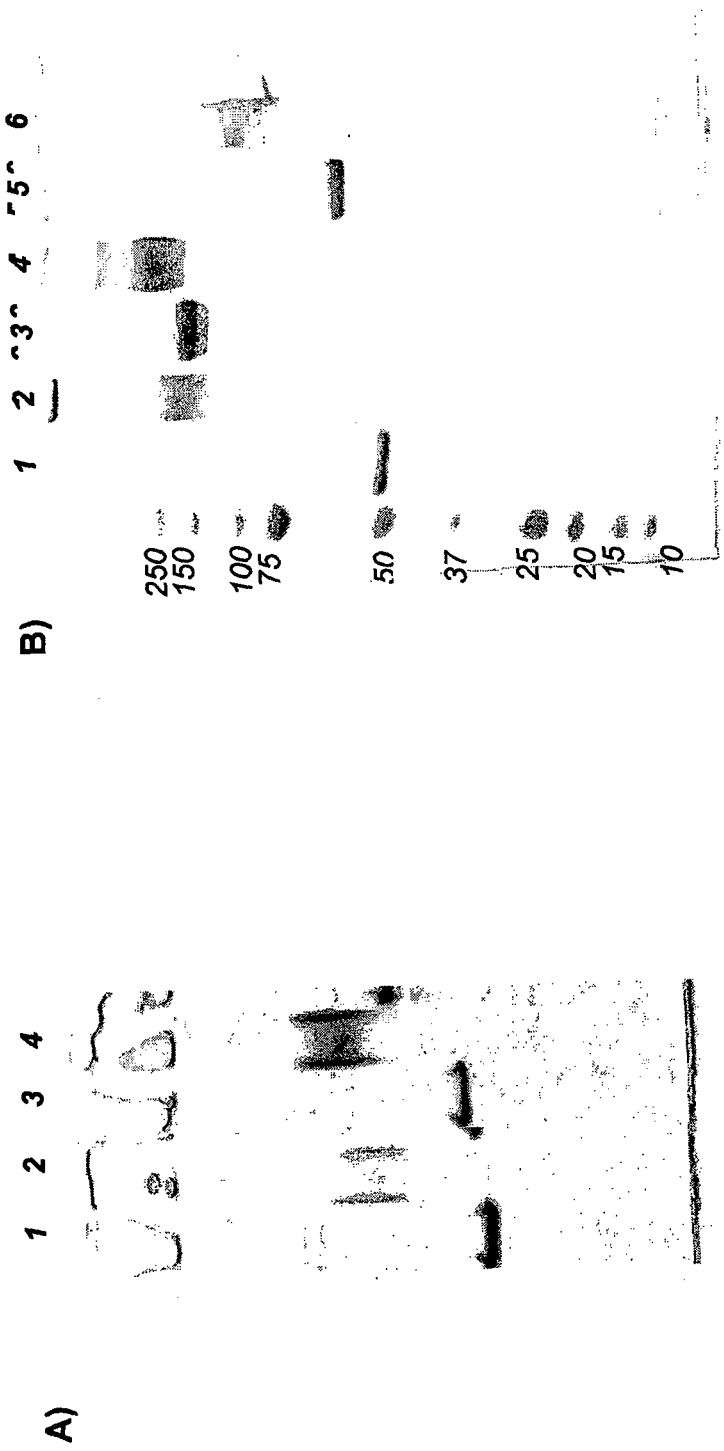
FIG. 1 (A) shows an SDS-Page (4-12% gradient) with the following (from left to right): (1) orf405B before conjugation, (2) orf405B after conjugation, (3) upec-5211 before conjugation, and (4) upec-5211 after conjugation; and (B) shows an SDS-Page (4-12% gradient) with the following (from left to right): molecular weight markers, (1) upec-5211 before conjugation, (2) upec-5211 after conjugation, (3) orf3526 before conjugation, (4) orf3526 after conjugation, (5) orf1364 before conjugation, and (6) orf1364 after conjugation.

| SEQ ID | Description |
|---|---|
| SEQ ID NOs: 1-22 = orf1364 amino acid sequences | |
| 1 | Orf1364 sequence from EPEC strain E110019 |
| 2 | Orf1364 sequence from EHEC strains Sakai, EDL933, EC508, EC869, EC4024, EC4042, EC4045, EC4076, EC4113, EC4115, EC4196, EC4206, EC4401, EC4486, EC4501 and TW14588 |
| 3 | Orf1364 sequence from EPEC strain B171 |
| 4 | Orf1364 sequence from EPEC strain E22 |
| 5 | Orf1364 sequence from EPEC strain B171 |
| 6 | Orf1364 sequence from EPEC strain B171 |
| 7 | Orf1364 sequence from ETEC strain E24377A and EAEC strain O42 |
| 8 | Orf1364 sequence from ETEC strain E24377A |
| 9 | Orf1364 sequence from UPEC strainUTI89 and NMEC strains RS218 and IHE3034 |
| 10 | Orf1364 sequence from EPEC strain E110019 |
| 11 | Orf1364 sequence from EPEC strain E22 |
| 12 | Orf1364 sequence from ETEC strain H10407 |
| 13 | Orf1364 sequence from UPEC strains F11 and 536 |
| 14 | Orf1364 sequence from antibiotic resistant strain SECEC |
| 15 | Orf1364 sequence from ETEC strain H10407 |
| 16 | Orf1364 sequence from commensal strains W3110 and DH10B |
| 17 | Orf1364 sequence from commensal strain MG1655 |

-continued

| SEQ ID | Description |
|---|---|
| 18 | Orf1364 sequence from EAEC strain O42 |
| 19 | Orf1364 sequence from ETEC strain B7A |
| 20 | Orf1364 sequence from UPEC strain CFT073 |
| 21 | Orf1364 sequence from EAEC strain O42 |
| 22 | Orf1364 sequence from UPEC strain CFT073 |
| | SEQ ID NOs: 23-25 = upec-5211 amino acid sequences |
| 23 | Upec-5211 sequence from UPEC strain CFT073 and from asymptomatic bacteriuria (ABU) strain 83972 |
| 24 | Upec-5211 sequence from commensal strain ED1a |
| 25 | Upec-5211 sequence from E. fergusonii ATCC 35469 |
| | SEQ ID NOs: 26-40 = orf3526 amino acid sequences |
| 26 | Orf3526 sequence from EAEC strain 101-1 (GI: 83587587) |
| 27 | Orf3526 sequence from UPEC strain 536 (GI: 110643204 - ECP_3050) |
| 28 | Orf3526 sequence from EAEC strain O42 |
| 29 | Orf3526 sequence from EPEC strain E2348/69 |
| 30 | Orf3526 sequence from EIEC strain 53638 (GI: 75515237) |
| 31 | Orf3526 sequence from commensal strain W3110 (GI: 89109748 - yghJ) |
| 32 | Orf3526 sequence from ETEC strain B7A (GI: 75227618) |
| 33 | Orf3526 sequence from EPEC strain E22 (GI: 75259912) |
| 34 | Orf3526 sequence from ETEC strain E24377A (GI: 157156747 - EcE24377A_3432) |
| 35 | Orf3526 sequence from ETEC strain H10407 |
| 36 | Orf3526 sequence from EPEC strain E110019 (GI: 75239450) |
| 37 | Orf3526 sequence from commensal strain HS (GI: 157162442 - EcHS_A3142) |
| 38 | Orf3526 sequence from antibiotic-resistant strain SECEC |
| 39 | Orf3526 sequence from NMEC strain IHE3034 |
| 40 | Orf3526 sequence from UPEC strain F11 (GI: 75241179) |
| 41 | pK1-0405B - Coding sequence for orf405B used in the Examples |
| 42 | pK1-0405B - Amino acid sequence of orf405B used in the Examples |
| 43 | pK1-1364 - Coding sequence for orf1364 used in the Examples |
| 44 | pK1-1364 - Amino acid sequence of orf1364 used in the Examples |
| 45 | Coding sequence for orf3613 used in the Examples |
| 46 | Amino acid sequence of orf3613 used in the Examples |
| 47 | Coding sequence for upec-5211 used in the Examples |
| 48 | Amino acid sequence of upec-5211 used in the Examples |
| 49 | Coding sequence for orf3526 used in the Examples |
| 50 | Amino acid sequence of orf3526 used in the Examples |
| 51 | dIdC polyoligonucleotide |
| 50 | Polycationic polymer peptide |

EXAMPLES

Conjugation Process

Five different recombinant proteins from different strains of Extraintestinal Pathogenic *E. coli* were compared for their ability to act as carrier proteins for polysaccharide immunogen (using laminarin as an exemplary polysaccharide immunogen): orf3613 (SEQ ID NO: 46), upec-5211 (SEQ ID NO: 48), orf3526 (SEQ ID NO: 50), orf1364 (SEQ ID NO: 44) and orf405B (SEQ ID NO: 42). The conjugate of orf3613 proved to be insoluble, so it was not tested further. After conjugation with laminarin, each of the four remaining conjugates were compared with a laminarin-CRM$_{197}$ conjugate given that CRM$_{197}$ is well characterized in its use as a carrier protein for polysaccharide immunogens.

These conjugates were prepared starting from a suitable solution of each protein and activated laminarin, prepared by the method disclosed in Torosantucci et al. (2005) *J. Exp. Med.* 202(5):597-606. Briefly, prior to conjugation, the saccharide was activated with an N-hydroxysuccinimide diester of adipic acid. Then the conjugation reaction for upec-5211 and orf405B was carried out in 50 mM NaH2PO4, 150 mM NaCl, 6 M guanidine HCl at pH 7.6 using a molar ratio of polysaccharide ester groups to protein of 30 and a protein concentration of 1.2-1.4 mg/ml. The results of these conjugation reactions were run on a gradient SDS-Page (4-12%) as shown in FIG. 1(A).

In a separate set of conjugation reactions, the conjugation reaction for upec-5211 (again), orf3526 and orf1364 was carried out in PBS using a molar ratio of polysaccharide ester groups to protein of 30 and a protein concentration of 5 mg/ml.

The reaction mixtures in each of the five reactions were mixed at room temperature and left overnight.

The resultant conjugates were purified by immobilized metal ion affinity chromatography (IMAC), a well known separation method for protein purification (see, for example, refs. 1 and 2). The purification was performed with HIS MULTITRAP HP™ plates (GE Healthcare), prepacked 96-well filter plates for small-scale purification of histidine-tagged proteins, with the use of a vacuum source.

The plates were pre-packed with IMAC matrix NI SEPHAROSE HIGH PERFORMANCE™ (GE Healthcare), which consists of 34-µm beads of highly cross-linked agarose to which iminodiacetic acid groups are covalently conjugated. The iminodiacetic acid groups were loaded with Ni$^{2+}$ in order to provide a group with affinity for the carrier protein with exposed histidine groups in the conjugate. The conjugates, prepared in solution as described above, were bound to the IMAC matrix. The IMAC matrix was then washed to remove the free saccharide. After washing, the purified conjugates were finally eluted.

Purification:
1. The matrix of the HIS MULTITRAP HP™ plate was washed with 0.5 ml of distilled water, and then equilibrated two times with 0.5 ml binding buffer, consisting of 6M Guanidine HCl, 20 mM NaPO$_4$, pH 7.6).
2. The conjugates (about 200 µl/well for 250 µg/well of protein) were loaded onto the plate and the plate was left on rocking platform for 1 hour at room temperature to allow the his-tagged protein to bind to the IMAC matrix. The plate was then washed two times with 0.5 ml binding buffer to remove free saccharide from the bound conjugates.
3. The conjugates were recovered by the addition to the matrix of with 0.2 ml elution buffer 6M Guanidine-HCl, 20 mM NaPO$_4$, 500 mM NaCl, 500 mM imidazole, pH 7.6. The plate was incubated for 10 minutes and the eluate containing the conjugates was collected. This elution procedure was repeated once. The two elution fractions were combined and dialyzed against 10 mM NaPO$_4$ pH 7.2 or 10 mM NaPO$_4$, 100 mM NaCl pH 7.2 or PBS with spectra Por membrane, 6-8 lcDa cut-off.

The purified conjugates of the invention were characterized by SDS-Page 4-12% (See FIGS. 1(A) and 1(B)), by MicroBCA to quantify the protein amount, and by HPAEC-PAD to quantify the saccharide amount. Table 1 summarizes the conjugation efficiencies as determined by MicroBCA and HPAEC-PAD.

TABLE 1

| Protein | CHO, mg/ml (HPAEC-PAD) | Protein, mg/ml (MicroBCA) | Sacch./Prot. w/w % | CHO mol/ Protein mol |
|---|---|---|---|---|
| orf405B | 0.04223 | 0.139 | 30.38 | 2.3 |
| upec-5211 | 0.04844 | 0.119 | 40.71 | 3.7 |
| upec-5211 (second preparation with PBS) | 0.2258 | 0.285 | 79.30 | 5.9 |
| orf3526 | 0.09179 | 0.471 | 19.53 | 4.9 |
| orf1364 | 0.162 | 0.458 | 35.37 | 2.9 |

Carrier Protein Immunization Study—*E. coli* Protein Tested as Carrier in Laminarin Conjugates Balb/c mice at 4-6 weeks old were immunized at days 0, 14 and 28 by subcutaneous injection with a 5 µg dose of polysaccharide immunogen in an injection volume of 150 µl. The mice were bled on days 0, 27 and 42.

Immunizations were carried out in groups of six mice for the first immunization study and eight mice for the second immunization study.

In the first immunization study, the mice were injected with laminarin conjugated to: upec-5211 (prepared via the first protocol above), orf405B, and (as a strong positive control) $CRM_{197}$.

Figure 2:
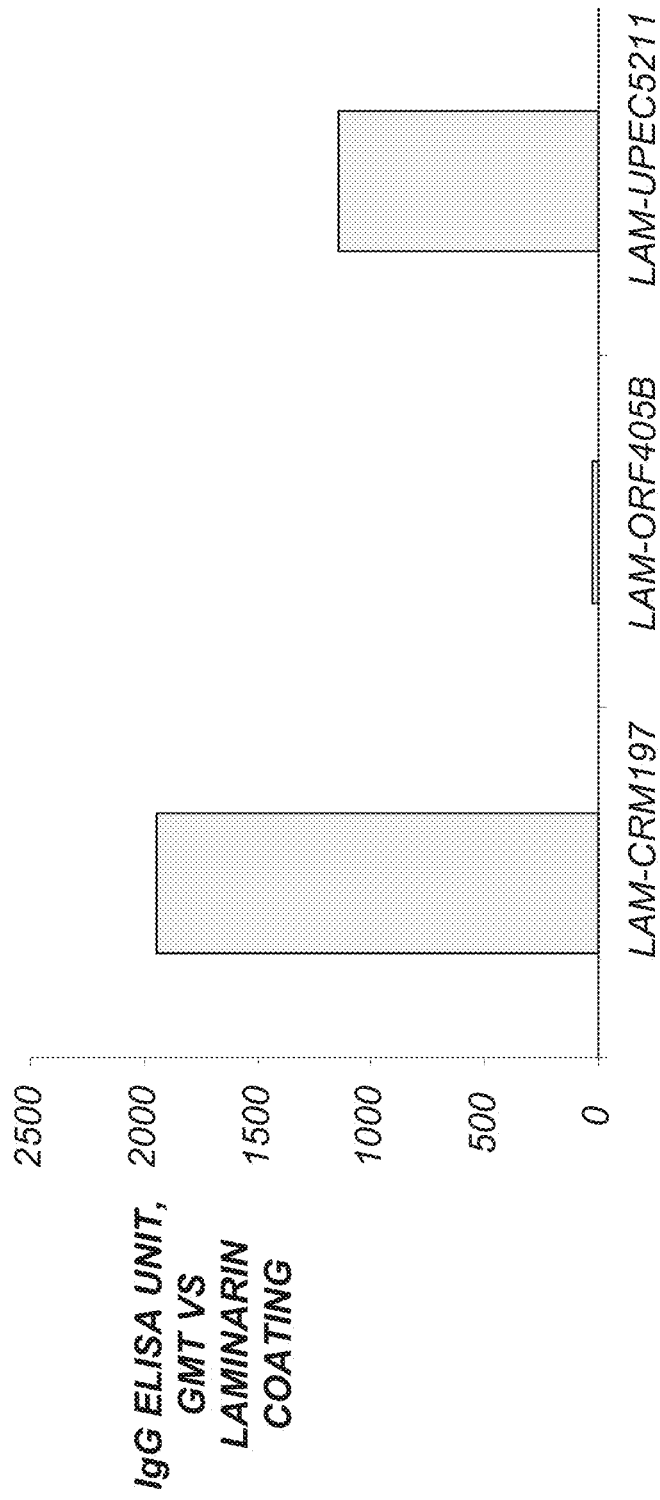
FIG. 2 shows the results of the first carrier protein immunization study. The y-axis shows the anti-laminarin IgG induction after immunization as measured by ELSA. The x-axis shows the ELISA results for the following conjugates (from left to right): laminarin conjugated to $CRM_{197}$, laminarin conjugated to orf405B, and laminarin conjugated to upec-5211.

The results show that upec-5211 as a carrier protein induced a decent antibody response against the polysaccharide portion (approximately two-thirds of the response induced by $CRM_{197}$), while orf405B as a carrier protein induced no antibody response to the polysaccharide portion (See FIG. 2).

In the second immunization study, the mice were injected with laminarin conjugated to: orf3526, orf1364, and (as a strong positive control) $CRM_{197}$.

Figure 3:
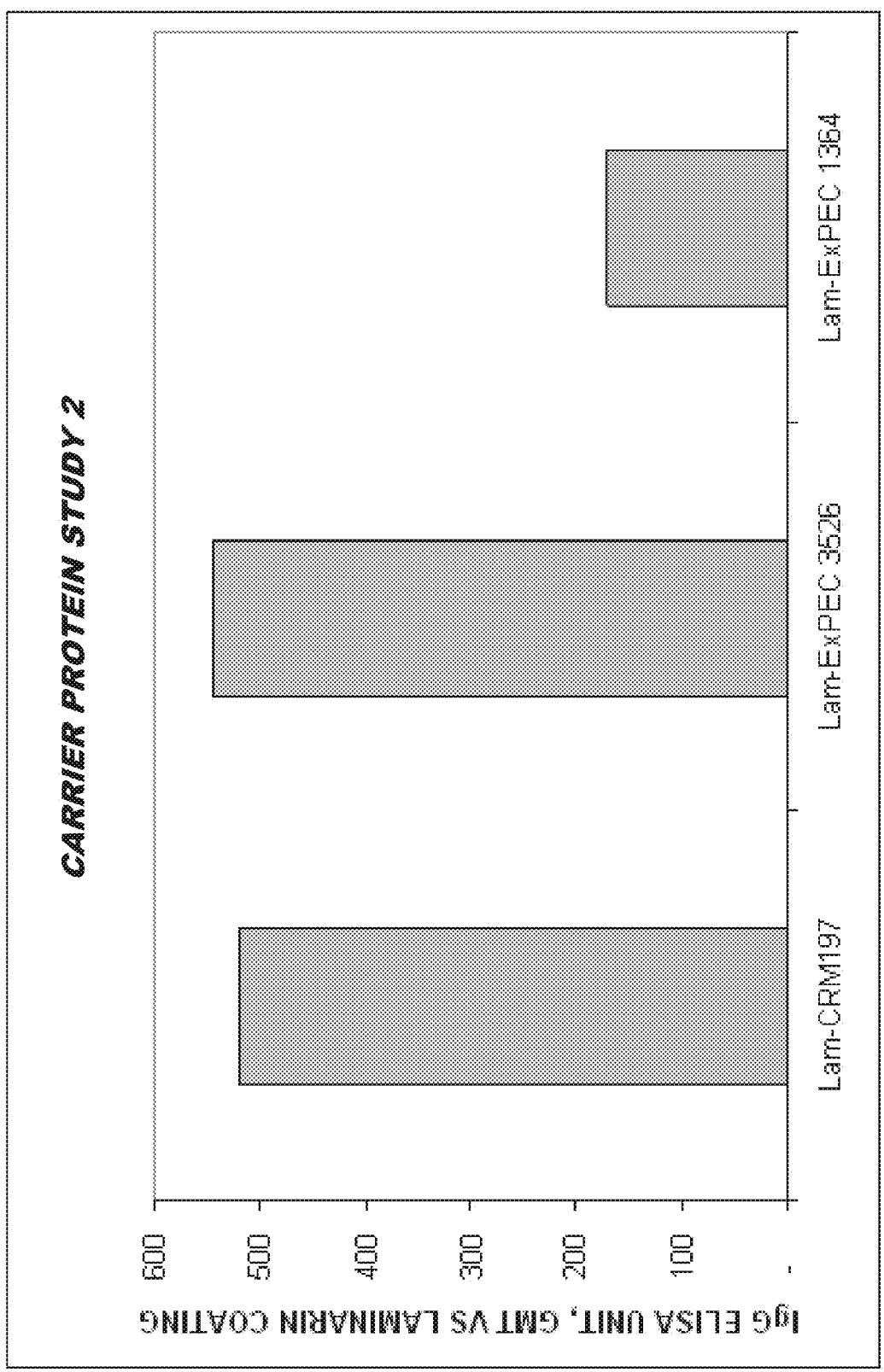
FIG. 3 shows the results of the second carrier protein immunization study. The y-axis shows the anti-laminarin IgG induction after immunization as measured by ELSA. The x-axis shows the ELISA results for the following conjugates (from left to right): laminarin conjugated to $CRM_{197}$, laminarin conjugated to orf3526, and laminarin conjugated to orf1364.

The results show that orf3526 as a carrier protein induced a strong antibody response against the polysaccharide portion (comparable or lightly great than that of $CRM_{197}$) while orf1364 give a lower, but still decent response (approximately one third of the response induced by $CRM_{197}$) (See FIG. 3).

It is especially noteworthy that the ability to induce an antibody response to a polysaccharide conjugate is not related to the ability of the carrier protein to induce a protective immune response to itself. Table 2 summarizes previous experiments using similar fragments (or in the case of upec-5211, orf1364, and orf405B, the exact same sequence) of the same protein to inoculate mice showed a very different response in the sepsis model. Each of upec-5211, orf1364 and orf405B provided relatively similar immune responses while each provides quite different degrees of induction of an immune response to a conjugated polysaccharide.

TABLE 2

| | Sepsis Animal Model | | |
|---|---|---|---|
| Candidate | Survival with vaccination (%) | Survival without vaccination (%) | P value |
| orf3526 | (75) | (0) | |
| upec-5211 | 30/93 (32) | 14/91 (15) | 0.009 |
| orf1364 (flu antigen 43 fragment) | 21/77 (27) | 8/84 (9) | 0.004 |
| orf405B (bacterial Ig-like domain (group 1) protein fragment) | 17/63 (26) | 9/66 (13) | 0.07 |

Immunogenicity—orf3526A, orf3526B, and orf3526C

To confirm that the three preferred fragments described in the alignment above had substantially the same immunogenicity as the full length AcfD (orf3526), the fragments based upon the full length sequence of SEQ ID NO: 39 were purified. The purified fragments were used in immunization experiments in mice, adjuvanted with Freund's complete adjuvant (orf3526A and orf3526B) or with alum (orf3526C). Immunized mice were then challenged with a lethal dose of *E. coli*. Results of the challenge are shown in Table 3 below.

TABLE 3

| | Sepsis animal model | | |
|---|---|---|---|
| Candidates | Survival with vaccination (%) | Survival without vaccination (%) | P value |
| orf3526A/FCA | 7/8 (87.5) | 1/8 (12.5) | 0.01 |
| orf3526B/FCA | 6/8 (75) | 1/8 (12.5) | 0.04 |
| orf3526C 2 µg/alum | 13/16 (81) | 0/7 (0) | 0.0005 |
| orf3526C 20 µg/alum | 15/16 (93) | 0/7 (0) | 0.0001 |

Thus, the fragments generate substantially similar immune responses in mice and will therefore be expected to provide substantially similar enhancement of the immune response to a conjugated polysaccharide as the full length orf3526.

It will be understood that the invention has been described by way of example only and modifications may be made whilst remaining within the scope and spirit of the invention.

[1] WO2006/089264.
[2] WO2006/091517.
[3] Needleman & Wunsch (1970) *J. Mol. Biol.* 48, 443-453.
[4] Rice et al. (2000) *Trends Genet.* 16:276-277.
[5] *Vaccine Design: The Subunit and Adjuvant Approach* (eds. Powell & Newman) Plenum Press 1995 (ISBN 0-306-44867-X).
[6] *Vaccine Adjuvants: Preparation Methods and Research Protocols* (Volume 42 of *Methods in Molecular Medicine* series). ISBN: 1-59259-083-7. Ed. O'Hagan.
[7] U.S. Pat. No. 6,355,271.
[8] WO00/23105.
[9] WO90/14837.
[10] WO90/14837.
[11] Podda & Del Giudice (2003) *Expert Rev Vaccines* 2:197-203.
[12] Podda (2001) *Vaccine* 19: 2673-2680.
[13] *Vaccine Design: The Subunit and Adjuvant Approach* (eds. Powell & Newman) Plenum Press 1995 (ISBN 0-306-44867-X).
[14] *Vaccine Adjuvants: Preparation Methods and Research Protocols* (Volume 42 of *Methods in Molecular Medicine* series). ISBN: 1-59259-083-7. Ed. O'Hagan.
[15] Allison & Byars (1992) *Res Immunol* 143:519-25.
[16] Hariharan et al. (1995) *Cancer Res* 55:3486-9.
[17] US-2007/014805.
[18] Suli et al. (2004) *Vaccine* 22(25-26):3464-9.
[19] WO95/11700.
[20] U.S. Pat. No. 6,080,725.
[21] WO2005/097181.
[22] WO2006/113373.
[23] Han et al. (2005) *Impact of Vitamin E on Immune Function and Infectious Diseases in the Aged at Nutrition, Immune functions* and Health EuroConference, Paris, 9-10 Jun. 2005.
[24] U.S. Pat. No. 6,630,161.
[25] U.S. Pat. No. 5,057,540.
[26] WO96/33739.
[27] EP-A-0109942.
[28] WO96/11711.
[29] WO00/07621.
[30] Barr et al. (1998) *Advanced Drug Delivery Reviews* 32:247-271.
[31] Sjolanderet et al. (1998) *Advanced Drug Delivery Reviews* 32:321-338.
[32] Niikura et al. (2002) *Virology* 293:273-280.
[33] Lenz et al. (2001) *J Immunol* 166:5346-5355.
[34] Pinto et al. (2003) *J Infect Dis* 188:327-338.
[35] Gerber et al. (2001) *J Virol* 75:4752-4760.

[36] WO03/024480.
[37] WO03/024481.
[38] Gluck et al. (2002) *Vaccine* 20:B10-B16.
[39] EP-A-0689454.
[40] Johnson et al. (1999) *Bioorg Med Chem Lett* 9:2273-2278.
[41] Evans et al. (2003) *Expert Rev Vaccines* 2:219-229.
[42] Meraldi et al. (2003) *Vaccine* 21:2485-2491.
[43] Pajak et al. (2003) *Vaccine* 21:836-842.
[44] Kandimalla et al. (2003) *Nucleic Acids Research* 31:2393-2400.
[45] WO02/26757.
[46] WO99/62923.
[47] Krieg (2003) *Nature Medicine* 9:831-835.
[48] McCluskie et al. (2002) *FEMS Immunology and Medical Microbiology* 32:179-185.
[49] WO98/40100.
[50] U.S. Pat. No. 6,207,646.
[51] U.S. Pat. No. 6,239,116.
[52] U.S. Pat. No. 6,429,199.
[53] Kandimalla et al. (2003) *Biochemical Society Transactions* 31 (part 3):654-658.
[54] Blackwell et al. (2003) *J Immunol* 170:4061-4068.
[55] Krieg (2002) *Trends Immunol* 23:64-65.
[56] WO01/95935.
[57] Kandimalla et al. (2003) *BBRC* 306:948-953.
[58] Bhagat et al. (2003) *BBRC* 300:853-861.
[59] WO03/035836.
[60] WO01/22972.
[61] Schellack et al. (2006) *Vaccine* 24:5461-72.
[62] WO95/17211.
[63] WO98/42375.
[64] Beignon et al. (2002) *Infect Immun* 70:3012-3019.
[65] Pizza et al. (2001) *Vaccine* 19:2534-2541.
[66] Pizza et al. (2000) *Int J Med Microbiol* 290:455-461.
[67] Scharton-Kersten et al. (2000) *Infect Immun* 68:5306-5313.
[68] Ryan et al. (1999) *Infect Immun* 67:6270-6280.
[69] Partidos et al. (1999) *Immunol Lett* 67:209-216.
[70] Peppoloni et al. (2003) *Expert Rev Vaccines* 2:285-293.
[71] Pine et al. (2002) *J Control Release* 85:263-270.
[72] Tebbey et al. (2000) *Vaccine* 18:2723-34.
[73] Domenighini et al. (1995) *Mol Microbiol* 15:1165-1167.
[74] WO99/40936.
[75] WO99/44636.
[76] Singh et al. (2001) *J Cont Release* 70:267-276.
[77] WO99/27960.
[78] U.S. Pat. No. 6,090,406.
[79] U.S. Pat. No. 5,916,588.
[80] EP-A-0626169.
[81] WO99/52549.
[82] WO01/21207.
[83] WO01/21152.
[84] Andrianov et al. (1998) *Biomaterials* 19:109-115.
[85] Payne et al. (1998) *Adv Drug Delivery Review* 31:185-196.
[86] U.S. Pat. No. 4,680,338.
[87] U.S. Pat. No. 4,988,815.
[88] WO92/15582.
[89] Stanley (2002) *Clin Exp Dermatol* 27:571-577.
[90] Wu et al. (2004) *Antiviral Res.* 64(2):79-83.
[91] Vasilakos et al. (2000) *Cell Immunol.* 204(1):64-74.
[92] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[93] Jones (2003) *Curr Opin Investig Drugs* 4:214-218.
[94] WO03/011223.
[95] Johnson et al. (1999) *Bioorg Med Chem Lett* 9:2273-2278.
[96] Evans et al. (2003) *Expert Rev Vaccines* 2:219-229.
[97] WO2004/060308.
[98] WO2004/064759.
[99] U.S. Pat. No. 6,924,271.
[100] US2005/0070556.
[101] U.S. Pat. No. 5,658,731.
[102] U.S. Pat. No. 5,011,828.
[103] WO2004/87153.
[104] U.S. Pat. No. 6,605,617.
[105] WO02/18383.
[106] WO2004/018455.
[107] WO03/082272.
[108] Wong et al. (2003) *J Clin Pharmacol* 43(7):735-42.
[109] US2005/0215517.
[110] Dyakonova et al. (2004) *Int Immunopharmacol* 4(13):1615-23.
[111] FR-2859633.
[112] Signorelli & Hadden (2003) *Int Immunopharmacol* 3(8):1177-86.
[113] WO2004/064715.
[114] De Libero et al, *Nature Reviews Immunology*, 2005, 5:485-496
[115] U.S. Pat. No. 5,936,076.
[116] Old et al, *J. Clin. Investig.*, 113: 1631-1640
[117] US2005/0192248
[118] Yang et al, *Angew. Chem. Int. Ed.*, 2004, 43: 3818-3822
[119] WO2005/102049
[120] Goff et al, *J. Am. Chem., Soc.*, 2004, 126: 13602-13603
[121] WO03/105769
[122] Cooper (1995) *Pharm Biotechnol* 6:559-80.
[123] WO99/11241.
[124] WO94/00153.
[125] WO98/57659.
[126] European patent applications 0835318, 0735898 and 0761231.
[127] Durant et al. (2007) *Infect Immun* 75:1916-25.
[128] WO02/081653.
[129] Gennaro (2000) *Remington: The Science and Practice of Pharmacy.* 20th edition, ISBN: 0683306472.
[130] *Methods In Enzymology* (S. Colowick and N. Kaplan, eds., Academic Press, Inc.)
[131] *Handbook of Experimental Immunology*, Vols. I-IV (D. M. Weir and C. C. Blackwell, eds, 1986, Blackwell Scientific Publications)
[132] Sambrook et al. (2001) *Molecular Cloning: A Laboratory Manual,* 3rd edition (Cold Spring Harbor Laboratory Press).
[133] *Handbook of Surface and Colloidal Chemistry* (Birdi, K. S. ed., CRC Press, 1997)
[134] Ausubel et al. (eds) (2002) *Short protocols in molecular biology,* 5th edition (Current Protocols).
[135] *Molecular Biology Techniques: An Intensive Laboratory Course,* (Ream et al., eds., 1998, Academic Press)
[136] *PCR (Introduction to Biotechniques Series),* 2nd ed. (Newton & Graham eds., 1997, *Springer* Verlag)
[137] *Current Protocols in Molecular Biology* (F. M. Ausubel et al., eds., 1987) Supplement 30
[138] Smith & Waterman (1981) *Adv. Appl. Math.* 2: 482-489.

SEQ ID NO: 41
GTTGCTGATGGTCAGCAAGCCTACACGCTGACACTGACAGCGGTGGACTCCGAGGGTAATCCGGTGAC

GGGAGAAGCCAGCCGCCTGCGACTTGTTCCGCAAGACACTAATGGTGTAACCGTTGGTGCCATTTCGG

AAATAAAACCAGGGGTTTACAGCGCCACGGTTTCTTCGACCCGTGCCGGAAACGTTGTTGTGCGTGCC

TTCAGCGAGCAGTATCAGCTGGGCACATTACAACAAACGCTGAAGTTTGTTGCCGGGCCGCTTGATGC

AGCACATTCGTCCATCACACTGAATCCTGATAAACCGGTGGTTGGCGGTACAGTTACGGCAATCTGGA

CGGCAAAAGATGCTAATGACAACCCTGTAACTGGCCTCAATCCGGATGCACCGTCATTATCGGGCGCA

GCTGCTGCTGGTTCTACGGCATCAGGCTGGACGGATAATGGCGACGGGACCTGGACTGCGCAGATTTC

TCTCGGCACTACGGCGGGTGAATTAGACGTTATGCCGAAGCTCAATGGGCAGGACGCGGCAGCAAATG

CGGCAAAAGTAACCGTGGTGGCTGATGCATTATCTTCAAACCAGTCGAAAGTCTCTGTCGCAGAAGAT

CACGTAAAAGCCGGTGAAAGCACAACCGTAACGCTGGTGGCGAAAGATGCGCATGGCAACGCTATCAG

TGGTCTTTCGTTGTCGGCAAGTTTGACGGGACCGCCTCTGAAGGGGCGACCGTTTCCAGTTGGACCG

AAAAAGGTGACGGTTCCTATGTTGCTACGTTAACTACAGGCGGAAAGACGGGCGAGCTTCGTGTCATG

CCGCTCTTCAACGGCCAGCCTGCAGCCACCGAAGCCGCGCAGCTGACTGTTATTGCCGGAGAGATGTC

ATCAGCGAACTCTACGCTTGTTGCGGACAATAAAACTCCAACGGTTAAAACGACGACGGAACTCACCT

TCACCATGAAGGATGCGTACGGGAATCCGGTCACCGGGCTGAAGCCAGATGCACCAGTGTTTAGTGGT

GCCGCCAGCACGGGGAGTGAGCGTCCTTCAGCAGGAAACTGGACAGAGAAAGGTAATGGGGTCTACGT

GTCGACCTTAACGCTGGGATCTGCCGCGGGTCAGTTGTCTGTGATGCCGCGAGTGAACGGCCAAAATG

CCGTTGCTCAGCCACTGGTGCTGAATGTTGCAGGTGACGCATCTAAGGCTGAGATTCGTGATATGACA

GTGAAGGTTAATAACCAA

SEQ ID NO: 42
VADGQQAYTLTLTAVDSEGNPVTGEASRLRLVPQDTNGVTVGAISEIKPGVYSATVSSTRAGNVVVRA

FSEQYQLGTLQQTLKFVAGPLDAAHSSITLNPDKPVVGGTVTAIWTAKDANDNPVTGLNPDAPSLSGA

AAAGSTASGWTDNGDGTWTAQISLGTTAGELDVMPKLNGQDAAANAAKVTVVADALSSNQSKVSVAED

HVKAGESTTVTLVAKDAHGNAISGLSLSASLTGTASEGATVSSWTEKGDGSYVATLTTGGKTGELRVM

PLFNGQPAATEAAQLTVIAGEMSSANSTLVADNKTPTVKTTTELTFTMKDAYGNPVTGLKPDAPVFSG

AASTGSERPSAGNWTEKGNGVYVSTLTLGSAAGQLSVMPRVNGQNAVAQPLVLNVAGDASKAEIRDMT

VKVNNQ

SEQ ID NO: 43
GCTGACACGGTTGTACAGGCGGGAGAAACCGTGAACGGCGGAACACTGACAAATCATGACAACCAGAT

TGTCCTCGGTACGGCCAACGGAATGACCATCAGTACCGGGCTGGAGTATGGGCCGGATAACGAGGCCA

ATACCGGCGGGCAATGGATACAAAATGGCGGTATCGCCAACAACACTACTGTCACCGGTGGTGGTCTT

CAGAGAGTGAATGCCGGAGGAAGCGTTTCAGACACGGTTATCAGTGCCGGAGGCGGACAGAGCCTTCA

GGGGCAGGCAGTGAACACCACTCTGAACGGCGGTGAGCAGTGGGTACATGAAGGCGGGATTGCAACGG

GTACCGTCATTAATGAGAAGGGCTGGCAGGCCGTCAAATCCGGTGCAATGGCAACCGACACGGTTGTG

AATACCGGCGCGGAAGGAGGACCGGATGCGGAAAATGGTGATACCGGGCAGACCGTCTACGGAGATGC

CGTACGCACCACCATCAATAAAAATGGTCGTCAGATTGTGGCTGCTGAAGGAACGGCAAATACCACTG

TGGTTTATGCCGGCGGCGACCAGACTGTACATGGTCACGCACTGGATACCACGCTGAATGGGGGTAC

CAGTATGTGCACAACGGAGGTACAGCATCTGACACTGTTGTTAACAGTGACGGCTGGCAGATTATCAA

GGAAGGTGGTCTGGCGGATTTCACCACCGTTAACCAGAAAGGTAAACTGCAGGTGAACGCCGGTGGTA

CAGCCACGAATGTCACCCTGACGCAGGGCGGCGCACTGGTCACCAGTACGGCGGCAACCGTCACCGGC

AGCAACCGTCTGGGCAATTTCACTGTGGAAAACGGTAATGCTGACGGTGTTGTTCTGGAGTCCGGTGG

-continued

```
TCGCCTGGATGTACTGGAGGGCCATTCAGCCTGGAAAACACTGGTGGATGACGGCGGTACCCTGGCAG

TGTCTGCCGGTGGTAAGGCAACAGATGTCACCATGACATCCGGTGGTGCCCTGATTGCAGACAGTGGT

GCCACTGTTGAGGGGACCAATGCCAGCGGTAAGTTCAGTATTGATGGCATATCCGGTCAGGCCAGCGG

CCTGCTGCTGGAAAATGGCGGCAGCTTTACGGTTAATGCCGGAGGACTGGCCAGCAACACCACTGTCG

GACATCGTGGAACACTGACGCTGGCCGCCGGGGGAAGTCTGAGTGGCAGAACACAGCTCAGTAAAGGC

GCCAGTATGGTACTGAATGGTGATGTGGTCAGTACCGGCGATATTGTTAACGCCGGAGAGATTCGCTT

TGATAATCAGACGACACCGGATGCCGCACTGAGCCGTGCTGTTGCAAAAGGCGACTCCCCGGTAACGT

TCCATAAACTGACCACCAGTAACCTCACCGGTCAGGGTGGCACCATCAATATGCGTGTTCGCCTTGAT

GGCAGCAATGCCTCTGACCAGCTGGTGATTAATGGTGGTCAGGCAACCGGCAAAACCTGGCTTGCGTT

TACAAATGTCGGAAACAGTAACCTCGGGGTGGCAACCTCCGGACAGGGTATCCGGGTTGTGGATGCAC

AGAATGGTGCCACCACAGAAGAAGGTGCGTTTGCCCTGAGTCGCCCGCTTCAGGCCGGCGCCTTTAAC

TACACCCTGAACCGTGACAGCGATGAAGACTGGTACCTGCGCAGTGAAAATGCTTATCGTGCTGAAGT

CCCC
```

SEQ ID NO: 44

```
ADTVVQAGETVNGGTLTNHDNQIVLGTANGMTISTGLEYGPDNEANTGGQWIQNGGIANNTTVTGGGL

QRVNAGGSVSDTVISAGGGQSLQGQAVNTTLNGGEQWVHEGGIATGTVINEKGWQAVKSGAMATDTVV

NTGAEGGPDAENGDTGQTVYGDAVRTTINKNGRQIVAAEGTANTTVVYAGGDQTVHGHALDTTLNGGY

QYVHNGGTASDTVVNSDGWQIIKEGGLADFTTVNQKGKLQVNAGGTATNVTLTQGGALVTSTAATVTG

SNRLGNFTVENGNADGVVLESGGRLDVLEGHSAWKTLVDDGGTLAVSAGGKATDVTMTSGGALIADSG

ATVEGTNASGKFSIDGISGQASGLLLENGGSFTVNAGGLASNTTVGHRGTLTLAAGGSLSGRTQLSKG

ASMVLNGDVVSTGDIVNAGEIRFDNQTTPDAALSRAVAKGDSPVTFHKLTTSNLTGQGGTINMRVRLD

GSNASDQLVINGGQATGKTWLAFTNVGNSNLGVATSGQGIRVVDAQNGATTEEGAFALSRPLQAGAFN

YTLNRDSDEDWYLRSENAYRAEVP
```

SEQ ID NO: 45

```
ATGTTAAAAAAAACATTGTTATCTATGTTCGCAACCGCATTGTTATCAGGCGTTGCTTTTAACGCTCT

TGCTGACGATGCTAATCAGGGTTCAGGTAAAATTACTTTTAAAGGTGAAGTTATCGATGCACCTTGTT

CTATTGCTCCTGGTGATGAAGATCAGACAATAAACCTCGGTGAAGTTGCTGATACCGTATTAAAAGC

GGTCAGAAATCACTGCCTGTAGATGTCACCATTCATTTGCAGGATTGTATTTTATCTGACGGCACTAA

CACTGTTGATAAAGTCAAAATCACCTTTAGTTCTGCCAGTGTTGACGCTACCGACTCCAACCTGCTTA

AAAACACTCTGGAAGGTAACATCGGCGGCGCAACTGATGTAGGCGTACGTCTGGTGAAATCAGACAAC

ACCAACGTGACTCTTGGCACTCCAATCACTATCAACTTCCCGACGACTAACTCTTACCAGGAGTTGAA

CTTTAAAGCCCGTATGGAGTCTCTGGGACGCACCGCGACCCCGGGTAACGTGCAGGCACAGGCTAATT

ACGTACTCGACTACAAG
```

SEQ ID NO: 46

```
MLKKTLLSMFATALLSGVAFNALADDANQGSGKITFKGEVIDAPCSIAPGDEDQTINLGEVADTVLKS

GQKSLPVDVTIHLQDCILSDGTNTVDKVKITFSSASVDATDSNLLKNTLEGNIGGATDVGVALVKSDN

TNVTLGTPITINFPTTNSYQELNFKARMESLGRTATPGNVQAQANYVLDYK
```

SEQ ID NO: 47

```
ATGAAAAAATCTCTTCTGGCTGTAATGCTGACAGGACTGTTTGCTCTCGTTTCTCTTCCCGCTCTGGG

AAATGTCAATCTCGAACAATTAAAGCAAAAAGCTGAAGTGGAGAAGCTAAAGCACAGTTGGAGCTGG

GATATCGCTATTTTCAGGGTAATGAAACGACAAAGGATCTCACCCAGGCGATGGACTGGTTTCGCCGT

GCCGCAGAGCAGGGATACACCCCGGCAGAATATGTACTGGGGTTACGCTATATGAACGGTGAAGGTGT

GCCGCAAGATTATGCTCAGGCAGTTATCTGGTACAAAAAAGCGGCACTGAAGGGGCTTCCGCAAGCGC
```

```
AGCAGAATCTGGGTGTAATGTACCATGAAGGTAATGGCGTGAAGGTTGATAAAGCCGAATCTGTGAAA

TGGTTTCGCCTGGCAGCAGAGCAAGGTCGTGACAGCGGCCAGCAAAGTATGGGAGACGCATATTTTGA

AGGCGATGGTGTGACGCGGGATTACGTTATGGCACGTGAGTGGTATAGCAAAGCAGCGGAACAAGGTA

ACGTCTGGTCCTGTAACCAGCTTGGTTATATGTATTCCAGAGGTTTAGGCGTTGAAAGAAACGATGCC

ATATCGGCACAATGGTATCGAAAATCAGCGACATCAGGCGACGAGTTGGGGCAGCTTCATTTAGCCGA

TATGTACTATTTCGGTATCGGTGTTACTCAGGATTACACTCAGTCACGGGTATTATTTTCCCAGTCGG

CAGAGCAGGGAAATTCTATTGCGCAGTTTCGTCTGGGATATATATTGGAGCAAGGTTTAGCGGGAGCG

AAAGAGCCGTTAAAAGCACTGGAGTGGTACCGTAAATCGGCAGAACAGGGAAATTCCGATGGTCAGTA

TTATTTGGCTCATCTGTATGATAAAGGCGCAGAAGGTGTAGCAAAAAATCGAGAACAAGCCATCTCCT

GGTACACGAAATCGGCAGAACAGGGGATGCTACCGCACAGGCTAATCTCGGCGCTATTTACTTCAGA

CTTGGTTCAGAAGAAGAACATAAAAAGGCGGTGGAATGGTTTCGCAAGGCCGCCGCAAAGGGTGAGAA

AGCGGCGCAATTTAATTTGGGTAATGCTTTACTCCAGGGAAAAGGTGTTAAAAAAGATGAGCAACAGG

CCGCAATCTGGATGCGAAAAGCCGCAGAGCAAGGATTAAGTGCAGCGCAGGTACAATTAGGTGAAATC

TATTATTATGGCTTGGGCGTAGAACGTGATTATGTGCAGGCCTGGGCGTGGTTCGATACCGCATCGAC

CAATGATATGAATCTTTTTGGTACAGAAAACCGCAACATTACAGAGAAAAAACTGACAGCCAAACAAC

TGCAACAGGCTGAATTATTATCGCAACAATATATAGAAAAATATGCCCCGGAAGCCTGGGCGAGAATG

CAAAAGCTTAAAGCGCAATCAGCGGTAAAGACGGGTAATAAA

SEQ ID NO: 48
MKKSLLAVMLTGLFALVSLPALGNVNLEQLKQKAESGEAKAQLELGYRYFQGNETTKDLTQAMDWFRR

AAEQGYTPAEYVLGLRYMNGEGVPQDYAQAVIWYKKAALKGLPQAQQNLGVMYHEGNGVKVDKAESVK

WFRLAAEQGRDSGQQSMGDAYFEGDGVTRDYVMAREWYSKAAEQGNVWSCNQLGYMYSRGLGVERNDA

ISAQWYRKSATSGDELGQLHLADMYYFGIGVTQDYTQSRVLFSQSAEQGNSIAQFRLGYILEQGLAGA

KEPLKALEWYRKSAEQGNSDGQYYLAHLYDKGAEGVAKNREQAISWYTKSAEQGDATAQANLGAIYFR

LGSEEEHKKAVEWFRKAAAKGEKAAQFNLGNALLQGKGVKKDEQQAAIWMRKAAEQGLSAAQVQLGEI

YYYGLGVERDYVQAWAWFDTASTNDMNLFGTENRNITEKKLTAKQLQQAELLSQQYIEKYAPEAWARM

QKLKAQSAVKTGNK
                                                           SEQ ID NO: 49
ATGAATAAGAAATTTAAATATAAGAAATCGCTTTTAGCGGCTATTTTAAGCGCAACCCTGTTAGCCGG

TTGTGATGGTGGTGGTTCAGGATCGTCCTCCGATACGCCGTCTGTAGATTCTGGATCAGGGACTTTGC

CGGAAGTGAAACCCGATCCAACACCAACCCCGGAGCCGACACCTGAGCCGACGCCGGACCCAGAACCT

ACGCCGGATCCAACACCTGATCCTGAGCCGACACCAGAACCGGAGCCAGAACCTGTTCCTACGAAAAC

GGGTTATCTGACCCTGGGCGGAAGCCAGCGGGTAACTGGTGCTACCTGTAATGGTGAATCCAGCGATG

GCTTTACCTTTACGCCAGGCAATACCGTGAGTTGTGTGGTGGGCAGTACGACCATTGCAACATTCAAC

ACCCAGTCAGAAGCTGCGCGTAGCCTGCGTGCGGTTGACAAAGTGTCGTTTAGCCTGGAGGACGCGCA

GGAGCTGGCGAATTCTGAAAATAAGAAAACCAACGCCATCTCTCTGGTGACGTCCAGCGACAGTTGCC

CCGCAGATGCAGAACAGCTTTGTCTTACTTTCTCGTCAGTGGTTGATCGCGCGCGATTTGAAAAACTG

TATAAGCAAATTGATCTGGCAACAGACAATTTCAGCAAGCTGGTCAATGAAGAGGTGGAAAACAATGC

TGCGACTGATAAAGCGCCGTCCACCCATACCTCAACGGTAGTGCCAGTCACGACAGAGGGAACAAAAC

CGGATCTGAACGCGTCCTTCGTGTCGGCTAACGCGGAACAGTTTTATCAGTATCAACCCACTGAAATC

ATTCTTTCCGAAGGCCAACTGGTGGATAGCCTGGGGAACGGTGTTGCTGGCGTTGACTACTACACCAA

TTCAGGCCGTGGCGTAACTGACGAAAACGGTAAATTTTCCTTTAGCTGGGGCGAAACCATCTCCTTTG
```

-continued

```
GTATCGATACCTTTGAACTGGGCTCAGTACGTGGCAATAAGTCGACCATTGCGCTGACTGAATTGGGT
GATGAAGTTCGCGGGGCAAATATCGATCAGCTCATTCATCGTTATTCGACGACTGGTCAAATAATAC
TCGTGTTGTTCCGGACGATGTACGCAAGGTCTTTGCCGAATATCCCAACGTGATCAACGAGATAATCA
ATCTTTCGTTATCCAACGGTGCGACGCTGGATGAAGGCGATCAAAACGTTGTGCTGCCTAACGAATTT
ATCGAGCAGTTTAAGACGGGTCAGGCCAAAGAGATCGATACCGCGATTTGTGCGAAAACCGACGGTTG
TAACGAGGCTCGCTGGTTCTCGCTGACAACGCGCAATGTTAATGACGGCCAGATTCAGGGCGTTATTA
ACAAGCTGTGGGCGTGGATACGAACTATCAGTCTGTCAGCAAGTTCCACGTCTTCCATGACTCTACC
AACTTCTATGGCAGCACCGGTAACGCGCGCGGTCAGGCGGTGGTAAATATCTCCAACTCGGCATTCCC
GATTCTGATGGCGCGTAATGATAAAAACTACTGGCTGGCGTTTGGCGAAAAACGCGCCTGGGATAAAA
ATGAGCTGGCGTACATTACGGAAGCGCCTTCCATTGTGCAGCCAGAGAACGTTACGCGCGATACTGCG
ACTTTCAACCTGCCGTTTATTTCGCTGGGGCAAGTCGGTGAAGGCAAACTGATGGTTATCGGTAACCC
GCACTACAACAGCATCCTGCGTTGCCCGAACGGTTACAGTTGGGGCGGTGGTGTTAATAGTAAAGGTG
AGTGTACGCTCAGCGGTGATTCTGATGACATGAAGCACTTTATGCAGAACGTACTGCGCTACTTGTCA
AATGACATCTGGCAGCCAAATACCAAGAGCATCATGACTGTCGGCACCAACCTGGAGAACGTTTATTT
CAAAAAAGCGGGCCAGGTATTGGGAAATAGTGCACCATTTGCTTTCCATGAGGATTTCACTGGTATCA
CGGTTAAACAGTTGACCAGCTATGGCGATCTGAATCCGGAAGAGATTCCGTTGCTGATCCTCAACGGC
TTTGAATATGTGACTCAGTGGTCTGGCGATCCCTATGCTGTGCCTCTGCGTGCAGATACCAGCAAACC
GAAGCTGACTCAGCAGGATGTGACCGATCTGATCGCTTATCTGAACAAAGGTGGCTCGGTGCTGATCA
TGGAAAACGTGATGAGCAATCTTAAGGAAGAGAGCGCGTCCAGTTTTGTGCGTCTGCTGGATGCCGCG
GGTCTGTCAATGGCTCTGAACAAATCGGTGGTGAACAACGATCCGCAAGGGTATCCGGATCGCGTTCG
TCAGCGTCGCGCGACTGGCATTTGGGTTTATGAACGTTATCCTGCTGCAGACGGCGCGCAACCGCCGT
ACACCATCGACCCAAATACAGGGGAAGTGACCTGGAAATACCAGCAAGACAACAAGCCTGATGACAAG
CCGAAACTGGAAGTTGCGAGCTGGCAGGAGGAAGTTGAGGGCAAACAGGTAACGCGTTATGCCTTTAT
TGATGAAGCGGAATACACAACAGAAGAATCTCTGGAAGCGGCAAAGGCAAAAATCTTTGAGAAGTTTC
CTGGGTTACAGGAGTGTAAGGACTCGACTTACCATTACGAGATTAACTGTTTGGAGCGCCGCCCAGGC
ACGGATGTTCCGGTAACAGGTGGCATGTATGTTCCGCGCTATACGCAACTGAATCTTGACGCCGACAC
CGCGAAAGCGATGGTGCAGGCGGCGGATTTAGGCACCAACATTCAGCGCCTGTATCAGCATGAGCTTT
ATTTCCGTACCAAAGGCAGTAAAGGTGAGCGTCTGAACAGTGTTGATCTGGAACGTCTGTACCAGAAC
ATGTCGGTCTGGCTGTGGAACGATACGAAATATCGTTACGAAGAGGGCAAGGAAGATGAGCTGGGCTT
TAAAACGTTCACCGAGTTCCTGAACTGCTACGCCAATGATGCCTATGCAGGCGGCACCAAGTGCTCCG
CAGATCTGAAAAAATCGCTGGTCGATAACAACATGATCTACGGTGACGGTAGCAGCAAAGCGGGCATG
ATGAACCCAAGCTATCCGCTCAACTATATGGAAAAACCGCTGACGCGTCTGATGCTGGGCCGTTCCTG
GTGGGATCTGAACATTAAGGTTGATGTGGAGAAGTACCCAGGATCCGTATCGGCAAAGGGTGAGAGCG
TTACGGAAAACATCAGCCTGTACTCGAATCCGACCAAATGGTTTGCGGGTAACATGCAGTCAACCGGC
CTGTGGGCACCGGCCCAGCAGGACGTCACCATTAAGTCTTCGGCGTCAGTCCCAGTGACTGTTACCGT
GGCGCTGGCTGACGACCTGACTGGACGTGAGAAGCATGAAGTTGCGCTGAACCGTCCGCCAAGAGTGA
CTAAAACGTATACTCTGGAGGCTAACGGTGAAGTGACCTTCAAGGTGCCTTATGGTGGTCTGATTTAT
ATCAAGGGCGACAGTAAGGATGATGTTTCTGCTAACTTCACCTTTACCGGTGTAGTAAAAGCGCCGTT
CTATAAAGACGGCGAATGGAAAAACGATCTGGACTCACCGGCGCCGCTGGGCGAGCTGGAGTCTGCGT
CGTTCGTCTATACCACGCCGAAGAAGAACCTTGAGGCCAGCAATTTCACTGGTGGTGTAGCAGAATTC
GCTAAAGATCTGGATACCTTTGCCAGCTCGATGAATGACTTCTACGGTCGTAATGATGAAGACGGTAA
```

```
GCACCGGATGTTTACCTATAAAAACTTGACGGGGCACAAGCATCGTTTCACCAACGATGTGCAGATCT

CCATCGGTGATGCGCACTCGGGTTATCCGGTAATGAACAGCAGCTTCTCGACGAACAGCACCACGCTG

CCGACGACGCCGCTGAACGACTGGCTGATTTGGCACGAAGTCGGTCATAACGCTGCAGAAACACCGCT

GAACGTACCGGGTGCAACTGAAGTGGCGAACAACGTGCTGGCGCTGTACATGCAGGATCGCTATCTCG

GTAAGATGAACCGTGTCGCTGACGACATTACCGTCGCGCCGGAATATCTGGACGAGAGCAACGGTCAG

GCCTGGGCGCGCGGCGGTGCGGGTGACCGTCTGCTGATGTACGCACAGTTGAAGGAGTGGGCAGAGGA

AAACTTTGATATCAAACAGTGGTATCCAGATGGTGAGCTGCCTAAGTTCTACAGCGATCGTAAAGGGA

TGAAGGGCTGGAACCTGTTCCAGTTGATGCACCGTAAAGCGCGCGGCGATGATGTTGGTAACAGCACC

TTTGGTGGCAAGAATTACTGTGCTGAATCCAATGGTAACGCTGCCGACACGCTGATGCTGTGTGCATC

CTGGGTCGCTCAGGCGGATCTTTCGGAATTCTTTAAGAAATGGAATCCGGGTGCAAGTGCTTACCAGT

TGCCGGGAGCAACGGAGATGAGTTTCCAGGGCGGTGTGAGCTCTTCGGCTTACAGCACGCTGGCGTCA

CTCAAGCTGCCGAAACCGGAAAAAGGGCCGGAAACCATTAACAAGGTTACCGAGCATAAGATGTCTGC

CGAG

SEQ ID NO: 50
MNKKFKYKKSLLAAILSATLLAGCDGGGSGSSSDTPSVDSGSGTLPEVKPDPTPTPEPTPEPTPDPEP

TPDPTPDPEPTPEPEPEPVPTKTGYLTLGGSQRVTGATCNGESSDGFTFTPGNTVSCVVGSTTIATFN

TQSEAARSLRAVDKVSFSLEDAQELANSENKKTNAISLVTSSDSCPADAEQLCLTFSSVVDRARFEKL

YKQIDLATDNFSKLVNEEVENNAATDKAPSTHTSTVVPVTTEGTKPDLNASFVSANAEQFYQYQPTEI

ILSEGQLVDSLGNGVAGVDYYTNSGRGVTDENGKFSFSWGETISFGIDTFELGSVRGNKSTIALTELG

DEVRGANIDQLIHRYSTTGQNNTRVVPDDVRKVFAEYPNVINEIINLSLSNGATLDEGDQNVVLPNEF

IEQFKTGQAKEIDTAICAKTDGCNEARWFSLTTRNVNDGQIQGVINKLWGVDTNYQSVSKFHVFHDST

NFYGSTGNARGQAVVNISNSAFPILMARNDKNYWLAFGEKRAWDKNELAYITEAPSIVQPENVTRDTA

TFNLPFISLGQVGEGKLMVIGNPHYNSILRCPNGYSWGGGVNSKGECTLSGDSDDMKHFMQNVLRYLS

NDIWQPNTKSIMTVGTNLENVYFKKAGQVLGNSAPFAFHEDFTGITVKQLTSYGDLNPEEIPLLILNG

FEYVTQWSGDPYAVPLRADTSKPKLTQQDVTDLIAYLNKGGSVLIMENVMSNLKEESASSFVRLLDAA

GLSMALNKSVVNNDPQGYPDRVRQRRATGIWVYERYPAADGAQPPYTIDPNTGEVTWKYQQDNKPDDK

PKLEVASWQEEVEGKQVTRYAFIDEAEYTTEESLEAAKAKIFEKFPGLQECKDSTYHYEINCLERRPG

TDVPVTGGMYVPRYTQLNLDADTAKAMVQAADLGTNIQRLYQHELYFRTKGSKGERLNSVDLERLYQN

MSVWLWNDTKYRYEEGKEDELGFKTFTEFLNCYANDAYAGGTKCSADLKKSLVDNNMIYGDGSSKAGM

MNPSYPLNYMEKPLTRLMLGRSWWDLNIKVDVEKYPGSVSAKGESVTENISLYSNPTKWFAGNMQSTG

LWAPAQQDVTIKSSASVPVTVTVALADDLTGREKHEVALNRPPRVTKTYTLEANGEVTFKVPYGGLIY

IKGDSKDDVSANFTFTGVVKAPFYKDGEWKNDLDSPAPLGELESASFVYTTPKKNLEASNFTGGVAEF

AKDLDTFASSMNDFYGRNDEDGKHRMFTYKNLTGHKHRFTNDVQISIGDAHSGYPVMNSSFSTNSTTL

PTTPLNDWLIWHEVGHNAAETPLNVPGATEVANNVLALYMQDRYLGKMNRVADDITVAPEYLDESNGQ

AWARGGAGDRLLMYAQLKEWAEENFDIKQWYPDGELPKFYSDRKGMKGWNLFQLMHRKARGDDVGNST

FGGKNYCAESNGNAADTLMLCASWVAQADLSEFFKKWNPGASAYQLPGATEMSFQGGVSSSAYSTLAS

LKLPKPEKGPETINKVTEHKMSAE
```

We claim:

1. A polysaccharide conjugate comprising a polysaccharide conjugated to a carrier polypeptide selected from the group consisting of an *E. coli* AcfD precursor polypeptide (orf3526 polypeptide), an *E. coli* Flu antigen 43 polypeptide (orf1364 polypeptide), and an *Escherichia* Sel1 repeat-containing polypeptide (upec-5211 polypeptide).

2. The polysaccharide conjugate of claim 1, wherein said carrier polypeptide is an *E. coli* AcfD precursor polypeptide (orf3526 polypeptide) which comprises a mutation reducing the toxicity and/or a deletion improving purification as compared to the *E. coli* AcfD precursor polypeptide (orf3526 polypeptide) having the amino acid sequence of SEQ ID NO: 39.

3. The polysaccharide conjugate of claim 2, wherein the mutation is selected from a deletion of all or a portion of the zincin metalloprotease domain and a point mutation in zincin metalloprotease domain which reduces the protease activity.

4. The polysaccharide conjugate of claim 2, wherein the carrier polypeptide does not comprise at least the last 100 C-terminal amino acids corresponding to the last 100 C-terminal amino acids of the *E. coli* AcfD precursor polypeptide (orf3526 polypeptide) having the amino acid sequence of SEQ ID NO: 39.

5. The polysaccharide conjugate of claim 1 wherein the carrier polypeptide is an *E. coli* AcfD precursor polypeptide (orf3526 polypeptide) which comprises:
   (a) the amino acid sequence selected from the group consisting of SEQ ID NOs 26-40;
   (b) from 1 to 10 single amino acid alterations compared to SEQ ID NOs: 26-40;
   (c) at least 85% sequence identity to any one of SEQ ID NOs: 26-40;
   (d) a fragment of at least 10 consecutive amino acids from any one of SEQ ID NOs: 26-40;
   and/or
   (e) an amino acid sequence that when aligned with any of SEQ ID NOs: 26-40 using a pairwise alignment algorithm, each moving window of x amino acids from N terminus to C terminus has at least x·y identical aligned amino acids, where x is 30 and y is 0.75.

6. The polysaccharide conjugate of claim 1 wherein the carrier polypeptide is an *E. coli* AcfD precursor polypeptide (orf3526 polypeptide) which comprises a deletion which increases solubility of the carrier polypeptide as compared to the *E. coli* AcfD precursor polypeptide (orf3526 polypeptide) having the amino acid sequence of SEQ ID NO: 39.

7. The polysaccharide conjugate of claim 6, wherein the deletion is removal of substantially all of the N-terminal amino acids up to the gly-ser region, removal of all or a part of the N-terminal proline-rich repeat, or both.

8. The polysaccharide conjugate of claim 6, wherein the deletion is removal of at least the first 10 N-terminal amino acids corresponding to the first 10 N-terminal amino acids of the *E. coli* AcfD precursor polypeptide (orf3526 polypeptide) having the amino acid sequence of SEQ ID NO: 39.

9. The polysaccharide conjugate of claim 1 wherein the carrier polypeptide is an *Escherichia* Sel1 repeat-containing polypeptide (upec-5211 polypeptide) which comprises:
   (a) the amino acid sequence selected from the group consisting of SEQ ID NOs 23-25;
   (b) from 1 to 10 single amino acid alterations compared to SEQ ID NOs: 23-25;
   (c) at least 85% sequence identity to any one of SEQ ID NOs: 23-25;
   (d) a fragment of at least 10 consecutive amino acids from any one of SEQ ID NOs:23-25;
   and/or
   (e) an amino acid sequence that when aligned with any of SEQ ID NOs: 23-25 using a pairwise alignment algorithm, each moving window of x amino acids from N terminus to C terminus has at least x·y identical aligned amino acids, where x is 30 and y is 0.75.

10. The polysaccharide conjugate of claim 1, wherein the polysaccharide is selected from the list comprising:
    (a) a glucan,
    (b) a capsular saccharide from at least one of serogroups A, C, W135 and Y of *Neisseria meningitidis*,
    (c) a saccharide antigen from *Streptococcus pneumoniae*,
    (d) a capsular polysaccharide from *Staphylococcus aureus*,
    (e) a *Haemophilus influenzae* B polysaccharide,
    (f) a saccharide antigen from *Streptococcus agalactiae*,
    (g) a lipopolysaccharide from *Vibrio cholerae*, or
    (h) a capsular polysaccharide from *Salmonella typhi*.

11. A vaccine comprising the polysaccharide conjugate of claim 1 and a pharmaceutically acceptable carrier.

12. The vaccine of claim 11 further comprising an additional vaccine component selected from: a *Neisseria meningitidis* antigen, a *Streptococcus pneumoniae* antigen, a *Streptococcus pyogenes* antigen, a *Moraxella catarrhalis* antigen, a *Bordetella pertussis* antigen, a *Staphylococcus aureus* antigen, a *Staphylococcus epidermidis* antigen, a *Clostridium tetani* antigen, a *Cornynebacterium diphtheriae* antigen, a *Haemophilus influenzae* type B (Hib) antigen, a *Pseudomonas aeruginosa* antigen, a *Legionella pneumophila* antigen, a *Streptococcus agalactiae* antigen, a *Neiserria gonorrhoeae* antigen, a *Chlamydia trachomatis* antigen, a *Treponema pallidum* antigen, a *Haemophilus ducreyi* antigen, an *Enterococcus faecalis* antigen, an *Enterococcus faecium* antigen, a *Helicobacter pylori* antigen, a *Staphylococcus saprophyticus* antigen, a *Yersinia enterocolitica* antigen, an additional *E. coli* antigen, a *Bacillus anthracis* antigen, a *Yersinia pestis* antigen, a *Mycobacterium tuberculosis* antigen, a *Rickettsia* antigen, a *Listeria monocytogenes* antigen, a *Chlamydia pneumoniae* antigen, a *Vibrio cholerae* antigen, a *Salmonella typhi* antigen, a *Borrelia burgdorferi* antigen, a *Porphyromonas gingivalis* antigen, a *Shigella* antigen and a *Klebsiella* antigen.

13. A method of inducing an enhanced immune response in a mammalian subject to polysaccharide comprising:
   administering the polysaccharide conjugate of claim 1 to the mammalian subject.

* * * * *

SEQUENCE LISTING

<160> NUMBER OF SEQ ID NOS: 55

<210> SEQ ID NO 1
<211> LENGTH: 949
<212> TYPE: PRT
<213> ORGANISM: Escherichia coli

<400> SEQUENCE: 1

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Arg Ala Gly Val Ala Val Ala Leu Ser Leu Ala Ala Val Thr Ser Val
        35                  40                  45

Pro Ala Leu Ala Ala Asp Lys Val Gln Ala Gly Glu Thr Val Asn
    50                  55                  60

Asp Gly Thr Leu Thr Asn His Asp Asn Gln Ile Val Phe Gly Thr Ala
65                  70                  75                  80

Asn Gly Met Thr Ile Ser Thr Gly Leu Glu Leu Gly Pro Asp Ser Glu
                85                  90                  95

Glu Asn Thr Gly Gly Gln Trp Ile Gln Asn Gly Gly Ile Ala Gly Asn
            100                 105                 110

Thr Thr Val Thr Thr Asn Gly Arg Gln Val Val Leu Glu Gly Gly Thr
        115                 120                 125

Ala Ser Asp Thr Val Ile Arg Asp Gly Gly Gln Ser Leu Asn Gly
    130                 135                 140

Leu Ala Val Asn Thr Thr Leu Asn Asn Arg Gly Glu Gln Trp Val His
145                 150                 155                 160

Glu Gly Gly Val Ala Thr Gly Thr Ile Ile Asn Arg Asp Gly Tyr Gln
                165                 170                 175

Ser Val Lys Ser Gly Gly Leu Ala Thr Gly Thr Ile Ile Asn Thr Gly
            180                 185                 190

Ala Glu Gly Gly Pro Asp Ser Asp Asn Ser Tyr Thr Gly Gln Lys Val
        195                 200                 205

Gln Gly Thr Ala Glu Ser Thr Thr Ile Asn Lys Asn Gly Arg Gln Ile
    210                 215                 220

Ile Leu Phe Ser Gly Leu Ala Arg Asp Thr Leu Ile Tyr Ala Gly Gly
225                 230                 235                 240

Asp Gln Ser Val His Gly Arg Ala Leu Asn Thr Thr Leu Asn Gly Gly
                245                 250                 255

Tyr Gln Tyr Val His Arg Asp Gly Leu Ala Leu Asn Thr Val Ile Asn
            260                 265                 270

Glu Gly Gly Trp Gln Val Val Lys Ala Gly Ala Ala Gly Asn Thr
        275                 280                 285

Thr Ile Asn Gln Asn Gly Glu Leu Arg Val His Ala Gly Gly Glu Ala
    290                 295                 300

Thr Ala Val Thr Gln Asn Thr Gly Gly Ala Leu Val Thr Ser Thr Ala
305                 310                 315                 320

Ala Thr Val Ile Gly Thr Asn Arg Leu Gly Asn Phe Thr Val Glu Asn
                325                 330                 335

Gly Lys Ala Asp Gly Val Val Leu Glu Ser Gly Gly Arg Leu Asp Val
            340                 345                 350

Leu Glu Ser His Ser Ala Gln Asn Thr Leu Val Asp Asp Gly Gly Thr
        355                 360                 365

Leu Ala Val Ser Ala Gly Gly Lys Ala Thr Ser Val Thr Ile Thr Ser
370                 375                 380

Gly Gly Ala Leu Ile Ala Asp Ser Gly Ala Thr Val Glu Gly Thr Asn
385                 390                 395                 400

Ala Ser Gly Lys Phe Ser Ile Asp Gly Thr Ser Gly Gln Ala Ser Gly
            405                 410                 415

Leu Leu Leu Glu Asn Gly Gly Ser Phe Thr Val Asn Ala Gly Gly Gln
            420                 425                 430

Ala Gly Asn Thr Thr Val Gly His Arg Gly Thr Leu Thr Leu Ala Ala
            435                 440                 445

Gly Gly Ser Leu Ser Gly Arg Thr Gln Leu Ser Lys Gly Ala Ser Met
450                 455                 460

Val Leu Asn Gly Asp Val Val Ser Thr Gly Asp Ile Val Asn Ala Gly
465                 470                 475                 480

Glu Ile Arg Phe Asp Asn Gln Thr Thr Pro Asn Ala Ala Leu Ser Arg
            485                 490                 495

Ala Val Ala Lys Ser Asn Ser Pro Val Thr Phe His Lys Leu Thr Thr
            500                 505                 510

Thr Asn Leu Thr Gly Gln Gly Gly Thr Ile Asn Met Arg Val Arg Leu
            515                 520                 525

Asp Gly Ser Asn Ala Ser Asp Gln Leu Val Ile Asn Gly Gly Gln Ala
530                 535                 540

Thr Gly Lys Thr Trp Leu Ala Phe Thr Asn Val Gly Asn Ser Asn Leu
545                 550                 555                 560

Gly Val Ala Thr Thr Gly Gln Gly Ile Arg Val Val Asp Ala Gln Asn
            565                 570                 575

Gly Ala Thr Thr Glu Glu Gly Ala Phe Ala Leu Ser Arg Pro Leu Gln
            580                 585                 590

Ala Gly Ala Phe Asn Tyr Thr Leu Asn Arg Asp Ser Asp Glu Asp Trp
            595                 600                 605

Tyr Leu Arg Ser Glu Asn Ala Tyr Arg Ala Glu Val Pro Leu Tyr Thr
610                 615                 620

Ser Met Leu Thr Gln Ala Met Asp Tyr Asp Arg Ile Leu Ala Gly Ser
625                 630                 635                 640

Arg Ser His Gln Thr Gly Val Asn Gly Glu Asn Asn Ser Val Arg Leu
            645                 650                 655

Ser Ile Gln Gly Gly His Leu Gly His Asp Asn Asn Gly Gly Ile Ala
            660                 665                 670

Arg Gly Ala Thr Pro Glu Ser Ser Gly Ser Tyr Gly Phe Val Arg Leu
            675                 680                 685

Glu Gly Asp Leu Leu Arg Thr Glu Val Ala Gly Met Ser Leu Thr Thr
690                 695                 700

Gly Val Tyr Gly Ala Ala Gly His Ser Ser Val Asp Val Lys Asp Asp
705                 710                 715                 720

Asp Gly Ser Arg Ala Gly Thr Val Arg Asp Ala Gly Ser Leu Gly
            725                 730                 735

Gly Tyr Leu Asn Leu Val His Thr Ser Ser Gly Leu Trp Ala Asp Ile
            740                 745                 750

Val Ala Gln Gly Thr Arg His Ser Met Lys Ala Ser Ser Asp Asn Asn
            755                 760                 765

Asp Phe Arg Ala Arg Gly Trp Gly Trp Leu Gly Ser Leu Glu Thr Gly
770                 775                 780

Leu Pro Phe Ser Ile Thr Asp Asn Leu Met Leu Glu Pro Gln Leu Gln

```
                785                 790                 795                 800
        Tyr Thr Trp Gln Gly Leu Ser Leu Asp Asp Gly Gln Asp Asn Ala Gly
                        805                 810                 815

Tyr Val Lys Phe Gly His Gly Ser Ala Gln His Val Arg Ala Gly Phe
                        820                 825                 830

Arg Leu Gly Ser His Asn Asp Met Thr Phe Gly Glu Gly Thr Ser Ser
                        835                 840                 845

Arg Asp Thr Leu Arg Asp Ser Ala Lys His Ser Val Ser Glu Leu Pro
                        850                 855                 860

Val Asn Trp Trp Val Gln Pro Ser Val Ile Arg Thr Phe Ser Ser Arg
        865                 870                 875                 880

Gly Asp Met Ser Met Gly Thr Ala Ala Ala Gly Ser Asn Met Thr Phe
                        885                 890                 895

Ser Pro Ser Arg Asn Gly Thr Ser Leu Asp Leu Gln Ala Gly Leu Glu
                        900                 905                 910

Ala Arg Ile Arg Glu Asn Ile Thr Leu Gly Val Gln Ala Gly Tyr Ala
                        915                 920                 925

His Ser Val Ser Gly Ser Ala Glu Gly Tyr Asn Gly Gln Ala Thr
                        930                 935                 940

Leu Asn Met Thr Phe
        945

<210> SEQ ID NO 2
<211> LENGTH: 949
<212> TYPE: PRT
<213> ORGANISM: Escherichia coli

<400> SEQUENCE: 2

Met Lys Arg His Leu Asn Thr Ser Tyr Arg Leu Val Trp Asn His Ile
        1               5                   10                  15

Thr Gly Thr Leu Val Val Ala Ser Glu Leu Ala Arg Ser Arg Gly Lys
                        20                  25                  30

Arg Ala Gly Val Ala Val Ala Leu Ser Leu Ala Ala Val Thr Ser Val
                        35                  40                  45

Pro Ala Leu Ala Ala Asp Lys Val Val Gln Ala Gly Glu Thr Val Asn
                        50                  55                  60

Asp Gly Thr Leu Thr Asn His Asp Asn Gln Ile Val Phe Gly Thr Ala
        65                  70                  75                  80

Asn Gly Met Thr Ile Ser Thr Gly Leu Glu Leu Gly Pro Asp Ser Glu
                        85                  90                  95

Glu Asn Thr Gly Gly Gln Trp Ile Gln Asn Gly Gly Ile Ala Gly Asn
                        100                 105                 110

Thr Thr Val Thr Thr Asn Gly Arg Gln Val Val Leu Glu Gly Gly Thr
                        115                 120                 125

Ala Ser Asp Thr Val Ile Arg Asp Gly Gly Gln Ser Leu Asn Gly
        130                 135                 140

Leu Ala Val Asn Thr Thr Leu Asn Asn Arg Gly Glu Gln Trp Val His
        145                 150                 155                 160

Glu Gly Gly Val Ala Thr Gly Thr Ile Ile Asn Arg Asp Gly Tyr Gln
                        165                 170                 175

Ser Val Lys Ser Gly Gly Leu Ala Thr Gly Thr Ile Ile Asn Thr Gly
                        180                 185                 190

Ala Glu Gly Gly Pro Asp Ser Asp Asn Ser Tyr Thr Gly Gln Lys Val
                        195                 200                 205
```

```
Gln Gly Thr Ala Glu Ser Thr Thr Ile Asn Lys Asn Gly Arg Gln Ile
210                 215                 220

Ile Leu Phe Ser Gly Leu Ala Arg Asp Thr Leu Ile Tyr Ala Gly Gly
225                 230                 235                 240

Asp Gln Ser Val His Gly Arg Ala Leu Asn Thr Thr Leu Asn Gly Gly
                245                 250                 255

Tyr Gln Tyr Val His Arg Asp Gly Leu Ala Leu Asn Thr Val Ile Asn
            260                 265                 270

Glu Gly Gly Trp Gln Val Val Lys Ala Gly Ala Ala Gly Asn Thr
            275                 280                 285

Thr Ile Asn Gln Asn Gly Glu Leu Arg Val His Ala Gly Gly Glu Ala
290                 295                 300

Thr Ala Val Thr Gln Asn Thr Gly Gly Ala Leu Val Thr Ser Thr Ala
305                 310                 315                 320

Ala Thr Val Ile Gly Thr Asn Arg Leu Gly Asn Phe Thr Val Glu Asn
                325                 330                 335

Gly Lys Ala Asp Gly Val Val Leu Glu Ser Gly Arg Leu Asp Val
            340                 345                 350

Leu Glu Ser His Ser Ala Gln Asn Thr Leu Val Asp Asp Gly Gly Thr
            355                 360                 365

Leu Ala Val Ser Ala Gly Gly Lys Ala Thr Ser Val Thr Ile Thr Ser
370                 375                 380

Gly Gly Ala Leu Ile Ala Asp Ser Gly Ala Thr Val Glu Gly Thr Asn
385                 390                 395                 400

Ala Ser Gly Lys Phe Ser Ile Asp Gly Thr Ser Gly Gln Ala Ser Gly
                405                 410                 415

Leu Leu Leu Glu Asn Gly Gly Ser Phe Thr Val Asn Ala Gly Gly Gln
            420                 425                 430

Ala Gly Asn Thr Thr Val Gly His Arg Gly Thr Leu Thr Leu Ala Ala
            435                 440                 445

Gly Gly Ser Leu Ser Gly Arg Thr Gln Leu Ser Lys Gly Ala Ser Met
450                 455                 460

Val Leu Asn Gly Asp Val Val Ser Thr Gly Asp Ile Val Asn Ala Gly
465                 470                 475                 480

Glu Ile Arg Phe Asp Asn Gln Thr Thr Pro Asn Ala Ala Leu Ser Arg
                485                 490                 495

Ala Val Ala Lys Ser Asn Ser Pro Val Thr Phe His Lys Leu Thr Thr
            500                 505                 510

Thr Asn Leu Thr Gly Gln Gly Gly Thr Ile Asn Met Arg Val Arg Leu
            515                 520                 525

Asp Gly Ser Asn Ala Ser Asp Gln Leu Val Ile Asn Gly Gly Gln Ala
530                 535                 540

Thr Gly Lys Thr Trp Leu Ala Phe Thr Asn Val Gly Asn Ser Asn Leu
545                 550                 555                 560

Gly Val Ala Thr Thr Gly Gln Gly Ile Arg Val Val Asp Ala Gln Asn
                565                 570                 575

Gly Ala Thr Thr Glu Glu Gly Ala Phe Ala Leu Ser Arg Pro Leu Gln
            580                 585                 590

Ala Gly Ala Phe Asn Tyr Thr Leu Asn Arg Asp Ser Asp Glu Asp Trp
            595                 600                 605

Tyr Leu Arg Ser Glu Asn Ala Tyr Arg Ala Glu Val Pro Leu Tyr Thr
610                 615                 620

Ser Met Leu Thr Gln Ala Met Asp Tyr Asp Arg Ile Leu Ala Gly Ser
```

```
                625                 630                 635                 640
        Arg Ser His Gln Thr Gly Val Asn Gly Glu Asn Asn Ser Val Arg Leu
                        645                 650                 655

Ser Ile Gln Gly Gly His Leu Gly His Asp Asn Asn Gly Gly Ile Ala
                        660                 665                 670

Arg Gly Ala Thr Pro Glu Ser Gly Ser Tyr Gly Phe Val Arg Leu
                        675                 680                 685

Glu Gly Asp Leu Leu Arg Thr Glu Val Ala Gly Met Ser Leu Thr Thr
                        690                 695                 700

Gly Val Tyr Gly Ala Ala Gly His Ser Ser Val Asp Val Lys Asp Asp
        705                 710                 715                 720

Asp Gly Ser Arg Ala Gly Thr Val Arg Asp Ala Gly Ser Leu Gly
                        725                 730                 735

Gly Tyr Leu Asn Leu Val His Thr Ser Ser Gly Leu Trp Ala Asp Ile
                        740                 745                 750

Val Ala Gln Gly Thr Arg His Ser Met Lys Ala Ser Ser Asp Asn Asn
                        755                 760                 765

Asp Phe Arg Ala Arg Gly Trp Gly Trp Leu Gly Ser Leu Glu Thr Gly
                        770                 775                 780

Leu Pro Phe Ser Ile Thr Asp Asn Leu Met Leu Glu Pro Gln Leu Gln
        785                 790                 795                 800

Tyr Thr Trp Gln Gly Leu Ser Leu Asp Asp Gly Gln Asp Asn Ala Gly
                        805                 810                 815

Tyr Val Lys Phe Gly His Gly Ser Ala Gln His Val Arg Ala Gly Phe
                        820                 825                 830

Arg Leu Gly Ser His Asn Asp Met Thr Phe Gly Glu Gly Thr Ser Ser
                        835                 840                 845

Arg Asp Thr Leu Arg Asp Ser Ala Lys His Ser Val Ser Glu Leu Pro
                        850                 855                 860

Val Asn Trp Trp Val Gln Pro Ser Val Ile Arg Thr Phe Ser Ser Arg
        865                 870                 875                 880

Gly Asp Met Ser Met Gly Thr Ala Ala Ala Gly Ser Asn Met Thr Phe
                        885                 890                 895

Ser Pro Ser Arg Asn Gly Thr Ser Leu Asp Leu Gln Ala Gly Leu Glu
                        900                 905                 910

Ala Arg Ile Arg Glu Asn Ile Thr Leu Gly Val Gln Ala Gly Tyr Ala
                        915                 920                 925

His Ser Val Ser Gly Ser Ser Ala Glu Gly Tyr Asn Gly Gln Ala Thr
                        930                 935                 940

Leu Asn Met Thr Phe
        945

<210> SEQ ID NO 3
<211> LENGTH: 949
<212> TYPE: PRT
<213> ORGANISM: Escherichia coli

<400> SEQUENCE: 3

Met Lys Arg His Leu Asn Thr Ser Tyr Arg Leu Val Trp Asn His Ile
        1               5                   10                  15

Thr Gly Thr Leu Val Val Ala Ser Glu Leu Ala Arg Ser Arg Gly Lys
                        20                  25                  30

Arg Ala Gly Val Ala Val Ala Leu Ser Leu Ala Ala Val Thr Ser Val
                        35                  40                  45
```

-continued

```
Pro Ala Leu Ala Ala Asp Thr Val Val Gln Ala Gly Glu Thr Val Asn
         50                  55                  60
Gly Gly Thr Leu Thr Asn His Asp Asn Gln Ile Val Leu Gly Thr Ala
 65                  70                  75                  80
Asn Gly Met Thr Ile Ser Thr Gly Leu Glu Leu Gly Pro Asp Ser Glu
                 85                  90                  95
Glu Asn Thr Gly Gly Gln Trp Ile Gln Asn Gly Gly Ile Ala Gly Asn
                100                 105                 110
Thr Thr Val Thr Thr Asn Gly Arg Gln Val Val Leu Glu Gly Gly Thr
            115                 120                 125
Ala Ser Asp Thr Val Ile Arg Asp Gly Gly Gln Ser Leu Asn Gly
        130                 135                 140
Leu Ala Val Asn Thr Thr Leu Asn Asn Arg Gly Glu Gln Trp Val His
145                 150                 155                 160
Glu Gly Gly Val Ala Thr Gly Thr Ile Ile Asn Arg Asp Gly Tyr Gln
                165                 170                 175
Ser Val Lys Ser Gly Gly Leu Ala Thr Gly Thr Ile Ile Asn Thr Gly
            180                 185                 190
Ala Glu Gly Gly Pro Asp Ser Asp Asn Ser Tyr Thr Gly Gln Lys Val
        195                 200                 205
Gln Gly Thr Ala Glu Ser Thr Thr Ile Asn Lys Asn Gly Arg Gln Ile
    210                 215                 220
Ile Leu Phe Ser Gly Leu Ala Arg Asp Thr Leu Ile Tyr Ala Gly Gly
225                 230                 235                 240
Asp Gln Ser Val His Gly Arg Ala Leu Asn Thr Thr Leu Asn Gly Gly
                245                 250                 255
Tyr Gln Tyr Val His Lys Asp Gly Leu Ala Leu Asn Thr Val Ile Asn
            260                 265                 270
Glu Gly Gly Trp Gln Val Val Lys Ala Gly Ala Val Gly Asn Thr
        275                 280                 285
Thr Ile Asn Gln Asn Gly Glu Leu Arg Val His Ala Gly Gly Glu Ala
    290                 295                 300
Thr Ala Val Thr Gln Asn Thr Gly Gly Ala Leu Val Thr Ser Thr Ala
305                 310                 315                 320
Ala Thr Val Thr Gly Ala Asn Arg Leu Gly His Phe Ser Val Gly Asn
                325                 330                 335
Gly Met Ala Asp Asn Val Val Leu Glu Asn Gly Gly Arg Leu Asp Val
            340                 345                 350
Leu Glu Gly His Ser Ala Gln Asn Thr Leu Val Asp Asp Gly Gly Thr
        355                 360                 365
Leu Ala Val Ser Ala Gly Gly Lys Ala Thr Asp Val Thr Met Thr Ser
    370                 375                 380
Gly Gly Ala Leu Ile Ala Asp Ser Gly Ala Thr Val Glu Gly Thr Asn
385                 390                 395                 400
Ala Ser Gly Lys Phe Ser Ile Asp Gly Ile Ser Gly Gln Ala Ser Gly
                405                 410                 415
Leu Leu Leu Glu Asn Gly Gly Ser Phe Thr Val Asn Ala Gly Gly Gln
            420                 425                 430
Ala Gly Asn Thr Thr Val Gly His Arg Gly Thr Leu Thr Leu Ala Ala
        435                 440                 445
Gly Gly Ser Leu Ser Gly Arg Thr Gln Leu Ser Lys Gly Ala Ser Met
    450                 455                 460
Val Leu Asn Gly Asp Val Val Ser Thr Gly Asp Ile Val Asn Ala Gly
```

```
              465                 470                 475                 480
        Glu Ile Arg Phe Asp Asn Gln Thr Thr Gln Asp Ala Val Leu Ser Arg
                        485                 490                 495

Ala Val Ala Lys Gly Asp Ser Pro Val Thr Phe His Lys Leu Thr Thr
                        500                 505                 510

Asn Asn Leu Thr Gly Gln Gly Thr Ile Asn Met Arg Val Arg Leu
                        515                 520                 525

Asp Gly Ser Asn Ala Ser Asp Gln Leu Val Ile Asn Gly Gly Gln Ala
                        530                 535                 540

Thr Gly Lys Thr Trp Leu Ala Phe Thr Asn Val Gly Asn Ser Asn Leu
        545                 550                 555                 560

Gly Val Ala Thr Ser Gly Gln Gly Ile Arg Val Val Asp Ala Gln Asn
                        565                 570                 575

Gly Ala Thr Thr Glu Gly Ala Phe Ala Leu Ser Arg Pro Leu Gln
                        580                 585                 590

Ala Gly Ala Phe Asn Tyr Thr Leu Asn Arg Asp Ser Asp Glu Asp Trp
                        595                 600                 605

Tyr Leu Arg Ser Glu Asn Ala Tyr Arg Ala Glu Val Pro Leu Tyr Ala
                        610                 615                 620

Ser Met Leu Thr Gln Ala Met Asp Tyr Asp Arg Ile Leu Ala Gly Ser
        625                 630                 635                 640

Arg Ser His Gln Thr Gly Val Asn Gly Glu Asn Asn Ser Val Arg Leu
                        645                 650                 655

Ser Ile Gln Gly Gly His Leu Gly His Asp Asn Asn Gly Gly Ile Ala
                        660                 665                 670

Arg Gly Ala Thr Pro Glu Ser Ser Gly Ser Tyr Gly Phe Val Arg Leu
                        675                 680                 685

Glu Gly Asp Leu Leu Arg Thr Glu Val Ala Gly Met Ser Leu Thr Thr
                        690                 695                 700

Gly Val Tyr Gly Ala Ala Gly His Ser Ser Val Asp Val Lys Asp Asp
        705                 710                 715                 720

Asp Gly Ser Arg Ala Gly Thr Val Arg Asp Ala Gly Ser Leu Gly
                        725                 730                 735

Gly Tyr Leu Asn Leu Thr His Thr Ser Ser Gly Leu Trp Ala Asp Ile
                        740                 745                 750

Val Ala Gln Gly Thr Arg His Ser Met Lys Ala Ser Ser Asp Asn Asn
                        755                 760                 765

Asp Phe Arg Ala Arg Gly Trp Gly Trp Leu Gly Ser Leu Glu Thr Gly
                        770                 775                 780

Leu Pro Phe Ser Ile Thr Asp Asn Leu Met Leu Glu Pro Gln Leu Gln
        785                 790                 795                 800

Tyr Thr Trp Gln Gly Leu Ser Leu Asp Asp Gly Gln Asp Asn Ala Gly
                        805                 810                 815

Tyr Val Lys Phe Gly His Gly Ser Ala Gln His Val Arg Ala Gly Phe
                        820                 825                 830

Arg Leu Gly Ser His Asn Asp Met Thr Phe Gly Glu Gly Thr Ser Ser
                        835                 840                 845

Arg Asp Thr Leu Arg Asp Ser Ala Lys His Ser Val Ser Glu Leu Pro
                        850                 855                 860

Val Asn Trp Trp Val Gln Pro Ser Val Ile Arg Thr Val Ser Ser Arg
        865                 870                 875                 880

Gly Asp Met Ser Met Gly Thr Ala Ala Ala Gly Ser Asn Met Thr Phe
                        885                 890                 895
```

```
Ser Pro Ser Arg Asn Gly Thr Ser Leu Asp Leu Gln Ala Gly Leu Glu
                900                 905                 910

Ala Arg Val Arg Glu Asn Ile Thr Leu Gly Val Gln Ala Gly Tyr Ala
            915                 920                 925

His Ser Val Ser Gly Ser Ala Glu Gly Tyr Asn Gly Gln Ala Thr
        930                 935                 940

Leu Asn Met Thr Phe
945

<210> SEQ ID NO 4
<211> LENGTH: 949
<212> TYPE: PRT
<213> ORGANISM: Escherichia coli

<400> SEQUENCE: 4

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Arg Ala Gly Val Ala Val Ala Leu Ser Leu Ala Ala Val Thr Ser Val
        35                  40                  45

Pro Ala Leu Ala Ala Asp Thr Val Gln Ala Gly Glu Thr Val Asn
    50                  55                  60

Gly Gly Thr Leu Thr Asn His Asp Asn Gln Ile Val Leu Gly Thr Ala
65                  70                  75                  80

Asn Gly Met Thr Ile Ser Thr Gly Leu Glu Leu Gly Pro Asp Ser Glu
                85                  90                  95

Glu Asn Thr Gly Gly Gln Trp Ile Gln Asn Gly Gly Ile Ala Gly Asn
            100                 105                 110

Thr Thr Val Thr Thr Asn Gly Arg Gln Val Val Leu Glu Gly Gly Thr
        115                 120                 125

Ala Ser Asp Thr Val Ile Arg Asp Gly Gly Gln Ser Leu Asn Gly
    130                 135                 140

Leu Ala Val Asn Thr Thr Leu Asn Asn Arg Gly Glu Gln Trp Val His
145                 150                 155                 160

Glu Gly Gly Val Ala Thr Gly Thr Ile Ile Asn Arg Asp Gly Tyr Gln
                165                 170                 175

Ser Val Lys Ser Gly Gly Leu Ala Thr Gly Thr Ile Ile Asn Thr Gly
            180                 185                 190

Ala Glu Gly Gly Pro Asp Ser Asp Asn Ser Tyr Thr Gly Gln Lys Val
        195                 200                 205

Gln Gly Thr Ala Glu Ser Thr Thr Ile Asn Lys Asn Gly Arg Gln Ile
    210                 215                 220

Ile Leu Phe Ser Gly Leu Ala Arg Asp Thr Leu Ile Tyr Ala Gly Gly
225                 230                 235                 240

Asp Gln Ser Val His Gly Arg Ala Leu Asn Thr Thr Leu Asn Gly Gly
                245                 250                 255

Tyr Gln Tyr Val His Lys Asp Gly Leu Ala Leu Asn Thr Val Ile Asn
            260                 265                 270

Glu Gly Gly Trp Gln Val Val Lys Ala Gly Gly Ala Val Gly Asn Thr
        275                 280                 285

Thr Ile Asn Gln Asn Gly Glu Leu Arg Val His Ala Gly Gly Glu Ala
    290                 295                 300

Thr Ala Val Thr Gln Asn Thr Gly Gly Ala Leu Val Thr Ser Thr Ala
```

```
             305                 310                 315                 320
        Ala Thr Val Thr Gly Ala Asn Arg Leu Gly His Phe Ser Val Gly Asn
                        325                 330                 335
        Gly Met Ala Asp Asn Val Val Leu Glu Asn Gly Gly Arg Leu Asp Val
                        340                 345                 350
        Leu Glu Gly His Ser Ala Gln Asn Thr Leu Val Asp Asp Gly Gly Thr
                        355                 360                 365
        Leu Ala Val Ser Ala Gly Gly Lys Ala Thr Asp Val Thr Met Thr Ser
        370                 375                 380
        Gly Gly Ala Leu Ile Ala Asp Ser Gly Ala Thr Val Glu Gly Thr Asn
        385                 390                 395                 400
        Ala Ser Gly Lys Phe Ser Ile Asp Gly Ile Ser Gly Gln Ala Ser Gly
                        405                 410                 415
        Leu Leu Leu Glu Asn Gly Gly Ser Phe Thr Val Asn Ala Gly Gly Gln
                        420                 425                 430
        Ala Gly Asn Thr Thr Val Gly His Arg Gly Thr Leu Thr Leu Ala Ala
                        435                 440                 445
        Gly Gly Ser Leu Ser Gly Arg Thr Gln Leu Ser Lys Gly Ala Ser Met
                        450                 455                 460
        Val Leu Asn Gly Asp Val Val Ser Thr Gly Asp Ile Val Asn Ala Gly
        465                 470                 475                 480
        Glu Ile Arg Phe Asp Asn Gln Thr Thr Gln Asp Ala Val Leu Ser Arg
                        485                 490                 495
        Ala Val Ala Lys Gly Asp Ser Pro Val Thr Phe His Lys Leu Thr Thr
                        500                 505                 510
        Asn Asn Leu Thr Gly Gln Gly Gly Thr Ile Asn Met Arg Val Arg Leu
                        515                 520                 525
        Asp Gly Ser Asn Ala Ser Asp Gln Leu Val Ile Asn Gly Gly Gln Ala
                        530                 535                 540
        Thr Gly Lys Thr Trp Leu Ala Phe Thr Asn Val Gly Asn Ser Asn Leu
        545                 550                 555                 560
        Gly Val Ala Thr Ser Gly Gln Gly Ile Arg Val Val Asp Ala Gln Asn
                        565                 570                 575
        Gly Ala Thr Thr Glu Glu Ser Ala Phe Ala Leu Ser Arg Pro Leu His
                        580                 585                 590
        Ala Gly Ala Phe Asn Tyr Thr Leu Asn Arg Asp Ser Asp Glu Asp Trp
                        595                 600                 605
        Tyr Leu Arg Ser Glu Asn Ala Tyr Arg Ala Glu Val Pro Leu Tyr Ala
                        610                 615                 620
        Ser Met Leu Thr Gln Ala Met Asp Tyr Asp Arg Ile Leu Ala Gly Ser
        625                 630                 635                 640
        Arg Ser His Gln Ser Gly Val Ser Gly Glu Asn Asn Ser Val Arg Leu
                        645                 650                 655
        Ser Ile Gln Gly Gly His Leu Gly His Asp Asn Asn Gly Gly Ile Ala
                        660                 665                 670
        Arg Gly Ala Thr Pro Glu Ser Asn Gly Ser Tyr Gly Phe Val Arg Leu
                        675                 680                 685
        Glu Gly Asp Leu Leu Arg Thr Glu Val Ala Gly Met Ser Leu Thr Thr
                        690                 695                 700
        Gly Val Tyr Gly Ala Ala Gly His Ser Ser Val Asp Val Lys Asn Asp
        705                 710                 715                 720
        Asp Gly Ser Arg Ala Gly Thr Val Arg Asp Asp Ala Gly Ser Leu Gly
                        725                 730                 735
```

-continued

```
Gly Tyr Leu Asn Leu Val His Thr Ser Ser Gly Leu Trp Ala Asp Ile
                740                 745                 750

Val Ala Gln Gly Thr His His Ser Met Lys Ala Ser Ser Asp Asn Asn
            755                 760                 765

Asp Phe Arg Ala Arg Gly Trp Gly Trp Leu Gly Ser Leu Glu Thr Gly
770                 775                 780

Leu Pro Phe Ser Ile Thr Asp Asn Leu Met Leu Glu Pro Gln Leu Gln
785                 790                 795                 800

Tyr Thr Trp Gln Gly Leu Ser Leu Asp Asp Gly Gln Asp Asn Ala Gly
                805                 810                 815

Tyr Val Lys Phe Gly His Gly Ser Ala Gln His Val Arg Ala Gly Phe
            820                 825                 830

Arg Leu Gly Ser His Asn Asp Met Thr Phe Gly Glu Gly Thr Ser Ser
        835                 840                 845

Arg Asp Thr Leu Arg Asp Ser Ala Lys His Arg Val Arg Glu Leu Pro
850                 855                 860

Val Asn Trp Trp Val Gln Pro Ser Val Ile Arg Thr Val Ser Ser Arg
865                 870                 875                 880

Gly Asp Met Ser Met Gly Thr Ala Ala Ala Gly Ser Asn Met Thr Phe
                885                 890                 895

Ser Pro Ser Arg Asn Gly Thr Ser Leu Asp Leu Gln Ala Gly Leu Glu
            900                 905                 910

Ala Arg Val Arg Glu Asn Ile Thr Leu Gly Val Gln Ala Gly Tyr Ala
        915                 920                 925

His Ser Val Ser Gly Ser Ser Ala Glu Gly Tyr Asn Gly Gln Ala Thr
    930                 935                 940

Leu Asn Met Thr Phe
945

<210> SEQ ID NO 5
<211> LENGTH: 948
<212> TYPE: PRT
<213> ORGANISM: Escherichia coli

<400> SEQUENCE: 5

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Arg Thr Gly Val Ala Val Ala Leu Ser Leu Ala Ala Val Thr Ser Val
        35                  40                  45

Pro Val Leu Ala Ala Asp Thr Val Val Gln Ala Gly Glu Thr Val Ser
    50                  55                  60

Gly Gly Thr Leu Thr Asn His Asp Asn Gln Ile Val Leu Gly Thr Ala
65                  70                  75                  80

Asn Gly Met Thr Ile Ser Thr Gly Leu Glu Tyr Gly Pro Asp Asn Glu
                85                  90                  95

Ala Asn Thr Gly Gly Gln Trp Ile Gln Asn Gly Gly Ile Ala Asn Asn
            100                 105                 110

Thr Thr Val Thr Gly Gly Leu Gln Arg Val Asn Ala Gly Gly Ser
        115                 120                 125

Val Ser Asp Thr Val Ile Ser Ala Gly Gly Gln Ser Leu Gln Gly
    130                 135                 140

Gln Ala Val Asn Thr Thr Leu Asn Gly Gly Glu Gln Trp Val His Glu
```

-continued

```
            145                 150                 155                 160
        Gly Gly Ile Ala Thr Gly Thr Val Ile Asn Glu Lys Gly Trp Gln Ala
                        165                 170                 175

Val Lys Ser Gly Ala Met Ala Thr Asp Thr Val Asn Thr Gly Ala
                        180                 185                 190

Glu Gly Gly Pro Asp Ala Glu Asn Gly Asp Thr Gly Gln Phe Val Arg
                        195                 200                 205

Gly Asn Ala Val Arg Thr Thr Ile Asn Lys Asn Gly Arg Gln Ile Val
        210                 215                 220

Ala Ala Glu Gly Thr Ala Asn Thr Thr Val Val Tyr Ala Gly Gly Asp
        225                 230                 235                 240

Gln Thr Val His Gly His Ala Leu Asp Thr Thr Leu Asn Gly Gly Tyr
                        245                 250                 255

Gln Tyr Val His Asn Gly Gly Thr Ala Ser Gly Thr Val Val Asn Ser
                        260                 265                 270

Asp Gly Trp Gln Ile Ile Lys Glu Gly Gly Leu Ala Asp Phe Thr Thr
                        275                 280                 285

Val Asn Gln Lys Gly Lys Leu Gln Val Asn Ala Gly Gly Thr Ala Thr
        290                 295                 300

His Val Thr Leu Lys Gln Gly Gly Ala Leu Val Thr Ser Thr Ala Ala
        305                 310                 315                 320

Thr Val Leu Gly Ser Asn Arg Leu Gly Asn Phe Thr Val Glu Asn Gly
                        325                 330                 335

Lys Ala Asp Gly Val Val Leu Glu Ser Gly Gly Arg Leu Asp Val Leu
                        340                 345                 350

Glu Gly His Ser Ala Gln Lys Thr Arg Val Asp Asp Gly Gly Thr Leu
                        355                 360                 365

Ala Val Ser Ala Gly Gly Lys Ala Thr Asp Val Thr Met Thr Ser Gly
                        370                 375                 380

Ser Ala Leu Ile Ala Asp Ser Gly Ala Thr Val Glu Gly Thr Asn Ala
        385                 390                 395                 400

Ser Gly Lys Phe Ser Ile Asp Gly Thr Ser Gln Ala Ser Gly Leu
                        405                 410                 415

Leu Leu Glu Asn Gly Gly Ser Phe Thr Val Asn Ala Gly Gly Leu Ala
                        420                 425                 430

Ser Asn Thr Thr Val Gly His Arg Gly Thr Leu Thr Leu Ala Ala Gly
                        435                 440                 445

Gly Ser Leu Ser Gly Arg Thr Gln Leu Ser Lys Gly Ala Ser Met Val
                        450                 455                 460

Leu Asn Gly Asp Val Val Ser Thr Gly Asp Ile Val Asn Ala Gly Glu
        465                 470                 475                 480

Ile Arg Phe Asp Asn Gln Thr Thr Gln Asp Ala Val Leu Ser Arg Ala
                        485                 490                 495

Val Ala Lys Gly Asp Ser Pro Val Thr Phe His Lys Leu Thr Thr Ser
                        500                 505                 510

Asn Leu Thr Gly Gln Gly Gly Thr Ile Asn Met Arg Val Arg Leu Asp
                        515                 520                 525

Gly Ser Asn Thr Ser Asp Gln Leu Val Ile Asn Gly Gly Gln Ala Thr
                        530                 535                 540

Gly Lys Thr Trp Leu Ala Phe Thr Asn Val Gly Asn Ser Asn Leu Gly
        545                 550                 555                 560

Val Ala Thr Ser Gly Gln Gly Ile Arg Val Val Asp Ala Gln Asn Gly
                        565                 570                 575
```

Ala Thr Thr Glu Glu Gly Ala Phe Ala Leu Ser Arg Pro Leu Gln Ala
            580                 585                 590

Gly Ala Phe Asn Tyr Thr Leu Asn Arg Asp Ser Asp Glu Asp Trp Tyr
        595                 600                 605

Leu Arg Ser Glu Asn Ala Tyr Arg Ala Glu Val Pro Leu Tyr Ala Ser
    610                 615                 620

Met Leu Thr Gln Ala Met Asp Tyr Asp Arg Ile Leu Ala Gly Ser Arg
625                 630                 635                 640

Ser His Gln Thr Gly Val Asn Gly Glu Asn Asn Ser Val Arg Leu Ser
                645                 650                 655

Ile Gln Gly Gly His Leu Gly His Asp Asn Asn Gly Ile Ala Arg
            660                 665                 670

Gly Ala Thr Pro Glu Ser Asn Gly Ser Tyr Gly Phe Val Arg Leu Glu
            675                 680                 685

Gly Asp Leu Leu Arg Thr Glu Val Ala Gly Met Ser Leu Thr Thr Gly
        690                 695                 700

Val Tyr Gly Ala Ala Gly His Ser Ser Val Asp Val Lys Asp Asp Asp
705                 710                 715                 720

Gly Ser Arg Ala Gly Thr Val Arg Asp Asp Ala Gly Ser Leu Gly Gly
                725                 730                 735

Tyr Leu Asn Leu Thr His Thr Ser Ser Gly Leu Trp Ala Asp Ile Val
            740                 745                 750

Ala Gln Gly Thr Arg His Ser Met Lys Ala Ser Ser Asp Asn Asn Asp
            755                 760                 765

Phe Arg Ala Arg Gly Trp Trp Leu Gly Ser Leu Glu Thr Gly Leu
770                 775                 780

Pro Phe Ser Ile Thr Asp Asn Val Met Leu Glu Pro Gln Leu Gln Tyr
785                 790                 795                 800

Thr Trp Gln Gly Leu Ser Leu Asp Asp Gly Gln Asp Asn Ala Gly Tyr
                805                 810                 815

Val Lys Phe Gly His Gly Ser Ala Gln His Val Arg Ala Gly Phe Arg
            820                 825                 830

Leu Gly Ser His Asn Asp Met Ser Phe Gly Glu Gly Thr Ser Ser Arg
            835                 840                 845

Asp Thr Leu Arg Asp Ser Ala Lys His Arg Val Arg Glu Leu Pro Val
    850                 855                 860

Asn Trp Trp Val Gln Pro Ser Val Ile Arg Thr Phe Ser Ser Arg Gly
865                 870                 875                 880

Asp Met Ser Met Gly Thr Ala Ala Gly Ser Asn Met Thr Phe Ser
                885                 890                 895

Pro Ser Arg Asn Gly Thr Ser Leu Asp Leu Gln Ala Gly Leu Glu Ala
                900                 905                 910

Arg Val Arg Glu Asn Ile Thr Leu Gly Val Gln Ala Gly Tyr Ala His
            915                 920                 925

Ser Val Ser Gly Ser Ser Ala Glu Gly Tyr Asn Gly Gln Ala Thr Leu
            930                 935                 940

Asn Val Thr Phe
945

<210> SEQ ID NO 6
<211> LENGTH: 948
<212> TYPE: PRT
<213> ORGANISM: Escherichia coli

<400> SEQUENCE: 6

```
Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Arg Thr Gly Val Ala Val Ala Leu Ser Leu Ala Ala Val Thr Ser Val
        35                  40                  45

Pro Val Leu Ala Ala Asp Thr Val Gln Ala Gly Glu Thr Val Ser
    50                  55                  60

Gly Gly Thr Leu Thr Asn His Asp Asn Gln Ile Val Leu Gly Thr Ala
65                  70                  75                  80

Asn Gly Met Thr Ile Ser Thr Gly Leu Glu Tyr Gly Pro Asp Asn Glu
                85                  90                  95

Ala Asn Thr Gly Gly Gln Trp Ile Gln Asn Gly Gly Ile Ala Asn Asn
            100                 105                 110

Thr Thr Val Thr Gly Gly Leu Gln Arg Val Asn Ala Gly Gly Ser
        115                 120                 125

Val Ser Asp Thr Val Ile Ser Ala Gly Gly Gln Ser Leu Gln Gly
    130                 135                 140

Gln Ala Val Asn Thr Thr Leu Asn Gly Gly Glu Gln Trp Val His Glu
145                 150                 155                 160

Gly Gly Ile Ala Thr Gly Thr Val Ile Asn Glu Lys Gly Trp Gln Ala
                165                 170                 175

Val Lys Ser Gly Ala Met Ala Thr Asp Thr Val Asn Thr Gly Ala
            180                 185                 190

Glu Gly Gly Pro Asp Ala Glu Asn Gly Asp Thr Gly Gln Phe Val Arg
        195                 200                 205

Gly Asn Ala Val Arg Thr Thr Ile Asn Lys Asn Gly Arg Gln Ile Val
    210                 215                 220

Ala Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
                245                 250                 255

Gln Tyr Val His Asn Gly Gly Thr Ala Ser Gly Thr Val Val Asn Ser
            260                 265                 270

Asp Gly Trp Gln Ile Ile Lys Glu Gly Gly Leu Ala Asp Phe Thr Thr
        275                 280                 285

Val Asn Gln Lys Gly Lys Leu Gln Val Asn Ala Gly Gly Thr Ala Thr
    290                 295                 300

His Val Thr Leu Lys Gln Gly Gly Ala Leu Val Thr Ser Thr Ala Ala
305                 310                 315                 320

Thr Val Leu Gly Ser Asn Arg Leu Gly Asn Phe Thr Val Glu Asn Gly
                325                 330                 335

Lys Ala Asp Gly Val Val Leu Glu Ser Gly Gly Arg Leu Asp Val Leu
            340                 345                 350

Glu Gly His Ser Ala Gln Lys Thr Arg Val Asp Asp Gly Gly Thr Leu
        355                 360                 365

Ala Val Ser Ala Gly Gly Lys Ala Thr Asp Val Thr Met Thr Ser Gly
    370                 375                 380

Ser Ala Leu Ile Ala Asp Ser Gly Ala Thr Val Glu Gly Thr Asn Ala
385                 390                 395                 400

Ser Gly Lys Phe Ser Ile Asp Gly Thr Ser Gly Gln Ala Ser Gly Leu
                405                 410                 415
```

```
Leu Leu Glu Asn Gly Gly Ser Phe Thr Val Asn Ala Gly Gly Leu Ala
            420                 425                 430

Ser Asn Thr Thr Val Gly His Arg Gly Thr Leu Thr Leu Ala Ala Gly
        435                 440                 445

Gly Ser Leu Ser Gly Arg Thr Gln Leu Ser Lys Gly Ala Ser Met Val
    450                 455                 460

Leu Asn Gly Asp Val Val Ser Thr Gly Asp Ile Val Asn Ala Gly Glu
465                 470                 475                 480

Ile Arg Phe Asp Asn Thr Thr Gln Asp Ala Val Leu Ser Arg Ala
                485                 490                 495

Val Ala Lys Gly Asp Ser Pro Val Thr Phe His Lys Leu Thr Thr Ser
            500                 505                 510

Asn Leu Thr Gly Gln Gly Gly Thr Ile Asn Met Arg Val Arg Leu Asp
        515                 520                 525

Gly Ser Asn Thr Ser Asp Gln Leu Val Ile Asn Gly Gln Ala Thr
    530                 535                 540

Gly Lys Thr Trp Leu Ala Phe Thr Asn Val Gly Asn Ser Asn Leu Gly
545                 550                 555                 560

Val Ala Thr Ser Gly Gln Gly Ile Arg Val Val Asp Ala Gln Asn Gly
                565                 570                 575

Ala Thr Thr Glu Glu Gly Ala Phe Ala Leu Ser Arg Pro Leu Gln Ala
            580                 585                 590

Gly Ala Phe Asn Tyr Thr Leu Asn Arg Asp Ser Asp Glu Asp Trp Tyr
        595                 600                 605

Leu Arg Ser Glu Asn Ala Tyr Arg Ala Glu Val Pro Leu Tyr Ala Ser
    610                 615                 620

Met Leu Thr Gln Ala Met Asp Tyr Asp Arg Ile Leu Ala Gly Ser Arg
625                 630                 635                 640

Ser His Gln Thr Gly Val Asn Gly Glu Asn Asn Ser Val Arg Leu Ser
                645                 650                 655

Ile Gln Gly Gly His Leu Gly His Asp Asn Asn Gly Gly Ile Ala Arg
            660                 665                 670

Gly Ala Thr Pro Glu Ser Asn Gly Ser Tyr Gly Phe Val Arg Leu Glu
        675                 680                 685

Gly Asp Leu Leu Arg Thr Glu Val Ala Gly Met Ser Leu Thr Thr Gly
    690                 695                 700

Val Tyr Gly Ala Ala Gly His Ser Ser Val Asp Val Lys Asp Asp Asp
705                 710                 715                 720

Gly Ser Arg Ala Gly Thr Val Arg Asp Asp Ala Gly Ser Leu Gly Gly
                725                 730                 735

Tyr Leu Asn Leu Thr His Thr Ser Ser Gly Leu Trp Ala Asp Ile Val
            740                 745                 750

Ala Gln Gly Thr Arg His Ser Met Lys Ala Ser Ser Asp Asn Asn Asp
        755                 760                 765

Phe Arg Ala Arg Gly Trp Gly Trp Leu Gly Ser Leu Glu Thr Gly Leu
    770                 775                 780

Pro Phe Ser Ile Thr Asp Asn Leu Met Leu Glu Pro Gln Leu Gln Tyr
785                 790                 795                 800

Thr Trp Gln Gly Leu Ser Leu Asp Asp Gly Gln Asp Asn Ala Gly Tyr
                805                 810                 815

Val Lys Phe Gly His Gly Ser Ala Gln His Val Arg Ala Gly Phe Arg
            820                 825                 830
```

```
Leu Gly Ser His Asn Asp Met Ser Phe Gly Glu Gly Thr Ser Ser Arg
            835                 840                 845

Asp Thr Leu Arg Asp Ser Ala Lys His Arg Val Arg Glu Leu Pro Val
    850                 855                 860

Asn Trp Trp Val Gln Pro Ser Val Ile Arg Thr Phe Ser Ser Arg Gly
865                 870                 875                 880

Asp Met Ser Met Gly Thr Ala Ala Gly Ser Asn Met Thr Phe Ser
                885                 890                 895

Pro Ser Arg Asn Gly Thr Ser Leu Asp Leu Gln Ala Gly Leu Glu Ala
                900                 905                 910

Arg Val Arg Glu Asn Ile Thr Leu Gly Val Gln Ala Gly Tyr Ala His
            915                 920                 925

Ser Val Ser Gly Ser Ser Ala Glu Gly Tyr Asn Gly Gln Ala Thr Leu
            930                 935                 940

Asn Val Thr Phe
945

<210> SEQ ID NO 7
<211> LENGTH: 948
<212> TYPE: PRT
<213> ORGANISM: Escherichia coli

<400> SEQUENCE: 7

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Arg Thr Gly Val Ala Val Ala Leu Ser Leu Ala Ala Val Thr Ser Val
        35                  40                  45

Pro Val Leu Ala Ala Asp Thr Val Gln Ala Gly Glu Thr Val Ser
    50                  55                  60

Gly Gly Thr Leu Thr Asn His Asp Asn Gln Ile Val Phe Gly Thr Ala
65                  70                  75                  80

Asn Gly Met Thr Ile Ser Thr Gly Leu Glu Tyr Gly Pro Asp Asn Glu
                85                  90                  95

Ala Asn Thr Gly Gly Gln Trp Ile Gln Asn Gly Gly Ile Ala Asn Asn
                100                 105                 110

Thr Thr Val Thr Gly Gly Gly Leu Gln Arg Val Asn Ala Gly Gly Ser
        115                 120                 125

Val Ser Asp Thr Val Ile Ser Ala Gly Gly Gln Ser Leu Gln Gly
    130                 135                 140

Gln Ala Val Asn Thr Thr Leu Asn Gly Gly Glu Gln Trp Val His Glu
145                 150                 155                 160

Gly Gly Ile Ala Thr Gly Thr Val Ile Asn Glu Lys Gly Trp Gln Ala
                165                 170                 175

Val Lys Ser Gly Ala Met Ala Thr Asp Thr Val Val Asn Thr Gly Ala
                180                 185                 190

Glu Gly Gly Pro Asp Ala Glu Asn Gly Asp Thr Gly Gln Phe Val Arg
        195                 200                 205

Gly Asn Ala Val Arg Thr Thr Ile Asn Glu Asn Gly Arg Gln Ile Val
    210                 215                 220

Ala Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
                245                 250                 255
```

-continued

```
Gln Tyr Val His Asn Gly Gly Thr Ala Ser Asp Thr Val Asn Ser
            260                 265                 270

Asp Gly Trp Gln Ile Val Lys Glu Gly Gly Leu Ala Asp Phe Thr Thr
            275                 280                 285

Val Asn Gln Lys Gly Lys Leu Gln Val Asn Ala Gly Gly Thr Ala Thr
290                 295                 300

Asn Val Thr Leu Lys Gln Gly Ala Leu Val Thr Ser Thr Ala Ala
305                 310                 315                 320

Thr Val Thr Gly Ser Asn Arg Leu Gly Asn Phe Thr Val Glu Asn Gly
            325                 330                 335

Asn Ala Asp Gly Val Val Leu Glu Ser Gly Arg Leu Asp Val Leu
            340                 345                 350

Glu Gly His Ser Ala Trp Lys Thr Leu Val Asp Asp Gly Gly Thr Leu
            355                 360                 365

Ala Val Ser Ala Gly Gly Lys Ala Thr Asp Val Thr Met Thr Ser Gly
    370                 375                 380

Ser Ala Leu Ile Ala Asp Ser Gly Ala Thr Val Glu Gly Thr Asn Ala
385                 390                 395                 400

Ser Gly Lys Phe Ser Ile Asp Gly Thr Ser Gly Gln Ala Ser Gly Leu
            405                 410                 415

Leu Leu Glu Asn Gly Gly Ser Phe Thr Val Asn Ala Gly Gly Leu Ala
            420                 425                 430

Ser Asn Thr Thr Val Gly His Arg Gly Thr Leu Thr Leu Ala Ala Gly
            435                 440                 445

Gly Ser Leu Ser Gly Arg Thr Gln Leu Ser Lys Gly Ala Ser Met Val
    450                 455                 460

Leu Asn Gly Asp Val Val Ser Thr Gly Asp Ile Val Asn Ala Gly Glu
465                 470                 475                 480

Ile Arg Phe Asp Asn Gln Thr Thr Pro Asp Ala Ala Leu Ser Arg Ala
            485                 490                 495

Val Ala Lys Gly Asp Ser Pro Val Thr Phe His Lys Leu Thr Thr Ser
            500                 505                 510

Asn Leu Thr Gly Gln Gly Gly Thr Ile Asn Met Arg Val Arg Leu Asp
            515                 520                 525

Gly Ser Asn Thr Ser Asp Gln Leu Val Ile Asn Gly Gly Gln Ala Thr
    530                 535                 540

Gly Lys Thr Trp Leu Ala Phe Thr Asn Val Gly Asn Ser Asn Leu Gly
545                 550                 555                 560

Val Ala Thr Ser Gly Gln Gly Ile Arg Val Val Asp Ala Gln Asn Gly
            565                 570                 575

Ala Thr Thr Glu Glu Gly Ala Phe Ala Leu Ser Arg Pro Leu Gln Ala
            580                 585                 590

Gly Ala Phe Asn Tyr Thr Leu Asn Arg Asp Ser Asp Glu Asp Trp Tyr
            595                 600                 605

Leu Arg Ser Glu Asn Ala Tyr Arg Ala Glu Val Pro Leu Tyr Thr Ser
            610                 615                 620

Met Leu Thr Gln Ala Met Asp Tyr Asp Arg Ile Leu Ala Gly Ser Arg
625                 630                 635                 640

Ser His Gln Thr Gly Val Asn Gly Glu Asn Asn Ser Val Arg Leu Ser
            645                 650                 655

Ile Gln Gly Gly His Leu Gly His Asp Asn Asn Gly Gly Ile Ala Arg
            660                 665                 670
```

```
Gly Ala Thr Pro Glu Ser Ser Gly Ser Tyr Gly Phe Val Arg Leu Glu
            675                 680                 685

Gly Asp Leu Leu Arg Thr Glu Val Ala Gly Met Ser Leu Thr Thr Gly
690                 695                 700

Val His Gly Ala Ala Gly His Ser Ser Val Asp Val Lys Asp Asp
705                 710                 715                 720

Gly Ser Arg Ala Gly Thr Val Arg Asp Asp Ala Gly Ser Leu Gly Gly
                725                 730                 735

Tyr Leu Asn Leu Thr His Thr Ser Ser Gly Leu Trp Ala Asp Ile Val
                740                 745                 750

Ala Gln Gly Thr Arg His Ser Met Lys Ala Ser Ser Asp Asn Asn Asp
                755                 760                 765

Phe Arg Ala Arg Gly Trp Gly Trp Leu Gly Ser Leu Glu Thr Gly Leu
                770                 775                 780

Pro Phe Ser Ile Thr Asp Asn Leu Met Leu Glu Pro Gln Leu Gln Tyr
785                 790                 795                 800

Thr Trp Gln Gly Leu Ser Leu Asp Asp Gly Asp Asn Ala Gly Tyr
                805                 810                 815

Val Lys Phe Gly His Gly Ser Ala Gln His Val Arg Ala Gly Phe Arg
                820                 825                 830

Leu Gly Ser His Asn Asp Met Ser Phe Gly Glu Gly Thr Ser Ser Arg
                835                 840                 845

Asp Thr Leu Arg Asp Ser Ala Lys His Arg Val Arg Glu Leu Pro Val
                850                 855                 860

Asn Trp Trp Val Gln Pro Ser Val Ile Arg Thr Phe Ser Ser Arg Gly
865                 870                 875                 880

Asp Met Ser Met Gly Thr Ala Ala Gly Ser Asn Met Thr Phe Ser
                885                 890                 895

Pro Ser Arg Asn Gly Thr Ser Leu Asp Leu Gln Ala Gly Leu Glu Ala
                900                 905                 910

Arg Val Arg Glu Asn Ile Thr Leu Gly Val Gln Ala Gly Tyr Ala His
                915                 920                 925

Ser Val Ser Gly Ser Ser Ala Glu Gly Tyr Asn Gly Gln Ala Thr Leu
                930                 935                 940

Asn Val Thr Phe
945

<210> SEQ ID NO 8
<211> LENGTH: 948
<212> TYPE: PRT
<213> ORGANISM: Escherichia coli

<400> SEQUENCE: 8

Met Lys Arg His Leu Asn Thr Ser Tyr Arg Leu Val Trp Asn His Ile
  1               5                  10                  15

Thr Gly Thr Leu Val Val Ala Ser Glu Leu Ala Arg Ser Arg Gly Lys
                20                  25                  30

Arg Ala Gly Val Ala Ile Ala Leu Ser Leu Ala Ala Val Thr Ser Val
                35                  40                  45

Pro Ala Leu Ala Ala Asp Thr Val Val Gln Ala Gly Glu Thr Val Asn
                50                  55                  60

Asp Gly Thr Leu Thr Asn His Asp Asn Gln Ile Val Leu Gly Thr Ala
 65                 70                  75                  80

Asn Gly Met Thr Ile Ser Thr Gly Leu Glu Tyr Gly Pro Asp Asn Glu
                85                  90                  95
```

```
Ala Asn Thr Gly Gly Gln Trp Ile Gln Asn Gly Gly Ile Ala Asn Asn
            100                 105                 110

Thr Thr Val Thr Gly Gly Leu Gln Arg Val Asn Ala Gly Gly Ser
        115                 120                 125

Val Ser Asp Thr Val Ile Ser Ala Gly Gly Gln Ser Leu Gln Gly
    130                 135                 140

Gln Ala Val Asn Thr Thr Leu Asn Gly Gly Glu Gln Trp Val His Glu
145                 150                 155                 160

Gly Gly Ile Ala Thr Gly Thr Val Ile Asn Glu Lys Gly Trp Gln Ala
                165                 170                 175

Val Lys Ser Gly Ala Met Ala Thr Asp Thr Val Asn Thr Gly Ala
            180                 185                 190

Glu Gly Gly Pro Asp Ala Glu Asn Gly Asp Thr Gly Gln Phe Val Arg
            195                 200                 205

Gly Asn Ala Val Arg Thr Thr Ile Asn Lys Asn Gly Arg Gln Ile Val
    210                 215                 220

Ala Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
            245                 250                 255

Gln Tyr Val His Asn Gly Gly Thr Ala Ser Gly Thr Val Val Asn Ser
            260                 265                 270

Asp Gly Trp Gln Ile Ile Lys Glu Gly Gly Leu Ala Asp Phe Thr Thr
            275                 280                 285

Val Asn Gln Lys Gly Lys Leu Gln Val Asn Ala Gly Gly Thr Ala Thr
    290                 295                 300

Asn Val Thr Leu Lys Gln Gly Gly Ala Leu Val Thr Ser Thr Ala Ala
305                 310                 315                 320

Thr Val Thr Gly Ser Asn Arg Leu Gly Asn Phe Thr Val Glu Asn Gly
            325                 330                 335

Lys Ala Asp Gly Val Val Leu Glu Ser Gly Gly Arg Leu Asp Val Leu
            340                 345                 350

Glu Gly His Ser Ala Trp Lys Thr Leu Val Asp Gly Gly Thr Leu
            355                 360                 365

Ala Val Ser Ala Gly Gly Lys Ala Thr Asp Val Thr Met Thr Ser Gly
    370                 375                 380

Gly Ala Leu Ile Ala Asp Ser Gly Ala Thr Val Glu Gly Thr Asn Ala
385                 390                 395                 400

Ser Gly Lys Phe Ser Ile Asp Gly Thr Ser Gly Gln Ala Ser Gly Leu
            405                 410                 415

Leu Leu Glu Asn Gly Gly Ser Phe Thr Val Asn Ala Gly Gly Leu Ala
            420                 425                 430

Ser Asn Thr Thr Val Gly His Arg Gly Thr Leu Thr Leu Ala Ala Gly
            435                 440                 445

Gly Ser Leu Ser Gly Arg Thr Gln Leu Ser Lys Gly Ala Ser Met Val
    450                 455                 460

Leu Asn Gly Asp Val Val Ser Thr Gly Asp Ile Val Asn Ala Gly Glu
465                 470                 475                 480

Ile Arg Phe Asp Asn Gln Thr Thr Pro Asp Ala Val Leu Ser Arg Ala
            485                 490                 495

Val Ala Lys Gly Asp Ser Pro Val Thr Phe His Lys Leu Thr Thr Ser
            500                 505                 510
```

```
Asn Leu Thr Gly Gln Gly Gly Thr Ile Asn Met Arg Val Arg Leu Asp
        515                 520                 525

Gly Ser Asn Thr Ser Asp Gln Leu Val Ile Asn Gly Gly Gln Ala Thr
        530                 535                 540

Gly Lys Thr Trp Leu Ala Phe Thr Asn Val Gly Asn Ser Asn Leu Gly
545                 550                 555                 560

Val Ala Thr Ser Gly Gln Gly Ile Arg Val Val Asp Ala Gln Asn Gly
                565                 570                 575

Ala Thr Thr Glu Glu Gly Ala Phe Leu Ser Arg Pro Leu Gln Ala
            580                 585                 590

Gly Ala Phe Asn Tyr Thr Leu Asn Arg Asp Ser Asp Glu Asp Trp Tyr
        595                 600                 605

Leu Arg Ser Glu Asn Ala Tyr Arg Ala Glu Val Pro Leu Tyr Ala Ser
        610                 615                 620

Met Leu Thr Gln Ala Met Asp Tyr Asp Arg Ile Leu Ala Gly Ser Arg
625                 630                 635                 640

Ser His Gln Thr Gly Val Ser Gly Glu Asn Asn Ser Val Arg Leu Ser
                645                 650                 655

Ile Gln Gly Gly His Leu Gly His Asp Asn Asn Gly Gly Ile Ala Arg
                660                 665                 670

Gly Ala Thr Pro Glu Ser Ser Gly Ser Tyr Gly Phe Val Arg Leu Glu
        675                 680                 685

Gly Asp Leu Leu Arg Thr Glu Val Ala Gly Met Ser Leu Thr Thr Gly
        690                 695                 700

Val Tyr Gly Ala Ala Gly His Ser Ser Val Asp Val Lys Asp Asp
705                 710                 715                 720

Gly Ser Arg Ala Gly Thr Ala Arg Asp Ala Gly Ser Leu Gly Gly
                725                 730                 735

Tyr Leu Asn Leu Val His Thr Ser Ser Gly Leu Trp Ala Asp Ile Val
                740                 745                 750

Ala Gln Gly Thr Arg His Ser Met Lys Ala Ser Ser Asp Asn Asn Asp
        755                 760                 765

Phe Arg Ala Arg Gly Trp Gly Trp Leu Gly Ser Leu Glu Thr Gly Leu
770                 775                 780

Pro Phe Ser Ile Thr Asp Asn Leu Met Leu Glu Pro Gln Leu Gln Tyr
785                 790                 795                 800

Thr Trp Gln Gly Leu Ser Leu Asp Asp Gly Gln Asp Asn Ala Gly Tyr
                805                 810                 815

Val Lys Phe Gly His Gly Ser Ala Gln His Val Arg Ala Gly Phe Arg
                820                 825                 830

Leu Gly Ser His Asn Asp Met Asn Phe Gly Lys Gly Thr Ser Ser Arg
        835                 840                 845

Asp Thr Leu Arg Asp Ser Ala Lys His Ser Val Arg Glu Leu Pro Val
850                 855                 860

Asn Trp Trp Val Gln Pro Ser Val Ile Arg Thr Phe Ser Ser Arg Gly
865                 870                 875                 880

Asp Met Ser Met Gly Thr Ala Ala Ala Gly Ser Asn Met Thr Phe Ser
                885                 890                 895

Pro Ser Arg Asn Gly Thr Ser Leu Asp Leu Gln Ala Gly Leu Glu Ala
                900                 905                 910

Arg Val Arg Glu Asn Ile Thr Leu Gly Val Gln Ala Gly Tyr Ala His
                915                 920                 925

Ser Val Ser Gly Ser Ser Ala Glu Gly Tyr Asn Gly Gln Ala Thr Leu
```

930                 935                 940

Asn Val Thr Phe
945

<210> SEQ ID NO 9
<211> LENGTH: 948
<212> TYPE: PRT
<213> ORGANISM: Escherichia coli

<400> SEQUENCE: 9

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Gly Ala Gly Val Ala Val Ala Leu Ser Leu Ala Ala Val Thr Ser Val
        35                  40                  45

Pro Ala Leu Ala Ala Asp Thr Val Gln Ala Gly Glu Thr Val Asn
    50                  55                  60

Gly Gly Thr Leu Thr Asn His Asp Asn Gln Ile Val Leu Gly Thr Ala
65                  70                  75                  80

Asn Gly Met Thr Ile Ser Thr Gly Leu Glu Tyr Gly Pro Asp Asn Glu
                85                  90                  95

Ala Asn Thr Gly Gly Gln Trp Ile Gln Asn Gly Gly Ile Ala Asn Asn
            100                 105                 110

Thr Thr Val Thr Gly Gly Gly Leu Gln Arg Val Asn Ala Gly Gly Ser
        115                 120                 125

Val Ser Asp Thr Val Ile Ser Ala Gly Gly Gln Ser Leu Gln Gly
    130                 135                 140

Gln Ala Val Asn Thr Thr Leu Asn Gly Gly Glu Gln Trp Val His Glu
145                 150                 155                 160

Gly Gly Ile Ala Thr Gly Thr Val Ile Asn Glu Lys Gly Trp Gln Ala
                165                 170                 175

Val Lys Ser Gly Ala Met Ala Thr Asp Thr Val Val Asn Thr Gly Ala
            180                 185                 190

Glu Gly Gly Pro Asp Ala Glu Asn Gly Asp Thr Gly Gln Thr Val Tyr
        195                 200                 205

Gly Asp Ala Val Arg Thr Thr Ile Asn Lys Asn Gly Arg Gln Ile Val
    210                 215                 220

Ala Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
                245                 250                 255

Gln Tyr Val His Asn Gly Gly Thr Ala Ser Asp Thr Val Asn Ser
            260                 265                 270

Asp Gly Trp Gln Ile Ile Lys Glu Gly Gly Leu Ala Asp Phe Thr Thr
        275                 280                 285

Val Asn Gln Lys Gly Lys Leu Gln Val Asn Ala Gly Gly Thr Ala Thr
    290                 295                 300

Asn Val Thr Leu Thr Gln Gly Gly Ala Leu Val Thr Ser Thr Ala Ala
305                 310                 315                 320

Thr Val Thr Gly Ser Asn Arg Leu Gly Asn Phe Thr Val Glu Asn Gly
                325                 330                 335

Asn Ala Asp Gly Val Val Leu Glu Ser Gly Gly Arg Leu Asp Val Leu
            340                 345                 350

-continued

```
Glu Gly His Ser Ala Trp Lys Thr Leu Val Asp Asp Gly Thr Leu
            355                 360                 365
Ala Val Ser Ala Gly Gly Lys Ala Thr Asp Val Thr Met Thr Ser Gly
370                 375                 380
Gly Ala Leu Ile Ala Asp Ser Gly Ala Thr Val Glu Gly Thr Asn Ala
385                 390                 395                 400
Ser Gly Lys Phe Ser Ile Asp Gly Ile Ser Gly Gln Ala Ser Gly Leu
                405                 410                 415
Leu Leu Glu Asn Gly Gly Ser Phe Thr Val Asn Ala Gly Leu Ala
            420                 425                 430
Ser Asn Thr Thr Val Gly His Arg Gly Thr Leu Thr Leu Ala Ala Gly
            435                 440                 445
Gly Ser Leu Ser Gly Arg Thr Gln Leu Ser Lys Gly Ala Ser Met Val
450                 455                 460
Leu Asn Gly Asp Val Val Ser Thr Gly Asp Ile Val Asn Ala Gly Glu
465                 470                 475                 480
Ile Arg Phe Asp Asn Gln Thr Thr Pro Asp Ala Ala Leu Ser Arg Ala
                485                 490                 495
Val Ala Lys Gly Asp Ser Pro Val Thr Phe His Lys Leu Thr Thr Ser
            500                 505                 510
Asn Leu Thr Gly Gln Gly Gly Thr Ile Asn Met Arg Val Arg Leu Asp
            515                 520                 525
Gly Ser Asn Ala Ser Asp Gln Leu Val Ile Asn Gly Gly Gln Ala Thr
            530                 535                 540
Gly Lys Thr Trp Leu Ala Phe Thr Asn Val Gly Asn Ser Asn Leu Gly
545                 550                 555                 560
Val Ala Thr Ser Gly Gln Gly Ile Arg Val Val Asp Ala Gln Asn Gly
                565                 570                 575
Ala Thr Thr Glu Glu Gly Ala Phe Ala Leu Ser Arg Pro Leu Gln Ala
            580                 585                 590
Gly Ala Phe Asn Tyr Thr Leu Asn Arg Asp Ser Asp Glu Asp Trp Tyr
            595                 600                 605
Leu Arg Ser Glu Asn Ala Tyr Arg Ala Glu Val Pro Leu Tyr Ala Ser
610                 615                 620
Met Leu Thr Gln Ala Met Asp Tyr Asp Arg Ile Leu Ala Gly Ser Arg
625                 630                 635                 640
Ser His Gln Ser Gly Val Ser Gly Glu Asn Asn Ser Val Arg Leu Ser
                645                 650                 655
Ile Gln Gly Gly His Leu Gly His Asp Asn Gly Gly Ile Ala Arg
            660                 665                 670
Gly Ala Thr Pro Glu Ser Asn Gly Ser Tyr Gly Phe Val Arg Leu Glu
            675                 680                 685
Gly Asp Leu Leu Arg Thr Glu Val Ala Gly Met Ser Leu Thr Thr Gly
            690                 695                 700
Val Tyr Gly Ala Ala Gly His Ser Ser Val Asp Val Lys Asp Asp
705                 710                 715                 720
Gly Ser Arg Ala Gly Thr Val Arg Asp Asp Ala Gly Ser Leu Gly Gly
                725                 730                 735
Tyr Leu His Leu Val His Thr Ser Ser Gly Leu Trp Ala Asp Ile Val
            740                 745                 750
Ala Gln Gly Thr Arg His Ser Met Lys Ala Ser Ser Asp Asn Asn Asp
            755                 760                 765
Phe Arg Ala Arg Gly Trp Gly Trp Leu Gly Ser Leu Glu Thr Gly Leu
```

```
                770               775               780
Pro Phe Ser Ile Thr Asp Asn Leu Met Leu Glu Pro Gln Leu Gln Tyr
785               790               795               800

Thr Trp Gln Gly Leu Ser Leu Asp Asp Gly Gln Asp Asn Ala Gly Tyr
                805               810               815

Val Lys Phe Gly His Gly Ser Ala Gln His Val Arg Ala Gly Phe Arg
                820               825               830

Leu Gly Ser His Asn Asp Met Asn Phe Gly Lys Gly Thr Ser Ser Arg
                835               840               845

Asp Thr Leu His Asp Ser Ala Lys His Ser Val Arg Glu Leu Pro Val
            850               855               860

Asn Trp Trp Val Gln Pro Ser Val Ile Arg Thr Phe Ser Ser Arg Gly
865               870               875               880

Asp Met Ser Met Gly Thr Ala Ala Ala Gly Ser Asn Met Thr Phe Ser
                885               890               895

Pro Ser Arg Asn Gly Thr Ser Leu Asp Leu Gln Ala Gly Leu Glu Ala
                900               905               910

Arg Val Arg Glu Asn Ile Thr Leu Gly Val Gln Ala Gly Tyr Ala His
                915               920               925

Ser Val Ser Gly Ser Ser Ala Glu Gly Tyr Asn Gly Gln Ala Thr Leu
                930               935               940

Asn Val Thr Phe
945

<210> SEQ ID NO 10
<211> LENGTH: 948
<212> TYPE: PRT
<213> ORGANISM: Escherichia coli

<400> SEQUENCE: 10

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
                20                  25                  30

Arg Thr Gly Val Ala Val Ala Leu Ser Leu Ala Ala Val Thr Ser Val
                35                  40                  45

Pro Val Leu Ala Ala Asp Thr Val Val Gln Ala Gly Glu Thr Val Ser
            50                  55                  60

Gly Gly Thr Leu Thr Asn His Asp Asn Gln Ile Val Phe Gly Thr Ala
65              70                  75                  80

Asn Gly Met Thr Ile Ser Thr Gly Leu Glu Tyr Gly Pro Asp Asn Glu
                85                  90                  95

Ala Asn Thr Gly Gly Gln Trp Ile Gln Asn Gly Gly Ile Ala Asn Asn
                100                 105                 110

Thr Thr Val Thr Gly Gly Leu Gln Arg Val Asn Ala Gly Gly Ser
                115                 120                 125

Val Ser Asp Thr Val Ile Ser Ala Gly Gly Gln Ser Leu Gln Gly
            130                 135                 140

Gln Ala Val Asn Thr Thr Leu Asn Gly Gly Glu Gln Trp Val His Glu
145                 150                 155                 160

Gly Gly Ile Ala Thr Val Thr Ile Asn Glu Lys Gly Trp Gln Ala
                165                 170                 175

Val Lys Ser Gly Ala Met Ala Thr Asp Thr Val Val Asn Thr Gly Ala
                180                 185                 190
```

-continued

```
Glu Gly Gly Pro Asp Ala Asp Asn Gly Asp Thr Gly Gln Phe Val Arg
        195                 200                 205
Gly Asn Ala Val Arg Thr Thr Ile Asn Lys Asn Gly Arg Gln Ile Val
    210                 215                 220
Ala Val Glu Gly Thr Ala Asn Thr Thr Val Val Tyr Ala Gly Gly Asp
225                 230                 235                 240
Gln Thr Val His Gly His Ala Leu Asp Thr Thr Leu Asn Gly Gly Tyr
                245                 250                 255
Gln Tyr Val His Asn Gly Gly Thr Ala Ser Asp Thr Val Val Asn Ser
                260                 265                 270
Asp Gly Trp Gln Ile Val Lys Glu Gly Gly Leu Ala Asp Phe Thr Thr
            275                 280                 285
Val Asn Gln Lys Gly Lys Leu Gln Val Asn Ala Gly Gly Thr Ala Thr
    290                 295                 300
Asn Val Thr Leu Lys Gln Gly Gly Ala Leu Val Thr Ser Thr Ala Ala
305                 310                 315                 320
Thr Val Thr Gly Ser Asn Arg Leu Gly Asn Phe Thr Val Glu Asn Gly
                325                 330                 335
Asn Ala Asp Gly Val Val Leu Glu Ser Gly Gly Arg Leu Asp Val Leu
                340                 345                 350
Glu Gly His Ser Ala Trp Lys Thr Arg Val Asp Asp Gly Gly Thr Leu
            355                 360                 365
Ala Val Ser Ala Gly Gly Lys Ala Thr Gly Val Thr Met Thr Ser Gly
    370                 375                 380
Gly Ala Leu Ile Ala Asp Ser Gly Ala Thr Val Glu Gly Thr Asn Ala
385                 390                 395                 400
Ser Gly Lys Phe Ser Ile Asp Gly Ile Ser Gly Gln Ala Ser Gly Leu
                405                 410                 415
Leu Leu Glu Asn Gly Gly Ser Phe Thr Val Asn Ala Gly Gly Gln Ala
                420                 425                 430
Ser Asn Thr Thr Val Gly His Arg Gly Thr Leu Met Leu Ala Ala Gly
            435                 440                 445
Gly Ser Leu Ser Gly Arg Thr Gln Leu Ser Lys Gly Ala Ser Met Val
    450                 455                 460
Leu Asn Gly Asp Val Val Ser Thr Gly Asp Ile Val Asn Ala Gly Glu
465                 470                 475                 480
Ile Tyr Phe Asp Asn Gln Thr Thr Pro Asp Ala Val Leu Ser Arg Ala
                485                 490                 495
Val Ala Lys Gly Asn Ala Pro Thr Phe His Lys Leu Thr Thr Ser
            500                 505                 510
Asn Leu Thr Gly Gln Gly Gly Thr Ile Asn Met Arg Val Arg Leu Asp
            515                 520                 525
Gly Ser Asn Ala Ser Asp Gln Leu Val Ile Asn Gly Gly Gln Ala Thr
    530                 535                 540
Gly Lys Thr Trp Leu Ala Phe Thr Asn Val Gly Asn Ser Asn Leu Gly
545                 550                 555                 560
Val Ala Thr Thr Gly Gln Gly Ile Arg Val Val Asp Ala Gln Asn Gly
                565                 570                 575
Ala Thr Thr Glu Glu Gly Val Phe Ala Leu Ser Arg Pro Leu Gln Ala
                580                 585                 590
Gly Ala Phe Asn Tyr Thr Leu Asn Arg Asp Ser Asp Glu Asp Trp Tyr
            595                 600                 605
Leu Arg Ser Glu Asn Ala Tyr Arg Ala Glu Val Pro Leu Tyr Thr Ser
```

```
                610                 615                 620
Met Leu Thr Gln Ala Met Asp Tyr Asp Arg Ile Leu Ala Gly Ser Arg
625                 630                 635                 640

Ser His Gln Thr Gly Val Asn Gly Glu Asn Asn Ser Val Arg Leu Ser
                645                 650                 655

Ile Gln Gly Gly His Leu Gly His Asp Asn Asn Gly Gly Ile Ala Arg
            660                 665                 670

Gly Ala Thr Pro Glu Ser Ser Gly Ser Tyr Gly Phe Val Arg Leu Glu
        675                 680                 685

Gly Asp Leu Leu Arg Thr Glu Val Ala Gly Met Ser Leu Thr Thr Gly
    690                 695                 700

Val Tyr Gly Ala Ala Gly His Ser Ser Val Asp Val Lys Asp Asp Asp
705                 710                 715                 720

Gly Ser Arg Ala Gly Thr Val Arg Asp Asp Ala Gly Ser Leu Gly Gly
                725                 730                 735

Tyr Leu Asn Leu Val His Thr Ser Ser Gly Leu Trp Ala Asp Ile Val
            740                 745                 750

Ala Gln Gly Thr Arg His Ser Met Lys Ala Ser Ser Asp Asn Asn Asp
        755                 760                 765

Phe Arg Ala Arg Gly Trp Gly Trp Leu Gly Ser Leu Glu Thr Gly Leu
    770                 775                 780

Pro Phe Ser Ile Thr Asp Asn Leu Met Leu Glu Pro Gln Leu Gln Tyr
785                 790                 795                 800

Thr Trp Gln Gly Leu Ser Leu Asp Asp Gly Gln Asp Asn Ala Gly Tyr
                805                 810                 815

Val Lys Phe Gly His Gly Ser Thr Gln His Val Arg Ala Gly Phe Arg
            820                 825                 830

Leu Gly Ser His Asn Asp Met Thr Phe Gly Glu Gly Thr Ser Ser Arg
        835                 840                 845

Asp Thr Leu Arg Asp Ser Ala Lys His Arg Val Arg Glu Leu Pro Val
    850                 855                 860

Asn Trp Trp Val Gln Pro Ser Val Ile Arg Thr Phe Ser Ser Arg Gly
865                 870                 875                 880

Asp Met Ser Met Gly Thr Ala Ala Gly Ser Asn Met Thr Phe Ser
                885                 890                 895

Pro Ser Arg Asn Gly Thr Ser Leu Asp Leu Gln Ala Gly Leu Glu Ala
            900                 905                 910

Arg Val Arg Glu Asn Ile Thr Leu Gly Val Gln Ala Gly Tyr Ala His
        915                 920                 925

Ser Val Ser Gly Ser Ser Ala Glu Gly Tyr Asn Gly Gln Ala Thr Leu
    930                 935                 940

Asn Val Thr Phe
945

<210> SEQ ID NO 11
<211> LENGTH: 948
<212> TYPE: PRT
<213> ORGANISM: Escherichia coli

<400> SEQUENCE: 11

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30
```

-continued

```
Arg Ala Gly Val Ala Val Ala Leu Ser Leu Ala Ala Val Thr Ser Val
             35                  40                  45
Pro Ala Leu Ala Ala Asp Thr Val Val Gln Ala Gly Glu Thr Val Ser
 50                  55                  60
Gly Gly Thr Leu Val Asn His Asp Asn Gln Ile Val Phe Gly Thr Ala
 65                  70                  75                  80
Asn Gly Met Thr Ile Ser Thr Gly Leu Glu Tyr Gly Pro Asp Asn Glu
                 85                  90                  95
Ala Asn Thr Gly Gly Gln Trp Ile Gln Asn Gly Gly Thr Ala Asn Asn
            100                 105                 110
Thr Thr Val Thr Gly Gly Leu Gln Arg Val Asn Thr Gly Gly Ser
            115                 120                 125
Val Ser Asp Thr Val Ile Ser Ala Gly Gly Gln Ser Leu Gln Gly
130                 135                 140
Gln Ala Val Asn Thr Thr Leu Asn Gly Gly Glu Gln Trp Val His Glu
145                 150                 155                 160
Gly Gly Ile Ala Thr Gly Thr Val Ile Asn Glu Lys Gly Trp Gln Ala
                165                 170                 175
Ile Lys Ser Gly Ala Val Ala Thr Asp Thr Val Val Asn Thr Gly Ala
            180                 185                 190
Glu Gly Gly Pro Asp Ala Glu Asn Gly Asp Thr Gly Gln Thr Val Tyr
            195                 200                 205
Gly Asp Ala Val Arg Thr Thr Ile Asn Lys Asn Gly Arg Gln Ile Val
210                 215                 220
Ala Ala Glu Gly Thr Ala Asn Thr Thr Val Val Tyr Ala Gly Gly Asp
225                 230                 235                 240
Gln Thr Val His Gly His Ala Leu Asp Thr Thr Leu Asn Gly Gly Tyr
                245                 250                 255
Gln Tyr Val His Asn Gly Gly Thr Ala Ser Gly Thr Val Val Asn Ser
            260                 265                 270
Asp Gly Trp Gln Ile Ile Lys Glu Gly Gly Leu Ala Asp Phe Thr Thr
            275                 280                 285
Val Asn Gln Lys Gly Lys Leu Gln Val Asn Ala Gly Gly Thr Ala Thr
290                 295                 300
Asn Val Thr Leu Lys Gln Gly Gly Ala Leu Val Thr Ser Thr Ala Ala
305                 310                 315                 320
Thr Val Leu Gly Ser Asn Arg Leu Gly Asn Phe Thr Val Glu Asn Gly
                325                 330                 335
Lys Ala Asp Gly Val Val Leu Glu Ser Gly Gly Arg Leu Asp Val Leu
            340                 345                 350
Glu Gly His Ser Ala Trp Lys Thr Leu Val Asp Asp Gly Gly Thr Leu
            355                 360                 365
Ala Val Ser Ala Gly Gly Lys Ala Thr Gly Val Thr Met Thr Ser Gly
370                 375                 380
Gly Ala Leu Ile Ala Asp Ser Gly Ala Thr Val Glu Gly Thr Asn Ala
385                 390                 395                 400
Ser Gly Lys Phe Ser Ile Asp Gly Ile Ser Gly Gln Ala Ser Gly Leu
                405                 410                 415
Leu Leu Glu Asn Gly Gly Ser Phe Thr Val Asn Ala Gly Gly Gln Ala
            420                 425                 430
Ser Asn Thr Thr Val Gly His Arg Gly Thr Leu Met Leu Ala Ala Gly
            435                 440                 445
Gly Ser Leu Ser Gly Arg Thr Gln Leu Ser Lys Gly Ala Ser Met Val
```

```
                450             455             460
Leu Asn Gly Asp Val Val Ser Thr Gly Asp Ile Val Asn Ala Gly Glu
465                 470                 475                 480

Ile Tyr Phe Asp Asn Gln Thr Thr Pro Asp Ala Val Leu Ser Arg Ala
            485                 490                 495

Val Ala Lys Gly Asn Ala Pro Val Thr Phe His Lys Leu Thr Thr Ser
        500                 505                 510

Asn Leu Thr Gly Gln Gly Thr Ile Asn Met Arg Val Arg Leu Asp
    515                 520                 525

Gly Ser Asn Thr Ser Asp Gln Leu Val Ile Asn Gly Gln Ala Thr
530                 535                 540

Gly Lys Thr Trp Leu Ala Phe Thr Asn Val Gly Asn Ser Asn Leu Gly
545                 550                 555                 560

Val Ala Thr Ser Gly Gln Gly Ile Arg Val Val Asp Ala Gln Asn Gly
            565                 570                 575

Ala Thr Thr Glu Glu Gly Ala Phe Ala Leu Ser Arg Pro Leu Gln Ala
        580                 585                 590

Gly Ala Phe Asn Tyr Thr Leu Asn Arg Asp Ser Asp Glu Asp Trp Tyr
    595                 600                 605

Leu Arg Ser Glu Asn Ala Tyr Arg Ala Glu Val Pro Leu Tyr Ala Ser
610                 615                 620

Met Leu Thr Gln Ala Met Asp Tyr Asp Arg Ile Leu Ala Gly Ser Arg
625                 630                 635                 640

Ser His Gln Ser Gly Val Ser Gly Glu Asn Asn Ser Val Arg Leu Ser
            645                 650                 655

Ile Gln Gly Gly His Leu Gly His Asp Asn Asn Gly Gly Ile Ala Arg
        660                 665                 670

Gly Ala Thr Pro Glu Ser Asn Gly Ser Tyr Gly Phe Val Arg Leu Glu
    675                 680                 685

Gly Asp Leu Leu Arg Thr Glu Val Ala Gly Met Ser Leu Thr Thr Gly
690                 695                 700

Val Tyr Gly Ala Ala Gly His Ser Ser Val Asp Val Lys Asp Asp
705                 710                 715                 720

Gly Ser Arg Ala Gly Thr Val Arg Asp Asp Ala Gly Ser Leu Gly Gly
            725                 730                 735

Tyr Leu Asn Leu Thr His Thr Ser Ser Gly Leu Trp Ala Asp Ile Val
        740                 745                 750

Ala Gln Gly Thr Arg His Ser Met Lys Ala Ser Ser Asp Asn Asn Asp
    755                 760                 765

Phe Arg Ala Arg Gly Trp Gly Trp Leu Gly Ser Leu Glu Thr Gly Leu
770                 775                 780

Pro Phe Ser Ile Thr Asp Asn Leu Met Leu Glu Pro Gln Leu Gln Tyr
785                 790                 795                 800

Thr Trp Gln Gly Leu Ser Leu Asp Asp Gly Gln Asp Asn Ala Gly Tyr
            805                 810                 815

Val Lys Phe Gly His Gly Ser Ala Gln His Val Arg Ala Gly Phe Arg
        820                 825                 830

Leu Gly Ser His Asn Asp Met Ser Phe Gly Glu Gly Thr Ser Ser Arg
    835                 840                 845

Asp Thr Leu Arg Asp Ser Ala Lys His Arg Val Arg Glu Leu Pro Val
850                 855                 860

Asn Trp Trp Val Gln Pro Ser Val Ile Arg Thr Phe Ser Ser Arg Gly
865                 870                 875                 880
```

```
Asp Met Ser Met Gly Thr Ala Ala Gly Ser Asn Met Thr Phe Ser
                885                 890                 895

Pro Ser Arg Asn Gly Thr Ser Leu Asp Leu Gln Ala Gly Leu Glu Ala
            900                 905                 910

Arg Val Arg Glu Asn Ile Thr Leu Gly Val Gln Ala Gly Tyr Ala His
        915                 920                 925

Ser Val Ser Gly Ser Ser Ala Glu Gly Tyr Asn Gly Gln Ala Thr Leu
930                 935                 940

Asn Val Thr Phe
945

<210> SEQ ID NO 12
<211> LENGTH: 948
<212> TYPE: PRT
<213> ORGANISM: Escherichia coli

<400> SEQUENCE: 12

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Arg Ala Gly Val Ala Ile Ala Leu Ser Leu Ala Ala Val Thr Ser Val
        35                  40                  45

Pro Ala Leu Ala Ala Asp Thr Val Val Gln Ala Gly Glu Thr Val Ser
    50                  55                  60

Gly Gly Thr Leu Thr Asn His Asp Asn Gln Ile Val Phe Gly Thr Ala
65                  70                  75                  80

Asn Gly Met Thr Ile Ser Ser Gly Leu Glu Tyr Gly Pro Asp Asn Glu
                85                  90                  95

Ala Asn Thr Gly Gly Gln Trp Ile Gln Asn Gly Gly Ile Ala Asn Asn
            100                 105                 110

Thr Thr Val Thr Gly Gly Leu Gln Arg Val Asn Ala Gly Gly Ser
        115                 120                 125

Val Ser Asp Thr Val Ile Ser Ala Gly Gly Gln Ser Leu Gln Gly
130                 135                 140

Gln Ala Val Asn Thr Thr Leu Asn Gly Gly Glu Gln Trp Val His Glu
145                 150                 155                 160

Gly Gly Ile Ala Thr Gly Thr Val Ile Asn Glu Lys Gly Trp Gln Ala
                165                 170                 175

Val Lys Ser Gly Ala Met Ala Thr Asp Thr Val Val Asn Thr Gly Ala
            180                 185                 190

Glu Gly Gly Pro Asp Ala Glu Asn Gly Asp Thr Gly Gln Phe Val Arg
        195                 200                 205

Gly Asn Ala Val Arg Thr Thr Ile Asn Lys Asn Gly Arg Gln Ile Val
    210                 215                 220

Ala Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
                245                 250                 255

Gln Tyr Val His Asn Gly Gly Thr Ala Ser Gly Thr Val Val Asn Ser
            260                 265                 270

Asp Gly Trp Gln Ile Ile Lys Glu Gly Leu Ala Asp Phe Thr Thr
        275                 280                 285

Val Asn Gln Lys Gly Lys Leu Gln Val Asn Ala Gly Gly Thr Ala Thr
```

```
              290                 295                 300
His Val Thr Leu Lys Gln Gly Gly Ala Leu Val Thr Ser Thr Ala Ala
305                 310                 315                 320

Thr Val Leu Gly Ser Asn Arg Leu Gly Asn Phe Thr Val Glu Asn Gly
                325                 330                 335

Lys Ala Asp Gly Val Val Leu Glu Ser Gly Gly Arg Leu Asp Val Leu
                340                 345                 350

Glu Gly His Ser Ala Gln Lys Thr Arg Val Asp Asp Gly Gly Thr Leu
                355                 360                 365

Ala Val Ser Ala Gly Gly Lys Ala Thr Gly Val Thr Met Thr Ser Gly
                370                 375                 380

Gly Ala Leu Ile Ala Asp Ser Gly Ala Thr Val Glu Gly Thr Asn Ala
385                 390                 395                 400

Ser Gly Lys Phe Ser Ile Asp Gly Thr Ser Gly Gln Ala Ser Gly Leu
                405                 410                 415

Leu Leu Glu Asn Gly Gly Ser Phe Thr Val Asn Ala Gly Gly Gln Ala
                420                 425                 430

Ser Asn Thr Thr Val Gly His Arg Gly Thr Leu Met Leu Ala Ala Gly
                435                 440                 445

Gly Ser Leu Ser Gly Arg Thr Gln Leu Ser Lys Gly Ala Ser Met Val
                450                 455                 460

Leu Asn Gly Asp Val Val Ser Thr Gly Asp Ile Val Asn Ala Gly Glu
465                 470                 475                 480

Ile His Phe Asp Asn Gln Thr Thr Gln Asp Ala Val Leu Ser Arg Ala
                485                 490                 495

Val Ala Lys Ser Asn Ser Pro Val Thr Phe His Lys Leu Thr Thr Thr
                500                 505                 510

Asn Leu Thr Gly Gln Gly Gly Thr Ile Asn Met Arg Val Ser Leu Asp
                515                 520                 525

Gly Ser Asn Ala Ser Asp Gln Leu Val Ile Asn Gly Gly Gln Ala Thr
                530                 535                 540

Gly Lys Thr Trp Leu Ala Phe Thr Asn Val Gly Asn Ser Asn Leu Gly
545                 550                 555                 560

Val Ala Thr Ser Gly Gln Gly Ile Arg Val Val Asp Ala Gln Asn Gly
                565                 570                 575

Ala Thr Thr Glu Glu Gly Ala Phe Ala Leu Ser Arg Pro Leu Gln Ala
                580                 585                 590

Gly Ala Phe Asn Tyr Thr Leu Asn Arg Asp Ser Asp Glu Asp Trp Tyr
                595                 600                 605

Leu Arg Ser Glu Asn Ala Tyr Arg Ala Glu Val Pro Leu Tyr Thr Ser
                610                 615                 620

Met Leu Thr Gln Ala Met Asp Tyr Asp Arg Ile Leu Ala Gly Ser Arg
625                 630                 635                 640

Ser His Gln Thr Gly Val Asn Gly Glu Asn Asn Ser Val Arg Leu Ser
                645                 650                 655

Ile Gln Gly Gly His Leu Gly His Asp Asn Asn Gly Gly Ile Ala Arg
                660                 665                 670

Gly Ala Thr Pro Glu Ser Ser Gly Ser Tyr Gly Phe Val Arg Leu Glu
                675                 680                 685

Gly Asp Leu Leu Arg Thr Glu Val Ala Gly Met Ser Leu Thr Thr Gly
                690                 695                 700

Val Tyr Gly Ala Ala Gly His Ser Ser Val Asp Val Lys Asp Asp Asp
705                 710                 715                 720
```

```
Gly Ser Arg Ala Gly Thr Val Arg Asp Asp Ala Gly Ser Leu Gly Gly
                725                 730                 735
Tyr Leu Asn Leu Thr His Thr Ser Ser Gly Leu Trp Ala Asp Ile Val
            740                 745                 750
Ala Gln Gly Thr Arg His Ser Met Lys Ala Ser Ser Asp Asn Asn Asp
        755                 760                 765
Phe Arg Ala Arg Gly Trp Gly Trp Leu Gly Ser Leu Glu Thr Gly Leu
770                 775                 780
Pro Phe Ser Ile Thr Asp Asn Leu Met Leu Glu Pro Gln Leu His Tyr
785                 790                 795                 800
Thr Trp Gln Gly Leu Ser Leu Asp Asp Gly Gln Asp Asn Ala Gly Tyr
                805                 810                 815
Val Lys Phe Gly His Gly Ser Ala Gln His Val Arg Ala Gly Phe Arg
            820                 825                 830
Leu Gly Ser His Asn Asp Met Thr Phe Gly Glu Gly Thr Ser Ser Arg
        835                 840                 845
Asp Thr Leu Arg Asp Ser Thr Lys His Gly Val Ser Glu Leu Pro Val
850                 855                 860
Asn Trp Trp Val Gln Pro Ser Val Ile Arg Thr Phe Ser Ser Arg Gly
865                 870                 875                 880
Asp Met Ser Met Gly Thr Ala Ala Gly Ser Asn Met Thr Phe Ser
                885                 890                 895
Pro Ser Arg Asn Gly Thr Ser Leu Asp Leu Gln Ala Gly Leu Glu Ala
            900                 905                 910
Arg Val Arg Glu Asn Ile Thr Leu Gly Val Gln Ala Gly Tyr Ala His
        915                 920                 925
Ser Val Ser Gly Asn Ser Ala Glu Gly Tyr Asn Gly Gln Ala Thr Leu
930                 935                 940
Asn Val Thr Phe
945

<210> SEQ ID NO 13
<211> LENGTH: 948
<212> TYPE: PRT
<213> ORGANISM: Escherichia coli

<400> SEQUENCE: 13

Met Lys Arg His Leu Asn Thr Ser Tyr Arg Leu Val Trp Asn His Ile
1               5                   10                  15
Thr Gly Thr Leu Val Val Ala Ser Glu Leu Ala Arg Ser Arg Gly Lys
            20                  25                  30
Arg Ala Gly Val Ala Val Ala Leu Ser Leu Ala Ala Val Thr Ser Val
        35                  40                  45
Pro Ala Leu Ala Ala Asp Thr Val Gln Ala Gly Glu Thr Val Asn
    50                  55                  60
Asp Gly Thr Leu Thr Asn His Asp Asn Gln Ile Val Leu Gly Thr Ala
65                  70                  75                  80
Asn Gly Met Thr Ile Ser Thr Gly Leu Glu Tyr Gly Pro Asp Asn Glu
                85                  90                  95
Ala Asn Thr Gly Gly Gln Trp Ile Gln Asn Gly Ile Ala Asn Asn
            100                 105                 110
Thr Thr Val Thr Gly Gly Gly Leu Gln Arg Val Asn Ala Gly Gly Ser
        115                 120                 125
Val Ser Asp Thr Val Ile Ser Ala Gly Gly Gly Gln Ser Leu Gln Gly
```

-continued

```
            130                 135                 140
Gln Ala Val Asn Thr Thr Leu Asn Gly Gly Glu Gln Trp Val His Glu
145                 150                 155                 160

Gly Gly Ile Ala Thr Gly Thr Val Ile Asn Glu Lys Gly Trp Gln Ala
                165                 170                 175

Val Lys Ser Gly Ala Met Ala Thr Asp Thr Val Asn Thr Gly Ala
                180                 185                 190

Glu Gly Gly Pro Asp Ala Glu Asn Gly Asp Thr Gly Gln Phe Val Arg
                195                 200                 205

Gly Asn Ala Val Arg Thr Thr Ile Asn Glu Asn Gly Arg Gln Ile Val
            210                 215                 220

Ala Ala Glu Gly Thr Ala Asn Thr Thr Val Val Tyr Ala Gly Gly Asp
225                 230                 235                 240

Gln Thr Val His Gly Tyr Ala Leu Asp Thr Thr Leu Asn Gly Gly Asn
                245                 250                 255

Gln Tyr Val His Asn Gly Gly Thr Ala Ser Gly Thr Val Val Asn Ser
                260                 265                 270

Asp Gly Trp Gln Ile Val Lys Glu Gly Gly Leu Ala Asp Phe Thr Ile
            275                 280                 285

Val Asn Gln Lys Gly Lys Leu Gln Val Asn Ala Gly Gly Thr Ala Thr
290                 295                 300

Asn Val Thr Leu Lys Gln Gly Gly Ala Leu Val Thr Ser Thr Ala Ala
305                 310                 315                 320

Thr Val Thr Gly Ser Asn Arg Leu Gly Asn Phe Thr Val Glu Asn Gly
                325                 330                 335

Asn Ala Asp Gly Val Val Leu Glu Ser Gly Gly Arg Leu Asp Val Leu
                340                 345                 350

Glu Gly His Ser Ala Trp Lys Thr Leu Val Asp Asp Gly Gly Thr Leu
                355                 360                 365

Ala Val Ser Ala Gly Gly Lys Ala Thr Asp Val Thr Met Thr Ser Gly
            370                 375                 380

Gly Ala Leu Ile Ala Asp Ser Gly Ala Thr Val Glu Gly Thr Asn Ala
385                 390                 395                 400

Ser Gly Lys Phe Ser Ile Asp Gly Ile Ser Gly Gln Ala Ser Gly Leu
                405                 410                 415

Leu Leu Glu Asn Gly Gly Ser Phe Thr Val Asn Ala Gly Gly Gln Ala
                420                 425                 430

Gly Asn Thr Thr Val Gly His Arg Gly Thr Leu Thr Leu Ala Ala Gly
            435                 440                 445

Gly Ser Leu Ser Gly Arg Thr Gln Leu Ser Lys Gly Ala Ser Met Val
            450                 455                 460

Leu Asn Gly Asp Val Val Ser Thr Gly Asp Ile Val Asn Ala Gly Glu
465                 470                 475                 480

Ile His Phe Asp Asn Gln Thr Thr Pro Asp Ala Ala Leu Ser Arg Ala
                485                 490                 495

Val Ala Lys Gly Asp Ser Pro Val Thr Phe His Lys Leu Thr Thr Ser
                500                 505                 510

Asn Leu Thr Gly Gln Gly Gly Thr Ile Asn Met Arg Val Arg Leu Asp
                515                 520                 525

Gly Ser Asn Thr Ser Asp Gln Leu Val Ile Asn Gly Gly Gln Ala Thr
            530                 535                 540

Gly Lys Thr Trp Leu Ala Phe Thr Asn Val Gly Asn Ser Asn Leu Gly
545                 550                 555                 560
```

Val Ala Thr Thr Gly Gln Gly Ile Arg Val Val Asp Ala Gln Asn Gly
            565                 570                 575

Ala Thr Thr Glu Glu Gly Ala Phe Ala Leu Ser Arg Pro Leu Gln Ala
            580                 585                 590

Gly Ala Phe Asn Tyr Thr Leu Asn Arg Asp Ser Asp Glu Asp Trp Tyr
            595                 600                 605

Leu Arg Ser Glu Asn Ala Tyr Arg Ala Glu Val Pro Leu Tyr Ala Ser
            610                 615                 620

Met Leu Thr Gln Ala Met Asp Tyr Asp Arg Ile Leu Ala Gly Ser Arg
625                 630                 635                 640

Ser His Gln Thr Gly Val Asn Gly Glu Asn Asn Ser Phe Arg Leu Ser
            645                 650                 655

Ile Gln Gly Gly His Leu Gly His Val Asn Asn Gly Gly Ile Ala Arg
            660                 665                 670

Gly Ala Thr Pro Glu Ser Ser Gly Ser Tyr Gly Leu Val Arg Leu Glu
            675                 680                 685

Gly Asp Leu Leu Arg Thr Glu Val Ala Gly Met Ser Leu Thr Thr Gly
            690                 695                 700

Val Tyr Gly Ala Ala Gly His Ser Ser Val Asp Val Lys Asp Asp
705                 710                 715                 720

Gly Ser Arg Ala Gly Thr Val Arg Asp Asp Ala Gly Ser Leu Gly Gly
            725                 730                 735

Tyr Leu Asn Leu Val His Thr Ser Ser Gly Leu Trp Ala Asp Ile Val
            740                 745                 750

Ala Gln Gly Thr Arg His Ser Met Lys Ala Ser Ser Asp Asn Asn Asp
            755                 760                 765

Phe Arg Ala Arg Gly Trp Gly Trp Leu Gly Ser Leu Glu Thr Gly Leu
            770                 775                 780

Pro Phe Ser Ile Thr Asp Asn Leu Met Leu Glu Pro Gln Leu Gln Tyr
785                 790                 795                 800

Thr Trp Gln Gly Leu Ser Leu Asp Asp Gly Gln Asp Asn Ala Gly Tyr
            805                 810                 815

Val Lys Phe Gly His Gly Ser Ala Gln His Val Arg Ala Gly Phe Arg
            820                 825                 830

Leu Gly Ser His Asn Asp Met Asn Phe Gly Lys Gly Thr Ser Ser Arg
            835                 840                 845

Asp Thr Leu Arg Asp Ser Ala Lys His Ser Val Arg Glu Leu Pro Val
            850                 855                 860

Asn Trp Trp Val Gln Pro Ser Val Ile Arg Thr Phe Ser Ser Arg Gly
865                 870                 875                 880

Asp Met Ser Met Gly Thr Ala Ala Gly Ser Asn Met Thr Phe Ser
            885                 890                 895

Pro Ser Gln Asn Gly Thr Thr Leu Asp Leu Gln Ala Gly Leu Glu Ala
            900                 905                 910

Arg Val Arg Glu Asn Ile Thr Leu Gly Val Gln Ala Gly Tyr Ala His
            915                 920                 925

Ser Val Ser Gly Ser Ser Ala Glu Gly Tyr Asn Gly Gln Ala Thr Leu
            930                 935                 940

Asn Val Thr Phe
945

<210> SEQ ID NO 14
<211> LENGTH: 948

<212> TYPE: PRT
<213> ORGANISM: Escherichia coli

<400> SEQUENCE: 14

```
Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Arg Ala Gly Val Ala Val Ala Leu Ser Leu Ala Ala Val Thr Pro Val
        35                  40                  45

Pro Ala Leu Ala Ala Asp Thr Val Glu Ala Gly Glu Thr Val Asn
50                  55                  60

Gly Gly Thr Leu Thr Asn His Asp Asn Gln Ile Val Phe Gly Thr Thr
65                  70                  75                  80

Asn Gly Met Thr Ile Ser Thr Gly Leu Glu Tyr Gly Asp Asn Glu
                85                  90                  95

Ala Asn Thr Gly Gly Gln Trp Val Gln Asp Gly Gly Thr Ala Ser Asn
            100                 105                 110

Thr Thr Ile Ser Ser Gly Gly Leu Gln Phe Val Gly Ala Gly Gly Lys
        115                 120                 125

Ala Thr Asp Thr Ile Ile Asn Glu Gly Gly Gly Gln Ser Leu Lys Gly
130                 135                 140

Leu Ala Leu Asn Thr Thr Leu Asn Gly Gly Glu Gln Trp Met His Glu
145                 150                 155                 160

Gly Ala Ile Ala Thr Gly Thr Val Ile Asn Asp Lys Gly Trp Gln Val
                165                 170                 175

Val Lys Pro Gly Ala Val Ala Thr Asp Thr Val Val Asn Thr Gly Ala
            180                 185                 190

Glu Gly Gly Pro Asp Ala Glu Asn Gly Asp Thr Gly Gln Phe Val Arg
        195                 200                 205

Gly Asn Ala Val Arg Thr Thr Ile Asn Lys Asn Gly Arg Gln Ile Val
210                 215                 220

Thr Val Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Asn
                245                 250                 255

Gln Tyr Val His Asn Gly Gly Thr Thr Ser Asp Thr Val Asn Ser
            260                 265                 270

Asp Gly Trp Gln Ile Ile Lys Glu Gly Gly Leu Ala Asp Phe Thr Thr
        275                 280                 285

Val Asn Gln Lys Gly Lys Leu Gln Val Asn Ala Gly Gly Thr Ala Thr
290                 295                 300

Asn Val Thr Leu Lys Gln Gly Gly Ala Leu Val Thr Ser Thr Ala Ala
305                 310                 315                 320

Thr Val Thr Gly Ser Asn Arg Leu Gly Asn Phe Ala Val Glu Asn Gly
                325                 330                 335

Lys Ala Asp Gly Val Val Leu Glu Ser Gly Gly Arg Leu Asp Val Leu
            340                 345                 350

Glu Gly His Ser Ala Gln Lys Thr Arg Val Asp Asp Gly Gly Thr Leu
        355                 360                 365

Ala Val Ser Ala Gly Gly Lys Ala Thr Gly Val Thr Met Thr Ser Gly
370                 375                 380

Gly Ala Leu Ile Ala Asp Ser Gly Ala Thr Val Glu Gly Thr Asn Ala
385                 390                 395                 400
```

-continued

```
Ser Gly Lys Phe Ser Ile Asp Gly Ile Ser Gly Gln Ala Ser Gly Leu
            405                 410                 415
Leu Leu Glu Asn Gly Gly Ser Phe Thr Val Asn Ala Gly Gly Gln Ala
        420                 425                 430
Gly Asn Thr Thr Val Gly His Arg Gly Thr Leu Thr Leu Ala Ala Gly
        435                 440                 445
Gly Ser Leu Ser Gly Arg Thr Gln Leu Ser Lys Gly Ala Ser Met Val
        450                 455                 460
Leu Asn Gly Asp Val Val Ser Thr Gly Asp Ile Val Asn Ala Gly Glu
465                 470                 475                 480
Ile Arg Phe Asp Asn Gln Thr Thr Gln Asp Ala Val Leu Ser Arg Ala
                485                 490                 495
Val Ala Lys Gly Asp Ala Pro Val Thr Phe His Lys Leu Thr Thr Ser
                500                 505                 510
Asn Leu Thr Gly Gln Gly Gly Thr Ile Asn Met Arg Val Arg Leu Asp
                515                 520                 525
Gly Ser Asn Ala Ser Asp Gln Leu Val Ile Asn Gly Gly Gln Ala Thr
        530                 535                 540
Gly Lys Thr Trp Leu Ala Phe Thr Asn Val Gly Asn Ser Asn Leu Gly
545                 550                 555                 560
Val Ala Thr Ser Gly Gln Gly Ile Arg Val Val Asp Ala Gln Asn Gly
                565                 570                 575
Ala Thr Thr Glu Glu Gly Ala Phe Ala Leu Ser Arg Pro Leu Gln Ala
                580                 585                 590
Gly Ala Phe Asn Tyr Thr Leu Asn Arg Asp Ser Asp Glu Asp Trp Tyr
                595                 600                 605
Leu Arg Ser Glu Asn Ala Tyr Arg Ala Glu Val Pro Leu Tyr Ala Ser
                610                 615                 620
Met Leu Thr Gln Ala Met Asp Tyr Asp Arg Ile Leu Ala Gly Ser Arg
625                 630                 635                 640
Ser His Gln Thr Gly Val Asn Gly Glu Asn Asn Ser Val Arg Leu Ser
                645                 650                 655
Ile Gln Gly Gly His Leu Gly His Asp Asn Asn Gly Gly Ile Ala Arg
                660                 665                 670
Gly Ala Thr Pro Glu Ser Ser Gly Ser Tyr Gly Phe Val Arg Leu Glu
                675                 680                 685
Ser Asp Leu Leu Arg Thr Glu Val Ala Gly Met Ser Val Thr Ala Gly
        690                 695                 700
Val Tyr Ser Ala Ala Gly His Ser Ser Val Asp Val Lys Asp Asp Asp
705                 710                 715                 720
Gly Ser Arg Ala Gly Thr Val Arg Asp Asp Ala Gly Ser Leu Gly Gly
                725                 730                 735
Tyr Leu Asn Leu Val His Thr Ser Ser Gly Leu Trp Ala Asp Ile Met
                740                 745                 750
Ala Gln Gly Thr Arg His Ser Met Lys Ala Ser Ser Asp Asn Asn Asp
                755                 760                 765
Phe Arg Ala Arg Gly Trp Gly Trp Leu Gly Ser Leu Glu Thr Gly Leu
        770                 775                 780
Pro Phe Ser Ile Thr Asp Asn Leu Met Leu Glu Pro Gln Leu Gln Tyr
785                 790                 795                 800
Thr Trp Gln Gly Leu Ser Leu Asp Asp Gly Gln Asp Asn Ala Gly Tyr
                805                 810                 815
```

```
Val Lys Phe Gly His Gly Ser Ala Gln His Met Arg Ala Gly Phe Arg
            820                 825                 830

Leu Gly Ser His Asn Asp Met Ser Phe Gly Glu Gly Thr Ser Ser Arg
        835                 840                 845

Asp Thr Leu Arg Asp Ser Ala Lys His Arg Val Arg Glu Leu Pro Val
    850                 855                 860

Asn Trp Trp Val Gln Pro Ser Val Ile Arg Thr Phe Ser Ser Arg Gly
865                 870                 875                 880

Asp Met Ser Met Gly Thr Ala Ala Gly Ser Asn Met Thr Phe Ser
                885                 890                 895

Pro Ser Gln Asn Gly Thr Ser Leu Asp Leu Gln Ala Gly Leu Glu Ala
            900                 905                 910

Arg Val Arg Glu Asn Ile Thr Leu Gly Val Gln Ala Gly Tyr Ala His
        915                 920                 925

Ser Val Ser Gly Ser Ser Ala Glu Gly Tyr Asn Gly Gln Ala Thr Leu
    930                 935                 940

Asn Val Thr Phe
945

<210> SEQ ID NO 15
<211> LENGTH: 948
<212> TYPE: PRT
<213> ORGANISM: Escherichia coli

<400> SEQUENCE: 15

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
            20                  25                  30

Arg Thr Gly Val Ala Val Ala Leu Ser Leu Ala Thr Ala Thr Ser Val
        35                  40                  45

Pro Ala Leu Ala Ala Asp Ser Val Val Gln Ala Gly Glu Thr Val Ser
    50                  55                  60

Gly Gly Thr Leu Glu Asn His Asp Asn Gln Ile Val Phe Gly Thr Thr
65                  70                  75                  80

Asn Gly Ile Thr Ile Ser Thr Gly Leu Glu Tyr Gly Pro Asp Asn Glu
                85                  90                  95

Ala Asn Thr Gly Gly Gln Trp Val Gln Asp Gly Gly Thr Ala Ser Asn
            100                 105                 110

Thr Thr Ile Ser Ser Gly Gly Leu Gln Phe Val Gly Ala Gly Gly Lys
        115                 120                 125

Ala Thr Asp Thr Ile Ile Asn Glu Gly Gly Gly Gln Ser Leu Lys Gly
    130                 135                 140

Leu Ala Leu Asn Thr Thr Leu Asn Gly Gly Glu Gln Trp Met His Glu
145                 150                 155                 160

Gly Ala Ile Ala Thr Gly Thr Val Ile Asn Asp Lys Gly Trp Gln Val
                165                 170                 175

Val Lys Pro Gly Ala Val Ala Thr Asp Thr Val Val Asn Thr Gly Ala
            180                 185                 190

Glu Gly Gly Pro Asp Ala Glu Asn Ala Asp Thr Gly Gln Phe Val Arg
        195                 200                 205

Gly Asp Ala Val Arg Thr Thr Ile Asn Lys Asn Gly Arg Gln Ile Val
    210                 215                 220

Val Ala Thr Gly Val Ala Asn Thr Thr Val Val Tyr Ala Gly Gly Asp
225                 230                 235                 240
```

```
Gln Thr Val His Gly Tyr Ala Leu Asp Thr Thr Leu Asn Gly Gly Asn
                245                 250                 255

Gln Tyr Val His Asn Gly Gly Thr Ala Ser Asp Thr Val Val Asn Ser
            260                 265                 270

Asp Gly Trp Gln Ile Ile Lys Glu Gly Leu Ala Asp Phe Thr Thr
        275                 280                 285

Val Asn Gln Lys Gly Lys Leu Gln Val Asn Ala Gly Gly Thr Ala Thr
    290                 295                 300

Asn Val Thr Leu Lys Gln Gly Gly Ala Leu Val Thr Ser Thr Ala Ala
305                 310                 315                 320

Thr Val Leu Gly Ser Asn Arg Leu Gly Asn Phe Thr Val Glu Asn Gly
                325                 330                 335

Lys Ala Asp Gly Val Val Leu Glu Ser Gly Gly Arg Leu Asp Val Leu
            340                 345                 350

Glu Gly His Ser Ala Trp Lys Thr Leu Val Asp Asp Gly Gly Ile Leu
        355                 360                 365

Ala Val Ser Ala Gly Gly Lys Ala Thr Asp Val Thr Met Thr Ser Gly
    370                 375                 380

Gly Ala Leu Ile Ala Asp Ser Gly Ala Thr Val Glu Gly Thr Asn Ala
385                 390                 395                 400

Ser Gly Lys Phe Ser Ile Asp Gly Ile Ser Gly Gln Ala Ser Gly Leu
                405                 410                 415

Leu Leu Glu Asn Gly Gly Ser Phe Thr Val Asn Ala Gly Gly Gln Ala
            420                 425                 430

Gly Asn Thr Thr Val Gly His Arg Gly Thr Leu Thr Leu Ala Ala Gly
        435                 440                 445

Gly Ser Leu Ser Gly Arg Thr Gln Leu Ser Lys Gly Ala Ser Met Val
    450                 455                 460

Leu Asn Gly Asp Val Val Ser Thr Gly Asp Ile Val Asn Ala Gly Glu
465                 470                 475                 480

Ile His Phe Asp Asn Gln Thr Thr Gln Asp Ala Val Leu Ser Arg Ala
                485                 490                 495

Val Ala Lys Ser Asn Ser Pro Val Thr Phe His Lys Leu Thr Thr Thr
            500                 505                 510

Asn Leu Thr Gly Gln Gly Gly Thr Ile Asn Met Arg Val Ser Leu Asp
        515                 520                 525

Gly Ser Asn Ala Ser Asp Gln Leu Val Ile Asn Gly Gly Gln Ala Thr
    530                 535                 540

Gly Lys Thr Trp Leu Ala Phe Thr Asn Val Gly Asn Ser Asn Leu Gly
545                 550                 555                 560

Val Ala Thr Ser Gly Gln Gly Ile Arg Val Val Asp Ala Gln Asn Gly
                565                 570                 575

Ala Thr Thr Glu Glu Gly Ala Phe Ala Leu Ser Arg Pro Leu Gln Ala
            580                 585                 590

Gly Ala Phe Asn Tyr Thr Leu Asn Arg Asp Ser Asp Glu Asp Trp Tyr
        595                 600                 605

Leu Arg Ser Glu Asn Ala Tyr Arg Ala Glu Val Pro Leu Tyr Thr Ser
    610                 615                 620

Met Leu Thr Gln Ala Met Asp Tyr Asp Arg Ile Leu Ala Gly Ser Arg
625                 630                 635                 640

Ser His Gln Thr Gly Val Asn Gly Glu Asn Asn Ser Val Arg Leu Ser
                645                 650                 655
```

```
Ile Gln Gly Gly His Leu Gly His Asp Asn Asn Gly Ile Ala Arg
            660                 665                 670

Gly Ala Thr Pro Glu Ser Ser Gly Ser Tyr Gly Phe Val Arg Leu Glu
            675                 680                 685

Gly Asp Leu Leu Arg Thr Glu Val Ala Gly Met Ser Val Thr Ala Gly
690                 695                 700

Val Tyr Gly Ala Ala Gly His Ser Ser Val Asp Val Lys Asp Asp Asp
705                 710                 715                 720

Gly Ser Arg Ala Gly Thr Val Arg Asp Asp Ala Gly Ser Leu Gly Gly
                725                 730                 735

Tyr Leu Asn Leu Val His Thr Ser Ser Gly Leu Trp Ala Asp Ile Val
            740                 745                 750

Ala Gln Gly Thr Arg His Ser Met Lys Ala Ser Thr Asp Asn Asn Asp
            755                 760                 765

Phe Arg Ala Arg Gly Trp Gly Trp Leu Gly Ser Leu Glu Thr Gly Leu
770                 775                 780

Pro Phe Ser Ile Thr Asp Asn Leu Met Leu Glu Pro Gln Leu Gln Tyr
785                 790                 795                 800

Thr Trp Gln Gly Leu Ser Leu Asp Asp Gly Lys Asp Asn Ala Gly Tyr
                805                 810                 815

Val Lys Phe Gly His Gly Ser Ala Gln His Val Arg Ala Gly Phe Arg
            820                 825                 830

Leu Gly Ser His Asn Asp Met Thr Phe Gly Glu Gly Thr Ser Ser Arg
            835                 840                 845

Ala Pro Leu Arg Asp Ser Ala Lys His Ser Met Arg Glu Leu Pro Val
850                 855                 860

Asn Trp Trp Val Gln Pro Ser Val Ile Arg Thr Phe Ser Ser Arg Gly
865                 870                 875                 880

Asp Met Ser Met Gly Thr Ala Ala Gly Ser Asn Met Thr Phe Ser
                885                 890                 895

Pro Ser Arg Asn Gly Thr Ser Leu Asp Leu Gln Ala Gly Leu Glu Ala
            900                 905                 910

Arg Val Arg Glu Asn Ile Thr Leu Gly Val Gln Ala Gly Tyr Ala His
            915                 920                 925

Ser Val Ile Gly Ser Ser Ala Glu Gly Tyr Asn Gly Gln Ala Thr Leu
930                 935                 940

Asn Val Thr Phe
945

<210> SEQ ID NO 16
<211> LENGTH: 1039
<212> TYPE: PRT
<213> ORGANISM: Escherichia coli

<400> SEQUENCE: 16

Met Lys Arg His Leu Asn Thr Cys Tyr Arg Leu Val Trp Asn His Met
1               5                   10                  15

Thr Gly Ala Phe Val Val Ala Ser Glu Leu Ala Arg Ala Arg Gly Lys
            20                  25                  30

Arg Gly Gly Val Ala Val Ala Leu Ser Leu Ala Ala Val Thr Ser Leu
        35                  40                  45

Pro Val Leu Ala Ala Asp Ile Val Val His Pro Gly Glu Thr Val Asn
    50                  55                  60

Gly Gly Thr Leu Ala Asn His Asp Asn Gln Ile Val Phe Gly Thr Thr
65                  70                  75                  80
```

-continued

Asn Gly Met Thr Ile Ser Thr Gly Leu Glu Tyr Gly Pro Asp Asn Glu
            85                  90                  95

Ala Asn Thr Gly Gly Gln Trp Val Gln Asp Gly Gly Thr Ala Asn Lys
                100                 105                 110

Thr Thr Val Thr Ser Gly Gly Leu Gln Arg Val Asn Pro Gly Gly Ser
            115                 120                 125

Val Ser Asp Thr Val Ile Ser Ala Gly Gly Gln Ser Leu Gln Gly
130                 135                 140

Arg Ala Val Asn Thr Thr Leu Asn Gly Gly Glu Gln Trp Met His Glu
145                 150                 155                 160

Gly Ala Ile Ala Thr Gly Thr Val Ile Asn Asp Lys Gly Trp Gln Val
                165                 170                 175

Val Lys Pro Gly Thr Val Ala Thr Asp Thr Val Asn Thr Gly Ala
            180                 185                 190

Glu Gly Gly Pro Asp Ala Glu Asn Gly Asp Thr Gly Gln Phe Val Arg
            195                 200                 205

Gly Asp Ala Val Arg Thr Thr Ile Asn Lys Asn Gly Arg Gln Ile Val
210                 215                 220

Arg Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
            245                 250                 255

Gln Tyr Val His Asn Gly Gly Thr Ala Ser Asp Thr Val Val Asn Ser
            260                 265                 270

Asp Gly Trp Gln Ile Val Lys Asn Gly Gly Val Ala Gly Asn Thr Thr
            275                 280                 285

Val Asn Gln Lys Gly Arg Leu Gln Val Asp Ala Gly Gly Thr Ala Thr
290                 295                 300

Asn Val Thr Leu Lys Gln Gly Gly Ala Leu Val Thr Ser Thr Ala Ala
305                 310                 315                 320

Thr Val Thr Gly Ile Asn Arg Leu Gly Ala Phe Ser Val Val Glu Gly
            325                 330                 335

Lys Ala Asp Asn Val Val Leu Glu Asn Gly Gly Arg Leu Asp Val Leu
            340                 345                 350

Thr Gly His Thr Ala Thr Asn Thr Arg Val Asp Asp Gly Gly Thr Leu
            355                 360                 365

Asp Val Arg Asn Gly Gly Thr Ala Thr Thr Val Ser Met Gly Asn Gly
            370                 375                 380

Gly Val Leu Leu Ala Asp Ser Gly Ala Ala Val Ser Gly Thr Arg Ser
385                 390                 395                 400

Asp Gly Lys Ala Phe Ser Ile Gly Gly Gln Ala Asp Ala Leu Met
            405                 410                 415

Leu Glu Lys Gly Ser Ser Phe Thr Leu Asn Ala Gly Asp Thr Ala Thr
            420                 425                 430

Asp Thr Thr Val Asn Gly Gly Leu Phe Thr Ala Arg Gly Gly Thr Leu
            435                 440                 445

Ala Gly Thr Thr Thr Leu Asn Asn Gly Ala Ile Leu Thr Leu Ser Gly
            450                 455                 460

Lys Thr Val Asn Asn Asp Thr Leu Thr Ile Arg Glu Gly Asp Ala Leu
465                 470                 475                 480

Leu Gln Gly Gly Ser Leu Thr Gly Asn Gly Ser Val Glu Lys Ser Gly
            485                 490                 495

```
Ser Gly Thr Leu Thr Val Ser Asn Thr Thr Leu Thr Gln Lys Ala Val
            500                 505                 510

Asn Leu Asn Glu Gly Thr Leu Thr Leu Asn Asp Ser Thr Val Thr Thr
        515                 520                 525

Asp Val Ile Ala Gln Arg Gly Thr Ala Leu Lys Leu Thr Gly Ser Thr
    530                 535                 540

Val Leu Asn Gly Ala Ile Asp Pro Thr Asn Val Thr Leu Ala Ser Gly
545                 550                 555                 560

Ala Thr Trp Asn Ile Pro Asp Asn Ala Thr Val Gln Ser Val Val Asp
                565                 570                 575

Asp Leu Ser His Ala Gly Gln Ile His Phe Thr Ser Thr Arg Thr Gly
            580                 585                 590

Lys Phe Val Pro Ala Thr Leu Lys Val Lys Asn Leu Asn Gly Gln Asn
        595                 600                 605

Gly Thr Ile Ser Leu Arg Val Arg Pro Asp Met Ala Gln Asn Asn Ala
    610                 615                 620

Asp Arg Leu Val Ile Asp Gly Gly Arg Ala Thr Gly Lys Thr Ile Leu
625                 630                 635                 640

Asn Leu Val Asn Ala Gly Asn Ser Ala Ser Gly Leu Ala Thr Ser Gly
                645                 650                 655

Lys Gly Ile Gln Val Val Glu Ala Ile Asn Gly Ala Thr Thr Glu Glu
            660                 665                 670

Gly Ala Phe Val Gln Gly Asn Arg Leu Gln Ala Gly Ala Phe Asn Tyr
        675                 680                 685

Ser Leu Asn Arg Asp Ser Asp Glu Ser Trp Tyr Leu Arg Ser Glu Asn
    690                 695                 700

Ala Tyr Arg Ala Glu Val Pro Leu Tyr Ala Ser Met Leu Thr Gln Ala
705                 710                 715                 720

Met Asp Tyr Asp Arg Ile Val Ala Gly Ser Arg Ser His Gln Thr Gly
                725                 730                 735

Val Asn Gly Glu Asn Asn Ser Val Arg Leu Ser Ile Gln Gly Gly His
            740                 745                 750

Leu Gly His Asp Asn Asn Gly Gly Ile Ala Arg Gly Ala Thr Pro Glu
        755                 760                 765

Ser Ser Gly Ser Tyr Gly Phe Val Arg Leu Glu Gly Asp Leu Met Arg
    770                 775                 780

Thr Glu Val Ala Gly Met Ser Val Thr Ala Gly Val Tyr Gly Ala Ala
785                 790                 795                 800

Gly His Ser Ser Val Asp Val Lys Asp Asp Gly Ser Arg Ala Gly
                805                 810                 815

Thr Val Arg Asp Asp Ala Gly Ser Leu Gly Gly Tyr Leu Asn Leu Val
        820                 825                 830

His Thr Ser Ser Gly Leu Trp Ala Asp Ile Val Ala Gln Gly Thr Arg
    835                 840                 845

His Ser Met Lys Ala Ser Ser Asp Asn Asp Phe Arg Ala Arg Gly
                855                 860

Trp Gly Trp Leu Gly Ser Leu Glu Thr Gly Leu Pro Phe Ser Ile Thr
865                 870                 875                 880

Asp Asn Leu Met Leu Glu Pro Gln Leu Gln Tyr Thr Trp Gln Gly Leu
                885                 890                 895

Ser Leu Asp Asp Gly Lys Asp Asn Ala Gly Tyr Val Lys Phe Gly His
            900                 905                 910

Gly Ser Ala Gln His Val Arg Ala Gly Phe Arg Leu Gly Ser His Asn
```

```
                915                 920                 925
Asp Met Thr Phe Gly Glu Gly Thr Ser Ser Arg Ala Pro Leu Arg Asp
    930                 935                 940

Ser Ala Lys His Ser Val Ser Glu Leu Pro Val Asn Trp Trp Val Gln
945                 950                 955                 960

Pro Ser Val Ile Arg Thr Phe Ser Ser Arg Gly Asp Met Arg Val Gly
            965                 970                 975

Thr Ser Thr Ala Gly Ser Gly Met Thr Phe Ser Pro Ser Gln Asn Gly
                980                 985                 990

Thr Ser Leu Asp Leu Gln Ala Gly Leu Glu Ala Arg Val Arg Glu Asn
            995                 1000                1005

Ile Thr Leu Gly Val Gln Ala Gly Tyr Ala His Ser Val Ser Gly Ser
    1010                1015                1020

Ser Ala Glu Gly Tyr Asn Gly Gln Ala Thr Leu Asn Val Thr Phe
1025                1030                1035

<210> SEQ ID NO 17
<211> LENGTH: 1039
<212> TYPE: PRT
<213> ORGANISM: Escherichia coli

<400> SEQUENCE: 17

Met Lys Arg His Leu Asn Thr Cys Tyr Arg Leu Val Trp Asn His Met
1               5                   10                  15

Thr Gly Ala Phe Val Val Ala Ser Glu Leu Ala Arg Ala Arg Gly Lys
            20                  25                  30

Arg Gly Gly Val Ala Val Ala Leu Ser Leu Ala Ala Val Thr Ser Leu
        35                  40                  45

Pro Val Leu Ala Ala Asp Ile Val Val His Pro Gly Glu Thr Val Asn
    50                  55                  60

Gly Gly Thr Leu Ala Asn His Asp Asn Gln Ile Val Phe Gly Thr Thr
65                  70                  75                  80

Asn Gly Met Thr Ile Ser Thr Gly Leu Glu Tyr Gly Pro Asp Asn Glu
                85                  90                  95

Ala Asn Thr Gly Gly Gln Trp Val Gln Asp Gly Gly Ala Asn Lys
            100                 105                 110

Thr Thr Val Thr Ser Gly Gly Leu Gln Arg Val Asn Pro Gly Gly Ser
        115                 120                 125

Val Ser Asp Thr Val Ile Ser Ala Gly Gly Gln Ser Leu Gln Gly
    130                 135                 140

Arg Ala Val Asn Thr Thr Leu Asn Gly Gly Glu Gln Trp Met His Glu
145                 150                 155                 160

Gly Ala Ile Ala Thr Gly Thr Val Ile Asn Asp Lys Gly Trp Gln Val
                165                 170                 175

Val Lys Pro Gly Thr Val Ala Thr Asp Thr Val Val Asn Thr Gly Ala
            180                 185                 190

Glu Gly Gly Pro Asp Ala Glu Asn Gly Asp Thr Gly Gln Phe Val Arg
        195                 200                 205

Gly Asp Ala Val Arg Thr Thr Ile Asn Lys Asn Gly Arg Gln Ile Val
    210                 215                 220

Arg Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
                245                 250                 255
```

-continued

```
Gln Tyr Val His Asn Gly Gly Thr Ala Ser Asp Thr Val Val Asn Ser
            260                 265                 270

Asp Gly Trp Gln Ile Val Lys Asn Gly Gly Val Ala Gly Asn Thr Thr
        275                 280                 285

Val Asn Gln Lys Gly Arg Leu Gln Val Asp Ala Gly Thr Ala Thr
    290                 295                 300

Asn Val Thr Leu Lys Gln Gly Gly Ala Leu Val Thr Ser Thr Ala Ala
305                 310                 315                 320

Thr Val Thr Gly Ile Asn Arg Leu Gly Ala Phe Ser Val Val Glu Gly
                325                 330                 335

Lys Ala Asp Asn Val Val Leu Glu Asn Gly Gly Arg Leu Asp Val Leu
            340                 345                 350

Thr Gly His Thr Ala Thr Asn Thr Arg Val Asp Asp Gly Gly Thr Leu
        355                 360                 365

Asp Val Arg Asn Gly Gly Thr Ala Thr Thr Val Ser Met Gly Asn Gly
    370                 375                 380

Gly Val Leu Leu Ala Asp Ser Gly Ala Ala Val Ser Gly Thr Arg Ser
385                 390                 395                 400

Asp Gly Lys Ala Phe Ser Ile Gly Gly Gly Gln Ala Asp Ala Leu Met
                405                 410                 415

Leu Glu Lys Gly Ser Ser Phe Thr Leu Asn Ala Gly Asp Thr Ala Thr
            420                 425                 430

Asp Thr Thr Val Asn Gly Gly Leu Phe Thr Ala Arg Gly Gly Thr Leu
        435                 440                 445

Ala Gly Thr Thr Thr Leu Asn Asn Gly Ala Ile Leu Thr Leu Ser Gly
    450                 455                 460

Lys Thr Val Asn Asn Asp Thr Leu Thr Ile Arg Glu Gly Asp Ala Leu
465                 470                 475                 480

Leu Gln Gly Gly Ser Leu Thr Gly Asn Gly Ser Val Glu Lys Ser Gly
                485                 490                 495

Ser Gly Thr Leu Thr Val Ser Asn Thr Thr Leu Thr Gln Lys Ala Val
            500                 505                 510

Asn Leu Asn Glu Gly Thr Leu Thr Leu Asn Asp Ser Thr Val Thr Thr
        515                 520                 525

Asp Val Ile Ala Gln Arg Gly Thr Ala Leu Lys Leu Thr Gly Ser Thr
    530                 535                 540

Val Leu Asn Gly Ala Ile Asp Pro Thr Asn Val Thr Leu Ala Ser Gly
545                 550                 555                 560

Ala Thr Trp Asn Ile Pro Asp Asn Ala Thr Val Gln Ser Val Val Asp
                565                 570                 575

Asp Leu Ser His Ala Gly Gln Ile His Phe Thr Ser Thr Arg Thr Gly
            580                 585                 590

Lys Phe Val Pro Ala Thr Leu Lys Val Lys Asn Leu Asn Gly Gln Asn
        595                 600                 605

Gly Thr Ile Ser Leu Arg Val Arg Pro Asp Met Ala Gln Asn Asn Ala
    610                 615                 620

Asp Arg Leu Val Ile Asp Gly Gly Arg Ala Thr Gly Lys Thr Ile Leu
625                 630                 635                 640

Asn Leu Val Asn Ala Gly Asn Ser Ala Ser Gly Leu Ala Thr Ser Gly
                645                 650                 655

Lys Gly Ile Gln Val Val Glu Ala Ile Asn Gly Ala Thr Thr Glu Glu
            660                 665                 670

Gly Ala Phe Val Gln Gly Asn Arg Leu Gln Ala Gly Ala Phe Asn Tyr
```

```
            675                 680                 685
Ser Leu Asn Arg Asp Ser Asp Glu Ser Trp Tyr Leu Arg Ser Glu Asn
    690                 695                 700

Ala Tyr Arg Ala Glu Val Pro Leu Tyr Ala Ser Met Leu Thr Gln Ala
705                 710                 715                 720

Met Asp Tyr Asp Arg Ile Val Ala Gly Ser Arg Ser His Gln Thr Gly
                725                 730                 735

Val Asn Gly Glu Asn Asn Ser Val Arg Leu Ser Ile Gln Gly Gly His
            740                 745                 750

Leu Gly His Asp Asn Asn Gly Gly Ile Ala Arg Gly Ala Thr Pro Glu
        755                 760                 765

Ser Ser Gly Ser Tyr Gly Phe Val Arg Leu Glu Gly Asp Leu Met Arg
    770                 775                 780

Thr Glu Val Ala Gly Met Ser Val Thr Ala Gly Val Tyr Gly Ala Ala
785                 790                 795                 800

Gly His Ser Ser Val Asp Val Lys Asp Asp Gly Ser Arg Ala Gly
                805                 810                 815

Thr Val Arg Asp Asp Ala Gly Cys Leu Gly Gly Tyr Leu Asn Leu Val
            820                 825                 830

His Thr Ser Ser Gly Leu Trp Ala Asp Ile Val Ala Gln Gly Thr Arg
        835                 840                 845

His Ser Met Lys Ala Ser Ser Asp Asn Asp Phe Arg Ala Arg Gly
850                 855                 860

Trp Gly Trp Leu Gly Ser Leu Glu Thr Gly Leu Pro Phe Ser Ile Thr
865                 870                 875                 880

Asp Asn Leu Met Leu Glu Pro Gln Leu Gln Tyr Thr Trp Gln Gly Leu
                885                 890                 895

Ser Leu Asp Asp Gly Lys Asp Asn Ala Gly Tyr Val Lys Phe Gly His
            900                 905                 910

Gly Ser Ala Gln His Val Arg Ala Gly Phe Arg Leu Gly Ser His Asn
        915                 920                 925

Asp Met Thr Phe Gly Glu Gly Thr Ser Ser Arg Ala Pro Leu Arg Asp
    930                 935                 940

Ser Ala Lys His Ser Val Ser Glu Leu Pro Val Asn Trp Trp Val Gln
945                 950                 955                 960

Pro Ser Val Ile Arg Thr Phe Ser Arg Gly Asp Met Arg Val Gly
                965                 970                 975

Thr Ser Thr Ala Gly Ser Gly Met Thr Phe Ser Pro Ser Gln Asn Gly
            980                 985                 990

Thr Ser Leu Asp Leu Gln Ala Gly Leu Glu Ala Arg Val Arg Glu Asn
        995                 1000                1005

Ile Thr Leu Gly Val Gln Ala Gly Tyr Ala His Ser Val Ser Gly Ser
    1010                1015                1020

Ser Ala Glu Gly Tyr Asn Gly Gln Ala Thr Leu Asn Val Thr Phe
1025                1030                1035

<210> SEQ ID NO 18
<211> LENGTH: 1039
<212> TYPE: PRT
<213> ORGANISM: Escherichia coli

<400> SEQUENCE: 18

Met Lys Arg His Leu Asn Thr Cys Tyr Arg Leu Val Trp Asn His Ile
1               5                   10                  15
```

Thr Gly Ala Phe Val Val Ala Ser Glu Leu Ala Arg Ala Arg Gly Lys
             20                  25                  30

Arg Gly Gly Val Ala Val Ala Leu Ser Leu Ala Ala Val Thr Ser Leu
         35                  40                  45

Pro Val Leu Ala Ala Asp Ile Val Val His Pro Gly Glu Thr Val Asn
     50                  55                  60

Gly Gly Thr Leu Ala Asn His Asp Asn Gln Ile Val Phe Gly Thr Thr
 65                  70                  75                  80

Asn Gly Met Thr Ile Ser Thr Gly Leu Glu Tyr Gly Pro Asp Asn Glu
                 85                  90                  95

Ala Asn Thr Gly Gly Gln Trp Val Gln Asp Gly Gly Thr Ala Asn Lys
            100                 105                 110

Thr Thr Val Thr Ser Gly Gly Leu Gln Arg Val Asn Pro Gly Gly Ser
            115                 120                 125

Val Ser Asp Thr Val Ile Ser Ala Gly Gly Gln Ser Leu Gln Gly
        130                 135                 140

Arg Ala Val Asn Thr Thr Leu Asn Gly Gly Glu Gln Trp Met His Glu
145                 150                 155                 160

Gly Ala Ile Ala Thr Gly Thr Val Ile Asn Asp Lys Gly Trp Gln Val
                165                 170                 175

Val Lys Pro Gly Thr Val Ala Thr Asp Thr Val Asn Thr Gly Ala
            180                 185                 190

Glu Gly Gly Pro Asp Ala Glu Asn Gly Asp Thr Gly Gln Phe Val Arg
                195                 200                 205

Gly Asp Ala Val Arg Thr Thr Ile Asn Lys Asn Gly Arg Gln Ile Val
210                 215                 220

Arg Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Tyr
                245                 250                 255

Gln Tyr Val His Asn Gly Gly Thr Ala Ser Asp Thr Val Val Asn Ser
        260                 265                 270

Asp Gly Trp Gln Ile Val Lys Asn Gly Gly Val Ala Gly Asn Thr Thr
        275                 280                 285

Val Asn Gln Lys Gly Arg Leu Gln Val Asp Ala Gly Gly Thr Ala Thr
290                 295                 300

Asn Val Thr Leu Lys Gln Gly Gly Ala Leu Val Thr Ser Thr Ala Ala
305                 310                 315                 320

Thr Val Thr Gly Ile Asn Arg Leu Gly Ala Phe Ser Val Glu Gly
                325                 330                 335

Lys Ala Asp Asn Val Val Leu Glu Asn Gly Gly Arg Leu Asp Val Leu
            340                 345                 350

Thr Gly His Thr Ala Thr Asn Thr Arg Val Asp Asp Gly Thr Leu
        355                 360                 365

Asp Val Arg Asn Gly Gly Thr Ala Thr Val Ser Met Gly Asn Gly
    370                 375                 380

Gly Val Leu Leu Ala Asp Ser Gly Ala Ala Val Ser Gly Thr Arg Ser
385                 390                 395                 400

Asp Gly Lys Ala Phe Ser Ile Gly Gly Gln Ala Asp Ala Leu Met
                405                 410                 415

Leu Glu Lys Gly Ser Ser Phe Thr Leu Asn Ala Gly Asp Thr Ala Thr
        420                 425                 430

Asp Thr Thr Val Asn Gly Gly Leu Phe Thr Ala Arg Gly Gly Thr Leu

-continued

```
            435                 440                 445
Ala Gly Thr Thr Thr Leu Asn Asn Gly Ala Ile Leu Thr Leu Ser Gly
450                 455                 460

Lys Thr Val Asn Asn Asp Thr Leu Thr Ile Arg Glu Gly Asp Ala Leu
465                 470                 475                 480

Leu Gln Gly Gly Ser Leu Thr Gly Asn Gly Ser Val Glu Lys Ser Gly
                    485                 490                 495

Ser Gly Thr Leu Thr Val Ser Asn Thr Thr Leu Thr Gln Lys Ala Val
                500                 505                 510

Asn Leu Asn Glu Gly Thr Leu Thr Leu Asn Asp Ser Thr Val Thr Thr
            515                 520                 525

Asp Val Ile Ala Gln Arg Gly Thr Ala Leu Lys Leu Thr Gly Ser Thr
530                 535                 540

Val Leu Asn Gly Ala Ile Asp Pro Thr Asn Val Thr Leu Ala Ser Gly
545                 550                 555                 560

Ala Thr Trp Asn Ile Pro Asp Asn Ala Thr Val Gln Ser Val Val Asp
                    565                 570                 575

Asp Leu Ser His Ala Gly Gln Ile His Phe Thr Ser Arg Thr Gly
                580                 585                 590

Lys Phe Val Pro Ala Thr Leu Lys Val Lys Asn Leu Asn Gly Gln Asn
            595                 600                 605

Gly Thr Ile Ser Leu Arg Val Arg Pro Asp Met Ala Gln Asn Asn Ala
610                 615                 620

Asp Arg Leu Val Ile Asp Gly Arg Ala Thr Gly Lys Thr Ile Leu
625                 630                 635                 640

Asn Leu Val Asn Ala Gly Asn Ser Ala Ser Gly Leu Ala Thr Ser Gly
                    645                 650                 655

Lys Gly Ile Gln Val Val Glu Ala Ile Asn Gly Ala Thr Thr Glu Glu
                660                 665                 670

Gly Ala Phe Val Gln Gly Asn Arg Leu Gln Ala Gly Ala Phe Asn Tyr
            675                 680                 685

Ser Leu Asn Arg Asp Ser Asp Glu Ser Trp Tyr Leu Arg Ser Glu Asn
690                 695                 700

Ala Tyr Arg Ala Glu Val Pro Leu Tyr Ala Ser Met Leu Thr Gln Ala
705                 710                 715                 720

Met Asp Tyr Asp Arg Ile Leu Ala Gly Ser Arg Ser His Gln Thr Gly
                    725                 730                 735

Val Ser Gly Glu Asn Asn Ser Val Arg Leu Ser Ile Gln Gly Gly His
                740                 745                 750

Leu Gly His Asp Asn Asn Gly Gly Ile Ala Arg Gly Ala Thr Pro Glu
            755                 760                 765

Ser Ser Gly Ser Tyr Gly Phe Val Arg Leu Glu Gly Asp Leu Leu Arg
770                 775                 780

Thr Glu Val Ala Gly Met Ser Leu Thr Thr Gly Val Tyr Gly Ala Ala
785                 790                 795                 800

Gly His Ser Ser Val Asp Val Lys Asp Asp Gly Ser Arg Ala Gly
                    805                 810                 815

Thr Val Arg Asp Asp Ala Gly Ser Leu Gly Gly Tyr Leu Asn Leu Thr
                820                 825                 830

His Thr Ser Ser Gly Leu Trp Ala Asp Ile Val Ala Gln Gly Thr Arg
            835                 840                 845

His Ser Met Lys Ala Ser Ser Asp Asn Asn Asp Phe Arg Ala Arg Gly
850                 855                 860
```

```
Trp Gly Trp Leu Gly Ser Leu Glu Thr Gly Leu Pro Phe Ser Ile Thr
865                 870                 875                 880

Asp Asn Leu Met Leu Glu Pro Gln Leu His Tyr Thr Trp Gln Gly Leu
            885                 890                 895

Ser Leu Asp Asp Gly Gln Asp Asn Ala Gly Tyr Val Lys Phe Gly His
        900                 905                 910

Gly Ser Ala Gln His Val Arg Ala Gly Phe Arg Leu Gly Ser His Asn
            915                 920                 925

Asp Met Thr Phe Gly Glu Gly Thr Ser Ser Arg Asp Thr Leu Arg Asp
930                 935                 940

Ser Thr Lys His Gly Val Ser Glu Leu Pro Val Asn Trp Trp Val Gln
945                 950                 955                 960

Pro Ser Val Ile Arg Thr Phe Ser Ser Arg Gly Asp Met Ser Met Gly
                965                 970                 975

Thr Ala Ala Gly Ser Asn Met Thr Phe Ser Pro Ser Gln Asn Gly
            980                 985                 990

Thr Ser Leu Asp Leu Gln Ala Gly Leu Glu Ala Arg Val Arg Glu Asn
            995                 1000                1005

Ile Thr Leu Gly Val Gln Ala Gly Tyr Ala His Ser Val Ser Gly Ser
    1010                1015                1020

Ser Ala Glu Gly Tyr Asn Gly Gln Ala Thr Leu Asn Val Thr Phe
1025                1030                1035

<210> SEQ ID NO 19
<211> LENGTH: 1039
<212> TYPE: PRT
<213> ORGANISM: Escherichia coli

<400> SEQUENCE: 19

Met Lys Arg His Leu Asn Thr Ser Tyr Arg Leu Val Trp Asn His Ile
1               5                   10                  15

Thr Gly Thr Leu Val Val Ala Ser Glu Leu Ala Arg Ser Arg Gly Lys
                20                  25                  30

Arg Ala Gly Val Ala Val Ala Leu Ser Leu Ala Ala Val Thr Ser Val
            35                  40                  45

Pro Ala Leu Ala Ala Asp Lys Val Val Gln Ala Gly Glu Thr Val Asn
    50                  55                  60

Asp Gly Thr Leu Thr Asn His Asp Asn Gln Ile Val Leu Gly Thr Ala
65                  70                  75                  80

Asn Gly Met Thr Ile Ser Thr Gly Leu Glu Tyr Gly Pro Asp Asn Glu
                85                  90                  95

Ala Asn Thr Gly Gly Gln Trp Ile Gln Asn Gly Gly Ile Ala Asn Asn
            100                 105                 110

Thr Thr Val Thr Gly Gly Leu Gln Arg Val Asn Ala Gly Gly Ser
        115                 120                 125

Val Ser Asp Thr Val Ile Ser Ala Gly Gly Gln Ser Leu Gln Gly
    130                 135                 140

Gln Ala Val Asn Thr Thr Leu Asn Gly Gly Glu Gln Trp Val His Glu
145                 150                 155                 160

Gly Gly Ile Ala Thr Gly Thr Val Ile Asn Glu Lys Gly Trp Gln Ala
                165                 170                 175

Ile Lys Ser Gly Ala Val Ala Thr Asp Thr Val Val Asn Thr Gly Ala
            180                 185                 190

Glu Gly Gly Pro Asp Ala Glu Asn Gly Asp Thr Gly Gln Thr Val Tyr
```

```
            195                 200                 205
Gly Asp Ala Val Arg Thr Thr Ile Asn Lys Asn Gly Arg Gln Ile Val
210                 215                 220

Ala Ala Glu Gly Thr Ala Asn Thr Thr Val Val Tyr Ala Gly Gly Asp
225                 230                 235                 240

Gln Thr Val His Gly His Ala Leu Asp Thr Thr Leu Asn Gly Gly Tyr
                245                 250                 255

Gln Tyr Val His Asn Gly Gly Thr Ala Ser Gly Thr Val Asn Ser
                260                 265                 270

Asp Gly Trp Gln Ile Val Lys Asn Gly Gly Val Ala Gly Asn Thr Thr
                275                 280                 285

Val Asn Gln Lys Gly Arg Leu Gln Val Asp Ala Gly Gly Thr Ala Thr
290                 295                 300

Asn Val Thr Leu Lys Gln Gly Gly Ala Leu Val Thr Ser Thr Ala Ala
305                 310                 315                 320

Thr Val Thr Gly Ile Asn Arg Leu Gly Ala Phe Ser Val Val Glu Gly
                325                 330                 335

Lys Ala Asp Asn Val Val Leu Glu Asn Gly Gly Arg Leu Asp Val Leu
                340                 345                 350

Thr Gly His Thr Ala Thr Asn Thr Arg Val Asp Asp Gly Gly Thr Leu
                355                 360                 365

Asp Val Arg Asn Gly Gly Thr Ala Thr Thr Val Ser Met Gly Asn Gly
370                 375                 380

Gly Val Leu Leu Ala Asp Ser Gly Ala Ala Val Ser Gly Thr Arg Ser
385                 390                 395                 400

Asp Gly Lys Ala Phe Ser Ile Gly Gly Gln Ala Asp Ala Leu Met
                405                 410                 415

Leu Glu Lys Gly Ser Ser Phe Thr Leu Asn Ala Gly Asp Thr Ala Thr
                420                 425                 430

Asp Thr Thr Val Asn Gly Gly Leu Phe Thr Ala Arg Gly Gly Thr Leu
                435                 440                 445

Ala Gly Thr Thr Thr Leu Asn Asn Gly Ala Ile Leu Thr Leu Ser Gly
450                 455                 460

Lys Thr Val Asn Asn Asp Thr Leu Thr Ile Arg Glu Gly Asp Ala Leu
465                 470                 475                 480

Leu Gln Gly Gly Ser Leu Thr Gly Asn Gly Ser Val Glu Lys Ser Gly
                485                 490                 495

Ser Gly Thr Leu Thr Val Ser Asn Thr Thr Leu Thr Gln Lys Ala Val
                500                 505                 510

Asn Leu Asn Glu Gly Thr Leu Thr Leu Asn Asp Ser Thr Val Thr Thr
                515                 520                 525

Asp Val Ile Ala Gln Arg Gly Thr Ala Leu Lys Leu Thr Gly Ser Thr
                530                 535                 540

Val Leu Asn Gly Ala Ile Asp Pro Thr Asn Val Thr Leu Ala Ser Gly
545                 550                 555                 560

Ala Thr Trp Asn Ile Pro Asp Asn Ala Thr Val Gln Ser Val Val Asp
                565                 570                 575

Asp Leu Ser His Ala Gly Gln Ile His Phe Thr Ser Thr Arg Thr Gly
                580                 585                 590

Lys Phe Val Pro Ala Thr Leu Lys Val Lys Asn Leu Asn Gly Gln Asn
                595                 600                 605

Gly Thr Ile Ser Leu Arg Val Arg Pro Asp Met Ala Gln Asn Asn Ala
                610                 615                 620
```

-continued

```
Asp Arg Leu Val Ile Asp Gly Gly Arg Ala Thr Gly Lys Thr Ile Leu
625                 630                 635                 640

Asn Leu Val Asn Ala Gly Asn Ser Ala Ser Gly Leu Ala Thr Ser Gly
            645                 650                 655

Lys Gly Ile Gln Val Val Glu Ala Ile Asn Gly Ala Thr Thr Glu Glu
            660                 665                 670

Gly Ala Phe Ile Gln Gly Asn Lys Leu Gln Ala Gly Ala Phe Asn Tyr
            675                 680                 685

Ser Leu Asn Arg Asp Ser Asp Glu Ser Trp Tyr Leu Arg Ser Glu Asn
690                 695                 700

Ala Tyr Arg Ala Glu Val Pro Leu Tyr Ala Ser Met Leu Thr Gln Ala
705                 710                 715                 720

Met Asp Tyr Asp Arg Ile Leu Ala Gly Ser Arg Ser His Gln Thr Gly
                725                 730                 735

Val Ser Gly Glu Asn Asn Ser Val Arg Leu Ser Ile Gln Gly Gly His
            740                 745                 750

Leu Gly His Asp Asn Asn Gly Gly Ile Ala Arg Gly Ala Thr Pro Glu
            755                 760                 765

Ser Ser Gly Ser Tyr Gly Phe Val Arg Leu Glu Gly Asp Leu Leu Arg
770                 775                 780

Thr Glu Val Ala Gly Met Ser Val Thr Ala Gly Val Tyr Gly Ala Ala
785                 790                 795                 800

Gly His Ser Ser Val Asp Val Lys Asp Asp Gly Ser Arg Ala Gly
                805                 810                 815

Thr Val Arg Asp Asp Ala Gly Ser Leu Gly Gly Tyr Leu Asn Leu Ile
                820                 825                 830

His Asn Ala Ser Gly Leu Trp Ala Asp Ile Val Ala Gln Gly Thr Arg
            835                 840                 845

His Ser Met Lys Ala Ser Ser Asp Asn Asn Asp Phe Arg Val Arg Gly
            850                 855                 860

Trp Gly Trp Leu Gly Ser Leu Glu Thr Gly Leu Pro Phe Ser Ile Thr
865                 870                 875                 880

Asp Asn Leu Met Leu Glu Pro Gln Leu Gln Tyr Thr Trp Gln Gly Leu
                885                 890                 895

Ser Leu Asp Asp Gly Gln Asp Asn Ala Ser Tyr Val Lys Phe Gly His
                900                 905                 910

Gly Ser Ala Gln His Val Arg Ala Gly Phe Arg Leu Gly Ser His His
            915                 920                 925

Asp Met Asn Phe Gly Lys Gly Thr Ser Ser Arg Asp Thr Leu Arg Gly
            930                 935                 940

Ser Ala Lys His Ser Val Arg Glu Leu Pro Val Asn Trp Trp Val Gln
945                 950                 955                 960

Pro Ser Val Ile Arg Thr Phe Ser Ser Arg Gly Asp Met Ser Met Gly
                965                 970                 975

Thr Ala Ala Ala Gly Ser Asn Met Thr Phe Ser Pro Ser Gln Asn Gly
                980                 985                 990

Thr Ser Leu Asp Leu Gln Ala Gly Leu Glu Ala Arg Val Arg Glu Asn
            995                 1000                1005

Ile Thr Leu Gly Val Gln Ala Gly Tyr Val His Ser Val Ser Gly Ser
    1010                1015                1020

Ser Ala Glu Gly Tyr Asn Gly Gln Ala Thr Leu Asn Val Thr Phe
1025                1030                1035
```

-continued

```
<210> SEQ ID NO 20
<211> LENGTH: 1039
<212> TYPE: PRT
<213> ORGANISM: Escherichia coli

<400> SEQUENCE: 20
```

| | | | | | | | | | | | | | | | |
|---|---|---|---|---|---|---|---|---|---|---|---|---|---|---|---|
| Met | Lys | Arg | His | Leu | Asn | Thr | Ser | Tyr | Arg | Leu | Val | Trp | Asn | His | Ile |
| 1 | | | | 5 | | | | | 10 | | | | | 15 | |
| Thr | Gly | Ala | Phe | Val | Val | Ala | Ser | Glu | Leu | Ala | Arg | Ala | Arg | Gly | Lys |
| | | | 20 | | | | | 25 | | | | | 30 | | |
| Arg | Ala | Gly | Val | Ala | Val | Ala | Leu | Ser | Leu | Ala | Ala | Ala | Thr | Ser | Leu |
| | | 35 | | | | | 40 | | | | | 45 | | | |
| Pro | Ala | Leu | Ala | Ala | Asp | Ser | Val | Val | Pro | Ala | Gly | Glu | Thr | Val | Asn |
| 50 | | | | | 55 | | | | | 60 | | | | | |
| Gly | Gly | Thr | Leu | Ile | Asn | His | Asp | Arg | Gln | Phe | Val | Ser | Gly | Thr | Ala |
| 65 | | | | | 70 | | | | | 75 | | | | | 80 |
| Asp | Gly | Met | Thr | Val | Ser | Thr | Gly | Leu | Glu | Leu | Gly | Ala | Asp | Ser | Asp |
| | | | | 85 | | | | | 90 | | | | | 95 | |
| Asn | Asn | Thr | Gly | Gly | Gln | Gln | Ile | Ala | Arg | Gly | Gly | Thr | Ala | Arg | Asn |
| | | | 100 | | | | | 105 | | | | | 110 | | |
| Thr | Arg | Val | Thr | Ala | Asn | Gly | Leu | Gln | Asp | Val | Met | Ala | Gly | Gly | Ser |
| | | 115 | | | | | 120 | | | | | 125 | | | |
| Thr | Ser | Asp | Thr | Val | Ile | Ser | Thr | Gly | Gly | Gln | Asn | Leu | Arg | Gly | |
| | 130 | | | | | 135 | | | | | 140 | | | | |
| Lys | Ala | Ser | Gly | Thr | Val | Leu | Asn | Gly | Gly | Asp | Gln | Trp | Ile | His | Ala |
| 145 | | | | | 150 | | | | | 155 | | | | | 160 |
| Gly | Gly | Arg | Ala | Ser | Gly | Thr | Val | Ile | Asn | Gln | Asp | Gly | Tyr | Gln | Thr |
| | | | | 165 | | | | | 170 | | | | | 175 | |
| Ile | Lys | His | Gly | Gly | Leu | Val | Thr | Gly | Thr | Ile | Val | Asn | Thr | Gly | Ala |
| | | | 180 | | | | | 185 | | | | | 190 | | |
| Glu | Gly | Gly | Pro | Asp | Ser | Glu | Asn | Val | Ser | Thr | Gly | Gln | Met | Val | Gly |
| | | 195 | | | | | 200 | | | | | 205 | | | |
| Gly | Ile | Ala | Glu | Ser | Thr | Thr | Ile | Asn | Lys | Asn | Gly | Arg | Gln | Val | Ile |
| | 210 | | | | | 215 | | | | | 220 | | | | |
| Trp | Ser | Ser | Gly | Ile | Ala | Arg | Asp | Thr | Leu | Ile | Tyr | Thr | Gly | Gly | Asp |
| 225 | | | | | 230 | | | | | 235 | | | | | 240 |
| Gln | Thr | Val | His | Gly | Glu | Ala | His | Asn | Thr | Arg | Leu | Glu | Gly | Gly | Asn |
| | | | | 245 | | | | | 250 | | | | | 255 | |
| Gln | Tyr | Val | His | Lys | Tyr | Gly | Leu | Ala | Leu | Asn | Thr | Val | Ile | Asn | Glu |
| | | | 260 | | | | | 265 | | | | | 270 | | |
| Gly | Gly | Trp | Gln | Val | Val | Lys | Ala | Gly | Gly | Thr | Ala | Gly | Asn | Thr | Thr |
| | | 275 | | | | | 280 | | | | | 285 | | | |
| Ile | Asn | Gln | Asn | Gly | Glu | Leu | Arg | Val | His | Ala | Gly | Gly | Glu | Ala | Ser |
| | 290 | | | | | 295 | | | | | 300 | | | | |
| Asp | Val | Thr | Gln | Asn | Thr | Gly | Gly | Ala | Leu | Val | Thr | Ser | Thr | Ala | Ala |
| 305 | | | | | 310 | | | | | 315 | | | | | 320 |
| Thr | Val | Thr | Gly | Thr | Asn | Arg | Leu | Gly | Ala | Phe | Ser | Val | Val | Glu | Gly |
| | | | | 325 | | | | | 330 | | | | | 335 | |
| Lys | Ala | Asp | Asn | Val | Val | Leu | Glu | Asn | Gly | Gly | Arg | Leu | Asp | Val | Leu |
| | | | 340 | | | | | 345 | | | | | 350 | | |
| Ser | Gly | His | Thr | Ala | Thr | Arg | Thr | Leu | Val | Asp | Asp | Gly | Gly | Thr | Leu |
| | | 355 | | | | | 360 | | | | | 365 | | | |
| Asp | Val | Arg | Asn | Gly | Gly | Thr | Ala | Thr | Ala | Val | Ser | Met | Gly | Asn | Gly |
| | 370 | | | | | 375 | | | | | 380 | | | | |

```
Gly Val Leu Leu Ala Asp Ser Gly Ala Ala Val Ser Gly Thr Arg Ser
385                 390                 395                 400

Asp Gly Thr Ala Phe Arg Ile Gly Gly Gln Ala Asp Ala Leu Met
                405                 410                 415

Leu Glu Lys Gly Ser Ser Phe Thr Leu Asn Ala Gly Asp Thr Ala Thr
            420                 425                 430

Asp Thr Thr Val Asn Gly Gly Leu Phe Thr Ala Arg Gly Gly Ser Leu
                435                 440                 445

Ala Gly Thr Thr Thr Leu Asn Asn Gly Ala Thr Phe Thr Leu Ala Gly
            450                 455                 460

Lys Thr Val Asn Asn Asp Thr Leu Thr Ile Arg Glu Gly Asp Ala Leu
465                 470                 475                 480

Leu Gln Gly Gly Ala Leu Thr Gly Asn Gly Arg Val Glu Lys Ser Gly
                485                 490                 495

Ser Gly Thr Leu Thr Val Ser Asn Thr Thr Leu Thr Gln Lys Ala Val
            500                 505                 510

Asn Leu Asn Glu Gly Thr Leu Thr Leu Asn Asp Ser Thr Val Thr Thr
            515                 520                 525

Asp Ile Ile Ala His Arg Gly Thr Ala Leu Lys Leu Thr Gly Ser Thr
530                 535                 540

Val Leu Asn Gly Ala Ile Asp Pro Thr Asn Val Thr Leu Thr Ser Gly
545                 550                 555                 560

Ala Thr Trp Asn Ile Pro Asp Asn Ala Thr Val Gln Ser Val Val Asp
                565                 570                 575

Asp Leu Ser His Ala Gly Gln Ile His Phe Thr Ser Ala Arg Thr Gly
                580                 585                 590

Lys Phe Val Pro Thr Thr Leu Gln Val Lys Asn Leu Asn Gly Gln Asn
                595                 600                 605

Gly Thr Ile Ser Leu Arg Val Arg Pro Asp Met Ala Gln Asn Asn Ala
                610                 615                 620

Asp Arg Leu Val Ile Asp Gly Gly Arg Ala Thr Gly Lys Thr Ile Leu
625                 630                 635                 640

Asn Leu Val Asn Ala Gly Asn Ser Gly Thr Gly Leu Ala Thr Thr Gly
                645                 650                 655

Lys Gly Ile Gln Val Val Glu Ala Ile Asn Gly Ala Thr Thr Glu Glu
            660                 665                 670

Gly Ala Phe Val Gln Gly Asn Met Leu Gln Ala Gly Ala Phe Asn Tyr
                675                 680                 685

Thr Leu Asn Arg Asp Ser Asp Glu Ser Trp Tyr Leu Arg Ser Glu Glu
            690                 695                 700

Arg Tyr Arg Ala Glu Val Pro Leu Tyr Ala Ser Met Leu Thr Gln Ala
705                 710                 715                 720

Met Asp Tyr Asp Arg Ile Leu Ala Gly Ser Arg Ser His Gln Thr Gly
                725                 730                 735

Val Asn Gly Glu Asn Asn Ser Val Arg Leu Ser Ile Gln Gly Gly His
                740                 745                 750

Leu Gly His Asp Asn Asn Gly Gly Ile Ala Arg Gly Ala Thr Pro Glu
            755                 760                 765

Ser Ser Gly Ser Tyr Gly Phe Val Arg Leu Glu Gly Asp Leu Leu Arg
            770                 775                 780

Thr Glu Val Ala Gly Met Ser Leu Thr Thr Gly Val Tyr Gly Ala Ala
785                 790                 795                 800
```

Gly His Ser Ser Val Asp Val Lys Asp Asp Gly Ser Arg Ala Gly
              805                 810                 815

Thr Val Arg Asp Asp Ala Gly Ser Leu Gly Gly Tyr Met Asn Leu Thr
        820                 825                 830

His Thr Ser Ser Gly Leu Trp Ala Asp Ile Val Ala Gln Gly Thr Arg
        835                 840                 845

His Ser Met Lys Ala Ser Ser Asp Asn Asn Asp Phe Arg Ala Arg Gly
        850                 855                 860

Arg Gly Trp Leu Gly Ser Leu Glu Thr Gly Leu Pro Phe Ser Ile Thr
865                 870                 875                 880

Asp Asn Leu Met Leu Glu Pro Arg Leu Gln Tyr Thr Trp Gln Gly Leu
                885                 890                 895

Ser Leu Asp Asp Gly Lys Asp Asn Ala Gly Tyr Val Lys Phe Gly His
                900                 905                 910

Gly Ser Ala Gln His Val Arg Ala Gly Phe Arg Leu Gly Ser His Asn
            915                 920                 925

Asp Met Thr Phe Gly Glu Gly Thr Ser Ser Arg Ala Pro Leu Arg Asp
        930                 935                 940

Ser Ala Lys His Ser Val Arg Glu Leu Pro Val Asn Trp Trp Val Gln
945                 950                 955                 960

Pro Ser Val Ile Arg Thr Phe Ser Ser Arg Gly Asp Met Arg Val Gly
                965                 970                 975

Thr Ser Thr Ala Gly Ser Gly Met Thr Phe Ser Pro Ser Gln Asn Gly
            980                 985                 990

Thr Ser Leu Asp Leu Gln Ala Gly Leu Glu Ala Arg Val Arg Glu Asn
        995                 1000                1005

Ile Thr Leu Gly Val Gln Ala Gly Tyr Ala His Ser Ile Asn Gly Ser
    1010                1015                1020

Ser Ala Glu Gly Tyr Asn Ser Gln Ala Thr Leu Asn Val Thr Phe
1025                1030                1035

<210> SEQ ID NO 21
<211> LENGTH: 1039
<212> TYPE: PRT
<213> ORGANISM: Escherichia coli

<400> SEQUENCE: 21

Met Lys Arg His Leu Asn Thr Cys Tyr Arg Leu Val Trp Asn His Ile
1               5                   10                  15

Thr Gly Ala Phe Val Val Ala Ser Glu Leu Ala Arg Ala Arg Gly Lys
            20                  25                  30

Arg Gly Gly Val Ala Val Ala Leu Ser Leu Ala Ala Val Thr Ser Leu
        35                  40                  45

Pro Val Leu Ala Ala Asp Ile Val Val His Pro Gly Glu Thr Val Asn
    50                  55                  60

Gly Gly Thr Leu Val Asn His Asp Asn Gln Phe Val Ser Gly Thr Ala
65                  70                  75                  80

Asp Gly Val Thr Val Ser Thr Gly Leu Glu Leu Gly Pro Asp Ser Asp
                85                  90                  95

Asp Asn Thr Gly Gly Gln Gln Ile Ala Arg Gly Gly Thr Ala Arg Asn
            100                 105                 110

Thr Thr Val Thr Ala Asn Gly Leu Gln Asp Val Met Ala Gly Gly Ser
        115                 120                 125

Ala Thr Asp Thr Val Ile Ser Ala Gly Gly Gln Asn Leu Arg Gly
    130                 135                 140

```
Gln Ala Tyr Gly Thr Val Leu Asn Gly Gly Glu Gln Trp Ile His Ala
145                 150                 155                 160

Gly Gly Ser Ala Ser Gly Thr Val Ile Asn Gln Ser Gly Tyr Gln Thr
            165                 170                 175

Ile Lys His Gly Gly Gln Ala Thr Gly Thr Ile Val Asn Thr Gly Ala
            180                 185                 190

Glu Gly Gly Pro Glu Ser Glu Asn Val Ser Ser Gly Gln Met Val Gly
            195                 200                 205

Gly Thr Ala Glu Ser Thr Thr Ile Asn Lys Asn Gly Arg Gln Val Ile
210                 215                 220

Trp Ser Ser Gly Met Ala Arg Asp Thr Leu Ile Tyr Ala Gly Gly Asp
225                 230                 235                 240

Gln Thr Val His Gly Glu Ala His Asn Thr Arg Leu Glu Gly Gly Asn
                245                 250                 255

Gln Tyr Val His Lys Tyr Gly Leu Ala Leu Asn Thr Val Ile Asn Glu
                260                 265                 270

Gly Gly Trp Gln Val Ile Lys Glu Gly Gly Thr Thr Ala His Thr Thr
            275                 280                 285

Ile Asn Gln Lys Gly Lys Leu Gln Val Asn Ala Gly Gly Lys Ala Ser
290                 295                 300

Asp Val Thr Gln Asn Thr Gly Gly Ala Leu Val Thr Ser Thr Ala Ala
305                 310                 315                 320

Thr Val Thr Gly Thr Asn Arg Leu Gly Ala Phe Ser Val Leu Ala Gly
                325                 330                 335

Lys Ala Asp Asn Val Val Leu Glu Asn Gly Gly Arg Leu Asp Val Leu
            340                 345                 350

Ser Gly His Thr Ala Thr Asn Thr Arg Val Asp Asp Gly Gly Thr Leu
            355                 360                 365

Asp Val Arg Asn Gly Gly Ala Ala Thr Thr Val Ser Met Gly Asn Gly
370                 375                 380

Gly Val Leu Leu Ala Asp Ser Gly Ala Ala Val Ser Gly Thr Arg Ser
385                 390                 395                 400

Asp Gly Thr Ala Phe Arg Ile Gly Gly Gln Ala Asp Ala Leu Met
                405                 410                 415

Leu Glu Lys Gly Ser Ser Phe Thr Leu Asn Ala Gly Asp Thr Ala Thr
            420                 425                 430

Asp Thr Thr Val Asn Gly Gly Leu Phe Thr Ala Arg Gly Gly Ser Leu
            435                 440                 445

Ala Gly Thr Thr Thr Leu Asn Asn Gly Ala Thr Leu Thr Leu Ser Gly
            450                 455                 460

Lys Thr Val Asn Asn Asp Thr Leu Thr Ile Arg Glu Gly Asp Ala Leu
465                 470                 475                 480

Leu Gln Gly Gly Ala Leu Thr Gly Asn Gly Arg Val Glu Lys Ser Gly
                485                 490                 495

Ser Gly Thr Leu Thr Val Ser Asn Thr Thr Leu Thr Gln Lys Thr Val
            500                 505                 510

Asn Leu Asn Glu Gly Thr Leu Thr Leu Asn Asp Ser Thr Val Thr Thr
            515                 520                 525

Asp Val Ile Ala Gln Arg Gly Thr Ala Leu Lys Leu Thr Gly Ser Thr
            530                 535                 540

Val Leu Asn Gly Ala Ile Asp Pro Thr Asn Val Thr Leu Thr Ser Gly
545                 550                 555                 560
```

```
Ala Thr Trp Asn Ile Pro Asp Asn Ala Thr Val Gln Ser Val Val Asp
                565                 570                 575

Asp Leu Ser His Ala Gly Gln Ile His Phe Thr Ser Thr Arg Thr Gly
            580                 585                 590

Lys Phe Val Pro Ala Thr Leu Gln Val Lys Asn Leu Asn Gly Gln Asn
            595                 600                 605

Gly Thr Ile Ser Leu Arg Val Arg Pro Asp Met Ala Gln Asn Asn Ala
            610                 615                 620

Asp Arg Leu Val Ile Asp Gly Arg Ala Thr Gly Lys Thr Ile Leu
625                 630                 635                 640

Asn Leu Val Asn Ala Gly Asn Ser Gly Thr Gly Leu Ala Thr Thr Gly
                645                 650                 655

Lys Gly Ile Gln Val Val Glu Ala Ile Asn Gly Ala Thr Thr Glu Glu
                660                 665                 670

Gly Ala Phe Val Gln Gly Asn Met Leu Gln Ala Gly Ala Phe Asn Tyr
                675                 680                 685

Thr Leu Asn Arg Asp Ser Asp Glu Ser Trp Tyr Leu Arg Ser Glu Glu
                690                 695                 700

Arg Tyr Arg Ala Glu Val Pro Leu Tyr Ala Ser Met Leu Thr Gln Ala
705                 710                 715                 720

Met Asp Tyr Asp Arg Ile Leu Ala Gly Ser Arg Ser His Gln Thr Gly
                725                 730                 735

Val Asn Gly Glu Asn Asn Ser Val Arg Leu Ser Ile Gln Gly His
                740                 745                 750

Leu Gly His Asp Asn Asn Gly Gly Ile Ala Arg Gly Ala Thr Pro Glu
                755                 760                 765

Ser Ser Gly Ser Tyr Gly Phe Val Arg Leu Glu Gly Asp Leu Leu Arg
                770                 775                 780

Thr Glu Val Ala Gly Met Ser Leu Thr Thr Gly Val Tyr Gly Ala Ala
785                 790                 795                 800

Gly His Ser Ser Val Asp Val Lys Asp Asp Gly Ser Arg Ala Gly
                805                 810                 815

Thr Val Arg Asp Asp Ala Gly Ser Leu Gly Gly Tyr Met Asn Leu Thr
                820                 825                 830

His Thr Ser Ser Gly Leu Trp Ala Asp Ile Val Ala Gln Gly Thr Arg
                835                 840                 845

His Ser Met Lys Ala Ser Ser Gly Asn Asn Asp Phe Arg Ala Arg Gly
                850                 855                 860

Trp Gly Trp Leu Gly Ser Leu Glu Thr Gly Leu Pro Phe Ser Ile Thr
865                 870                 875                 880

Asp Asn Leu Met Leu Glu Pro Arg Leu Gln Tyr Thr Trp Gln Gly Leu
                885                 890                 895

Ser Leu Asp Asp Gly Lys Asp Asn Ala Gly Tyr Val Lys Phe Gly His
                900                 905                 910

Gly Ser Ala Gln His Val Arg Ala Gly Phe Arg Leu Gly Ser His Asn
                915                 920                 925

Asp Met Thr Phe Gly Glu Gly Thr Ser Ser Arg Ala Pro Leu Arg Asp
                930                 935                 940

Ser Ala Lys His Ser Val Arg Glu Leu Pro Val Asn Trp Trp Val Gln
945                 950                 955                 960

Pro Ser Val Ile Arg Thr Phe Ser Ser Arg Gly Asp Met Arg Val Gly
                965                 970                 975

Thr Ser Thr Ala Gly Ser Gly Met Thr Phe Ser Pro Ser Gln Asn Gly
```

```
                 980             985             990
Thr Ser Leu Asp Leu Gln Ala Gly Leu Glu Ala Arg Val Arg Glu Asn
            995                1000                1005

Ile Thr Leu Gly Val Gln Ala Gly Tyr Ala His Ser Val Ser Gly Ser
        1010                1015                1020

Ser Ala Glu Gly Tyr Asn Ser Gln Ala Thr Leu Asn Val Thr Phe
1025                1030                1035

<210> SEQ ID NO 22
<211> LENGTH: 1040
<212> TYPE: PRT
<213> ORGANISM: Escherichia coli

<400> SEQUENCE: 22

Met Lys Arg His Leu Asn Thr Cys Tyr Arg Leu Val Trp Asn His Ile
 1               5                  10                  15

Thr Gly Ala Phe Val Val Ala Ser Glu Leu Ala Arg Ala Arg Gly Lys
             20                  25                  30

Arg Gly Gly Val Ala Val Ala Leu Ser Leu Ala Ala Val Thr Pro Leu
         35                  40                  45

Pro Val Leu Ser Ala Asp Ile Val Val His Pro Gly Glu Thr Val Asn
 50                  55                  60

Gly Gly Thr Leu Val Asn His Asp Asn Gln Phe Val Ser Gly Thr Ala
65                  70                  75                  80

Asn Gly Val Thr Val Ser Thr Gly Leu Glu Leu Gly Pro Asp Ser Asp
                 85                  90                  95

Glu Asn Thr Gly Gly Gln Trp Ile Lys Ala Gly Gly Thr Gly Arg Asn
            100                 105                 110

Thr Thr Val Thr Ala Asn Gly Arg Gln Ile Val Gln Ala Gly Gly Thr
        115                 120                 125

Ala Ser Asp Thr Val Ile Arg Asp Gly Gly Gln Ser Leu Asn Gly
130                 135                 140

Leu Ala Val Asn Thr Thr Leu Asp Asn Arg Gly Glu Gln Trp Val His
145                 150                 155                 160

Gly Gly Gly Lys Ala Ala Gly Thr Ile Ile Asn Gln Asp Gly Tyr Gln
                165                 170                 175

Thr Ile Lys His Gly Gly Leu Ala Thr Gly Thr Ile Val Asn Thr Gly
            180                 185                 190

Ala Glu Gly Gly Pro Glu Ser Glu Asn Val Ser Ser Gly Gln Met Val
        195                 200                 205

Gly Gly Thr Ala Glu Ser Thr Thr Ile Asn Lys Asn Gly Arg Gln Val
    210                 215                 220

Ile Trp Ser Ser Gly Met Ala Arg Asp Thr Leu Ile Tyr Ala Gly Gly
225                 230                 235                 240

Asp Gln Thr Val His Gly Glu Ala His Asn Thr Arg Leu Glu Gly Gly
                245                 250                 255

Asn Gln Tyr Val His Asn Gly Gly Thr Ala Thr Glu Thr Leu Ile Asn
            260                 265                 270

Arg Asp Gly Trp Gln Val Ile Lys Glu Gly Gly Thr Ala Ala His Thr
        275                 280                 285

Thr Ile Asn Gln Lys Gly Lys Leu Gln Val Asn Ala Gly Gly Lys Ala
    290                 295                 300

Ser Asp Val Thr Gln Asn Thr Gly Gly Ala Leu Val Thr Ser Thr Ala
305                 310                 315                 320
```

```
Ala Thr Val Thr Gly Thr Asn Arg Leu Gly Ala Phe Ser Val Val Ala
            325                 330                 335

Gly Lys Ala Asp Asn Val Val Leu Glu Asn Gly Gly Arg Leu Asp Val
        340                 345                 350

Leu Ser Gly His Thr Ala Thr Asn Thr Arg Val Asp Asp Gly Gly Thr
    355                 360                 365

Leu Asp Ile Arg Asn Gly Gly Ala Ala Thr Thr Val Ser Met Gly Asn
370                 375                 380

Gly Gly Val Leu Leu Ala Asp Ser Gly Ala Ala Val Ser Gly Thr Arg
385                 390                 395                 400

Ser Asp Gly Lys Ala Phe Ser Ile Gly Gly Gln Ala Asp Ala Leu
            405                 410                 415

Met Leu Glu Lys Gly Ser Ser Phe Thr Leu Asn Ala Gly Asp Thr Ala
        420                 425                 430

Thr Asp Thr Thr Val Asn Gly Gly Leu Phe Thr Ala Arg Gly Gly Thr
    435                 440                 445

Leu Ala Gly Thr Thr Thr Leu Asn Asn Gly Ala Ile Leu Thr Leu Ser
    450                 455                 460

Gly Lys Thr Val Asn Asn Asp Thr Leu Thr Ile Arg Glu Gly Asp Ala
465                 470                 475                 480

Leu Leu Gln Gly Gly Ser Leu Thr Gly Asn Gly Ser Val Glu Lys Ser
            485                 490                 495

Gly Ser Gly Thr Leu Thr Val Ser Asn Thr Thr Leu Thr Gln Lys Ala
            500                 505                 510

Val Asn Leu Asn Glu Gly Thr Leu Thr Leu Asn Asp Ser Thr Val Thr
        515                 520                 525

Thr Asp Val Ile Ala Gln Arg Gly Thr Ala Leu Lys Leu Thr Gly Ser
    530                 535                 540

Thr Val Leu Asn Gly Ala Ile Asp Pro Thr Asn Val Thr Leu Ala Ser
545                 550                 555                 560

Asp Ala Thr Trp Asn Ile Pro Asn Ala Thr Val Gln Ser Val Val
            565                 570                 575

Asp Asp Leu Ser His Ala Gly Gln Ile His Phe Thr Ser Ser Arg Thr
            580                 585                 590

Gly Thr Phe Val Pro Ala Thr Leu Lys Val Lys Asn Leu Asn Gly Gln
        595                 600                 605

Asn Gly Thr Ile Ser Leu Arg Val Arg Pro Asp Met Ala Gln Asn Asn
        610                 615                 620

Ala Asp Arg Leu Val Ile Asp Gly Gly Arg Ala Thr Gly Lys Thr Ile
625                 630                 635                 640

Leu Asn Leu Val Asn Ala Gly Asn Ser Ala Ser Gly Leu Ala Thr Ser
                645                 650                 655

Gly Lys Gly Ile Gln Val Val Glu Ala Ile Asn Gly Ala Thr Thr Glu
        660                 665                 670

Glu Gly Ala Phe Val Gln Gly Asn Arg Leu Gln Ala Gly Ala Phe Asn
    675                 680                 685

Tyr Ser Leu Asn Arg Asp Ser Asp Glu Ser Trp Tyr Leu Arg Ser Glu
    690                 695                 700

Asn Ala Tyr Arg Ala Glu Val Pro Leu Tyr Ala Ser Met Leu Thr Gln
705                 710                 715                 720

Ala Met Asp Tyr Asp Arg Ile Leu Ala Gly Ser Arg Ser His Gln Thr
            725                 730                 735

Gly Val Asn Gly Glu Asn Asn Ser Val Arg Leu Ser Ile Gln Gly Gly
```

His Leu Gly His Asp Asn Asn Gly Gly Ile Ala Arg Gly Ala Thr Pro
        740                 745                 750

Glu Ser Ser Gly Ser Tyr Gly Phe Val Arg Leu Glu Gly Asp Leu Leu
    755                 760                 765

Arg Thr Asp Val Ala Gly Met Ser Val Thr Ala Gly Ile Tyr Gly Ala
770                 775                 780

Ala Gly His Ser Ser Val Asp Val Lys Asp Asp Gly Ser Arg Ala
785                 790                 795                 800

Gly Thr Val Arg Asp Asp Ala Gly Ser Leu Gly Gly Tyr Met Asn Leu
    805                 810                 815

Thr His Thr Ser Ser Gly Leu Trp Ala Asp Ile Val Ala Gln Gly Thr
820                 825                 830

Arg His Ser Met Lys Ala Ser Ser Gly Asn Asn Asp Phe Arg Ala Arg
    835                 840                 845

Gly Arg Gly Trp Leu Gly Ser Leu Glu Thr Gly Leu Pro Phe Ser Ile
865                 870                 875                 880

Thr Asp Asn Leu Met Leu Glu Pro Arg Leu Gln Tyr Thr Trp Gln Gly
            885                 890                 895

Leu Ser Leu Asp Asp Gly Lys Asp Asn Ala Gly Tyr Val Lys Phe Gly
                900                 905                 910

His Gly Ser Ala Gln His Val Arg Ala Gly Phe Arg Leu Gly Ser His
    915                 920                 925

Asn Asp Met Thr Phe Gly Glu Gly Thr Ser Ser Arg Ala Pro Leu Arg
930                 935                 940

Asp Ser Ala Lys His Ser Val Arg Glu Leu Pro Val Asn Trp Trp Val
945                 950                 955                 960

Gln Pro Ser Val Ile Arg Thr Phe Ser Arg Gly Asp Met Arg Val
                965                 970                 975

Gly Thr Ser Thr Ala Gly Ser Gly Met Thr Phe Ser Pro Ser Gln Asn
            980                 985                 990

Gly Thr Ser Leu Asp Leu Gln Ala Gly Leu Glu Ala Arg Val Arg Glu
    995                 1000                1005

Asn Ile Thr Leu Gly Val Gln Ala Gly Tyr Ala His Ser Val Ser Gly
    1010                1015                1020

Ser Ser Ala Glu Gly Tyr Asn Gly Gln Ala Thr Leu Asn Val Thr Phe
1025                1030                1035                1040

<210> SEQ ID NO 23
<211> LENGTH: 490
<212> TYPE: PRT
<213> ORGANISM: Escherichia coli

<400> SEQUENCE: 23

Met Lys Lys Ser Leu Leu Ala Val Met Leu Thr Gly Leu Phe Ala Leu
1               5                   10                  15

Val Ser Leu Pro Ala Leu Gly Asn Val Asn Leu Glu Gln Leu Lys Gln
            20                  25                  30

Lys Ala Glu Ser Gly Glu Ala Lys Ala Gln Leu Glu Leu Gly Tyr Arg
        35                  40                  45

Tyr Phe Gln Gly Asn Glu Thr Thr Lys Asp Leu Thr Gln Ala Met Asp
    50                  55                  60

Trp Phe Arg Arg Ala Ala Glu Gln Gly Tyr Thr Pro Ala Glu Tyr Val
65                  70                  75                  80

-continued

```
Leu Gly Leu Arg Tyr Met Asn Gly Glu Gly Val Pro Gln Asp Tyr Ala
                 85                  90                  95

Gln Ala Val Ile Trp Tyr Lys Lys Ala Ala Leu Lys Gly Leu Pro Gln
            100                 105                 110

Ala Gln Gln Asn Leu Gly Val Met Tyr His Glu Gly Asn Gly Val Lys
        115                 120                 125

Val Asp Lys Ala Glu Ser Val Lys Trp Phe Arg Leu Ala Ala Glu Gln
    130                 135                 140

Gly Arg Asp Ser Gly Gln Gln Ser Met Gly Asp Ala Tyr Phe Glu Gly
145                 150                 155                 160

Asp Gly Val Thr Arg Asp Tyr Val Met Ala Arg Glu Trp Tyr Ser Lys
                165                 170                 175

Ala Ala Glu Gln Gly Asn Val Trp Ser Cys Asn Gln Leu Gly Tyr Met
            180                 185                 190

Tyr Ser Arg Gly Leu Gly Val Glu Arg Asn Asp Ala Ile Ser Ala Gln
        195                 200                 205

Trp Tyr Arg Lys Ser Ala Thr Ser Gly Asp Glu Leu Gly Gln Leu His
    210                 215                 220

Leu Ala Asp Met Tyr Tyr Phe Gly Ile Gly Val Thr Gln Asp Tyr Thr
225                 230                 235                 240

Gln Ser Arg Val Leu Phe Ser Gln Ser Ala Glu Gln Gly Asn Ser Ile
                245                 250                 255

Ala Gln Phe Arg Leu Gly Tyr Ile Leu Glu Gln Gly Leu Ala Gly Ala
            260                 265                 270

Lys Glu Pro Leu Lys Ala Leu Glu Trp Tyr Arg Lys Ser Ala Glu Gln
        275                 280                 285

Gly Asn Ser Asp Gly Gln Tyr Tyr Leu Ala His Leu Tyr Asp Lys Gly
    290                 295                 300

Ala Glu Gly Val Ala Lys Asn Arg Glu Gln Ala Ile Ser Trp Tyr Thr
305                 310                 315                 320

Lys Ser Ala Glu Gln Gly Asp Ala Thr Ala Gln Ala Asn Leu Gly Ala
                325                 330                 335

Ile Tyr Phe Arg Leu Gly Ser Glu Glu Glu His Lys Lys Ala Val Glu
            340                 345                 350

Trp Phe Arg Lys Ala Ala Ala Lys Gly Glu Lys Ala Ala Gln Phe Asn
        355                 360                 365

Leu Gly Asn Ala Leu Leu Gln Gly Lys Gly Val Lys Lys Asp Glu Gln
    370                 375                 380

Gln Ala Ala Ile Trp Met Arg Lys Ala Ala Glu Gln Gly Leu Ser Ala
385                 390                 395                 400

Ala Gln Val Gln Leu Gly Glu Ile Tyr Tyr Tyr Gly Leu Gly Val Glu
                405                 410                 415

Arg Asp Tyr Val Gln Ala Trp Ala Trp Phe Asp Thr Ala Ser Thr Asn
            420                 425                 430

Asp Met Asn Leu Phe Gly Thr Glu Asn Arg Asn Ile Thr Glu Lys Lys
        435                 440                 445

Leu Thr Ala Lys Gln Leu Gln Gln Ala Glu Leu Leu Ser Gln Gln Tyr
    450                 455                 460

Ile Glu Lys Tyr Ala Pro Glu Ala Trp Ala Arg Met Gln Lys Leu Lys
465                 470                 475                 480

Ala Gln Ser Ala Val Lys Thr Gly Asn Lys
                485                 490
```

```
<210> SEQ ID NO 24
<211> LENGTH: 490
<212> TYPE: PRT
<213> ORGANISM: Escherichia coli

<400> SEQUENCE: 24

Met Lys Lys Ser Leu Leu Ala Val Met Leu Thr Gly Leu Phe Ala Leu
  1               5                  10                  15

Val Ser Leu Pro Ala Leu Gly Asn Val Asn Leu Glu Gln Leu Lys Gln
             20                  25                  30

Lys Ala Glu Ser Gly Glu Ala Lys Ala Gln Leu Glu Leu Gly Tyr Arg
         35                  40                  45

Tyr Phe Gln Gly Asn Glu Thr Thr Lys Asp Leu Thr Leu Ala Met Asp
     50                  55                  60

Trp Phe Arg Arg Ala Ala Glu Gln Gly Tyr Thr Pro Ala Glu Tyr Val
 65                  70                  75                  80

Leu Gly Leu Arg Tyr Met Asn Gly Glu Gly Val Pro Gln Asp Tyr Ala
                 85                  90                  95

Gln Ala Val Ile Trp Tyr Lys Lys Ala Leu Lys Gly Leu Pro Gln
            100                 105                 110

Ala Gln Gln Asn Leu Gly Val Met Tyr His Glu Gly Asn Gly Val Lys
        115                 120                 125

Val Asp Lys Ala Glu Ser Val Lys Trp Phe Arg Leu Ala Ala Glu Gln
    130                 135                 140

Gly Arg Asp Ser Gly Gln Gln Ser Met Gly Asp Ala Tyr Phe Glu Gly
145                 150                 155                 160

Asp Gly Val Thr Arg Asp Tyr Val Met Ala Arg Glu Trp Tyr Ser Lys
                165                 170                 175

Ala Ala Glu Gln Gly Asn Val Trp Ser Cys Asn Gln Leu Gly Tyr Met
            180                 185                 190

Tyr Ser Arg Gly Leu Gly Val Glu Arg Asn Asp Ala Ile Ser Ala Gln
        195                 200                 205

Trp Tyr Arg Lys Ser Ala Thr Ser Gly Asp Glu Leu Gly Gln Leu His
    210                 215                 220

Leu Ala Asp Met Tyr Tyr Phe Gly Ile Gly Val Thr Gln Asp Tyr Thr
225                 230                 235                 240

Gln Ser Arg Val Leu Phe Ser Gln Ser Ala Glu Gln Gly Asn Ser Ile
                245                 250                 255

Ala Gln Phe Arg Leu Gly Tyr Ile Leu Glu Gln Gly Leu Ala Gly Ala
            260                 265                 270

Lys Glu Pro Leu Lys Ala Leu Glu Trp Tyr Arg Lys Ser Ala Glu Gln
        275                 280                 285

Gly Asn Ser Asp Gly Gln Tyr Tyr Leu Ala His Leu Tyr Asp Lys Gly
    290                 295                 300

Ala Glu Gly Val Ala Lys Asn Arg Glu Gln Ala Ile Ser Trp Tyr Thr
305                 310                 315                 320

Lys Ser Ala Glu Gln Gly Asp Ala Thr Ala Gln Ala Asn Leu Gly Ala
                325                 330                 335

Ile Tyr Phe Arg Leu Gly Ser Glu Glu His Lys Lys Ala Val Glu
            340                 345                 350

Trp Phe Arg Lys Ala Ala Ala Lys Gly Glu Lys Ala Ala Gln Phe Asn
        355                 360                 365

Leu Gly Asn Ala Leu Leu Gln Gly Lys Gly Val Lys Lys Asp Glu Gln
    370                 375                 380
```

```
Gln Ala Ala Ile Trp Met Arg Lys Ala Ala Glu Gln Gly Leu Ser Ala
385                 390                 395                 400

Ala Gln Val Gln Leu Gly Glu Ile Tyr Tyr Tyr Gly Leu Gly Val Glu
                405                 410                 415

Arg Asp Tyr Val Gln Ala Trp Ala Trp Phe Asp Thr Ala Ser Thr Asn
            420                 425                 430

Asp Met Asn Leu Phe Gly Thr Glu Asn Arg Asn Ile Thr Glu Lys Lys
        435                 440                 445

Leu Thr Thr Lys Gln Leu Gln Gln Ala Glu Leu Leu Ser Gln Gln Tyr
    450                 455                 460

Ile Glu Lys Tyr Ala Thr Glu Ala Trp Ala Arg Met Gln Lys Leu Lys
465                 470                 475                 480

Ala Gln Ser Ala Val Lys Thr Gly Asn Lys
                485                 490

<210> SEQ ID NO 25
<211> LENGTH: 490
<212> TYPE: PRT
<213> ORGANISM: Escherichia fergusonii

<400> SEQUENCE: 25

Met Lys Lys Ser Leu Leu Ala Ala Leu Leu Thr Gly Leu Phe Ala Leu
1               5                   10                  15

Val Ser Leu Pro Ala Leu Gly Asn Val Asn Phe Glu Gln Leu Lys Gln
            20                  25                  30

Lys Ala Glu Arg Gly Glu Ala Lys Ala Gln Leu Glu Leu Gly Tyr Arg
        35                  40                  45

Tyr Phe Gln Gly Asn Glu Thr Thr Lys Asp Leu Thr Gln Ala Ile Asp
    50                  55                  60

Trp Phe Arg Arg Ala Ala Glu Gln Gly Tyr Thr Pro Ala Glu Phe Val
65                  70                  75                  80

Leu Gly Leu Arg Tyr Met Asn Gly Glu Gly Val Pro Lys Asp Tyr Ala
                85                  90                  95

Gln Ala Val Ile Trp Tyr Lys Lys Ala Ala Leu Lys Gly Leu Pro Gln
            100                 105                 110

Ala Gln Gln Asn Leu Gly Val Met Tyr His Asp Gly Lys Gly Val Lys
        115                 120                 125

Ile Asp Lys Ala Glu Ser Val Lys Trp Phe Arg Leu Ala Ala Glu Gln
    130                 135                 140

Gly Arg Asp Ser Gly Gln Gln Ser Met Gly Asp Ala Tyr Phe Glu Gly
145                 150                 155                 160

Asp Gly Val Thr Arg Asp Tyr Val Met Ala Arg Glu Trp Tyr Ser Lys
                165                 170                 175

Ala Ala Glu Gln Gly Asn Val Trp Ser Cys Asn Gln Leu Gly Tyr Ile
            180                 185                 190

Tyr Ser Lys Gly Leu Gly Val Glu Lys Asn Asp Ala Ile Ser Ala Gln
        195                 200                 205

Trp Tyr Arg Lys Ser Ala Thr Ser Gly Asp Glu Leu Gly Gln Leu His
    210                 215                 220

Leu Ala Asp Met Tyr Tyr Phe Gly Ile Gly Val Thr Gln Asp Tyr Thr
225                 230                 235                 240

Gln Ser Arg Ile Leu Phe Thr Gln Ser Ala Glu Gln Gly Asn Ala Ile
                245                 250                 255

Ala Gln Tyr Arg Leu Gly Tyr Ile Leu Glu Glu Gly Leu Ala Gly Ala
            260                 265                 270
```

```
Lys Glu Pro Leu Lys Ala Leu Glu Trp Tyr Arg Lys Ser Ala Glu Gln
            275                 280                 285

Gly Asn Ala Ile Gly Gln Tyr Tyr Leu Ala Glu Ile Tyr Ile Arg Arg
        290                 295                 300

Ala Glu Gly Ile Pro Tyr Asn Arg Glu Gln Ala Ile Tyr Trp Tyr Thr
305                 310                 315                 320

Lys Ser Ala Glu Gln Gly Asp Thr Asp Ala Gln Val Asn Leu Gly Ala
                325                 330                 335

Leu Leu Tyr Arg His Gly Ser Glu Glu Gln Arg Arg Ala Val Asp
                340                 345                 350

Trp Tyr Arg Lys Ala Ala Glu Gly Val Ala Met Ala Gln Phe Asn
                355                 360                 365

Leu Gly Asn Ala Leu Leu Gln Gly Lys Gly Val Lys Lys Asp Glu Gln
            370                 375                 380

Gln Ala Ala Ile Trp Met Arg Lys Ala Ala Glu Gln Gly Phe Ser Ser
385                 390                 395                 400

Ala Gln Val Gln Leu Gly Glu Ile Tyr Tyr Tyr Gly Leu Gly Val Glu
                405                 410                 415

Arg Asp Tyr Val Gln Ala Trp Ala Trp Phe Asp Thr Ala Ser Thr Asn
                420                 425                 430

Asp Met Asn Leu Phe Gly Thr Glu Asn Arg Asn Ile Thr Glu Lys Lys
                435                 440                 445

Leu Thr Ala Lys Gln Leu Gln Gln Ala Glu Leu Leu Ser Gln Gln Tyr
            450                 455                 460

Ile Glu Lys Tyr Ala Pro Glu Ala Trp Ala Arg Met Gln Lys Leu Asn
465                 470                 475                 480

Ala Arg Ser Thr Val Thr Thr Gly Asn Lys
                485                 490

<210> SEQ ID NO 26
<211> LENGTH: 1461
<212> TYPE: PRT
<213> ORGANISM: Escherichia coli

<400> SEQUENCE: 26

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
                20                  25                  30

Ser Asp Thr Pro Pro Val Asp Ser Gly Thr Gly Ser Leu Pro Glu Val
                35                  40                  45

Lys Pro Asp Pro Thr Pro Asn Pro Glu Pro Thr Pro Glu Pro Thr Pro
            50                  55                  60

Asp Pro Glu Pro Thr Pro Glu Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Ile Thr Gly Ala Thr Cys Asn Gly Glu Ser Ser
                100                 105                 110

Asp Gly Phe Thr Phe Thr Pro Gly Asp Lys Val Thr Cys Val Ala Gly
                115                 120                 125

Asn Asn Thr Thr Ile Ala Thr Phe Asp Thr Gln Ser Glu Ala Ala Arg
            130                 135                 140

Ser Leu Arg Ala Val Glu Lys Val Ser Phe Ser Leu Glu Asp Ala Gln
```

-continued

```
            145                 150                 155                 160
        Glu Leu Ala Ala Ser Asp Asp Lys Lys Ser Asn Ala Val Ser Leu Val
                        165                 170                 175

Thr Ser Ser Asn Ser Cys Pro Ala Asn Thr Glu Gln Val Cys Leu Thr
                        180                 185                 190

Phe Ser Ser Val Ile Glu Ser Lys Arg Phe Asp Ser Leu Tyr Lys Gln
                        195                 200                 205

Ile Asp Leu Ala Pro Glu Glu Phe Lys Lys Leu Val Asn Glu Glu Val
        210                 215                 220

Glu Asn Asn Ala Ala Thr Asp Lys Ala Pro Ser Thr His Thr Ser Pro
        225                 230                 235                 240

Val Val Pro Val Thr Thr Pro Gly Thr Lys Pro Asp Leu Asn Ala Ser
                        245                 250                 255

Phe Val Ser Ala Asn Ala Glu Gln Phe Tyr Gln Tyr Gln Pro Thr Glu
                        260                 265                 270

Ile Ile Leu Ser Glu Gly Arg Leu Val Asp Ser Met Gly Asn Gly Val
                        275                 280                 285

Val Gly Val Asn Tyr Tyr Thr Ser Ser Gly Arg Gly Val Thr Gly Glu
                        290                 295                 300

Asn Gly Lys Phe Asn Phe Ser Trp Gly Glu Thr Ile Ser Phe Gly Ile
        305                 310                 315                 320

Asp Thr Phe Glu Leu Gly Ser Val Arg Gly Asn Lys Ser Thr Ile Ala
                        325                 330                 335

Leu Thr Glu Leu Gly Asp Glu Val Arg Gly Ala Asn Ile Asp Gln Leu
                        340                 345                 350

Ile His Arg Tyr Ser Gln Ala Gly Lys Asn Asp Glu Arg Glu Val Pro
                        355                 360                 365

Asp Val Val Arg Lys Val Phe Ala Glu Tyr Pro Asn Val Ile Asn Glu
                        370                 375                 380

Ile Ile Asn Leu Ser Leu Ser Asn Gly Glu Ala Leu Ser Glu Gly Asp
        385                 390                 395                 400

Gln Thr Phe Glu Arg Thr Asn Glu Phe Leu Glu Gln Phe Glu Ser Gly
                        405                 410                 415

Gln Ala Lys Glu Ile Asp Thr Ala Ile Cys Asp Ser Leu Gly Gly Cys
                        420                 425                 430

Asn Ser Gln Arg Trp Phe Ser Leu Thr Ala Arg Asn Val Asn Glu Gly
                        435                 440                 445

Gln Ile Gln Gly Val Ile Asn Lys Leu Trp Gly Val Asp Lys Asp Tyr
        450                 455                 460

Lys Ser Val Thr Lys Phe His Val Phe His Asp Ser Thr Asn Phe Tyr
        465                 470                 475                 480

Gly Ser Thr Gly Asn Ala Arg Gly Gln Ala Val Val Asn Ile Ser Asn
                        485                 490                 495

Ala Ala Phe Pro Ile Leu Met Ala Arg Asn Asp Lys Asn Tyr Trp Leu
                        500                 505                 510

Ala Phe Gly Glu Lys Arg Ala Trp Asp Lys Asn Glu Leu Ala Tyr Ile
                        515                 520                 525

Thr Glu Ala Pro Ser Leu Val Glu Pro Glu Asn Val Thr Arg Asp Thr
                        530                 535                 540

Ala Thr Phe Asn Leu Pro Phe Ile Ser Leu Gly Gln Val Gly Glu Gly
        545                 550                 555                 560

Lys Leu Met Val Ile Gly Asn Pro His Tyr Asn Ser Ile Leu Arg Cys
                        565                 570                 575
```

```
Pro Asn Gly Tyr Ser Trp Glu Gly Gly Val Asp Lys Asn Gly Gln Cys
            580                 585                 590

Thr Arg Asn Ser Asp Ser Asn Asp Met Lys His Phe Met Gln Asn Val
        595                 600                 605

Leu Arg Tyr Leu Ser Asp Lys Trp Thr Pro Asp Ala Lys Ala Ser
610                 615                 620

Met Thr Val Gly Thr Asn Leu Asp Thr Val Tyr Phe Lys Arg His Gly
625                 630                 635                 640

Gln Val Thr Gly Asn Ser Ala Glu Phe Gly Phe His Pro Asp Phe Ala
                645                 650                 655

Gly Ile Ser Val Glu His Leu Ser Tyr Gly Asp Leu Asp Pro Gln
            660                 665                 670

Glu Met Pro Leu Leu Ile Leu Asn Gly Phe Glu Tyr Val Thr Gln Val
                675                 680                 685

Gly Asn Asp Pro Tyr Ala Ile Pro Leu Arg Ala Asp Thr Ser Lys Pro
690                 695                 700

Lys Leu Thr Gln Gln Asp Val Thr Asp Leu Ile Ala Tyr Leu Asn Lys
705                 710                 715                 720

Gly Gly Ser Val Leu Ile Met Glu Asn Val Met Ser Asn Leu Lys Glu
                725                 730                 735

Glu Ser Ala Ser Gly Phe Val Arg Leu Leu Asp Ala Ala Gly Leu Ser
                740                 745                 750

Met Ala Leu Asn Lys Ser Val Val Asn Asn Asp Pro Gln Gly Tyr Pro
            755                 760                 765

Asn Arg Val Arg Gln Gln Arg Ala Thr Gly Ile Trp Val Tyr Glu Arg
770                 775                 780

Tyr Pro Ala Val Asp Gly Ala Leu Pro Tyr Thr Ile Asp Ser Lys Thr
785                 790                 795                 800

Gly Glu Val Lys Trp Lys Tyr Gln Val Glu Asn Lys Pro Asp Asp Lys
                805                 810                 815

Pro Lys Leu Glu Val Ala Ser Trp Leu Glu Asp Val Asp Gly Lys Gln
                820                 825                 830

Glu Thr Arg Tyr Ala Phe Ile Asp Glu Ala Asp His Lys Thr Glu Asp
            835                 840                 845

Ser Leu Lys Ala Ala Lys Ala Lys Ile Phe Glu Lys Phe Pro Gly Leu
850                 855                 860

Lys Glu Cys Lys Asp Pro Thr Tyr His Tyr Glu Val Asn Cys Leu Glu
865                 870                 875                 880

Tyr Arg Pro Gly Thr Gly Val Pro Val Thr Gly Met Tyr Val Pro
            885                 890                 895

Gln Tyr Thr Gln Leu Ser Leu Asn Ala Asp Thr Ala Lys Ala Met Val
                900                 905                 910

Gln Ala Ala Asp Leu Gly Thr Asn Ile Gln Arg Leu Tyr Gln His Glu
            915                 920                 925

Leu Tyr Phe Arg Thr Asn Gly Arg Lys Gly Glu Arg Leu Ser Ser Val
            930                 935                 940

Asp Leu Glu Arg Leu Tyr Gln Asn Met Ser Val Trp Leu Trp Asn Lys
945                 950                 955                 960

Ile Glu Tyr Arg Tyr Glu Asn Asp Lys Asp Glu Leu Gly Phe Lys
                965                 970                 975

Thr Phe Thr Glu Phe Leu Asn Cys Tyr Ala Asn Asp Ala Tyr Thr Gly
            980                 985                 990
```

```
Gly Thr Gln Cys Ser Asp Glu Leu Lys Lys Ser Leu Val Asp Asn Asn
            995                 1000                1005

Met Ile Tyr Gly Glu Lys Ser Val Asn Lys Ala Gly Met Met Asn Pro
    1010                1015                1020

Ser Tyr Pro Leu Asn Tyr Met Glu Lys Pro Leu Thr Arg Leu Met Leu
1025                1030                1035                1040

Gly Arg Ser Trp Trp Asp Leu Asn Ile Lys Val Asp Val Glu Lys Tyr
                1045                1050                1055

Pro Gly Ala Val Ser Ala Glu Gly Lys Val Thr Glu Thr Ile Ser
            1060                1065                1070

Leu Tyr Ser Asn Pro Thr Lys Trp Phe Ala Gly Asn Met Gln Ser Thr
                1075                1080                1085

Gly Leu Trp Ala Pro Ala Gln Lys Glu Val Thr Ile Glu Ser Ser Ala
    1090                1095                1100

Ser Val Pro Val Thr Val Thr Val Ala Leu Ala Asp Asp Leu Thr Gly
1105                1110                1115                1120

Arg Glu Lys His Glu Val Ala Leu Asn Arg Pro Pro Lys Val Thr Lys
                1125                1130                1135

Thr Tyr Glu Leu Lys Ala Asn Gly Glu Val Lys Phe Thr Val Pro Tyr
                1140                1145                1150

Gly Gly Leu Ile Tyr Ile Lys Gly Asn Ser Pro Gln Asn Glu Ser Ala
    1155                1160                1165

Glu Phe Thr Phe Thr Gly Val Val Lys Ala Pro Phe Tyr Lys Asp Gly
            1170                1175                1180

Ala Trp Lys Asn Ala Leu Asn Ser Pro Ala Pro Leu Gly Glu Leu Glu
1185                1190                1195                1200

Ser Asp Ala Phe Val Tyr Thr Thr Pro Lys Lys Asn Leu Glu Ala Ser
                1205                1210                1215

Asn Phe Thr Gly Gly Val Ala Glu Phe Ala Lys Asp Leu Asp Thr Phe
            1220                1225                1230

Ala Ser Ser Met Asn Asp Phe Tyr Gly Arg Asn Asp Glu Asp Gly Lys
            1235                1240                1245

His Arg Met Phe Glu Thr Pro Leu Thr Val Pro Gly Ala Thr Glu Val
    1250                1255                1260

Ala Asn Asn Val Leu Ala Leu Tyr Met Gln Asp Arg Tyr Leu Gly Lys
1265                1270                1275                1280

Met Asn Arg Val Ala Asp Asp Ile Thr Val Ala Pro Glu Tyr Leu Glu
            1285                1290                1295

Glu Ser Asn Gly Gln Ala Trp Ala Arg Gly Gly Ala Gly Asp Arg Leu
            1300                1305                1310

Leu Met Tyr Ala Gln Leu Lys Glu Trp Ala Glu Lys Asn Phe Asp Ile
    1315                1320                1325

Lys Gln Trp Tyr Pro Glu Gly Asp Leu Pro Lys Phe Tyr Ser Asp Arg
    1330                1335                1340

Glu Gly Met Lys Gly Trp Asn Leu Phe Gln Leu Met His Arg Lys Ala
1345                1350                1355                1360

Arg Gly Asp Glu Val Gly Lys Thr Lys Phe Gly Glu Arg Asn Tyr Cys
            1365                1370                1375

Ala Glu Ser Asn Gly Asn Ala Ala Asp Lys Leu Met Leu Cys Ala Ser
            1380                1385                1390

Trp Val Ala Gln Thr Asp Leu Ser Glu Phe Phe Lys Lys Trp Asn Pro
    1395                1400                1405

Gly Ala Asn Ala Tyr Gln Leu Pro Gly Ala Ser Glu Met Asn Phe Glu
```

```
                1410              1415                 1420
Gly Gly Val Ser Gln Ser Ala Tyr Glu Thr Leu Ala Ala Leu Asn Leu
1425                1430                1435                1440

Pro Lys Pro Gln Gln Gly Pro Glu Thr Ile Asn Gln Val Thr Glu His
                1445                1450                1455

Lys Met Ser Ala Glu
            1460

<210> SEQ ID NO 27
<211> LENGTH: 1461
<212> TYPE: PRT
<213> ORGANISM: Escherichia coli

<400> SEQUENCE: 27

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
            20                  25                  30

Ser Asp Thr Pro Pro Val Asp Ser Gly Thr Gly Ser Leu Pro Glu Val
            35                  40                  45

Lys Pro Asp Pro Thr Pro Asn Pro Glu Pro Thr Pro Glu Pro Thr Pro
50                  55                  60

Asp Pro Glu Pro Thr Pro Glu Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Ile Thr Gly Ala Thr Cys Asn Gly Glu Ser Ser
            100                 105                 110

Asp Gly Phe Thr Phe Thr Pro Gly Asp Lys Val Thr Cys Val Ala Gly
            115                 120                 125

Asn Asn Thr Thr Ile Ala Thr Phe Asp Thr Gln Ser Glu Ala Ala Arg
130                 135                 140

Ser Leu Arg Ala Val Glu Lys Val Ser Phe Ser Leu Glu Asp Ala Gln
145                 150                 155                 160

Glu Leu Ala Ala Ser Asp Asp Lys Lys Ser Asn Ala Val Ser Leu Val
                165                 170                 175

Thr Ser Ser Asn Ser Cys Pro Ala Asp Thr Glu Gln Val Cys Leu Thr
            180                 185                 190

Phe Ser Ser Val Ile Glu Ser Lys Arg Phe Asp Ser Leu Tyr Lys Gln
            195                 200                 205

Ile Asp Leu Ala Pro Glu Glu Phe Lys Lys Leu Val Asn Glu Glu Val
210                 215                 220

Glu Asn Asn Ala Ala Thr Asp Lys Ala Pro Ser Thr His Thr Ser Pro
225                 230                 235                 240

Val Val Pro Val Thr Thr Pro Gly Thr Lys Pro Asp Leu Asn Ala Ser
                245                 250                 255

Phe Val Ser Ala Asn Ala Glu Gln Phe Tyr Gln Tyr Gln Pro Thr Glu
            260                 265                 270

Ile Ile Leu Ser Glu Gly Arg Leu Val Asp Ser Met Gly Asn Gly Val
            275                 280                 285

Val Gly Val Asn Tyr Tyr Thr Ser Ser Gly Arg Gly Val Thr Gly Glu
            290                 295                 300

Asn Gly Lys Phe Asn Phe Ser Trp Gly Glu Thr Ile Ser Phe Gly Ile
305                 310                 315                 320
```

```
Asp Thr Phe Glu Leu Gly Ser Val Arg Gly Asn Lys Ser Thr Ile Ala
            325                 330                 335

Leu Thr Glu Leu Gly Asp Glu Val Arg Gly Ala Asn Ile Asp Gln Leu
            340                 345                 350

Ile His Arg Tyr Ser Gln Ala Gly Lys Asn Asp Glu Arg Glu Val Pro
            355                 360                 365

Asp Val Val Arg Lys Val Phe Ala Glu Tyr Pro Asn Val Ile Asn Glu
370                 375                 380

Ile Ile Asn Leu Ser Leu Ser Asn Gly Glu Ala Leu Ser Glu Gly Asp
385                 390                 395                 400

Gln Thr Phe Glu Arg Thr Asn Glu Phe Leu Glu Gln Phe Glu Ser Gly
            405                 410                 415

Gln Ala Lys Glu Ile Asp Thr Ala Ile Cys Asp Ser Leu Gly Gly Cys
            420                 425                 430

Asn Ser Gln Arg Trp Phe Ser Leu Thr Ala Arg Asn Val Asn Asp Gly
            435                 440                 445

Gln Ile Gln Gly Val Ile Asn Lys Leu Trp Gly Val Asp Thr Asn Tyr
            450                 455                 460

Lys Ser Val Ser Lys Phe His Val Phe His Asp Ser Thr Asn Phe Tyr
465                 470                 475                 480

Gly Ser Thr Gly Asn Ala Arg Gly Gln Ala Val Val Asn Ile Ser Asn
            485                 490                 495

Ala Ala Phe Pro Ile Leu Met Ala Arg Asn Asp Lys Asn Tyr Trp Leu
            500                 505                 510

Ala Phe Gly Glu Lys Arg Ala Trp Asp Lys Asn Glu Leu Ala Tyr Ile
            515                 520                 525

Thr Glu Ala Pro Ser Leu Val Glu Pro Glu Asn Val Thr Arg Asp Thr
            530                 535                 540

Ala Thr Phe Asn Leu Pro Phe Ile Ser Leu Gly Gln Val Gly Glu Gly
545                 550                 555                 560

Lys Leu Met Val Ile Gly Asn Pro His Tyr Asn Ser Ile Leu Arg Cys
            565                 570                 575

Pro Asn Gly Tyr Ser Trp Glu Gly Gly Val Asp Lys Asn Gly Gln Cys
            580                 585                 590

Thr Arg Asn Ser Asp Ser Asn Asp Met Lys His Phe Met Gln Asn Val
            595                 600                 605

Leu Arg Tyr Leu Ser Asp Asp Lys Trp Thr Pro Asp Ala Lys Ala Ser
            610                 615                 620

Met Thr Val Gly Thr Asn Leu Asp Thr Val Tyr Phe Lys Arg His Gly
625                 630                 635                 640

Gln Val Thr Gly Asn Ser Ala Glu Phe Gly Phe His Pro Asp Phe Ala
            645                 650                 655

Gly Ile Ser Val Glu His Leu Ser Ser Tyr Gly Asp Leu Asp Pro Gln
            660                 665                 670

Glu Met Pro Leu Leu Ile Leu Asn Gly Phe Glu Tyr Val Thr Gln Val
            675                 680                 685

Gly Asn Asp Pro Tyr Ala Ile Pro Leu Arg Ala Asp Thr Ser Lys Pro
            690                 695                 700

Lys Leu Thr Gln Gln Asp Val Thr Asp Leu Ile Ala Tyr Leu Asn Lys
705                 710                 715                 720

Gly Gly Ser Val Leu Ile Met Glu Asn Val Met Ser Asn Leu Lys Glu
            725                 730                 735

Glu Ser Ala Ser Gly Phe Val Arg Leu Leu Asp Ala Ala Gly Leu Ser
```

```
                    740                 745                 750
Met Ala Leu Asn Lys Ser Val Val Asn Asp Pro Gln Gly Tyr Pro
            755                 760                 765

Asn Arg Val Arg Gln Arg Ala Thr Gly Ile Trp Val Tyr Glu Arg
        770                 775                 780

Tyr Pro Ala Val Asp Gly Ala Leu Pro Tyr Thr Ile Asp Ser Lys Thr
785                 790                 795                 800

Gly Glu Val Lys Trp Lys Tyr Gln Val Glu Asn Lys Pro Asp Asp Lys
                805                 810                 815

Pro Lys Leu Glu Val Ala Ser Trp Leu Glu Asp Val Asp Gly Lys Gln
            820                 825                 830

Glu Thr Arg Tyr Ala Phe Ile Asp Glu Ala Asp His Lys Thr Glu Asp
            835                 840                 845

Ser Leu Lys Ala Ala Lys Ala Lys Ile Phe Glu Lys Phe Pro Gly Leu
            850                 855                 860

Lys Glu Cys Lys Asp Pro Thr Tyr His Tyr Glu Val Asn Cys Leu Glu
865                 870                 875                 880

Tyr Arg Pro Gly Thr Gly Val Pro Val Thr Gly Gly Met Tyr Val Pro
                885                 890                 895

Gln Tyr Thr Gln Leu Ser Leu Asn Ala Asp Thr Ala Lys Ala Met Val
            900                 905                 910

Gln Ala Ala Asp Leu Gly Thr Asn Ile Gln Arg Leu Tyr Gln His Glu
            915                 920                 925

Leu Tyr Phe Arg Thr Asn Gly Arg Lys Gly Glu Arg Leu Ser Ser Val
            930                 935                 940

Asp Leu Glu Arg Leu Tyr Gln Asn Met Ser Val Trp Leu Trp Asn Lys
945                 950                 955                 960

Ile Glu Tyr Arg Tyr Glu Asn Asp Lys Asp Glu Leu Gly Phe Lys
                965                 970                 975

Thr Phe Thr Glu Phe Leu Asn Cys Tyr Ala Asn Asp Ala Tyr Thr Gly
            980                 985                 990

Gly Thr Gln Cys Ser Asp Glu Leu Lys Lys Ser Leu Val Asp Asn Asn
        995                 1000                1005

Met Ile Tyr Gly Glu Lys Ser Val Asn Lys Ala Gly Met Met Asn Pro
    1010                1015                1020

Ser Tyr Pro Leu Asn Tyr Met Glu Lys Pro Leu Thr Arg Leu Met Leu
1025                1030                1035                1040

Gly Arg Ser Trp Trp Asp Leu Asn Ile Lys Val Asp Val Glu Lys Tyr
                1045                1050                1055

Pro Gly Ala Val Ser Ala Glu Gly Glu Lys Val Thr Glu Thr Ile Ser
            1060                1065                1070

Leu Tyr Ser Asn Pro Thr Lys Trp Phe Ala Gly Asn Met Gln Ser Thr
        1075                1080                1085

Gly Leu Trp Ala Pro Ala Gln Lys Glu Val Thr Ile Glu Ser Thr Ala
    1090                1095                1100

Ser Val Ala Val Thr Val Thr Val Ala Leu Ala Asp Asp Leu Thr Gly
1105                1110                1115                1120

Arg Glu Lys His Glu Val Ala Leu Asn Arg Pro Pro Val Thr Lys
                1125                1130                1135

Thr Tyr Glu Leu Lys Ala Asn Gly Glu Val Lys Phe Thr Val Pro Tyr
        1140                1145                1150

Gly Gly Leu Ile Tyr Ile Lys Gly Asn Ser Pro Gln Asn Glu Ser Ala
    1155                1160                1165
```

Glu Phe Thr Phe Thr Gly Val Val Lys Ala Pro Phe Tyr Lys Asp Gly
   1170                1175                1180

Ala Trp Lys Asn Ala Leu Asn Ser Pro Ala Pro Leu Gly Glu Leu Glu
1185                1190                1195                1200

Ser Asp Ala Phe Val Tyr Thr Thr Pro Lys Lys Asn Leu Glu Ala Ser
            1205                1210                1215

Asn Tyr Lys Gly Gly Gln Glu Gln Phe Ala Glu Leu Asp Thr Phe
        1220                1225                1230

Ala Ser Ser Met Asn Asp Phe Tyr Gly Arg Asn Asp Glu Asp Gly Lys
        1235                1240                1245

His Arg Met Phe Glu Thr Pro Leu Thr Val Pro Gly Ala Thr Glu Val
    1250                1255                1260

Ala Asn Asn Val Leu Ala Leu Tyr Met Gln Asp Arg Tyr Leu Gly Lys
1265                1270                1275                1280

Met Asn Arg Val Ala Asp Asp Ile Thr Val Ala Pro Glu Tyr Leu Glu
            1285                1290                1295

Glu Ser Asn Asn Gln Ala Trp Ala Arg Gly Gly Ala Gly Asp Arg Leu
        1300                1305                1310

Leu Met Tyr Ala Gln Leu Lys Glu Trp Ala Lys Asn Phe Asp Ile
    1315                1320                1325

Thr Lys Trp Tyr Pro Glu Gly Asn Leu Pro Lys Phe Tyr Ser Glu Arg
1330                1335                1340

Glu Gly Met Lys Gly Trp Asn Leu Phe Gln Leu Met His Arg Lys Ala
1345                1350                1355                1360

Arg Gly Asp Glu Val Gly Lys Thr Lys Phe Gly Glu Arg Asn Tyr Cys
            1365                1370                1375

Ala Glu Ser Asn Gly Asn Ala Asp Thr Leu Met Leu Cys Ala Ser
        1380                1385                1390

Trp Val Ala Gln Thr Asp Leu Ser Ala Phe Phe Lys Lys Trp Asn Pro
    1395                1400                1405

Gly Ala Asn Ala Tyr Gln Leu Pro Gly Ala Ser Glu Met Asn Phe Glu
    1410                1415                1420

Gly Gly Val Ser Gln Ser Ala Tyr Glu Thr Leu Ala Ala Leu Asn Leu
1425                1430                1435                1440

Pro Lys Pro Gln Gln Gly Pro Glu Thr Ile Asn Lys Val Thr Glu Tyr
            1445                1450                1455

Ser Met Pro Ala Glu
        1460

<210> SEQ ID NO 28
<211> LENGTH: 1463
<212> TYPE: PRT
<213> ORGANISM: Escherichia coli

<400> SEQUENCE: 28

Met Asn Lys Lys Phe Lys Tyr Lys Lys Ser Leu Leu Ala Ala Ile Leu
 1               5                  10                  15

Ser Ala Thr Leu Leu Ala Gly Cys Asp Gly Gly Gly Gly Ser Ser Ser
            20                  25                  30

Ser Asp Thr Pro Pro Val Asp Ser Gly Thr Gly Ser Leu Pro Glu Val
        35                  40                  45

Lys Pro Asp Pro Thr Pro Asn Pro Glu Pro Thr Pro Glu Pro Thr Pro
    50                  55                  60

Asp Pro Glu Pro Thr Pro Glu Pro Thr Pro Asp Pro Glu Pro Thr Pro

-continued

```
                65                  70                  75                  80
            Glu Pro Glu Pro Glu Pro Val Pro Thr Lys Thr Gly Tyr Leu Thr Leu
                            85                  90                  95
            Gly Gly Ser Gln Arg Ile Thr Gly Ala Thr Cys Asn Gly Glu Ser Ser
                            100                 105                 110
            Asp Gly Phe Thr Phe Thr Pro Gly Asp Lys Val Thr Cys Val Ala Gly
                            115                 120                 125
            Asn Asn Thr Thr Ile Ala Thr Phe Asp Thr Gln Ser Glu Ala Ala Arg
                            130                 135                 140
            Ser Leu Arg Ala Val Glu Lys Val Ser Phe Ser Leu Glu Asp Ala Gln
            145                 150                 155                 160
            Glu Leu Ala Ala Ser Asp Asp Lys Lys Ser Asn Ala Val Ser Leu Val
                            165                 170                 175
            Thr Ser Ser Asn Ser Cys Pro Ala Asn Thr Glu Gln Val Cys Leu Thr
                            180                 185                 190
            Phe Ser Ser Val Ile Glu Ser Lys Arg Phe Asp Ser Leu Tyr Lys Gln
                            195                 200                 205
            Ile Asp Leu Ala Pro Glu Glu Phe Lys Lys Leu Val Asn Glu Glu Val
                            210                 215                 220
            Glu Asn Asn Ala Ala Thr Asp Lys Ala Pro Ser Thr His Thr Ser Pro
            225                 230                 235                 240
            Val Val Pro Val Thr Thr Pro Gly Thr Lys Pro Asp Leu Asn Ala Ser
                            245                 250                 255
            Phe Val Ser Ala Asn Ala Glu Gln Phe Tyr Gln Tyr Gln Pro Thr Glu
                            260                 265                 270
            Ile Ile Leu Ser Glu Gly Arg Leu Val Asp Ser Met Gly Asn Gly Val
                            275                 280                 285
            Val Gly Val Asn Tyr Tyr Thr Ser Ser Gly Arg Gly Val Thr Gly Glu
                            290                 295                 300
            Asn Gly Lys Phe Asn Phe Ser Trp Gly Glu Thr Ile Ser Phe Gly Ile
            305                 310                 315                 320
            Asp Thr Phe Glu Leu Gly Ser Val Arg Gly Asn Lys Ser Thr Ile Ala
                            325                 330                 335
            Leu Thr Glu Leu Gly Asp Glu Val Arg Gly Ala Asn Ile Asp Gln Leu
                            340                 345                 350
            Ile His Arg Tyr Ser Gln Ala Gly Lys Asn Asp Glu Arg Glu Val Pro
                            355                 360                 365
            Asp Val Val Arg Lys Val Phe Ala Ala Tyr Pro Asn Val Ile Asn Glu
                            370                 375                 380
            Ile Ile Asn Leu Ser Leu Ser Asn Gly Glu Ala Leu Ser Glu Gly Asp
            385                 390                 395                 400
            Gln Thr Phe Glu Arg Thr Asn Glu Phe Leu Glu Gln Phe Glu Ser Gly
                            405                 410                 415
            Gln Ala Lys Glu Ile Asp Thr Ala Ile Cys Asp Ser Leu Gly Gly Cys
                            420                 425                 430
            Asn Ser Gln Arg Trp Phe Ser Leu Thr Ala Arg Asn Val Asn Glu Gly
                            435                 440                 445
            Gln Ile Gln Gly Val Ile Asn Lys Leu Trp Gly Val Asp Lys Asp Tyr
                            450                 455                 460
            Lys Ser Val Thr Lys Phe His Val Phe His Asp Ser Thr Asn Phe Tyr
            465                 470                 475                 480
            Gly Ser Thr Gly Asn Ala Arg Gly Gln Ala Val Val Asn Ile Ser Asn
                            485                 490                 495
```

```
Ala Ala Phe Pro Ile Leu Met Ala Arg Asn Asp Lys Asn Tyr Trp Leu
            500                 505                 510
Ala Phe Gly Glu Lys Arg Ala Trp Asp Lys Asn Glu Leu Ala Tyr Ile
        515                 520                 525
Thr Glu Ala Pro Ser Leu Val Glu Pro Glu Asn Val Thr Arg Asp Thr
    530                 535                 540
Ala Thr Phe Asn Leu Pro Phe Ile Ser Leu Gly Gln Val Gly Glu Gly
545                 550                 555                 560
Lys Leu Met Val Ile Gly Asn Pro His Tyr Asn Ser Ile Leu Arg Cys
                565                 570                 575
Pro Asn Gly Tyr Ser Trp Glu Gly Val Asp Lys Asn Gly Gln Cys
            580                 585                 590
Thr Arg Asn Ser Asp Ser Asn Asp Met Lys His Phe Met Gln Asn Val
        595                 600                 605
Leu Arg Tyr Leu Ser Asn Asp Lys Trp Thr Pro Asp Ala Lys Ala Ser
    610                 615                 620
Met Thr Val Gly Thr Asn Leu Asp Thr Val Tyr Phe Lys Arg His Gly
625                 630                 635                 640
Gln Val Thr Gly Asn Ser Ala Glu Phe Gly Phe His Pro Asp Phe Ala
                645                 650                 655
Gly Ile Ser Val Glu His Leu Ser Ser Tyr Gly Asp Leu Asp Pro Gln
            660                 665                 670
Lys Met Pro Leu Leu Ile Leu Asn Gly Phe Glu Tyr Val Thr Gln Val
        675                 680                 685
Gly Gly Asp Pro Tyr Ala Val Pro Leu Arg Ala Asp Thr Ser Lys Pro
    690                 695                 700
Lys Leu Ser Gln Gln Asp Val Thr Asp Leu Ile Ala Tyr Leu Asn Lys
705                 710                 715                 720
Gly Gly Ser Val Leu Ile Met Glu Asn Val Met Ser Asn Leu Lys Glu
                725                 730                 735
Glu Ser Ala Ser Gly Phe Val Arg Leu Leu Asp Ala Ala Gly Leu Ser
            740                 745                 750
Met Ala Leu Asn Lys Ser Val Val Asn Asn Asp Pro Gln Gly Tyr Pro
        755                 760                 765
Asp Arg Val Arg Gln Arg Arg Ala Thr Gly Ile Trp Val Tyr Glu Arg
    770                 775                 780
Tyr Pro Val Val Glu Gly Glu Leu Pro Tyr Thr Ile Asp Ser Lys Thr
785                 790                 795                 800
Gly Lys Val Thr Trp Lys Tyr Gln Ile Asp Asn Lys Pro Asp Lys Lys
                805                 810                 815
Pro Lys Leu Glu Val Ala Ser Trp Gln Glu Glu Val Asp Gly Lys Gln
            820                 825                 830
Val Thr Gln Phe Ala Phe Ile Asp Glu Ala Asp His Lys Thr Thr Glu
        835                 840                 845
Ser Leu Asp Ala Ala Lys Lys Lys Ile Leu Glu Lys Phe Lys Gly Leu
    850                 855                 860
Glu Glu Cys Lys Asp Ser Thr Tyr His Tyr Glu Ile Asn Cys Leu Glu
865                 870                 875                 880
Tyr Arg Pro Gly Thr Asn Val Pro Ala Thr Gly Gly Met Tyr Val Pro
                885                 890                 895
Arg Tyr Thr Gln Leu Asn Leu Ser Ala Asp Thr Ala Lys Ala Met Val
            900                 905                 910
```

-continued

```
Gln Ala Ala Asp Leu Gly Thr Asn Ile Gln Arg Leu Tyr Gln His Glu
            915                 920                 925

Leu Tyr Phe Arg Thr Asn Gly Arg Lys Gly Glu Arg Leu Ser Ser Val
        930                 935                 940

Asp Leu Glu Arg Leu Tyr Gln Asn Met Ser Val Trp Leu Trp Asn Glu
945                 950                 955                 960

Ile Glu Tyr Ser Tyr Asp Ser Ser Lys Glu Asp Leu Gly Phe Lys
                965                 970                 975

Thr Phe Thr Glu Phe Leu Asn Cys Tyr Ala Asn Asp Ala Tyr Thr Gly
            980                 985                 990

Gly Thr Gln Cys Ser Asp Glu Leu Lys Lys Ser Leu Val Asp Asn Asn
        995                 1000                1005

Met Ile Tyr Gly Glu Lys Ser Val Asn Lys Ala Gly Met Met Asn Pro
    1010                1015                1020

Ser Tyr Pro Leu Asn Tyr Met Glu Lys Pro Leu Thr Arg Leu Met Leu
1025                1030                1035                1040

Gly Arg Ser Trp Trp Asp Leu Asn Ile Lys Val Asp Val Glu Lys Tyr
            1045                1050                1055

Pro Gly Ala Val Ser Glu Glu Gly Gln Glu Val Thr Glu Ser Ile Ser
            1060                1065                1070

Leu Tyr Ser Asn Pro Thr Lys Trp Phe Ala Gly Asn Met Gln Ser Thr
        1075                1080                1085

Gly Leu Trp Ala Pro Ala Gln Lys Glu Val Thr Ile Lys Ser Asn Ala
        1090                1095                1100

Asp Val Pro Val Thr Val Thr Val Ala Leu Ala Asp Asp Leu Thr Gly
1105                1110                1115                1120

Arg Glu Lys His Glu Val Ala Leu Asn Arg Pro Pro Lys Val Thr Lys
            1125                1130                1135

Thr Tyr Glu Leu Lys Ala Asn Gly Glu Val Lys Phe Thr Val Pro Tyr
        1140                1145                1150

Gly Gly Leu Ile Tyr Ile Lys Gly Asn Ser Lys Glu Asn Asn Lys Ser
        1155                1160                1165

Ala Ser Phe Thr Phe Thr Gly Val Val Lys Ala Pro Phe Tyr Lys Asn
    1170                1175                1180

Gly Ala Trp Lys Asn Ala Leu Asn Ser Pro Ala Pro Leu Gly Glu Leu
1185                1190                1195                1200

Glu Ser Asp Ala Phe Val Tyr Thr Thr Pro Lys Lys Asn Leu Glu Ala
                1205                1210                1215

Ser Asn Phe Thr Gly Gly Val Ala Glu Phe Ala Lys Asp Leu Asp Thr
                1220                1225                1230

Phe Ala Ser Ser Met Asn Asp Phe Tyr Gly Arg Asn Asp Glu Asp Gly
            1235                1240                1245

Lys His Arg Met Phe Glu Thr Pro Leu Thr Val Pro Gly Ala Thr Glu
    1250                1255                1260

Val Ala Asn Asn Val Leu Ala Leu Tyr Met Gln Asp Arg Tyr Leu Gly
1265                1270                1275                1280

Lys Met Asn Arg Val Ala Asp Asp Ile Thr Val Ala Pro Glu Tyr Leu
            1285                1290                1295

Glu Glu Ser Asn Asn Gln Ala Trp Ala Arg Gly Gly Ala Gly Asp Arg
            1300                1305                1310

Leu Leu Met Tyr Ala Gln Leu Lys Glu Trp Ala Glu Lys Asn Phe Asp
        1315                1320                1325

Ile Lys Lys Trp Tyr Pro Asp Gly Thr Pro Leu Pro Glu Phe Tyr Ser
```

```
                      1330                1335                1340
Glu Arg Glu Gly Met Lys Gly Trp Asn Leu Phe Gln Leu Met His Arg
1345                1350                1355                1360

Lys Ala Arg Gly Asp Glu Val Ser Asn Asp Lys Phe Gly Arg Asn
                1365                1370                1375

Tyr Cys Ala Glu Ser Asn Gly Asn Thr Ala Asp Thr Leu Met Leu Cys
                1380                1385                1390

Ala Ser Trp Val Ala Gln Thr Asp Leu Ser Glu Phe Phe Lys Lys Trp
                1395                1400                1405

Asn Pro Gly Ala Asn Ala Tyr Gln Leu Pro Gly Ala Thr Glu Met Ser
                1410                1415                1420

Phe Glu Gly Gly Val Ser Gln Ser Ala Tyr Asn Thr Leu Ala Ser Leu
1425                1430                1435                1440

Asp Leu Pro Lys Pro Lys Gln Gly Pro Glu Thr Ile Asn Lys Val Thr
                1445                1450                1455

Glu Tyr Ser Met Pro Ala Glu
                1460

<210> SEQ ID NO 29
<211> LENGTH: 1464
<212> TYPE: PRT
<213> ORGANISM: Escherichia coli

<400> SEQUENCE: 29

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Pro Ser
                20                  25                  30

Ser Asp Thr Pro Pro Val Asp Ser Gly Thr Gly Ser Leu Pro Glu Val
                35                  40                  45

Lys Pro Asp Pro Thr Pro Asn Pro Glu Pro Thr Pro Glu Pro Thr Pro
                50                  55                  60

Asp Pro Glu Pro Thr Pro Asp Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Ile Thr Gly Ala Thr Cys Asn Gly Glu Ser Ser
                100                 105                 110

Asp Gly Phe Thr Phe Thr Pro Gly Asp Lys Val Thr Cys Val Ala Gly
                115                 120                 125

Asn Asn Thr Thr Ile Ala Thr Phe Asp Thr Gln Ser Glu Ala Ala Arg
                130                 135                 140

Ser Leu Arg Ala Val Glu Lys Val Ser Phe Ser Leu Glu Asp Ala Gln
145                 150                 155                 160

Glu Leu Ala Ala Ser Asp Asp Lys Lys Ser Asn Ala Val Ser Leu Val
                165                 170                 175

Thr Ser Ser Asn Ser Cys Pro Ala Asp Thr Glu Gln Val Cys Leu Thr
                180                 185                 190

Phe Ser Ser Val Ile Glu Ser Lys Arg Phe Asp Ser Leu Tyr Lys Gln
                195                 200                 205

Ile Asp Leu Ala Pro Glu Glu Phe Lys Lys Leu Val Asn Glu Glu Val
                210                 215                 220

Glu Asn Asn Ala Ala Thr Asp Lys Ala Pro Ser Thr His Thr Ser Pro
225                 230                 235                 240
```

-continued

```
Val Val Pro Val Thr Thr Pro Gly Thr Lys Pro Asp Leu Asn Ala Ser
            245                 250                 255
Phe Val Ser Ala Asn Ala Glu Gln Phe Tyr Gln Tyr Gln Pro Thr Glu
        260                 265                 270
Ile Ile Leu Ser Glu Gly Arg Leu Val Asp Ser Gln Gly Tyr Gly Val
    275                 280                 285
Ala Gly Val Asn Tyr Tyr Thr Asn Ser Gly Arg Gly Val Thr Gly Glu
290                 295                 300
Asn Gly Glu Phe Ser Phe Ser Trp Gly Glu Thr Ile Ser Phe Gly Ile
305                 310                 315                 320
Asp Thr Phe Glu Leu Gly Ser Val Arg Gly Asn Lys Ser Thr Ile Ala
                325                 330                 335
Leu Thr Glu Leu Gly Asp Glu Val Arg Gly Ala Asn Ile Asp Gln Leu
            340                 345                 350
Ile His Arg Tyr Ser Thr Thr Gly Gln Asn Asn Thr Arg Val Val Pro
        355                 360                 365
Asp Asp Val Arg Lys Val Phe Ala Glu Tyr Pro Asn Val Ile Asn Glu
    370                 375                 380
Ile Ile Asn Leu Ser Leu Ser Asn Gly Ala Thr Leu Asp Glu Gly Asp
385                 390                 395                 400
Gln Asn Val Val Leu Pro Asn Glu Phe Ile Glu Gln Phe Lys Thr Gly
                405                 410                 415
Gln Ala Lys Glu Ile Asp Thr Ala Ile Cys Ala Lys Thr Asp Gly Cys
            420                 425                 430
Asn Glu Ala Arg Trp Phe Ser Leu Thr Thr Arg Asn Val Asn Asp Gly
        435                 440                 445
Gln Ile Gln Gly Val Ile Asn Lys Leu Trp Gly Val Asp Lys Asp Tyr
    450                 455                 460
Lys Ser Val Thr Lys Phe His Val Phe His Asp Ser Thr Asn Phe Tyr
465                 470                 475                 480
Gly Ser Thr Gly Asn Ala Arg Gly Gln Ala Val Val Asn Ile Ser Asn
                485                 490                 495
Ala Ala Phe Pro Ile Leu Met Ala Arg Asn Asp Lys Asn Tyr Trp Leu
            500                 505                 510
Ala Phe Gly Glu Lys Arg Ala Trp Asp Lys Asn Glu Leu Ala Tyr Ile
        515                 520                 525
Thr Glu Ala Pro Ser Ile Val Gln Pro Glu Asn Val Thr Arg Asp Thr
    530                 535                 540
Ala Thr Phe Asn Leu Pro Phe Ile Ser Leu Gly Gln Val Gly Glu Gly
545                 550                 555                 560
Lys Leu Met Val Ile Gly Asn Pro His Tyr Asn Ser Ile Leu Arg Cys
                565                 570                 575
Pro Asn Gly Tyr Ser Trp Asn Gly Val Asn Lys Asp Gly Gln Cys
            580                 585                 590
Thr Leu Ser Gly Asp Ser Asp Met Lys His Phe Met Gln Asn Val
    595                 600                 605
Leu Arg Tyr Leu Ser Asp Asp Lys Trp Thr Pro Asp Ala Lys Ala Ser
    610                 615                 620
Met Thr Val Gly Thr Asn Leu Asp Thr Val Tyr Phe Lys Arg His Gly
625                 630                 635                 640
Gln Val Thr Gly Asn Ser Ala Glu Phe Gly Phe His Pro Asp Phe Ala
                645                 650                 655
Gly Ile Ser Val Glu His Leu Ser Ser Tyr Gly Asp Leu Asp Pro Gln
```

-continued

```
                660                 665                 670
Glu Met Pro Leu Leu Ile Leu Asn Gly Phe Glu Tyr Val Thr Gln Val
            675                 680                 685
Gly Asn Asp Pro Tyr Ala Ile Pro Leu Arg Ala Asp Thr Ser Lys Pro
        690                 695                 700
Lys Leu Thr Gln Gln Asp Val Thr Asp Leu Ile Ala Tyr Leu Asn Lys
705                 710                 715                 720
Gly Gly Ser Val Leu Ile Met Glu Asn Val Met Ser Asn Leu Lys Glu
                725                 730                 735
Glu Ser Ala Ser Gly Phe Val Arg Leu Leu Asp Ala Ala Gly Leu Ser
            740                 745                 750
Met Ala Leu Asn Lys Ser Val Val Asn Thr Asp Pro Gln Gly Tyr Pro
        755                 760                 765
Asn Arg Val Arg Gln Gln Arg Glu Lys Gly Ile Trp Val Tyr Glu Arg
    770                 775                 780
Tyr Pro Ala Val Asp Ser Ala Gln Pro Pro Tyr Thr Ile Asp Pro Asp
785                 790                 795                 800
Thr Gly Lys Val Thr Trp Lys Tyr Gln Glu Glu Gly Lys Pro Asp Asp
                805                 810                 815
Lys Pro Lys Leu Glu Val Ala Ser Trp Gln Glu Asp Val Asp Gly Lys
            820                 825                 830
Gln Val Thr Arg Tyr Ala Phe Ile Asp Glu Ala Glu His Ser Thr Glu
        835                 840                 845
Glu Ser Leu Glu Ala Ala Lys Ala Lys Ile Phe Glu Lys Phe Pro Gly
    850                 855                 860
Leu Gln Glu Cys Lys Asp Ser Thr Tyr His Tyr Glu Ile Asn Cys Leu
865                 870                 875                 880
Glu Arg Arg Pro Gly Thr Asp Val Pro Val Thr Gly Gly Met Tyr Val
                885                 890                 895
Pro Arg Tyr Thr Gln Leu Asn Leu Asp Ala Asp Thr Ala Lys Ala Met
            900                 905                 910
Val Gln Ala Ala Asp Leu Gly Thr Asn Ile Gln Arg Leu Tyr Gln His
        915                 920                 925
Glu Leu Tyr Phe Arg Thr Asn Gly Arg Lys Gly Glu Arg Leu Ser Ser
    930                 935                 940
Val Asp Leu Glu Arg Leu Tyr Gln Asn Met Ser Val Trp Leu Trp Asn
945                 950                 955                 960
Lys Ile Glu Tyr Arg Tyr Glu Asn Asp Lys Asp Glu Leu Gly Phe
                965                 970                 975
Lys Thr Phe Thr Glu Phe Leu Asn Cys Tyr Ala Asn Asn Ala Tyr Ser
            980                 985                 990
Glu Gly Thr Gln Cys Ser Ala Asp Leu Lys Lys Ser Leu Val Asp Asn
        995                1000                1005
Asn Met Ile Tyr Gly Asp Gly Ser Ser Lys Ala Gly Met Met Asn Pro
    1010                1015                1020
Ser Tyr Pro Leu Asn Tyr Met Glu Lys Pro Leu Thr Arg Leu Met Leu
1025                1030                1035                1040
Gly Arg Ser Trp Trp Asp Leu Asn Ile Lys Val Asp Val Glu Lys Tyr
                1045                1050                1055
Pro Gly Ala Val Ser Ala Glu Gly Lys Val Thr Glu Thr Ile Ser
            1060                1065                1070
Leu Tyr Ser Asn Pro Thr Lys Trp Phe Ala Gly Asn Met Gln Ser Thr
    1075                1080                1085
```

Gly Leu Trp Ala Pro Ala Gln Gln Glu Val Thr Ile Glu Ser Thr Ala
        1090                1095                1100

Ser Val Pro Val Thr Val Thr Val Ala Leu Ala Asp Asp Leu Thr Gly
1105                1110                1115                1120

Arg Glu Lys His Glu Val Ala Leu Asn Arg Pro Pro Lys Val Thr Lys
            1125                1130                1135

Thr Tyr Asp Leu Lys Ala Asn Asp Lys Val Thr Phe Lys Val Pro Tyr
        1140                1145                1150

Gly Gly Leu Ile Tyr Ile Lys Gly Asn Ser Pro Lys Asn Glu Ser Ala
            1155                1160                1165

Glu Phe Thr Phe Thr Gly Val Val Lys Ala Pro Phe Tyr Lys Asp Gly
        1170                1175                1180

Glu Trp Lys Asn Ala Leu Asn Ser Pro Ala Pro Leu Gly Glu Leu Glu
1185                1190                1195                1200

Ser Asp Ser Phe Val Tyr Thr Ala Pro Lys Asn Asn Leu Asn Ala Ser
            1205                1210                1215

Asn Tyr Ser Asn Tyr Thr Asp Gly Val Ala Glu Phe Ala Lys Glu Leu
        1220                1225                1230

Asp Thr Phe Ala Ser Ser Met Asn Asp Phe Tyr Gly Arg Asp Gly Glu
        1235                1240                1245

Ser Gly Asn His Arg Met Phe Glu Thr Pro Leu Asn Val Pro Gly Ala
        1250                1255                1260

Thr Glu Val Ala Asn Asn Val Leu Ala Leu Tyr Met Gln Asp Arg Tyr
1265                1270                1275                1280

Leu Gly Lys Met Asn Arg Val Ala Asp Ile Thr Val Ala Pro Glu
                1285                1290                1295

Tyr Leu Asp Glu Ser Asn Gly Gln Ala Trp Ala Arg Gly Ala Gly
        1300                1305                1310

Asp Arg Leu Leu Met Tyr Ala Gln Leu Lys Glu Trp Ala Glu Glu Asn
        1315                1320                1325

Phe Asp Ile Lys Gln Trp Tyr Pro Asp Gly Glu Leu Pro Lys Phe Tyr
        1330                1335                1340

Ser Asp Arg Lys Gly Met Lys Gly Trp Asn Leu Phe Gln Leu Met His
1345                1350                1355                1360

Arg Lys Ala Arg Gly Asp Asp Val Ser Asn Asp Lys Phe Gly Gly Arg
                1365                1370                1375

Asn Tyr Cys Ala Glu Ser Asn Gly Asn Ala Ala Asp Thr Leu Met Leu
            1380                1385                1390

Cys Ala Ser Trp Val Ala Gln Ala Asp Leu Ser Glu Phe Phe Lys Lys
        1395                1400                1405

Trp Asn Pro Gly Ala Asn Ala Tyr Gln Leu Pro Gly Ala Ser Glu Met
        1410                1415                1420

Ser Phe Glu Gly Gly Val Ser Gln Ser Ala Tyr Asn Thr Leu Ala Ala
1425                1430                1435                1440

Met His Leu Ser Lys Pro Glu Lys Gly Pro Glu Thr Ile Asn Lys Val
                1445                1450                1455

Thr Glu Tyr Ser Met Pro Ala Glu
            1460

<210> SEQ ID NO 30
<211> LENGTH: 1460
<212> TYPE: PRT
<213> ORGANISM: Escherichia coli

```
<400> SEQUENCE: 30

Met Asn Lys Lys Phe Lys Tyr Lys Lys Ser Leu Leu Ala Ala Ile Leu
 1               5                  10                  15

Ser Ala Thr Leu Leu Ala Gly Cys Asp Gly Gly Ser Gly Ser Ser
            20                  25                  30

Ser Asp Thr Pro Pro Val Asp Ser Gly Thr Gly Ser Leu Pro Glu Val
            35                  40                  45

Lys Pro Asp Pro Thr Pro Asn Pro Glu Pro Thr Pro Glu Pro Thr Pro
 50                  55                  60

Asp Pro Glu Pro Thr Pro Glu Pro Ile Pro Asp Pro Glu Pro Thr Pro
 65                  70                  75                  80

Glu Pro Glu Pro Glu Pro Val Pro Thr Lys Thr Gly Tyr Leu Thr Leu
                 85                  90                  95

Gly Gly Ser Gln Arg Val Thr Gly Ala Thr Cys Asn Gly Glu Ser Ser
                100                 105                 110

Asp Gly Phe Thr Phe Lys Pro Gly Glu Asp Val Thr Cys Val Ala Gly
                115                 120                 125

Asn Thr Thr Ile Ala Thr Phe Asn Thr Gln Ser Glu Ala Ala Arg Ser
130                 135                 140

Leu Arg Ala Val Glu Lys Val Ser Phe Ser Leu Glu Asp Ala Gln Glu
145                 150                 155                 160

Leu Ala Gly Ser Asp Asp Lys Lys Ser Asn Ala Val Ser Leu Val Thr
                165                 170                 175

Ser Ser Asn Ser Cys Pro Ala Asn Thr Glu Gln Val Cys Leu Thr Phe
                180                 185                 190

Ser Ser Val Ile Glu Ser Lys Arg Phe Asp Ser Leu Tyr Lys Gln Ile
                195                 200                 205

Asp Leu Ala Pro Glu Glu Phe Lys Lys Leu Val Asn Glu Glu Val Glu
                210                 215                 220

Asn Asn Ala Ala Thr Asp Lys Ala Pro Ser Thr His Thr Ser Pro Val
225                 230                 235                 240

Val Pro Val Thr Thr Pro Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
                260                 265                 270

Ile Leu Ser Glu Gly Arg Leu Val Asp Ser Gln Gly Tyr Gly Val Ala
                275                 280                 285

Gly Val Asn Tyr Tyr Thr Asn Ser Gly Arg Gly Val Thr Gly Glu Asn
                290                 295                 300

Gly Glu Phe Ser Phe Ser Trp Gly Glu Thr Ile Ser Phe Gly Ile Asp
305                 310                 315                 320

Thr Phe Glu Leu Gly Ser Val Arg Gly Asn Lys Ser Thr Ile Ala Leu
                325                 330                 335

Thr Glu Leu Gly Asp Glu Val Arg Gly Ala Asn Ile Asp Gln Leu Ile
                340                 345                 350

His Arg Tyr Ser Thr Thr Gly Gln Asn Asn Thr Arg Val Val Pro Asp
                355                 360                 365

Asp Val Arg Lys Val Phe Ala Glu Tyr Pro Asn Val Ile Asn Glu Ile
                370                 375                 380

Ile Asn Leu Ser Leu Ser Asn Gly Ala Thr Leu Gly Glu Gly Glu Gln
385                 390                 395                 400

Val Val Asn Leu Pro Asn Glu Phe Ile Glu Gln Phe Asn Thr Gly Gln
                405                 410                 415
```

-continued

Ala Lys Glu Ile Asp Thr Ala Ile Cys Ala Lys Thr Asp Gly Cys Asn
            420                 425                 430

Glu Ala Arg Trp Phe Ser Leu Thr Thr Arg Asn Val Asn Asp Gly Gln
            435                 440                 445

Ile Gln Gly Val Ile Asn Lys Leu Trp Gly Val Asp Thr Asn Tyr Lys
            450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ala
                485                 490                 495

Ala Phe Pro Ile Leu Met Ala Arg Asn Asp Lys Asn Tyr Trp Leu Ala
            500                 505                 510

Phe Gly Glu Lys Arg Ala Trp Asp Lys Asn Glu Leu Ala Tyr Ile Thr
            515                 520                 525

Glu Ala Pro Ser Leu Val Glu Pro Glu Asn Val Thr Arg Asp Thr Ala
            530                 535                 540

Thr Phe Asn Leu Pro Phe Ile Ser Leu Gly Gln Val Gly Glu Gly Lys
545                 550                 555                 560

Leu Met Val Ile Gly Asn Pro His Tyr Asn Ser Ile Leu Arg Cys Pro
                565                 570                 575

Asn Gly Tyr Ser Trp Asn Gly Gly Val Asn Lys Asp Gly Gln Cys Thr
            580                 585                 590

Leu Asn Ser Asp Ser Asp Met Lys His Phe Met Gln Asn Val Leu
            595                 600                 605

Arg Tyr Leu Ser Asp Asp Lys Trp Thr Pro Asp Ala Lys Ala Ser Met
610                 615                 620

Thr Val Gly Thr Asn Leu Asp Thr Val Tyr Phe Lys Arg His Gly Gln
625                 630                 635                 640

Val Thr Gly Asn Ser Ala Ala Phe Asp Phe His Pro Asp Phe Ala Gly
                645                 650                 655

Ile Ser Val Glu His Leu Ser Ser Tyr Gly Asp Leu Asp Pro Gln Glu
            660                 665                 670

Met Pro Leu Leu Ile Leu Asn Gly Phe Glu Tyr Val Thr Gln Val Gly
            675                 680                 685

Asn Asp Pro Tyr Ala Ile Pro Leu Arg Ala Asp Thr Ser Lys Pro Lys
            690                 695                 700

Leu Thr Gln Gln Asp Val Thr Asp Leu Ile Ala Tyr Leu Asn Lys Gly
705                 710                 715                 720

Gly Ser Val Leu Ile Met Glu Asn Val Met Ser Asn Leu Lys Glu Glu
                725                 730                 735

Ser Ala Ser Gly Phe Val Arg Leu Leu Asp Ala Ala Gly Leu Ser Met
            740                 745                 750

Ala Leu Asn Lys Ser Val Asn Asn Asp Pro Gln Gly Tyr Pro Asn
            755                 760                 765

Arg Val Arg Gln Gln Arg Ala Thr Gly Ile Trp Val Tyr Glu Arg Tyr
            770                 775                 780

Pro Ala Val Asp Gly Ala Leu Pro Tyr Thr Ile Asp Ser Lys Thr Gly
785                 790                 795                 800

Glu Val Lys Trp Lys Tyr Gln Val Glu Asn Lys Pro Asp Asp Lys Pro
                805                 810                 815

Lys Leu Glu Val Ala Ser Trp Leu Glu Asp Val Asp Gly Lys Gln Glu
            820                 825                 830

-continued

Thr Arg Tyr Ala Phe Ile Asp Glu Ala Asp His Lys Thr Glu Asp Ser
        835                 840                 845

Leu Lys Ala Ala Lys Glu Lys Ile Phe Ala Ala Phe Pro Gly Leu Lys
850                 855                 860

Glu Cys Thr Asn Pro Ala Tyr His Tyr Glu Val Asn Cys Leu Glu Tyr
865                 870                 875                 880

Arg Pro Gly Thr Gly Val Pro Val Thr Gly Met Tyr Val Pro Gln
            885                 890                 895

Tyr Thr Gln Leu Ser Leu Asn Ala Asp Thr Ala Lys Ala Met Val Gln
        900                 905                 910

Ala Ala Asp Leu Gly Thr Asn Ile Gln Arg Leu Tyr Gln His Glu Leu
        915                 920                 925

Tyr Phe Arg Thr Asn Gly Arg Lys Gly Glu Arg Leu Ser Ser Val Asp
930                 935                 940

Leu Glu Arg Leu Tyr Gln Asn Met Ser Val Trp Leu Trp Asn Asp Thr
945                 950                 955                 960

Ser Tyr Arg Tyr Glu Glu Gly Lys Asn Asp Glu Leu Gly Phe Lys Thr
            965                 970                 975

Phe Thr Glu Phe Leu Asn Cys Tyr Ala Asn Asp Ala Tyr Ala Gly Gly
        980                 985                 990

Thr Lys Cys Ser Ala Asp Leu Lys Lys Ser Leu Val Asp Asn Asn Met
        995                 1000                1005

Ile Tyr Gly Asp Gly Ser Ser Lys Ala Gly Met Met Asn Pro Ser Tyr
        1010                1015                1020

Pro Leu Asn Tyr Met Glu Lys Pro Leu Thr Arg Leu Met Leu Gly Arg
1025                1030                1035                1040

Ser Trp Trp Asp Leu Asn Ile Lys Val Asp Val Glu Lys Tyr Pro Gly
            1045                1050                1055

Ala Val Ser Glu Glu Gly Gln Asn Val Thr Glu Thr Ile Ser Leu Tyr
        1060                1065                1070

Ser Asn Pro Thr Lys Trp Phe Ala Gly Asn Met Gln Ser Thr Gly Leu
        1075                1080                1085

Trp Ala Pro Ala Gln Lys Glu Val Thr Ile Lys Ser Asn Ala Asn Val
        1090                1095                1100

Pro Val Thr Val Thr Val Ala Leu Ala Asp Asp Leu Thr Gly Arg Glu
1105                1110                1115                1120

Lys His Glu Val Ala Leu Asn Arg Pro Pro Arg Val Thr Lys Thr Tyr
            1125                1130                1135

Ser Leu Asp Ala Ser Gly Thr Val Lys Phe Lys Val Pro Tyr Gly Gly
        1140                1145                1150

Leu Ile Tyr Ile Lys Gly Asn Ser Ser Thr Asn Glu Ser Ala Ser Phe
        1155                1160                1165

Thr Phe Thr Gly Val Val Lys Ala Pro Phe Tyr Lys Asp Gly Ala Trp
        1170                1175                1180

Lys Asn Asp Leu Asn Ser Pro Ala Pro Leu Gly Glu Leu Glu Ser Asp
1185                1190                1195                1200

Ala Phe Val Tyr Thr Thr Pro Lys Lys Asn Leu Asn Ala Ser Asn Tyr
            1205                1210                1215

Thr Gly Gly Leu Glu Gln Phe Ala Asn Asp Leu Asp Thr Phe Ala Ser
        1220                1225                1230

Ser Met Asn Asp Phe His Gly Arg Asp Ser Glu Asp Gly Lys His Arg
        1235                1240                1245

Met Phe Glu Thr Pro Leu Thr Val Pro Gly Ala Thr Glu Val Ala Asn

```
                    1250            1255            1260
Asn Val Leu Ala Leu Tyr Met Gln Asp Arg Tyr Leu Gly Lys Met Asn
1265            1270            1275            1280

Arg Val Ala Asp Asp Ile Thr Val Ala Pro Glu Tyr Leu Glu Glu Ser
            1285            1290            1295

Asn Asn Gln Ala Trp Ala Arg Gly Gly Ala Gly Asp Arg Leu Leu Met
        1300            1305            1310

Tyr Ala Gln Leu Lys Glu Trp Ala Glu Lys Asn Phe Asp Ile Lys Lys
        1315            1320            1325

Trp Tyr Pro Asp Gly Thr Pro Leu Pro Glu Phe Tyr Ser Glu Arg Glu
        1330            1335            1340

Gly Met Lys Gly Trp Asn Leu Phe Gln Leu Met His Arg Lys Ala Arg
1345            1350            1355            1360

Gly Asp Glu Val Ser Asn Asp Lys Phe Gly Gly Lys Asn Tyr Cys Ala
            1365            1370            1375

Glu Ser Asn Gly Asn Ala Ala Asp Thr Leu Met Leu Cys Ala Ser Trp
        1380            1385            1390

Val Ala Gln Thr Asp Leu Ser Glu Phe Phe Lys Lys Trp Asn Pro Gly
        1395            1400            1405

Ala Asn Ala Tyr Gln Leu Pro Gly Ala Ser Glu Met Ser Phe Glu Gly
        1410            1415            1420

Gly Val Ser Gln Ser Ala Tyr Asn Thr Leu Ala Ser Leu Asp Leu Pro
1425            1430            1435            1440

Lys Pro Glu Gln Gly Pro Glu Thr Ile Asn Gln Val Thr Glu His Lys
            1445            1450            1455

Met Ser Ala Glu
            1460

<210> SEQ ID NO 31
<211> LENGTH: 1460
<212> TYPE: PRT
<213> ORGANISM: Escherichia coli

<400> SEQUENCE: 31

Met Asn Lys Lys Phe Lys Tyr Lys Lys Ser Leu Leu Ala Ala Ile Leu
1               5               10              15

Ser Ala Thr Leu Leu Ala Gly Cys Asp Gly Gly Gly Ser Gly Ser Ser
            20              25              30

Ser Asp Thr Pro Pro Val Asp Ser Gly Thr Gly Ser Leu Pro Glu Val
        35              40              45

Lys Pro Asp Pro Thr Pro Asn Pro Glu Pro Thr Glu Pro Thr Pro
50              55              60

Asp Pro Glu Pro Thr Pro Glu Pro Ile Pro Asp Pro Glu Pro Thr Pro
65              70              75              80

Glu Pro Glu Pro Glu Pro Val Pro Thr Lys Thr Gly Tyr Leu Thr Leu
            85              90              95

Gly Gly Ser Gln Arg Val Thr Gly Ala Thr Cys Asn Gly Glu Ser Ser
        100             105             110

Asp Gly Phe Thr Phe Lys Pro Gly Glu Asp Val Thr Cys Val Ala Gly
        115             120             125

Asn Thr Thr Ile Ala Thr Phe Asn Thr Gln Ser Glu Ala Ala Arg Ser
        130             135             140

Leu Arg Ala Val Glu Lys Val Ser Phe Ser Leu Glu Asp Ala Gln Glu
145             150             155             160
```

```
Leu Ala Gly Ser Asp Asp Lys Lys Ser Asn Ala Val Ser Leu Val Thr
            165                 170                 175

Ser Ser Asn Ser Cys Pro Ala Asn Thr Glu Gln Val Cys Leu Thr Phe
            180                 185                 190

Ser Ser Val Ile Glu Ser Lys Arg Phe Asp Ser Leu Tyr Lys Gln Ile
            195                 200                 205

Asp Leu Ala Pro Glu Glu Phe Lys Lys Leu Val Asn Glu Glu Val Glu
210                 215                 220

Asn Asn Ala Ala Thr Asp Lys Ala Pro Ser Thr His Thr Ser Pro Val
225                 230                 235                 240

Val Pro Val Thr Thr Pro Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
            260                 265                 270

Ile Leu Ser Glu Gly Arg Leu Val Asp Ser Gln Gly Tyr Gly Val Ala
            275                 280                 285

Gly Val Asn Tyr Tyr Thr Asn Ser Gly Arg Gly Val Thr Gly Glu Asn
            290                 295                 300

Gly Glu Phe Ser Phe Ser Trp Gly Glu Thr Ile Ser Phe Gly Ile Asp
305                 310                 315                 320

Thr Phe Glu Leu Gly Ser Val Arg Gly Asn Lys Ser Thr Ile Ala Leu
                325                 330                 335

Thr Glu Leu Gly Asp Glu Val Arg Gly Ala Asn Ile Asp Gln Leu Ile
            340                 345                 350

His Arg Tyr Ser Thr Thr Gly Gln Asn Asn Thr Arg Val Val Pro Asp
            355                 360                 365

Asp Val Arg Lys Val Phe Ala Glu Tyr Pro Asn Val Ile Asn Glu Ile
            370                 375                 380

Ile Asn Leu Ser Leu Ser Asn Gly Ala Thr Leu Gly Glu Gly Glu Gln
385                 390                 395                 400

Val Val Asn Leu Pro Asn Glu Phe Ile Glu Gln Phe Asn Thr Gly Gln
                405                 410                 415

Ala Lys Glu Ile Asp Thr Ala Ile Cys Ala Lys Thr Asp Gly Cys Asn
            420                 425                 430

Glu Ala Arg Trp Phe Ser Leu Thr Thr Arg Asn Val Asn Asp Gly Gln
            435                 440                 445

Ile Gln Gly Val Ile Asn Lys Leu Trp Gly Val Asp Thr Asn Tyr Lys
            450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ala
                485                 490                 495

Ala Phe Pro Ile Leu Met Ala Arg Asn Asp Lys Asn Tyr Trp Leu Ala
            500                 505                 510

Phe Gly Glu Lys Arg Ala Trp Asp Lys Asn Glu Leu Ala Tyr Ile Thr
            515                 520                 525

Glu Ala Pro Ser Leu Val Glu Pro Glu Asn Val Thr Arg Asp Thr Ala
530                 535                 540

Thr Phe Asn Leu Pro Phe Ile Ser Leu Gly Gln Val Gly Glu Gly Lys
545                 550                 555                 560

Leu Met Val Ile Gly Asn Pro His Tyr Asn Ser Ile Leu Arg Cys Pro
                565                 570                 575

Asn Gly Tyr Ser Trp Asn Gly Gly Val Asn Lys Asp Gly Gln Cys Thr
```

```
                580              585              590
Leu Asn Ser Asp Pro Asp Asp Met Lys Asn Phe Met Glu Asn Val Leu
            595                  600                  605

Arg Tyr Leu Ser Asp Asp Lys Trp Lys Pro Asp Ala Lys Ala Ser Met
        610                  615                  620

Thr Val Gly Thr Asn Leu Asp Thr Val Tyr Phe Lys Arg His Gly Gln
625                  630                  635                  640

Val Thr Gly Asn Ser Ala Ala Phe Asp Phe His Pro Asp Phe Ala Gly
                645                  650                  655

Ile Ser Val Glu His Leu Ser Ser Tyr Gly Asp Leu Asp Pro Gln Glu
            660                  665                  670

Met Pro Leu Leu Ile Leu Asn Gly Phe Glu Tyr Val Thr Gln Val Gly
        675                  680                  685

Asn Asp Pro Tyr Ala Ile Pro Leu Arg Ala Asp Thr Ser Lys Pro Lys
    690                  695                  700

Leu Thr Gln Gln Asp Val Thr Asp Leu Ile Ala Tyr Leu Asn Lys Gly
705                  710                  715                  720

Gly Ser Val Leu Ile Met Glu Asn Val Met Ser Asn Leu Lys Glu Glu
                725                  730                  735

Ser Ala Ser Gly Phe Val Arg Leu Leu Asp Ala Ala Gly Leu Ser Met
            740                  745                  750

Ala Leu Asn Lys Ser Val Val Asn Asn Asp Pro Gln Gly Tyr Pro Asn
        755                  760                  765

Arg Val Arg Gln Gln Arg Ala Thr Gly Ile Trp Val Tyr Glu Arg Tyr
    770                  775                  780

Pro Ala Val Asp Gly Ala Leu Pro Tyr Thr Ile Asp Ser Lys Thr Gly
785                  790                  795                  800

Glu Val Lys Trp Lys Tyr Gln Val Glu Asn Lys Pro Asp Asp Lys Pro
                805                  810                  815

Lys Leu Glu Val Ala Ser Trp Leu Glu Asp Val Asp Gly Lys Gln Glu
            820                  825                  830

Thr Arg Tyr Ala Phe Ile Asp Glu Ala Asp His Lys Thr Glu Asp Ser
        835                  840                  845

Leu Lys Ala Ala Lys Glu Lys Ile Phe Ala Ala Phe Pro Gly Leu Lys
    850                  855                  860

Glu Cys Thr Asn Pro Ala Tyr His Tyr Glu Val Asn Cys Leu Glu Tyr
865                  870                  875                  880

Arg Pro Gly Thr Gly Val Pro Val Thr Gly Gly Met Tyr Val Pro Gln
                885                  890                  895

Tyr Thr Gln Leu Ser Leu Asn Ala Asp Thr Ala Lys Ala Met Val Gln
            900                  905                  910

Ala Ala Asp Leu Gly Thr Asn Ile Gln Arg Leu Tyr Gln His Glu Leu
        915                  920                  925

Tyr Phe Arg Thr Asn Gly Arg Lys Gly Glu Arg Leu Ser Ser Val Asp
    930                  935                  940

Leu Glu Arg Leu Tyr Gln Asn Met Ser Val Trp Leu Trp Asn Asp Thr
945                  950                  955                  960

Ser Tyr Arg Tyr Glu Glu Gly Lys Asn Asp Glu Leu Gly Phe Lys Thr
                965                  970                  975

Phe Thr Glu Phe Leu Asn Cys Tyr Ala Asn Asp Ala Tyr Ala Gly Gly
            980                  985                  990

Thr Lys Cys Ser Ala Asp Leu Lys Lys Ser Leu Val Asp Asn Asn Met
        995                  1000                 1005
```

```
Ile Tyr Gly Asp Gly Ser Ser Lys Ala Gly Met Met Asn Pro Ser Tyr
    1010                1015                1020

Pro Leu Asn Tyr Met Glu Lys Pro Leu Thr Arg Leu Met Leu Gly Arg
1025                1030                1035                1040

Ser Trp Trp Asp Leu Asn Ile Lys Val Asp Val Glu Lys Tyr Pro Gly
                1045                1050                1055

Ala Val Ser Glu Glu Gly Gln Asn Val Thr Glu Thr Ile Ser Leu Tyr
            1060                1065                1070

Ser Asn Pro Thr Lys Trp Phe Ala Gly Asn Met Gln Ser Thr Gly Leu
        1075                1080                1085

Trp Ala Pro Ala Gln Lys Glu Val Thr Ile Lys Ser Asn Ala Asn Val
    1090                1095                1100

Pro Val Thr Val Thr Val Ala Leu Ala Asp Asp Leu Thr Gly Arg Glu
1105                1110                1115                1120

Lys His Glu Val Ala Leu Asn Arg Pro Pro Arg Val Thr Lys Thr Tyr
                1125                1130                1135

Ser Leu Asp Ala Ser Gly Thr Val Lys Phe Lys Val Pro Tyr Gly Gly
            1140                1145                1150

Leu Ile Tyr Ile Lys Gly Asn Ser Ser Thr Asn Glu Ser Ala Ser Phe
        1155                1160                1165

Thr Phe Thr Gly Val Val Lys Ala Pro Phe Tyr Lys Asp Gly Ala Trp
    1170                1175                1180

Lys Asn Asp Leu Asn Ser Pro Ala Pro Leu Gly Glu Leu Glu Ser Asp
1185                1190                1195                1200

Ala Phe Val Tyr Thr Thr Pro Lys Lys Asn Leu Asn Ala Ser Asn Tyr
                1205                1210                1215

Thr Gly Gly Leu Glu Gln Phe Ala Asn Asp Leu Asp Thr Phe Ala Ser
            1220                1225                1230

Ser Met Asn Asp Phe Tyr Gly Arg Asp Ser Glu Asp Gly Lys His Arg
        1235                1240                1245

Met Phe Glu Thr Pro Leu Thr Val Pro Gly Ala Thr Glu Val Ala Asn
    1250                1255                1260

Asn Val Leu Ala Leu Tyr Met Gln Asp Arg Tyr Leu Gly Lys Met Asn
1265                1270                1275                1280

Arg Val Ala Asp Ile Thr Val Ala Pro Glu Tyr Leu Glu Glu Ser
                1285                1290                1295

Asn Asn Gln Ala Trp Ala Arg Gly Gly Ala Gly Asp Arg Leu Leu Met
            1300                1305                1310

Tyr Ala Gln Leu Lys Glu Trp Ala Glu Lys Asn Phe Asp Ile Lys Lys
        1315                1320                1325

Trp Tyr Pro Asp Gly Thr Pro Leu Pro Glu Phe Tyr Ser Glu Arg Glu
    1330                1335                1340

Gly Met Lys Gly Trp Asn Leu Phe Gln Leu Met His Arg Lys Ala Arg
1345                1350                1355                1360

Gly Asp Glu Val Ser Asn Asp Lys Phe Gly Lys Asn Tyr Cys Ala
                1365                1370                1375

Glu Ser Asn Gly Asn Ala Ala Asp Thr Leu Met Leu Cys Ala Ser Trp
            1380                1385                1390

Val Ala Gln Thr Asp Leu Ser Glu Phe Phe Lys Lys Trp Asn Pro Gly
        1395                1400                1405

Ala Asn Ala Tyr Gln Leu Pro Gly Ala Ser Glu Met Ser Phe Glu Gly
    1410                1415                1420
```

```
Gly Val Ser Gln Ser Ala Tyr Asn Thr Leu Ala Ser Leu Asp Leu Pro
1425                1430                1435                1440

Lys Pro Glu Gln Gly Pro Glu Thr Ile Asn Gln Val Thr Glu His Lys
            1445                1450                1455

Met Ser Ala Glu
            1460

<210> SEQ ID NO 32
<211> LENGTH: 1462
<212> TYPE: PRT
<213> ORGANISM: Escherichia coli

<400> SEQUENCE: 32

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Gly Ser Gly Ser Ser
            20                  25                  30

Ser Asp Thr Pro Pro Val Asp Ser Gly Thr Gly Ser Leu Pro Glu Val
            35                  40                  45

Lys Pro Asp Pro Thr Pro Asn Pro Glu Pro Thr Pro Glu Pro Thr Pro
50                  55                  60

Asp Pro Glu Pro Thr Pro Glu Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Leu Arg Val Thr Gly Asp Ile Thr Cys Asn Asp Glu Ser
            100                 105                 110

Ser Asp Gly Phe Thr Phe Thr Pro Gly Asp Lys Val Thr Cys Val Ala
            115                 120                 125

Gly Asn Asn Thr Thr Ile Ala Thr Phe Asp Thr Gln Ser Glu Ala Ala
        130                 135                 140

Arg Ser Leu Arg Ala Val Glu Lys Val Ser Phe Ser Leu Glu Asp Ala
145                 150                 155                 160

Gln Glu Leu Ala Gly Ser Asp Asn Lys Lys Ser Asn Ala Leu Ser Leu
                165                 170                 175

Val Thr Ser Met Asn Ser Cys Pro Ala Asn Thr Glu Gln Val Cys Leu
            180                 185                 190

Glu Phe Ser Val Ile Glu Ser Lys Arg Phe Asp Ser Leu Tyr Lys
            195                 200                 205

Gln Ile Asp Leu Ala Pro Glu Glu Phe Lys Lys Leu Val Asn Glu Glu
        210                 215                 220

Val Glu Asn Asn Ala Ala Thr Asp Lys Ala Pro Ser Thr His Thr Ser
225                 230                 235                 240

Pro Val Val Pro Val Thr Thr Pro Gly Thr Lys Pro Asp Leu Asn Ala
                245                 250                 255

Ser Phe Val Ser Ala Asn Ala Glu Gln Phe Tyr Gln Tyr Gln Pro Ser
            260                 265                 270

Glu Ile Ile Leu Ser Glu Gly Arg Leu Val Asp Ser Gln Gly Tyr Gly
            275                 280                 285

Val Ala Gly Val Asn Tyr Tyr Thr Asn Ser Gly Arg Gly Val Thr Gly
        290                 295                 300

Glu Asn Gly Glu Phe Ser Phe Ser Trp Gly Glu Thr Ile Ser Phe Gly
305                 310                 315                 320

Ile Asp Thr Phe Glu Leu Gly Ser Val Arg Gly Asn Lys Ser Thr Ile
                325                 330                 335
```

```
Ala Leu Thr Glu Leu Gly Asp Glu Val Arg Gly Ala Asn Ile Asp Gln
            340                 345                 350

Leu Ile His Arg Tyr Ser Thr Thr Gly Gln Asn Asn Thr Arg Val Val
            355                 360                 365

Pro Asp Asp Val Arg Lys Val Phe Ala Glu Tyr Pro Asn Val Ile Asn
370                 375                 380

Glu Ile Ile Asn Leu Ser Leu Ser Asn Gly Ala Thr Leu Asp Glu Gly
385                 390                 395                 400

Glu Gln Val Val Asn Leu Pro Asn Glu Phe Ile Glu Gln Phe Lys Thr
                405                 410                 415

Gly Gln Ala Lys Glu Ile Asp Thr Ala Ile Cys Ala Lys Thr Asp Gly
            420                 425                 430

Cys Asn Glu Ala Arg Trp Phe Ser Leu Thr Thr Arg Asn Val Asn Asp
            435                 440                 445

Gly Gln Ile Gln Gly Val Ile Asn Lys Leu Trp Gly Val Asp Thr Asn
450                 455                 460

Tyr Lys Ser Val Ser Lys Phe His Val Phe His Asp Ser Thr Asn Phe
465                 470                 475                 480

Tyr Gly Ser Thr Gly Asn Ala Arg Gly Gln Ala Val Val Asn Ile Ser
            485                 490                 495

Asn Ala Ala Phe Pro Ile Leu Met Ala Arg Asn Asp Lys Asn Tyr Trp
            500                 505                 510

Leu Ala Phe Gly Glu Lys Arg Ala Trp Asp Lys Asn Glu Leu Ala Tyr
            515                 520                 525

Ile Thr Glu Ala Pro Ser Leu Val Glu Pro Glu Asn Val Thr Arg Asp
            530                 535                 540

Thr Ala Thr Phe Asn Leu Pro Phe Ile Ser Leu Gly Gln Val Gly Glu
545                 550                 555                 560

Gly Lys Leu Met Val Ile Gly Asn Pro His Tyr Asn Ser Ile Leu Arg
            565                 570                 575

Cys Pro Asn Gly Tyr Ser Trp Asn Gly Val Asn Lys Asp Gly Gln
            580                 585                 590

Cys Thr Leu Asn Ser Asp Pro Asp Met Lys Asn Phe Met Glu Asn
            595                 600                 605

Val Leu Arg Tyr Leu Ser Asp Asp Lys Trp Thr Pro Asp Ala Lys Ala
            610                 615                 620

Ser Met Thr Val Gly Thr Asn Leu Asp Thr Val Tyr Phe Lys Arg His
625                 630                 635                 640

Gly Gln Val Thr Gly Asn Ser Ala Ala Phe Asp Phe His Pro Asp Phe
                645                 650                 655

Ala Gly Ile Ser Val Glu His Leu Ser Ser Tyr Gly Asp Leu Asp Pro
            660                 665                 670

Gln Glu Met Pro Leu Leu Ile Leu Asn Gly Phe Glu Tyr Val Thr Gln
            675                 680                 685

Val Gly Asn Asp Pro Tyr Ala Ile Pro Leu Arg Ala Asp Thr Ser Lys
            690                 695                 700

Pro Lys Leu Thr Gln Gln Asp Val Thr Asp Leu Ile Ala Tyr Leu Asn
705                 710                 715                 720

Lys Gly Gly Ser Val Leu Ile Met Glu Asn Val Met Ser Asn Leu Lys
                725                 730                 735

Glu Glu Ser Ala Ser Gly Phe Val Arg Leu Leu Asp Ala Ala Gly Leu
            740                 745                 750
```

```
Ser Met Ala Leu Asn Lys Ser Val Asn Asn Asp Pro Gln Gly Tyr
        755                 760                 765

Pro Asn Arg Val Arg Gln Gln Arg Ala Thr Gly Ile Trp Val Tyr Glu
770                 775                 780

Arg Tyr Pro Ala Val Asp Gly Ala Leu Pro Tyr Thr Ile Asp Ser Lys
785                 790                 795                 800

Thr Gly Glu Val Lys Trp Lys Tyr Gln Val Glu Asn Lys Pro Asp Asp
                805                 810                 815

Lys Pro Lys Leu Glu Val Ala Ser Trp Leu Asp Val Asp Gly Lys
                820                 825                 830

Gln Glu Thr Arg Tyr Ala Phe Ile Asp Glu Ala Asp His Lys Thr Glu
        835                 840                 845

Asp Ser Leu Lys Ala Ala Lys Glu Lys Ile Phe Ala Ala Phe Pro Gly
        850                 855                 860

Leu Lys Glu Cys Thr Asn Pro Ala Tyr His Tyr Glu Val Asn Cys Leu
865                 870                 875                 880

Glu Tyr Arg Pro Gly Thr Gly Val Pro Val Thr Gly Gly Met Tyr Val
                885                 890                 895

Pro Gln Tyr Thr Gln Leu Ser Leu Asn Ala Asp Thr Ala Lys Ala Met
                900                 905                 910

Val Gln Ala Ala Asp Leu Gly Thr Asn Ile Gln Arg Leu Tyr Gln His
        915                 920                 925

Glu Leu Tyr Phe Arg Thr Asn Gly Arg Lys Gly Glu Arg Leu Ser Cys
        930                 935                 940

Val Asp Leu Glu Arg Leu Tyr Gln Asn Met Ser Val Trp Leu Trp Asn
945                 950                 955                 960

Asp Thr Ser Tyr Arg Tyr Glu Glu Gly Lys Asn Asp Glu Leu Gly Phe
                965                 970                 975

Lys Thr Phe Thr Glu Phe Leu Asn Cys Tyr Ala Asn Asp Ala Tyr Ala
                980                 985                 990

Gly Gly Thr Lys Cys Ser Ala Asp Leu Lys Lys Ser Leu Val Asp Asn
        995                 1000                1005

Asn Met Ile Tyr Gly Asp Gly Ser Ser Lys Ala Gly Met Met Asn Pro
    1010                1015                1020

Ser Tyr Pro Leu Asn Tyr Met Glu Lys Pro Leu Thr Arg Leu Met Leu
1025                1030                1035                1040

Gly Arg Ser Trp Trp Asp Leu Asn Ile Lys Val Asp Val Glu Lys Tyr
                1045                1050                1055

Pro Gly Ala Val Ser Glu Glu Gly Gln Asn Val Thr Glu Thr Ile Ser
                1060                1065                1070

Leu Tyr Ser Asn Pro Thr Lys Trp Phe Ala Gly Asn Met Gln Ser Thr
    1075                1080                1085

Gly Leu Trp Ala Pro Ala Gln Lys Glu Val Thr Ile Lys Ser Asn Ala
    1090                1095                1100

Asn Val Pro Val Thr Val Thr Val Ala Leu Ala Asp Asp Leu Thr Gly
1105                1110                1115                1120

Arg Glu Lys His Glu Val Ala Leu Asn Arg Pro Pro Arg Val Thr Lys
                1125                1130                1135

Thr Tyr Ser Leu Asp Ala Ser Gly Thr Val Lys Phe Lys Val Pro Tyr
        1140                1145                1150

Gly Gly Leu Ile Tyr Ile Lys Gly Asn Ser Thr Asn Glu Ser Ala
        1155                1160                1165

Ser Phe Thr Phe Thr Gly Val Val Lys Ala Pro Phe Tyr Lys Asp Gly
```

```
            1170                1175                1180
Ala Trp Lys Asn Asp Leu Asn Ser Pro Ala Pro Leu Gly Glu Leu Glu
1185                1190                1195                1200

Ser Asp Ala Phe Val Tyr Thr Thr Pro Lys Lys Asn Leu Asn Ala Ser
                1205                1210                1215

Asn Tyr Thr Gly Gly Leu Glu Gln Phe Ala Asn Asp Leu Asp Thr Phe
            1220                1225                1230

Ala Ser Ser Met Asn Asp Phe Tyr Gly Arg Asp Ser Glu Asp Gly Lys
                1235                1240                1245

His Arg Met Phe Glu Thr Pro Leu Thr Val Pro Gly Ala Thr Glu Val
            1250                1255                1260

Ala Asn Asn Val Leu Ala Leu Tyr Met Gln Asp Arg Tyr Leu Gly Lys
1265                1270                1275                1280

Met Asn Arg Val Ala Asp Asp Ile Thr Val Ala Pro Glu Tyr Leu Glu
                1285                1290                1295

Glu Ser Asn Gly Gln Ala Trp Ala Arg Gly Gly Ala Gly Asp Arg Leu
            1300                1305                1310

Leu Met Tyr Ala Gln Leu Lys Glu Trp Ala Glu Lys Asn Phe Asp Ile
            1315                1320                1325

Lys Lys Trp Tyr Pro Asp Gly Thr Pro Leu Pro Glu Phe Tyr Ser Glu
            1330                1335                1340

Arg Glu Gly Met Lys Gly Trp Asn Leu Phe Gln Leu Met His Arg Lys
1345                1350                1355                1360

Ala Arg Gly Asp Glu Val Ser Asn Asp Lys Phe Gly Gly Lys Asn Tyr
                1365                1370                1375

Cys Ala Glu Ser Asn Gly Asn Ala Ala Asp Thr Leu Met Leu Cys Ala
            1380                1385                1390

Ser Trp Val Ala Gln Thr Asp Leu Ser Glu Phe Lys Lys Trp Asn
            1395                1400                1405

Pro Gly Ala Asn Ala Tyr Gln Leu Pro Gly Ala Ser Glu Met Ser Phe
            1410                1415                1420

Glu Gly Gly Val Ser Gln Ser Ala Tyr Asn Thr Leu Ala Ser Leu Lys
1425                1430                1435                1440

Leu Pro Lys Pro Glu Gln Gly Pro Glu Thr Ile Asn Lys Val Thr Glu
                1445                1450                1455

His Lys Met Ser Val Glu
            1460

<210> SEQ ID NO 33
<211> LENGTH: 1461
<212> TYPE: PRT
<213> ORGANISM: Escherichia coli

<400> SEQUENCE: 33

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
                20                  25                  30

Ser Asp Thr Pro Pro Val Asp Ser Gly Thr Gly Ser Leu Pro Glu Val
            35                  40                  45

Lys Pro Asp Pro Thr Pro Asn Pro Glu Pro Thr Pro Glu Pro Thr Pro
        50                  55                  60

Asp Pro Glu Pro Thr Pro Glu Pro Thr Pro Asp Pro Glu Pro Thr Pro
65                  70                  75                  80
```

```
Glu Pro Glu Pro Glu Pro Val Pro Thr Lys Thr Gly Tyr Leu Thr Leu
                85                  90                  95

Gly Gly Ser Leu Arg Val Thr Gly Asp Ile Thr Cys Asn Asp Glu Ser
            100                 105                 110

Ser Asp Gly Phe Thr Phe Thr Pro Gly Asp Lys Val Thr Cys Val Ala
        115                 120                 125

Gly Asn Asn Thr Thr Ile Ala Thr Phe Asp Thr Gln Ser Glu Ala Ala
    130                 135                 140

Arg Ser Leu Arg Ala Val Glu Lys Val Ser Phe Ser Leu Glu Asp Ala
145                 150                 155                 160

Gln Glu Leu Ala Gly Ser Asp Asn Lys Lys Ser Asn Ala Leu Ser Leu
                165                 170                 175

Val Thr Ser Met Asn Ser Cys Pro Ala Asn Thr Glu Gln Val Cys Leu
            180                 185                 190

Glu Phe Ser Ser Val Ile Glu Ser Lys Arg Phe Asp Ser Leu Tyr Lys
        195                 200                 205

Gln Ile Asp Leu Ala Pro Glu Glu Phe Lys Lys Leu Val Asn Glu Glu
    210                 215                 220

Val Glu Asn Asn Ala Ala Thr Asp Lys Ala Pro Ser Thr His Thr Ser
225                 230                 235                 240

Pro Val Val Pro Val Thr Thr Pro Gly Thr Lys Pro Asp Leu Asn Ala
                245                 250                 255

Ser Phe Val Ser Ala Asn Ala Glu Gln Phe Tyr Gln Tyr Gln Pro Ser
            260                 265                 270

Glu Ile Ile Leu Ser Glu Gly Arg Leu Val Asp Ser Gln Gly Tyr Gly
        275                 280                 285

Val Ala Gly Val Asn Tyr Tyr Thr Asn Ser Gly Arg Gly Val Thr Gly
    290                 295                 300

Glu Asn Gly Glu Phe Ser Phe Ser Trp Gly Glu Thr Ile Ser Phe Gly
305                 310                 315                 320

Ile Asp Thr Phe Glu Leu Gly Ser Val Arg Gly Asn Lys Ser Thr Ile
                325                 330                 335

Ala Leu Thr Glu Leu Gly Asp Glu Val Arg Gly Ala Asn Ile Asp Gln
            340                 345                 350

Leu Ile His Arg Tyr Ser Thr Thr Gly Gln Asn Asn Thr Arg Val Val
        355                 360                 365

Pro Asp Asp Val Arg Lys Val Phe Ala Glu Tyr Pro Asn Val Ile Asn
    370                 375                 380

Glu Ile Ile Asn Leu Ser Leu Ser Asn Gly Ala Thr Leu Asp Glu Gly
385                 390                 395                 400

Glu Gln Val Val Asn Leu Pro Asn Glu Phe Ile Glu Gln Phe Lys Thr
                405                 410                 415

Gly Gln Ala Lys Glu Ile Asp Thr Ala Ile Cys Ala Lys Thr Asp Gly
            420                 425                 430

Cys Asn Glu Ala Arg Trp Phe Ser Leu Thr Thr Arg Asn Val Asn Asp
        435                 440                 445

Gly Gln Ile Gln Gly Val Ile Asn Lys Leu Trp Gly Val Asp Thr Asn
    450                 455                 460

Tyr Lys Ser Val Ser Lys Phe His Val Phe His Asp Ser Thr Asn Phe
465                 470                 475                 480

Tyr Gly Ser Thr Gly Asn Ala Arg Gly Gln Ala Val Val Asn Ile Ser
                485                 490                 495

Asn Ala Ala Phe Pro Ile Leu Met Ala Arg Asn Asp Lys Asn Tyr Trp
```

```
              500             505             510
Leu Ala Phe Gly Glu Lys Arg Ala Trp Asp Lys Asn Glu Leu Ala Tyr
            515             520             525
Ile Thr Glu Ala Pro Ser Leu Val Glu Pro Glu Asn Val Thr Arg Asp
        530             535             540
Thr Ala Thr Phe Asn Leu Pro Phe Ile Ser Leu Gly Gln Val Gly Glu
545             550             555             560
Gly Lys Leu Met Val Ile Gly Asn Pro His Tyr Asn Ser Ile Leu Arg
                565             570             575
Cys Pro Asn Gly Tyr Ser Trp Asn Gly Gly Val Asn Lys Asp Gly Gln
            580             585             590
Cys Thr Leu Asn Ser Asp Pro Asp Met Lys Asn Phe Met Glu Asn
        595             600             605
Val Leu Arg Tyr Leu Ser Asp Asp Lys Trp Thr Pro Asp Ala Lys Ala
    610             615             620
Ser Met Thr Val Gly Thr Asn Leu Asp Thr Val Tyr Phe Lys Arg His
625             630             635             640
Gly Gln Val Thr Gly Asn Ser Ala Ala Phe Asp Phe His Pro Asp Phe
                645             650             655
Ala Gly Ile Ser Val Glu His Leu Ser Ser Tyr Gly Asp Leu Asp Pro
            660             665             670
Gln Glu Met Pro Leu Leu Ile Leu Asn Gly Phe Glu Tyr Val Thr Gln
        675             680             685
Val Gly Asn Asp Pro Tyr Ala Ile Pro Leu Arg Ala Asp Thr Ser Lys
    690             695             700
Pro Lys Leu Thr Gln Gln Asp Val Thr Asp Leu Ile Ala Tyr Leu Asn
705             710             715             720
Lys Gly Gly Ser Val Leu Ile Met Glu Asn Val Met Ser Asn Leu Lys
                725             730             735
Glu Glu Ser Ala Ser Gly Phe Val Arg Leu Leu Asp Ala Ala Gly Leu
            740             745             750
Ser Met Ala Leu Asn Lys Ser Val Val Asn Asn Asp Pro Gln Gly Tyr
        755             760             765
Pro Asn Arg Val Arg Gln Gln Arg Ala Thr Gly Ile Trp Val Tyr Glu
    770             775             780
Arg Tyr Pro Ala Val Asp Gly Ala Leu Pro Tyr Thr Ile Asp Ser Lys
785             790             795             800
Thr Gly Glu Val Lys Trp Lys Tyr Gln Val Glu Asn Lys Pro Asp Asp
                805             810             815
Lys Pro Lys Leu Glu Val Ala Ser Trp Leu Glu Asp Val Asp Gly Lys
            820             825             830
Gln Glu Thr Arg Tyr Ala Phe Ile Asp Glu Ala Asp His Lys Thr Glu
        835             840             845
Asp Ser Leu Lys Ala Ala Lys Glu Lys Ile Phe Ala Ala Phe Pro Gly
    850             855             860
Leu Lys Glu Cys Thr Asn Pro Ala Tyr His Tyr Glu Val Asn Cys Leu
865             870             875             880
Glu Tyr Arg Pro Gly Thr Gly Val Pro Val Thr Gly Gly Met Tyr Val
                885             890             895
Pro Gln Tyr Thr Gln Leu Ser Leu Asn Ala Asp Thr Ala Lys Ala Met
            900             905             910
Val Gln Ala Ala Asp Leu Gly Thr Asn Ile Gln Arg Leu Tyr Gln His
        915             920             925
```

```
Glu Leu Tyr Phe Arg Thr Asn Gly Arg Lys Gly Glu Arg Leu Ser Ser
    930                 935                 940

Val Asp Leu Glu Arg Leu Tyr Gln Asn Met Ser Val Trp Leu Trp Asn
945                 950                 955                 960

Asp Thr Ser Tyr Arg Tyr Glu Glu Gly Lys Asn Asp Glu Leu Gly Phe
                965                 970                 975

Lys Thr Phe Thr Glu Phe Leu Asn Cys Tyr Ala Asn Asp Ala Tyr Ala
            980                 985                 990

Gly Gly Thr Lys Cys Ser Ala Asp Leu Lys Lys Ser Leu Val Asp Asn
            995                 1000                1005

Asn Met Ile Tyr Gly Asp Gly Ser Ser Lys Ala Gly Met Met Asn Pro
    1010                1015                1020

Ser Tyr Pro Leu Asn Tyr Met Glu Lys Pro Leu Thr Arg Leu Met Leu
1025                1030                1035                1040

Gly Arg Ser Trp Trp Asp Leu Asn Ile Lys Val Asp Val Glu Lys Tyr
                1045                1050                1055

Pro Gly Ala Val Ser Glu Glu Gly Gln Asn Val Thr Glu Thr Ile Ser
                1060                1065                1070

Leu Tyr Ser Asn Pro Thr Lys Trp Phe Ala Gly Asn Met Gln Ser Thr
    1075                1080                1085

Gly Leu Trp Ala Pro Ala Gln Lys Glu Val Thr Ile Lys Ser Asn Ala
    1090                1095                1100

Asn Val Pro Val Thr Val Thr Val Ala Leu Ala Asp Asp Leu Thr Gly
1105                1110                1115                1120

Arg Glu Lys His Glu Val Ala Leu Asn Arg Pro Pro Arg Val Thr Lys
                1125                1130                1135

Thr Tyr Ser Leu Asp Ala Ser Gly Thr Val Lys Phe Lys Val Pro Tyr
                1140                1145                1150

Gly Gly Leu Ile Tyr Ile Lys Gly Asn Ser Ser Thr Asn Glu Ser Ala
            1155                1160                1165

Ser Phe Thr Phe Thr Gly Val Val Lys Ala Pro Phe Tyr Lys Asp Gly
    1170                1175                1180

Ala Trp Lys Asn Asp Leu Asn Ser Pro Ala Pro Leu Gly Glu Leu Glu
1185                1190                1195                1200

Ser Asp Ala Phe Val Tyr Thr Thr Pro Lys Lys Asn Leu Asn Ala Ser
                1205                1210                1215

Asn Tyr Thr Gly Gly Leu Glu Gln Phe Ala Asn Asp Leu Asp Thr Phe
                1220                1225                1230

Ala Ser Ser Met Asn Asp Phe Tyr Gly Arg Asp Glu Thr Ser Gly Lys
            1235                1240                1245

His Arg Met Phe Glu Thr Pro Leu Thr Val Pro Gly Ala Thr Glu Val
    1250                1255                1260

Ala Asn Asn Val Leu Ala Leu Tyr Met Gln Asp Arg Tyr Leu Gly Lys
1265                1270                1275                1280

Met Asn Arg Val Ala Asp Asp Ile Thr Val Ala Pro Glu Tyr Leu Glu
                1285                1290                1295

Glu Ser Asn Gly Gln Ala Trp Ala Arg Gly Gly Ala Gly Asp Arg Leu
                1300                1305                1310

Leu Met Tyr Ala Gln Leu Lys Glu Trp Ala Glu Lys Asn Phe Asp Ile
            1315                1320                1325

Lys Lys Trp Tyr Pro Gly Gly Leu Pro Lys Phe Phe Ser Asp Arg
    1330                1335                1340
```

Glu Gly Met Lys Gly Trp Asn Leu Phe Gln Leu Met His Arg Lys Ala
1345                1350                1355                1360

Arg Gly Asp Asp Val Gly Asp Lys Thr Phe Gly Gly Lys Asn Tyr Cys
            1365                1370                1375

Ala Glu Ser Asn Gly Asn Ala Ala Asp Thr Leu Met Leu Cys Ala Ser
        1380                1385                1390

Trp Val Ala Gln Thr Asp Leu Ser Ala Phe Phe Lys Lys Trp Asn Pro
    1395                1400                1405

Gly Ala Asn Ala Tyr Gln Leu Pro Gly Ala Thr Glu Met Ser Phe Glu
1410                1415                1420

Gly Gly Val Ser Gln Ser Ala Tyr Ser Thr Leu Ala Ser Leu Lys Leu
1425                1430                1435                1440

Pro Lys Pro Glu Gln Gly Pro Glu Thr Ile Asn Lys Val Thr Glu His
                1445                1450                1455

Lys Met Ser Leu Glu
            1460

<210> SEQ ID NO 34
<211> LENGTH: 1461
<212> TYPE: PRT
<213> ORGANISM: Escherichia coli

<400> SEQUENCE: 34

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
            20                  25                  30

Ser Asp Thr Pro Pro Val Asp Ser Gly Thr Gly Ser Leu Pro Glu Val
        35                  40                  45

Lys Pro Asp Pro Thr Pro Asn Pro Glu Pro Thr Pro Glu Pro Thr Pro
50                  55                  60

Asp Pro Glu Pro Thr Pro Glu Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Leu Arg Val Thr Gly Asp Ile Thr Cys Asn Asp Glu Ser
            100                 105                 110

Ser Asp Gly Phe Thr Phe Thr Pro Gly Asp Lys Val Thr Cys Val Ala
        115                 120                 125

Gly Asn Asn Thr Thr Ile Ala Thr Phe Asp Thr Gln Ser Glu Ala Ala
    130                 135                 140

Arg Ser Leu Arg Ala Val Glu Lys Val Ser Phe Ser Leu Glu Asp Ala
145                 150                 155                 160

Gln Glu Leu Ala Gly Ser Asp Asn Lys Lys Ser Asn Ala Leu Ser Leu
                165                 170                 175

Val Thr Ser Met Asn Ser Cys Pro Ala Asn Thr Glu Gln Val Cys Leu
            180                 185                 190

Glu Phe Ser Ser Val Ile Glu Ser Lys Arg Phe Asp Ser Leu Tyr Lys
        195                 200                 205

Gln Ile Asp Leu Ala Pro Glu Glu Phe Lys Lys Leu Val Asn Glu Glu
    210                 215                 220

Val Glu Asn Asn Ala Ala Thr Asp Lys Ala Pro Ser Thr His Thr Ser
225                 230                 235                 240

Pro Val Val Pro Ala Thr Thr Pro Gly Thr Lys Pro Asp Leu Asn Ala
                245                 250                 255

```
Ser Phe Val Ser Ala Asn Ala Glu Gln Phe Tyr Gln Tyr Gln Pro Thr
                260                 265                 270

Glu Ile Ile Leu Ser Glu Gly Arg Leu Val Asp Ser Gln Gly Asp Gly
            275                 280                 285

Val Val Gly Val Asn Tyr Tyr Thr Asn Ser Gly Arg Gly Val Thr Gly
290                 295                 300

Glu Asn Gly Glu Phe Ser Phe Ser Trp Gly Glu Thr Ile Ser Phe Gly
305                 310                 315                 320

Ile Asp Thr Phe Glu Leu Gly Ser Val Arg Gly Asn Lys Ser Thr Ile
                325                 330                 335

Ala Leu Thr Glu Leu Gly Asp Glu Val Arg Gly Ala Asn Ile Asp Gln
            340                 345                 350

Leu Ile His Arg Tyr Ser Lys Ala Gly Gln Asn His Thr Arg Val Val
        355                 360                 365

Pro Asp Glu Val Arg Lys Val Phe Ala Glu Tyr Pro Asn Val Ile Asn
370                 375                 380

Glu Ile Ile Asn Leu Ser Leu Ser Asn Gly Ala Thr Leu Gly Glu Gly
385                 390                 395                 400

Glu Gln Val Val Asn Leu Pro Asn Glu Phe Ile Glu Gln Phe Lys Thr
                405                 410                 415

Gly Gln Ala Lys Glu Ile Asp Thr Ala Ile Cys Ala Lys Thr Asp Gly
            420                 425                 430

Cys Asn Glu Ala Arg Trp Phe Ser Leu Thr Thr Arg Asn Val Asn Asp
        435                 440                 445

Gly Lys Ile Gln Gly Val Ile Asn Lys Leu Trp Gly Val Asp Thr Asn
450                 455                 460

Tyr Lys Ser Val Ser Lys Phe His Val Phe His Asp Ser Thr Asn Phe
465                 470                 475                 480

Tyr Gly Ser Thr Gly Asn Ala Arg Gly Gln Ala Val Val Asn Ile Ser
                485                 490                 495

Asn Ala Ala Phe Pro Ile Leu Met Ala Arg Asn Asp Lys Asn Tyr Trp
            500                 505                 510

Leu Ala Phe Gly Glu Lys Arg Ala Trp Asp Lys Asn Glu Leu Ala Tyr
        515                 520                 525

Ile Thr Glu Ala Pro Ser Ile Val Arg Pro Glu Asn Val Thr Arg Glu
530                 535                 540

Thr Ala Thr Phe Asn Leu Pro Phe Ile Ser Leu Gly Gln Val Gly Asp
545                 550                 555                 560

Gly Lys Leu Met Val Ile Gly Asn Pro His Tyr Asn Ser Ile Leu Arg
                565                 570                 575

Cys Pro Asn Gly Tyr Ser Trp Asn Gly Gly Val Asn Lys Asp Gly Gln
            580                 585                 590

Cys Thr Leu Asn Ser Asp Pro Asp Met Lys Asn Phe Met Glu Asn
        595                 600                 605

Val Leu Arg Tyr Leu Ser Asp Asp Lys Trp Thr Pro Asp Ala Lys Ala
610                 615                 620

Ser Met Thr Val Gly Thr Asn Leu Asp Thr Val Tyr Phe Lys Arg His
625                 630                 635                 640

Gly Gln Val Thr Gly Asn Ser Ala Ala Phe Asp Phe His Pro Asp Phe
                645                 650                 655

Ala Gly Ile Ser Val Glu His Leu Ser Ser Tyr Gly Asp Leu Asp Pro
            660                 665                 670
```

```
Gln Glu Met Pro Leu Leu Ile Leu Asn Gly Phe Tyr Val Thr Gln
            675                 680                 685

Val Gly Asn Asp Pro Tyr Ala Ile Pro Leu Arg Ala Asp Thr Ser Lys
690                 695                 700

Pro Lys Leu Thr Gln Gln Asp Val Thr Asp Leu Ile Ala Tyr Leu Asn
705                 710                 715                 720

Lys Gly Gly Ser Val Leu Ile Met Glu Asn Val Met Ser Asn Leu Lys
            725                 730                 735

Glu Glu Ser Ala Ser Gly Phe Val Arg Leu Leu Asp Ala Ala Gly Leu
            740                 745                 750

Ser Met Ala Leu Asn Lys Ser Val Val Asn Asn Asp Pro Gln Gly Tyr
            755                 760                 765

Pro Asn Arg Val Arg Gln Arg Ser Thr Gly Ile Trp Val Tyr Glu
            770                 775                 780

Arg Tyr Pro Ala Val Asp Gly Lys Pro Pro Tyr Thr Ile Asp Asp Thr
785                 790                 795                 800

Thr Lys Glu Val Ile Trp Lys Tyr Gln Gln Asn Lys Pro Asp Asp
            805                 810                 815

Lys Pro Lys Leu Glu Val Ala Ser Trp Gln Glu Glu Val Glu Gly Lys
            820                 825                 830

Gln Val Thr Gln Phe Ala Phe Ile Asp Glu Ala Asp His Lys Thr Pro
            835                 840                 845

Glu Ser Leu Ala Ala Ala Lys Gln Arg Ile Leu Asp Ala Phe Pro Gly
            850                 855                 860

Leu Glu Val Cys Lys Asp Ser Asp Tyr His Tyr Glu Val Asn Cys Leu
865                 870                 875                 880

Glu Tyr Arg Pro Gly Thr Asp Val Pro Val Thr Gly Gly Met Tyr Val
            885                 890                 895

Pro Gln Tyr Thr Gln Leu Asp Leu Ser Ala Asp Thr Ala Lys Ala Met
            900                 905                 910

Leu Gln Ala Ala Asp Leu Gly Thr Asn Ile Gln Arg Leu Tyr Gln His
            915                 920                 925

Glu Leu Tyr Phe Arg Thr Asn Gly Arg Gln Gly Glu Arg Leu Asn Ser
            930                 935                 940

Val Asp Leu Glu Arg Leu Tyr Gln Asn Met Ser Val Trp Leu Trp Asn
945                 950                 955                 960

Glu Thr Lys Tyr Arg Tyr Glu Glu Gly Lys Glu Asp Glu Leu Gly Phe
            965                 970                 975

Lys Thr Phe Thr Glu Phe Leu Asn Cys Tyr Thr Asn Asn Ala Tyr Val
            980                 985                 990

Gly Thr Gln Cys Ser Ala Glu Leu Lys Lys Ser Leu Ile Asp Asn Lys
            995                 1000                1005

Met Ile Tyr Gly Glu Glu Ser Ser Lys Ala Gly Met Met Asn Pro Ser
    1010                1015                1020

Tyr Pro Leu Asn Tyr Met Glu Lys Pro Leu Thr Arg Leu Met Leu Gly
1025                1030                1035                1040

Arg Ser Trp Trp Asp Leu Asn Ile Lys Val Asp Val Glu Lys Tyr Pro
                1045                1050                1055

Gly Val Val Asn Thr Asn Gly Glu Thr Val Thr Gln Asn Ile Asn Leu
                1060                1065                1070

Tyr Ser Ala Pro Thr Lys Trp Phe Ala Gly Asn Met Gln Ser Thr Gly
                1075                1080                1085

Leu Trp Ala Pro Ala Gln Gln Glu Val Ser Ile Glu Ser Lys Ala Thr
```

```
                1090                1095                1100
Val Pro Val Thr Val Thr Val Ala Leu Ala Asp Asp Leu Thr Gly Arg
1105                1110                1115                1120

Glu Lys His Glu Val Ser Leu Asn Arg Pro Pro Arg Val Thr Lys Thr
                1125                1130                1135

Tyr Asp Leu Lys Ala Asn Asp Lys Val Thr Phe Lys Val Pro Tyr Gly
                1140                1145                1150

Gly Leu Ile Tyr Ile Lys Gly Asp Ser Lys Glu Val Gln Ser Ala Asp
                1155                1160                1165

Phe Thr Phe Thr Gly Val Val Lys Ala Pro Phe Tyr Lys Asp Gly Lys
                1170                1175                1180

Trp Gln His Asp Leu Asn Ser Pro Ala Pro Leu Gly Glu Leu Glu Ser
1185                1190                1195                1200

Ala Ser Phe Val Tyr Thr Thr Pro Lys Lys Asn Leu Asn Ala Ser Asn
                1205                1210                1215

Tyr Thr Gly Gly Leu Glu Gln Phe Ala Asn Asp Leu Asp Thr Phe Ala
                1220                1225                1230

Ser Ser Met Asn Asp Phe Tyr Gly Arg Asp Ser Glu Asp Gly Lys His
                1235                1240                1245

Arg Met Phe Glu Thr Pro Leu Thr Val Pro Gly Ala Thr Glu Val Ala
                1250                1255                1260

Asn Asn Val Leu Ala Leu Tyr Met Gln Asp Arg Tyr Leu Gly Lys Met
1265                1270                1275                1280

Asn Arg Val Ala Asp Asp Ile Thr Val Ala Pro Glu Tyr Leu Glu Glu
                1285                1290                1295

Ser Asn Gly Gln Ala Trp Ala Arg Gly Gly Ala Gly Asp Arg Leu Leu
                1300                1305                1310

Met Tyr Ala Gln Leu Lys Glu Trp Ala Glu Lys Asn Phe Asp Ile Lys
                1315                1320                1325

Lys Trp Tyr Pro Asp Gly Thr Pro Leu Pro Glu Phe Tyr Ser Glu Arg
                1330                1335                1340

Glu Gly Met Lys Gly Trp Asn Leu Phe Gln Leu Met His Arg Lys Ala
1345                1350                1355                1360

Arg Gly Asp Glu Val Ser Asn Asp Lys Phe Gly Lys Asn Tyr Cys
                1365                1370                1375

Ala Glu Ser Asn Gly Asn Ala Ala Asp Thr Leu Met Leu Cys Ala Ser
                1380                1385                1390

Trp Val Ala Gln Thr Asp Leu Ser Glu Phe Lys Lys Trp Asn Pro
                1395                1400                1405

Gly Ala Asn Ala Tyr Gln Leu Pro Gly Ala Ser Glu Met Ser Phe Glu
                1410                1415                1420

Gly Gly Val Ser Gln Ser Ala Tyr Asn Thr Leu Ala Ser Leu Lys Leu
1425                1430                1435                1440

Pro Lys Pro Glu Gln Gly Pro Glu Thr Ile Asn Lys Val Thr Glu His
                1445                1450                1455

Lys Met Ser Val Glu
                1460

<210> SEQ ID NO 35
<211> LENGTH: 1459
<212> TYPE: PRT
<213> ORGANISM: Escherichia coli

<400> SEQUENCE: 35
```

```
Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Gly Ser Gly Ser Ser
            20                  25                  30

Ser Asp Thr Pro Pro Val Asp Ser Gly Thr Gly Ser Leu Pro Glu Val
            35                  40                  45

Lys Pro Asp Pro Thr Pro Asn Pro Glu Pro Thr Pro Glu Pro Thr Pro
50                  55                  60

Asp Pro Glu Pro Thr Pro Glu Pro Ile Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
            100                 105                 110

Asp Gly Phe Thr Phe Lys Pro Gly Glu Asp Val Thr Cys Val Ala Gly
            115                 120                 125

Asn Thr Thr Ile Ala Thr Phe Asn Thr Gln Ser Glu Ala Ala Arg Ser
            130                 135                 140

Leu Arg Ala Val Glu Lys Val Ser Phe Ser Leu Glu Asp Ala Gln Glu
145                 150                 155                 160

Leu Ala Gly Ser Asp Asp Lys Lys Ser Asn Ala Val Ser Leu Val Thr
                165                 170                 175

Ser Ser Asn Ser Cys Pro Ala Asn Thr Glu Gln Val Cys Leu Thr Phe
            180                 185                 190

Ser Ser Val Ile Glu Ser Lys Arg Phe Asp Ser Leu Tyr Lys Gln Ile
            195                 200                 205

Asp Leu Ala Pro Glu Glu Phe Lys Lys Leu Val Asn Glu Glu Val Glu
            210                 215                 220

Asn Asn Ala Ala Thr Asp Lys Ala Pro Ser Thr His Thr Ser Pro Val
225                 230                 235                 240

Val Pro Val Thr Thr Pro Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
            260                 265                 270

Ile Leu Ser Glu Gly Arg Leu Val Asp Ser Gln Gly Tyr Gly Val Ala
            275                 280                 285

Gly Val Asn Tyr Tyr Thr Asn Ser Gly Arg Gly Val Thr Gly Glu Asn
            290                 295                 300

Gly Glu Phe Ser Phe Ser Trp Gly Glu Ala Ile Ser Phe Gly Ile Asp
305                 310                 315                 320

Thr Phe Glu Leu Gly Ser Val Arg Gly Asn Lys Ser Thr Ile Ala Leu
            325                 330                 335

Thr Glu Leu Gly Asp Glu Val Arg Gly Ala Asn Ile Asp Gln Leu Ile
            340                 345                 350

His Arg Tyr Ser Thr Thr Gly Gln Asn Thr Arg Val Val Pro Asp
            355                 360                 365

Asp Val Arg Lys Val Phe Ala Glu Tyr Pro Asn Val Ile Asn Glu Ile
            370                 375                 380

Ile Asn Leu Ser Leu Ser Asn Gly Ala Thr Leu Gly Glu Gly Glu Gln
385                 390                 395                 400

Val Val Asn Leu Pro Asn Glu Phe Ile Glu Gln Phe Asn Thr Gly Gln
                405                 410                 415

Ala Lys Glu Ile Asp Thr Ala Ile Cys Ala Lys Thr Asp Gly Cys Asn
```

-continued

```
            420                 425                 430
Glu Ala Arg Trp Phe Ser Leu Thr Thr Arg Asn Val Asn Asp Gly Gln
            435                 440                 445

Ile Gln Gly Val Ile Asn Lys Leu Trp Gly Val Asp Thr Asn Tyr Lys
450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ala
                485                 490                 495

Ala Phe Pro Ile Leu Met Ala Arg Asn Asp Lys Asn Tyr Trp Leu Ala
                500                 505                 510

Phe Gly Glu Lys Arg Ala Trp Asp Lys Asn Glu Leu Ala Tyr Ile Thr
                515                 520                 525

Glu Ala Pro Ser Ile Val Arg Pro Glu Asn Val Thr Arg Glu Thr Ala
                530                 535                 540

Ser Phe Asn Leu Pro Phe Ile Ser Leu Gly Gln Val Gly Asp Gly Lys
545                 550                 555                 560

Leu Met Val Ile Gly Asn Pro His Tyr Asn Ser Ile Leu Arg Cys Pro
                565                 570                 575

Asn Gly Tyr Ser Trp Asn Gly Val Asn Lys Asp Gly Gln Cys Thr
                580                 585                 590

Leu Asn Ser Asp Pro Asp Asp Met Lys Asn Phe Met Glu Asn Val Leu
                595                 600                 605

Arg Tyr Leu Ser Asn Asp Arg Trp Leu Pro Asp Ala Lys Ser Ser Met
                610                 615                 620

Thr Val Gly Thr Asn Leu Glu Thr Val Tyr Phe Lys Lys His Gly Gln
625                 630                 635                 640

Val Leu Gly Asn Ser Ala Pro Phe Ala Phe His Lys Asp Phe Thr Gly
                645                 650                 655

Ile Thr Val Lys Pro Met Thr Ser Tyr Gly Asn Leu Asn Pro Asp Glu
                660                 665                 670

Val Pro Leu Leu Ile Leu Asn Gly Phe Glu Tyr Val Thr Gln Trp Gly
                675                 680                 685

Ser Asp Pro Tyr Ser Ile Pro Leu Arg Ala Asp Thr Ser Lys Pro Lys
690                 695                 700

Leu Thr Gln Gln Asp Val Thr Asp Leu Ile Ala Tyr Met Asn Lys Gly
705                 710                 715                 720

Gly Ser Val Leu Ile Met Glu Asn Val Met Ser Asn Leu Lys Glu Glu
                725                 730                 735

Ser Ala Ser Gly Phe Val Arg Leu Leu Asp Ala Ala Gly Leu Ser Met
                740                 745                 750

Ala Leu Asn Lys Ser Val Val Asn Asp Pro Gln Gly Tyr Pro Asp
                755                 760                 765

Arg Val Arg Gln Arg Arg Ser Thr Gly Ile Trp Val Tyr Glu Arg Tyr
770                 775                 780

Pro Ala Val Asp Gly Lys Pro Pro Tyr Thr Ile Asp Thr Thr Lys
785                 790                 795                 800

Glu Val Ile Trp Lys Tyr Gln Gln Glu Asn Lys Pro Asp Asp Lys Pro
                805                 810                 815

Lys Leu Glu Val Ala Ser Trp Gln Glu Val Glu Gly Lys Gln Val
                820                 825                 830

Thr Gln Phe Ala Phe Ile Asp Glu Ala Asp His Lys Thr Pro Glu Ser
                835                 840                 845
```

```
Leu Ala Ala Ala Lys Gln Arg Ile Leu Asp Ala Phe Pro Gly Leu Glu
        850                 855                 860

Val Cys Lys Asp Ser Asp Tyr His Tyr Glu Val Asn Cys Leu Glu Tyr
865                 870                 875                 880

Arg Pro Gly Thr Asp Val Pro Val Thr Gly Gly Met Tyr Val Pro Gln
                    885                 890                 895

Tyr Thr Gln Leu Asp Leu Ser Ala Asp Thr Ala Lys Ala Met Leu Gln
                900                 905                 910

Ala Ala Asp Leu Gly Thr Asn Ile Gln Arg Leu Tyr Gln His Glu Leu
                915                 920                 925

Tyr Phe Arg Thr Asn Gly Arg Gln Gly Glu Arg Leu Asn Ser Val Asp
        930                 935                 940

Leu Glu Arg Leu Tyr Gln Asn Met Ser Val Trp Leu Trp Asn Glu Thr
945                 950                 955                 960

Lys Tyr Arg Tyr Glu Glu Gly Lys Glu Asp Glu Leu Gly Phe Lys Thr
                965                 970                 975

Phe Thr Glu Phe Leu Asn Cys Tyr Thr Asn Asn Ala Tyr Val Gly Thr
                980                 985                 990

Gln Cys Ser Ala Glu Leu Lys Lys Ser Leu Ile Asp Asn Lys Met Ile
        995                 1000                1005

Tyr Gly Glu Glu Ser Ser Lys Ala Gly Met Met Asn Pro Ser Tyr Pro
    1010                1015                1020

Leu Asn Tyr Met Glu Lys Pro Leu Thr Arg Leu Met Leu Gly Arg Ser
1025                1030                1035                1040

Trp Trp Asp Leu Asn Ile Lys Val Asp Val Glu Lys Tyr Pro Gly Val
                1045                1050                1055

Val Asn Thr Asn Gly Glu Thr Val Thr Gln Asn Ile Asn Leu Tyr Ser
                1060                1065                1070

Ala Pro Thr Lys Trp Phe Ala Gly Asn Met Gln Ser Thr Gly Leu Trp
            1075                1080                1085

Ala Pro Ala Gln Gln Glu Val Ser Ile Glu Ser Lys Ser Thr Val Pro
            1090                1095                1100

Val Thr Val Thr Val Ala Leu Ala Asp Asp Leu Thr Gly Arg Glu Lys
1105                1110                1115                1120

His Glu Val Ser Leu Asn Arg Pro Pro Arg Val Thr Lys Thr Tyr Asp
                1125                1130                1135

Leu Lys Ala Asn Asp Lys Val Thr Phe Lys Val Pro Tyr Gly Gly Leu
                1140                1145                1150

Ile Tyr Ile Lys Gly Asp Ser Lys Glu Val Gln Ser Ala Asp Phe Thr
            1155                1160                1165

Phe Thr Gly Val Val Lys Ala Pro Phe Tyr Lys Asp Gly Lys Trp Gln
    1170                1175                1180

His Asp Leu Asn Ser Pro Ala Pro Leu Gly Glu Leu Glu Ser Ala Ser
1185                1190                1195                1200

Phe Val Tyr Thr Thr Pro Lys Lys Asn Leu Asn Ala Ser Asn Tyr Thr
                1205                1210                1215

Gly Gly Leu Glu Gln Phe Ala Asn Asp Leu Asp Thr Phe Ala Ser Ser
                1220                1225                1230

Met Asn Asp Phe Tyr Gly Arg Asp Ser Glu Asp Gly Lys His Arg Met
            1235                1240                1245

Phe Glu Thr Pro Leu Thr Val Pro Gly Ala Thr Glu Val Ala Asn Asn
    1250                1255                1260
```

-continued

Val Leu Ala Leu Tyr Met Gln Asp Arg Tyr Leu Gly Lys Met Asn Arg
1265                1270                1275                1280

Val Ala Asp Asp Ile Thr Val Ala Pro Glu Tyr Leu Glu Glu Ser Asn
                1285                1290                1295

Gly Gln Ala Trp Ala Arg Gly Ala Gly Asp Arg Leu Leu Met Tyr
            1300                1305                1310

Ala Gln Leu Lys Glu Trp Ala Glu Lys Asn Phe Asp Ile Lys Lys Trp
        1315                1320                1325

Tyr Pro Asp Gly Thr Pro Leu Pro Glu Phe Tyr Ser Glu Arg Glu Gly
        1330                1335                1340

Met Lys Gly Trp Asn Leu Phe Gln Leu Met His Arg Lys Ala Arg Gly
1345                1350                1355                1360

Asp Glu Val Ser Asn Asp Lys Phe Gly Gly Lys Asn Tyr Cys Ala Glu
                1365                1370                1375

Ser Asn Gly Asn Ala Ala Asp Thr Leu Met Leu Cys Ala Ser Trp Val
            1380                1385                1390

Ala Gln Thr Asp Leu Ser Glu Phe Phe Lys Lys Trp Asn Pro Gly Ala
        1395                1400                1405

Asn Ala Tyr Gln Leu Pro Gly Ala Ser Glu Met Ser Phe Glu Gly Gly
        1410                1415                1420

Val Ser Gln Ser Ala Tyr Asn Thr Leu Ala Ser Leu Asp Leu Pro Lys
1425                1430                1435                1440

Pro Glu Gln Gly Pro Glu Thr Ile Asn Gln Val Thr Glu His Lys Met
                1445                1450                1455

Ser Ala Glu

<210> SEQ ID NO 36
<211> LENGTH: 1460
<212> TYPE: PRT
<213> ORGANISM: Escherichia coli

<400> SEQUENCE: 36

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
            20                  25                  30

Ser Asp Thr Pro Pro Val Asp Ser Gly Thr Gly Ser Leu Pro Glu Val
        35                  40                  45

Lys Pro Asp Pro Thr Pro Asn Pro Glu Pro Thr Pro Glu Pro Thr Pro
50                  55                  60

Asp Pro Glu Pro Thr Pro Glu Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Leu Arg Val Thr Gly Asp Ile Thr Cys Asn Asp Glu Ser
            100                 105                 110

Ser Asp Gly Phe Thr Phe Thr Pro Gly Asp Lys Val Thr Cys Val Ala
        115                 120                 125

Gly Asn Asn Thr Thr Ile Ala Thr Phe Asp Thr Gln Ser Glu Ala Ala
    130                 135                 140

Arg Ser Leu Arg Ala Val Glu Lys Val Ser Phe Ser Leu Glu Asp Ala
145                 150                 155                 160

Gln Glu Leu Ala Gly Ser Asp Asn Lys Lys Ser Asn Ala Leu Ser Leu
                165                 170                 175

Val Thr Ser Met Asn Ser Cys Pro Ala Asn Thr Glu Gln Val Cys Leu
            180                 185                 190

Glu Phe Ser Ser Val Ile Glu Ser Lys Arg Phe Asp Ser Leu Tyr Lys
            195                 200                 205

Gln Ile Asp Leu Ala Pro Glu Glu Phe Lys Lys Leu Val Asn Glu Glu
210                 215                 220

Val Glu Asn Asn Ala Ala Thr Asp Lys Ala Pro Ser Thr His Thr Ser
225                 230                 235                 240

Pro Val Val Pro Val Thr Thr Pro Gly Thr Lys Pro Asp Leu Asn Ala
            245                 250                 255

Ser Phe Val Ser Ala Asn Ala Glu Gln Phe Tyr Gln Tyr Gln Pro Ser
            260                 265                 270

Glu Ile Ile Leu Ser Glu Gly Arg Leu Val Asp Ser Gln Gly Tyr Gly
            275                 280                 285

Val Ala Gly Val Asn Tyr Tyr Thr Asn Ser Gly Arg Gly Val Thr Gly
            290                 295                 300

Glu Asn Gly Glu Phe Ser Phe Ser Trp Gly Glu Thr Ile Ser Phe Gly
305                 310                 315                 320

Ile Asp Thr Phe Glu Leu Gly Ser Val Arg Gly Asn Lys Ser Thr Ile
            325                 330                 335

Ala Leu Thr Glu Leu Gly Asp Glu Val Arg Gly Ala Asn Ile Asp Gln
            340                 345                 350

Leu Ile His Arg Tyr Ser Thr Thr Gly Gln Asn Asn Thr Arg Val Val
            355                 360                 365

Pro Asp Asp Val Arg Lys Val Phe Ala Glu Tyr Pro Asn Val Ile Asn
370                 375                 380

Glu Ile Ile Asn Leu Ser Leu Ser Asn Gly Ala Thr Leu Gly Glu Gly
385                 390                 395                 400

Glu Gln Val Val Asn Leu Pro Asn Glu Phe Ile Glu Gln Phe Lys Thr
            405                 410                 415

Gly Gln Ala Lys Glu Ile Asp Thr Ala Ile Cys Ala Lys Thr Asp Gly
            420                 425                 430

Cys Asn Glu Ala Arg Trp Phe Ser Leu Thr Thr Arg Asn Val Asn Asp
            435                 440                 445

Gly Gln Ile Gln Gly Val Ile Asn Lys Leu Trp Gly Val Asp Thr Asn
450                 455                 460

Tyr Lys Ser Val Ser Lys Phe His Val Phe His Asp Ser Thr Asn Phe
465                 470                 475                 480

Tyr Gly Ser Thr Gly Asn Ala Arg Gly Gln Ala Val Val Asn Ile Ser
            485                 490                 495

Asn Ala Ala Phe Pro Ile Leu Met Ala Arg Asn Asp Lys Asn Tyr Trp
            500                 505                 510

Leu Ala Phe Gly Glu Lys Arg Ala Trp Asp Lys Asn Asp Leu Ala Tyr
            515                 520                 525

Ile Thr Glu Ala Pro Ser Ile Val Arg Pro Glu Asn Val Thr Arg Glu
            530                 535                 540

Thr Ala Thr Phe Asn Leu Pro Phe Ile Ser Leu Gly Gln Val Gly Asp
545                 550                 555                 560

Gly Lys Leu Met Val Ile Gly Asn Pro His Tyr Asn Ser Ile Leu Arg
            565                 570                 575

Cys Pro Asn Gly Tyr Ser Trp Asn Gly Gly Val Asn Lys Asp Gly Gln
            580                 585                 590

Cys Thr Leu Asn Ser Asp Pro Asp Asp Met Lys Asn Phe Met Glu Asn

-continued

```
              595                 600                 605
Val Leu Arg Tyr Leu Ser Asn Asp Arg Trp Leu Pro Asp Ala Lys Ser
610                 615                 620

Ser Met Thr Val Gly Thr Asn Leu Asp Thr Val Tyr Phe Lys Lys His
625                 630                 635                 640

Gly Gln Val Leu Gly Asn Ser Ala Pro Phe Ala Phe His Lys Asp Phe
                645                 650                 655

Thr Gly Ile Thr Val Lys Pro Met Thr Ser Tyr Gly Asn Leu Asn Pro
                660                 665                 670

Asp Glu Val Pro Leu Leu Ile Leu Asn Gly Phe Glu Tyr Val Thr Gln
                675                 680                 685

Trp Gly Ser Asp Pro Tyr Ser Ile Pro Leu Arg Ala Asp Thr Ser Lys
690                 695                 700

Pro Lys Leu Thr Gln Gln Asp Val Thr Asp Leu Ile Ala Tyr Met Asn
705                 710                 715                 720

Lys Gly Gly Ser Val Leu Ile Met Glu Asn Val Met Ser Asn Leu Lys
                725                 730                 735

Glu Glu Ser Ala Ser Gly Phe Val Arg Leu Leu Asp Ala Ala Gly Leu
                740                 745                 750

Ser Met Ala Leu Asn Lys Ser Val Val Asn Asn Asp Pro Gln Gly Tyr
                755                 760                 765

Pro Asp Arg Val Arg Gln Arg Arg Ser Thr Gly Ile Trp Val Tyr Glu
770                 775                 780

Arg Tyr Pro Ala Val Asp Gly Lys Pro Pro Tyr Thr Ile Asp Asp Thr
785                 790                 795                 800

Thr Lys Glu Val Ile Trp Lys Tyr Gln Gln Glu Asn Lys Pro Asp Asp
                805                 810                 815

Lys Pro Lys Leu Glu Val Ala Ser Trp Gln Glu Val Glu Gly Lys
                820                 825                 830

Gln Val Thr Gln Phe Ala Phe Ile Asp Glu Ala Asp His Lys Thr Pro
                835                 840                 845

Glu Ser Leu Ala Ala Ala Lys Gln Arg Ile Leu Asp Ala Phe Pro Gly
850                 855                 860

Leu Glu Val Cys Lys Asp Ser Asp Tyr His Tyr Glu Val Asn Cys Leu
865                 870                 875                 880

Glu Tyr Arg Pro Gly Ser Gly Val Pro Val Thr Gly Gly Met Tyr Val
                885                 890                 895

Pro Gln Tyr Thr Gln Leu Asp Leu Gly Ala Asp Thr Ala Lys Ala Met
                900                 905                 910

Leu Gln Ala Ala Asp Leu Gly Thr Asn Ile Gln Arg Leu Tyr Gln His
                915                 920                 925

Glu Leu Tyr Phe Arg Thr Asn Gly Arg Gln Gly Glu Arg Leu Asn Ser
930                 935                 940

Val Asp Leu Glu Arg Leu Tyr Gln Asn Met Ser Val Trp Leu Trp Asn
945                 950                 955                 960

Glu Thr Lys Tyr Arg Tyr Glu Glu Gly Lys Glu Asp Glu Leu Gly Phe
                965                 970                 975

Lys Thr Phe Thr Glu Phe Leu Asn Cys Tyr Thr Asn Asn Ala Tyr Val
                980                 985                 990

Gly Thr Gln Cys Ser Ala Glu Leu Lys Lys Ser Leu Ile Asp Asn Lys
                995                 1000                1005

Met Ile Tyr Gly Glu Glu Ser Ser Lys Ala Gly Met Met Asn Pro Ser
                1010                1015                1020
```

```
Tyr Pro Leu Asn Tyr Met Glu Lys Pro Leu Thr Arg Leu Met Leu Gly
1025                1030                1035                1040

Arg Ser Trp Trp Asp Leu Asn Ile Lys Val Asp Val Glu Lys Tyr Pro
            1045                1050                1055

Gly Ala Val Ser Glu Glu Gly Gln Asn Val Thr Glu Thr Ile Ser Leu
        1060                1065                1070

Tyr Ser Asn Pro Thr Lys Trp Phe Ala Gly Asn Met Gln Ser Thr Gly
    1075                1080                1085

Leu Trp Ala Pro Ala Gln Lys Glu Val Thr Ile Lys Ser Asn Ala Asn
1090                1095                1100

Val Pro Val Thr Val Thr Val Ala Leu Ala Asp Asp Leu Thr Gly Arg
1105                1110                1115                1120

Glu Lys His Glu Val Ala Leu Asn Arg Pro Pro Arg Val Thr Lys Thr
            1125                1130                1135

Tyr Ser Leu Asp Ala Ser Gly Thr Val Lys Phe Lys Val Pro Tyr Gly
        1140                1145                1150

Gly Leu Ile Tyr Ile Lys Gly Asn Ser Ser Thr Asn Glu Ser Ala Ser
    1155                1160                1165

Phe Thr Phe Thr Gly Val Val Lys Ala Pro Phe Tyr Lys Asp Gly Ala
1170                1175                1180

Trp Lys Asn Asp Leu Asn Ser Pro Ala Pro Leu Gly Glu Leu Glu Ser
1185                1190                1195                1200

Asp Ala Phe Val Tyr Thr Thr Pro Lys Lys Asn Leu Asn Ala Ser Asn
            1205                1210                1215

Tyr Thr Gly Gly Leu Glu Gln Phe Ala Asn Asp Leu Asp Thr Phe Ala
        1220                1225                1230

Ser Ser Met Asn Asp Phe Tyr Gly Arg Asp Ser Glu Ser Gly Lys His
    1235                1240                1245

Arg Met Phe Glu Thr Pro Leu Thr Val Pro Gly Ala Thr Glu Val Ala
1250                1255                1260

Asn Asn Val Leu Ala Leu Tyr Met Gln Asp Arg Tyr Leu Gly Lys Met
1265                1270                1275                1280

Asn Arg Val Ala Asp Asp Ile Thr Val Ala Pro Glu Tyr Leu Glu Glu
            1285                1290                1295

Ser Asn Gly Gln Ala Trp Ala Arg Gly Gly Ala Gly Asp Arg Leu Leu
        1300                1305                1310

Met Tyr Ala Gln Leu Lys Glu Trp Ala Glu Lys Asn Phe Asp Ile Lys
    1315                1320                1325

Lys Trp Tyr Pro Glu Gly Glu Leu Pro Lys Phe Phe Ser Asp Arg Glu
        1330                1335                1340

Gly Met Lys Gly Trp Asn Leu Phe Gln Leu Met His Arg Lys Ala Arg
1345                1350                1355                1360

Gly Asp Asp Val Gly Asn Lys Thr Phe Gly Gly Lys Asn Tyr Cys Ala
            1365                1370                1375

Glu Ser Asn Gly Asn Ala Ala Asp Ser Leu Met Leu Cys Ala Ser Trp
        1380                1385                1390

Val Ala Gln Thr Asp Leu Ser Ala Phe Phe Lys Lys Trp Asn Pro Gly
    1395                1400                1405

Ala Asn Ala Tyr Gln Leu Pro Gly Ala Thr Glu Met Ser Phe Glu Gly
        1410                1415                1420

Gly Val Ser Gln Ser Ala Tyr Ser Thr Leu Ala Ser Leu Lys Leu Pro
1425                1430                1435                1440
```

```
Lys Pro Glu Gln Gly Pro Glu Thr Ile Asn Lys Val Thr Glu His Lys
                1445                1450                1455

Met Ser Leu Glu
        1460

<210> SEQ ID NO 37
<211> LENGTH: 1458
<212> TYPE: PRT
<213> ORGANISM: Escherichia coli

<400> SEQUENCE: 37

Met Asn Lys Lys Phe Lys Tyr Lys Lys Ser Leu Leu Ala Ala Ile Leu
 1               5                  10                  15

Ser Ala Thr Leu Leu Ala Gly Cys Asp Gly Gly Ser Gly Ser Ser
                20                  25                  30

Ser Asp Thr Pro Pro Val Asp Ser Gly Thr Gly Ser Leu Pro Glu Val
                35                  40                  45

Lys Pro Asp Pro Thr Pro Asn Pro Glu Pro Thr Pro Glu Pro Thr Pro
    50                  55                  60

Asp Pro Glu Pro Thr Pro Glu Pro Ile Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
                100                 105                 110

Asp Gly Phe Thr Phe Lys Pro Gly Glu Asp Val Thr Cys Val Ala Gly
                115                 120                 125

Asn Thr Thr Ile Ala Thr Phe Asn Thr Gln Ser Glu Ala Ala Arg Ser
            130                 135                 140

Leu Arg Ala Val Glu Lys Val Ser Phe Ser Leu Glu Asp Ala Gln Glu
145                 150                 155                 160

Leu Ala Gly Ser Asp Asp Lys Lys Ser Asn Ala Val Ser Leu Val Thr
                165                 170                 175

Ser Ser Asn Ser Cys Pro Ala Asn Thr Glu Gln Val Cys Leu Thr Phe
                180                 185                 190

Ser Ser Val Ile Glu Ser Lys Arg Phe Asp Ser Leu Tyr Lys Gln Ile
                195                 200                 205

Asp Leu Ala Pro Glu Glu Phe Lys Lys Leu Val Asn Glu Glu Val Glu
            210                 215                 220

Asn Asn Ala Ala Thr Asp Lys Ala Pro Ser Thr His Thr Ser Pro Val
225                 230                 235                 240

Val Pro Val Thr Thr Pro Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
                260                 265                 270

Ile Leu Ser Glu Gly Arg Leu Val Asp Ser Gln Gly Tyr Gly Val Ala
            275                 280                 285

Gly Val Asn Tyr Tyr Thr Asn Ser Gly Arg Gly Val Thr Gly Glu Asn
            290                 295                 300

Gly Glu Phe Ser Phe Ser Trp Gly Glu Thr Ile Ser Phe Gly Ile Asp
305                 310                 315                 320

Thr Phe Glu Leu Gly Ser Val Arg Gly Asn Lys Ser Thr Ile Ala Leu
                325                 330                 335

Thr Glu Leu Gly Asp Glu Val Arg Gly Ala Asn Ile Asp Gln Leu Ile
                340                 345                 350
```

His Arg Tyr Ser Thr Thr Gly Gln Asn Asn Thr Arg Val Val Pro Asp
         355                 360                 365

Asp Val Arg Lys Val Phe Ala Glu Tyr Pro Asn Val Ile Asn Glu Ile
        370                 375                 380

Ile Asn Leu Ser Leu Ser Asn Gly Ala Thr Leu Gly Glu Gly Glu Gln
385                 390                 395                 400

Val Val Asn Leu Pro Asn Glu Phe Ile Glu Gln Phe Asn Thr Gly Gln
                405                 410                 415

Ala Lys Glu Ile Asp Thr Ala Ile Cys Ala Lys Thr Asp Gly Cys Asn
            420                 425                 430

Glu Ala Arg Trp Phe Ser Leu Thr Thr Arg Asn Val Asn Asp Gly Gln
        435                 440                 445

Ile Gln Gly Val Ile Asn Lys Leu Trp Gly Val Asp Thr Asn Tyr Lys
        450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ala
                485                 490                 495

Ala Phe Pro Ile Leu Met Ala Arg Asn Asp Lys Asn Tyr Trp Leu Ala
            500                 505                 510

Phe Gly Glu Lys Arg Ala Trp Asp Lys Asn Glu Leu Ala Tyr Ile Thr
        515                 520                 525

Glu Ala Pro Ser Ile Val Arg Pro Glu Asn Val Thr Arg Glu Thr Ala
        530                 535                 540

Thr Phe Asn Leu Pro Phe Ile Ser Leu Gly Gln Val Gly Asp Gly Lys
545                 550                 555                 560

Leu Met Val Ile Gly Asn Pro His Tyr Asn Ser Ile Leu Arg Cys Pro
                565                 570                 575

Asn Gly Tyr Ser Trp Asn Gly Gly Val Asn Lys Asp Gly Gln Cys Thr
            580                 585                 590

Leu Asn Ser Asp Pro Asp Asp Met Lys Asn Phe Met Glu Asn Val Leu
        595                 600                 605

Arg Tyr Leu Ser Asn Asp Arg Trp Leu Pro Asp Ala Lys Ser Asn Met
        610                 615                 620

Thr Val Gly Thr Asn Leu Asp Thr Val Tyr Phe Lys Lys His Gly Gln
625                 630                 635                 640

Val Thr Gly Asn Ser Ala Ala Phe Gly Phe His Pro Asp Phe Ala Gly
                645                 650                 655

Ile Ser Val Glu His Leu Ser Ser Tyr Gly Asp Leu Asp Pro Gln Glu
            660                 665                 670

Met Pro Leu Leu Ile Leu Asn Gly Phe Glu Tyr Val Thr Gln Val Gly
        675                 680                 685

Asn Asp Pro Tyr Ala Ile Pro Leu Arg Ala Asp Thr Ser Lys Pro Lys
        690                 695                 700

Leu Thr Gln Gln Asp Val Thr Asp Leu Ile Ala Tyr Met Asn Lys Gly
705                 710                 715                 720

Gly Ser Val Leu Ile Met Glu Asn Val Met Ser Asn Leu Lys Glu Glu
                725                 730                 735

Ser Ala Ser Gly Phe Val Arg Leu Leu Asp Ala Ala Gly Leu Ser Met
            740                 745                 750

Ala Leu Asn Lys Ser Val Val Asn Asn Asp Pro Gln Gly Tyr Pro Asp
        755                 760                 765

```
Arg Val Arg Gln Arg Arg Ser Thr Gly Ile Trp Val Tyr Glu Arg Tyr
770             775                 780

Pro Ala Val Asp Gly Lys Pro Pro Tyr Thr Ile Asp Asp Thr Thr Lys
785             790             795                 800

Glu Val Ile Trp Lys Tyr Gln Gln Glu Asn Lys Pro Asp Asp Lys Pro
                805             810              815

Lys Leu Glu Val Ala Ser Trp Gln Glu Val Glu Gly Lys Gln Val
                820             825             830

Thr Gln Phe Ala Phe Ile Asp Glu Ala Asp His Lys Thr Pro Glu Ser
            835             840             845

Leu Ala Ala Ala Lys Lys Arg Ile Leu Asp Ala Phe Pro Gly Leu Glu
850             855             860

Glu Cys Lys Asp Ser Asp Tyr His Tyr Glu Val Asn Cys Leu Glu Tyr
865             870             875             880

Arg Pro Gly Thr Gly Val Pro Val Thr Gly Met Tyr Val Pro Gln
                885             890             895

Tyr Thr Gln Leu Ser Leu Asn Ala Asp Thr Ala Lys Ala Met Val Gln
                900             905             910

Ala Ala Asp Leu Gly Thr Asn Ile Gln Arg Leu Tyr Gln His Glu Leu
                915             920             925

Tyr Phe Arg Thr Asn Gly Arg Lys Gly Glu Arg Leu Ser Ser Val Asp
930             935             940

Leu Glu Arg Leu Tyr Gln Asn Met Ser Val Trp Leu Trp Asn Lys Ile
945             950             955             960

Glu Tyr Arg Tyr Glu Asn Asp Lys Asp Glu Leu Gly Phe Lys Thr
                965             970             975

Phe Thr Glu Phe Leu Asn Cys Tyr Ala Asn Asn Ala Tyr Asp Gly Gly
                980             985             990

Thr Gln Cys Ser Ala Glu Leu Lys Gln Ser Leu Ile Asp Asn Lys Met
            995             1000            1005

Ile Tyr Gly Glu Gly Ser Lys Ala Gly Met Met Asn Pro Ser Tyr Pro
    1010            1015            1020

Leu Asn Tyr Met Glu Lys Pro Leu Thr Arg Leu Met Leu Gly Arg Ser
1025            1030            1035            1040

Trp Trp Asp Leu Asn Ile Lys Val Asp Val Glu Lys Tyr Pro Gly Ala
                1045            1050            1055

Val Ser Ala Glu Gly Glu Val Thr Glu Thr Ile Asn Leu Tyr Ser
            1060            1065            1070

Asn Pro Thr Lys Trp Phe Ala Gly Asn Met Gln Ser Thr Gly Leu Trp
    1075            1080            1085

Ala Pro Ala Gln Gln Glu Val Ser Ile Lys Ser Asn Ala Lys Val Pro
    1090            1095            1100

Val Thr Val Thr Val Ala Leu Ala Asp Asp Leu Thr Gly Arg Glu Lys
1105            1110            1115            1120

His Glu Val Ala Leu Asn Arg Pro Arg Val Thr Lys Thr Tyr Ser
                1125            1130            1135

Leu Asp Ala Ser Gly Thr Val Lys Phe Lys Val Pro Tyr Gly Gly Leu
                1140            1145            1150

Ile Tyr Ile Lys Ser Asp Ser Lys Glu Lys Ser Ala Asn Phe Thr
                1155            1160            1165

Phe Thr Gly Val Val Lys Ala Pro Phe Tyr Lys Asp Gly Lys Trp Lys
    1170            1175            1180

Asn Asp Leu Lys Ser Pro Ala Pro Leu Gly Glu Leu Glu Ser Ala Ser
```

```
                    1185                1190                1195                1200
        Phe Val Tyr Thr Thr Pro Lys Lys Asn Leu Glu Ala Ser Asn Tyr Lys
                        1205                1210                1215

Gly Gly Leu Lys Gln Phe Ala Glu Asp Leu Asp Thr Phe Ala Ser Ser
                        1220                1225                1230

Met Asn Asp Phe Tyr Gly Arg Asp Gly Glu Ser Gly Lys His Arg Met
                        1235                1240                1245

Phe Glu Thr Pro Leu Thr Val Pro Gly Ala Thr Glu Val Ala Asn Asn
                        1250                1255                1260

Val Leu Ala Leu Tyr Met Gln Asp Arg Tyr Leu Gly Lys Met Asn Arg
        1265                1270                1275                1280

Val Ala Asp Asp Ile Thr Val Ala Pro Glu Tyr Leu Glu Ser Asn
                        1285                1290                1295

Gly Gln Ala Trp Ala Arg Gly Ala Gly Asp Arg Leu Leu Met Tyr
                        1300                1305                1310

Ala Gln Leu Lys Glu Trp Ala Glu Lys Asn Phe Asp Ile Lys Gln Trp
                        1315                1320                1325

Tyr Pro Glu Gly Ser Leu Pro Ala Phe Tyr Ser Glu Arg Glu Gly Met
                        1330                1335                1340

Lys Gly Trp Asn Leu Phe Gln Leu Met His Arg Lys Ala Arg Gly Asp
        1345                1350                1355                1360

Asp Val Gly Asn Asp Lys Phe Gly Asn Arg Asn Tyr Cys Ala Glu Ser
                        1365                1370                1375

Asn Gly Asn Ala Ala Asp Thr Leu Met Leu Cys Ala Ser Trp Val Ala
                        1380                1385                1390

Gln Thr Asp Leu Ser Ala Phe Phe Lys Lys Trp Asn Pro Gly Ala Asn
                        1395                1400                1405

Ala Tyr Gln Leu Pro Gly Ala Thr Glu Met Ser Phe Glu Gly Gly Val
                        1410                1415                1420

Ser Gln Ser Ala Tyr Asn Thr Leu Ala Ser Leu Asp Leu Pro Lys Pro
        1425                1430                1435                1440

Lys Gln Gly Pro Glu Thr Ile Asn Lys Val Thr Glu Tyr Ser Met Pro
                        1445                1450                1455

Ala Glu

<210> SEQ ID NO 38
<211> LENGTH: 1458
<212> TYPE: PRT
<213> ORGANISM: Escherichia coli

<400> SEQUENCE: 38

Met Asn Lys Lys Phe Lys Tyr Lys Lys Ser Leu Leu Ala Ala Ile Leu
        1               5                   10                  15

Ser Ala Thr Leu Leu Ala Gly Cys Asp Gly Gly Ser Gly Ser Ser
                        20                  25                  30

Ser Asp Thr Pro Pro Val Asp Ser Gly Thr Gly Ser Leu Pro Glu Val
                        35                  40                  45

Lys Pro Asp Pro Thr Pro Asn Pro Glu Pro Thr Pro Glu Pro Thr Pro
                50                  55                  60

Asp Pro Glu Pro Thr Pro Glu Pro Ile Pro Asp Pro Glu Pro Thr Pro
        65                  70                  75                  80

Glu Pro Glu Pro Glu Pro Val Pro Thr Lys Thr Gly Tyr Leu Thr Leu
                        85                  90                  95

Gly Gly Ser Gln Arg Val Thr Gly Ala Thr Cys Asn Gly Glu Ser Ser
```

```
                100             105               110
Asp Gly Phe Thr Phe Lys Pro Gly Glu Asp Val Thr Cys Val Ala Gly
            115                 120             125

Asn Thr Thr Ile Ala Thr Phe Asn Thr Gln Ser Glu Ala Ala Arg Ser
        130                 135             140

Leu Arg Ala Val Glu Lys Val Ser Phe Ser Leu Glu Asp Ala Gln Glu
145                 150                 155                 160

Leu Ala Gly Ser Asp Asp Lys Lys Ser Asn Ala Val Ser Leu Val Thr
                165                 170                 175

Ser Ser Asn Ser Cys Pro Ala Asn Thr Glu Gln Val Cys Leu Thr Phe
            180                 185             190

Ser Ser Val Ile Glu Ser Lys Arg Phe Asp Ser Leu Tyr Lys Gln Ile
        195                 200             205

Asp Leu Ala Pro Glu Glu Phe Lys Lys Leu Val Asn Glu Val Glu
    210                 215             220

Asn Asn Ala Ala Thr Asp Lys Ala Pro Ser Thr His Thr Ser Pro Val
225                 230                 235                 240

Val Pro Val Thr Thr Pro Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
            260                 265             270

Ile Leu Ser Glu Gly Arg Leu Val Asp Ser Gln Gly Tyr Gly Val Ala
        275                 280             285

Gly Val Asn Tyr Tyr Thr Asn Ser Gly Arg Gly Val Thr Gly Glu Asn
    290                 295             300

Gly Glu Phe Ser Phe Ser Trp Gly Glu Thr Ile Ser Phe Gly Ile Asp
305                 310                 315                 320

Thr Phe Glu Leu Gly Ser Val Arg Gly Asn Lys Ser Thr Ile Ala Leu
                325                 330                 335

Thr Glu Leu Gly Asp Glu Val Arg Gly Ala Asn Ile Asp Gln Leu Ile
            340                 345             350

His Arg Tyr Ser Thr Thr Gly Gln Asn Asn Thr Arg Val Val Pro Glu
        355                 360             365

Asp Val Arg Lys Val Phe Ala Glu Tyr Pro Asn Val Ile Asn Glu Ile
    370                 375             380

Ile Asn Leu Ser Leu Ser Asn Gly Ala Thr Leu Gly Glu Gly Glu Gln
385                 390                 395                 400

Val Val Asn Leu Pro Asn Glu Phe Ile Glu Gln Phe Asn Thr Gly Gln
                405                 410                 415

Ala Lys Glu Ile Asp Thr Ala Ile Cys Ala Lys Thr Asp Gly Cys Asn
            420                 425             430

Glu Ala Arg Trp Phe Ser Leu Thr Arg Asn Val Asn Asp Gly Gln
        435                 440             445

Ile Gln Gly Val Ile Asn Lys Leu Trp Gly Val Asp Thr Asn Tyr Lys
    450                 455             460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ala
                485                 490                 495

Ala Phe Pro Ile Leu Met Ala Arg Asn Asp Lys Asn Tyr Trp Leu Ala
            500                 505             510

Phe Gly Glu Lys Arg Ala Trp Asp Lys Asn Glu Leu Ala Tyr Ile Thr
        515                 520             525
```

```
Glu Ala Pro Ser Ile Val Arg Pro Glu Asn Val Thr Arg Glu Thr Ala
    530                 535                 540

Thr Phe Asn Leu Pro Phe Ile Ser Leu Gly Gln Val Gly Asp Gly Lys
545                 550                 555                 560

Leu Met Val Ile Gly Asn Pro His Tyr Asn Ser Ile Leu Arg Cys Pro
                565                 570                 575

Asn Gly Tyr Ser Trp Asn Gly Val Asn Lys Asp Gly Gln Cys Thr
                580                 585                 590

Leu Asn Ser Asp Pro Asp Asp Met Lys Asn Phe Met Glu Asn Val Leu
        595                 600                 605

Arg Tyr Leu Ser Asn Asp Arg Trp Leu Pro Asp Ala Lys Ser Asn Met
    610                 615                 620

Thr Val Gly Thr Asn Leu Asp Thr Val Tyr Phe Lys Lys His Gly Gln
625                 630                 635                 640

Val Thr Gly Asn Ser Ala Ala Phe Gly Phe His Pro Asp Phe Ala Gly
                645                 650                 655

Ile Ser Val Glu His Leu Ser Ser Tyr Gly Asp Leu Asp Pro Gln Glu
                660                 665                 670

Met Pro Leu Leu Ile Leu Asn Gly Phe Glu Tyr Val Thr Gln Val Gly
            675                 680                 685

Asn Asp Pro Tyr Ala Ile Pro Leu Arg Ala Asp Thr Ser Lys Pro Lys
    690                 695                 700

Leu Thr Gln Gln Asp Val Thr Asp Leu Ile Ala Tyr Met Asn Lys Gly
705                 710                 715                 720

Gly Ser Val Leu Ile Met Glu Asn Val Met Ser Asn Leu Lys Glu Glu
                725                 730                 735

Ser Ala Ser Gly Phe Val Arg Leu Leu Asp Ala Ala Gly Leu Ser Met
            740                 745                 750

Ala Leu Asn Lys Ser Val Val Asn Asn Asp Pro Gln Gly Tyr Pro Asp
        755                 760                 765

Arg Val Arg Gln Arg Arg Ser Thr Gly Ile Trp Val Tyr Glu Arg Tyr
    770                 775                 780

Pro Ala Val Asp Gly Lys Pro Tyr Thr Ile Asp Asp Thr Thr Lys
785                 790                 795                 800

Glu Val Ile Trp Lys Tyr Gln Gln Glu Asn Lys Pro Asp Asp Lys Pro
                805                 810                 815

Lys Leu Glu Val Ala Ser Trp Gln Glu Glu Val Glu Gly Lys Gln Val
            820                 825                 830

Thr Gln Phe Ala Phe Ile Asp Glu Ala Asp His Lys Thr Pro Glu Ser
        835                 840                 845

Leu Ala Ala Ala Lys Lys Arg Ile Leu Asp Ala Phe Pro Gly Leu Glu
    850                 855                 860

Glu Cys Lys Asp Ser Asp Tyr His Tyr Glu Val Asn Cys Leu Glu Tyr
865                 870                 875                 880

Arg Pro Gly Thr Gly Val Pro Val Thr Gly Met Tyr Val Pro Gln
                885                 890                 895

Tyr Thr Gln Leu Ser Leu Asn Ala Asp Thr Ala Lys Ala Met Val Gln
            900                 905                 910

Ala Ala Asp Leu Gly Thr Asn Ile Gln Arg Leu Tyr Gln His Glu Leu
        915                 920                 925

Tyr Phe Arg Thr Asn Gly Arg Lys Gly Glu Arg Leu Ser Ser Val Asp
    930                 935                 940
```

```
Leu Glu Arg Leu Tyr Gln Asn Met Ser Val Trp Leu Trp Asn Lys Ile
945                 950                 955                 960

Glu Tyr Arg Tyr Glu Asn Asp Lys Asp Glu Leu Gly Phe Lys Thr
            965                 970                 975

Phe Thr Glu Phe Leu Asn Cys Tyr Ala Asn Asn Ala Tyr Asp Gly Gly
            980                 985                 990

Thr Gln Cys Ser Ala Glu Leu Lys Gln Ser Leu Ile Asp Asn Lys Met
        995                 1000                1005

Ile Tyr Gly Glu Gly Ser Lys Ala Gly Met Met Asn Pro Ser Tyr Pro
    1010                1015                1020

Leu Asn Tyr Met Glu Lys Pro Leu Thr Arg Leu Met Leu Gly Arg Ser
1025                1030                1035                1040

Trp Trp Asp Leu Asn Ile Lys Val Asp Val Glu Lys Tyr Pro Gly Ala
            1045                1050                1055

Val Ser Ala Glu Gly Glu Val Thr Glu Thr Ile Asn Leu Tyr Ser
            1060                1065                1070

Asn Pro Thr Lys Trp Phe Ala Gly Asn Met Gln Ser Thr Gly Leu Trp
        1075                1080                1085

Ala Pro Ala Gln Gln Glu Val Ser Ile Lys Ser Asn Ala Lys Val Pro
    1090                1095                1100

Val Thr Val Thr Val Ala Leu Ala Asp Asp Leu Thr Gly Arg Glu Lys
1105                1110                1115                1120

His Glu Val Ala Leu Asn Arg Pro Pro Arg Val Thr Lys Thr Tyr Ser
            1125                1130                1135

Leu Asp Ala Ser Gly Thr Val Lys Phe Lys Val Pro Tyr Gly Gly Leu
        1140                1145                1150

Ile Tyr Ile Lys Ser Asp Ser Lys Glu Glu Lys Ser Ala Asn Phe Thr
    1155                1160                1165

Phe Thr Gly Val Val Lys Ala Pro Phe Tyr Lys Asp Gly Lys Trp Lys
    1170                1175                1180

Asn Asp Leu Lys Ser Pro Ala Pro Leu Gly Leu Glu Ser Ala Ser
1185                1190                1195                1200

Phe Val Tyr Thr Thr Pro Lys Lys Asn Leu Glu Ala Ser Asn Tyr Lys
            1205                1210                1215

Gly Gly Leu Lys Gln Phe Ala Glu Asp Leu Asp Thr Phe Ala Ser Ser
        1220                1225                1230

Met Asn Asp Phe Tyr Gly Arg Asp Gly Glu Ser Gly Lys His Arg Met
            1235                1240                1245

Phe Glu Thr Pro Leu Thr Val Pro Gly Ala Thr Glu Val Ala Asn Asn
    1250                1255                1260

Val Leu Ala Leu Tyr Met Gln Asp Arg Tyr Leu Gly Lys Met Asn Arg
1265                1270                1275                1280

Val Ala Asp Asp Ile Thr Val Ala Pro Glu Tyr Leu Glu Glu Ser Asn
            1285                1290                1295

Gly Gln Ala Trp Ala Arg Gly Gly Ala Gly Asp Arg Leu Leu Met Tyr
        1300                1305                1310

Ala Gln Leu Lys Glu Trp Ala Glu Lys Asn Phe Asp Ile Lys Gln Trp
            1315                1320                1325

Tyr Pro Glu Gly Ser Leu Pro Ala Phe Tyr Ser Glu Arg Glu Gly Met
    1330                1335                1340

Lys Gly Trp Asn Leu Phe Gln Leu Met His Arg Lys Ala Arg Gly Asp
1345                1350                1355                1360

Asp Val Gly Asn Asp Lys Phe Gly Asn Arg Asn Tyr Cys Ala Glu Ser
```

```
                        1365              1370              1375
Asn Gly Asn Ala Ala Asp Thr Leu Met Leu Cys Ala Ser Trp Val Ala
                1380              1385              1390

Gln Thr Asp Leu Ser Ala Phe Phe Lys Lys Trp Asn Pro Gly Ala Asn
                1395              1400              1405

Ala Tyr Gln Leu Pro Gly Ala Thr Glu Met Ser Phe Glu Gly Gly Val
                1410              1415              1420

Ser Gln Ser Ala Tyr Asn Thr Leu Ala Ser Leu Asp Leu Pro Lys Pro
1425              1430              1435              1440

Glu Gln Gly Pro Glu Thr Ile Asn Gln Val Thr Glu His Lys Met Ser
                1445              1450              1455

Ala Glu

<210> SEQ ID NO 39
<211> LENGTH: 1460
<212> TYPE: PRT
<213> ORGANISM: Escherichia coli

<400> SEQUENCE: 39

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
                20                  25                  30

Ser Asp Thr Pro Ser Val Asp Ser Gly Ser Gly Thr Leu Pro Glu Val
                35                  40                  45

Lys Pro Asp Pro Thr Pro Thr Pro Glu Pro Thr Pro Glu Pro Thr Pro
50                  55                  60

Asp Pro Glu Pro Thr Pro Asp Pro Thr Pro Asp Pro Glu Pro Thr Pro
65                  70                  75                  80

Glu Pro Glu Pro Glu Pro Val Pro Thr Lys Thr Gly Tyr Leu Thr Leu
                85                  90                  95

Gly Gly Ser Gln Arg Val Thr Gly Ala Thr Cys Asn Gly Glu Ser Ser
                100                 105                 110

Asp Gly Phe Thr Phe Thr Pro Gly Asn Thr Val Ser Cys Val Val Gly
                115                 120                 125

Ser Thr Thr Ile Ala Thr Phe Asn Thr Gln Ser Glu Ala Ala Arg Ser
130                 135                 140

Leu Arg Ala Val Asp Lys Val Ser Phe Ser Leu Glu Asp Ala Gln Glu
145                 150                 155                 160

Leu Ala Asn Ser Glu Asn Lys Lys Thr Asn Ala Ile Ser Leu Val Thr
                165                 170                 175

Ser Ser Asp Ser Cys Pro Ala Asp Ala Glu Gln Leu Cys Leu Thr Phe
                180                 185                 190

Ser Ser Val Val Asp Arg Ala Arg Phe Glu Lys Leu Tyr Lys Gln Ile
                195                 200                 205

Asp Leu Ala Thr Asp Asn Phe Ser Lys Leu Val Asn Glu Glu Val Glu
                210                 215                 220

Asn Asn Ala Ala Thr Asp Lys Ala Pro Ser Thr His Thr Ser Thr Val
225                 230                 235                 240

Val Pro Val Thr Thr Glu Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
                260                 265                 270

Ile Leu Ser Glu Gly Gln Leu Val Asp Ser Leu Gly Asn Gly Val Ala
```

```
                275                 280                 285
Gly Val Asp Tyr Tyr Thr Asn Ser Gly Arg Gly Val Thr Asp Glu Asn
290                 295                 300
Gly Lys Phe Ser Phe Ser Trp Gly Glu Thr Ile Ser Phe Gly Ile Asp
305                 310                 315                 320
Thr Phe Glu Leu Gly Ser Val Arg Gly Asn Lys Ser Thr Ile Ala Leu
                325                 330                 335
Thr Glu Leu Gly Asp Glu Val Arg Gly Ala Asn Ile Asp Gln Leu Ile
                340                 345                 350
His Arg Tyr Ser Thr Thr Gly Gln Asn Asn Thr Arg Val Val Pro Asp
                355                 360                 365
Asp Val Arg Lys Val Phe Ala Glu Tyr Pro Asn Val Ile Asn Glu Ile
            370                 375                 380
Ile Asn Leu Ser Leu Ser Asn Gly Ala Thr Leu Asp Glu Gly Asp Gln
385                 390                 395                 400
Asn Val Val Leu Pro Asn Glu Phe Ile Glu Gln Phe Lys Thr Gly Gln
                405                 410                 415
Ala Lys Glu Ile Asp Thr Ala Ile Cys Ala Lys Thr Asp Gly Cys Asn
                420                 425                 430
Glu Ala Arg Trp Phe Ser Leu Thr Thr Arg Asn Val Asn Asp Gly Gln
                435                 440                 445
Ile Gln Gly Val Ile Asn Lys Leu Trp Gly Val Asp Thr Asn Tyr Gln
450                 455                 460
Ser Val Ser Lys Phe His Val Phe His Asp Ser Thr Asn Phe Tyr Gly
465                 470                 475                 480
Ser Thr Gly Asn Ala Arg Gly Gln Ala Val Val Asn Ile Ser Asn Ser
                485                 490                 495
Ala Phe Pro Ile Leu Met Ala Arg Asn Asp Lys Asn Tyr Trp Leu Ala
                500                 505                 510
Phe Gly Glu Lys Arg Ala Trp Asp Lys Asn Glu Leu Ala Tyr Ile Thr
                515                 520                 525
Glu Ala Pro Ser Ile Val Gln Pro Glu Asn Val Thr Arg Asp Thr Ala
530                 535                 540
Thr Phe Asn Leu Pro Phe Ile Ser Leu Gly Gln Val Gly Glu Gly Lys
545                 550                 555                 560
Leu Met Val Ile Gly Asn Pro His Tyr Asn Ser Ile Leu Arg Cys Pro
                565                 570                 575
Asn Gly Tyr Ser Trp Gly Gly Val Asn Ser Lys Gly Glu Cys Thr
                580                 585                 590
Leu Ser Gly Asp Ser Asp Met Lys His Phe Met Gln Asn Val Leu
                595                 600                 605
Arg Tyr Leu Ser Asn Asp Ile Trp Gln Pro Asn Thr Lys Ser Ile Met
            610                 615                 620
Thr Val Gly Thr Asn Leu Glu Asn Val Tyr Phe Lys Lys Ala Gly Gln
625                 630                 635                 640
Val Leu Gly Asn Ser Ala Pro Phe Ala Phe His Glu Asp Phe Thr Gly
                645                 650                 655
Ile Thr Val Lys Gln Leu Thr Ser Tyr Gly Asp Leu Asn Pro Glu Glu
                660                 665                 670
Ile Pro Leu Leu Ile Leu Asn Gly Phe Glu Tyr Val Thr Gln Trp Ser
                675                 680                 685
Gly Asp Pro Tyr Ala Val Pro Leu Arg Ala Asp Thr Ser Lys Pro Lys
690                 695                 700
```

```
Leu Thr Gln Gln Asp Val Thr Asp Leu Ile Ala Tyr Leu Asn Lys Gly
705                 710                 715                 720

Gly Ser Val Leu Ile Met Glu Asn Val Met Ser Asn Leu Lys Glu Glu
            725                 730                 735

Ser Ala Ser Ser Phe Val Arg Leu Leu Asp Ala Ala Gly Leu Ser Met
            740                 745                 750

Ala Leu Asn Lys Ser Val Val Asn Asn Asp Pro Gln Gly Tyr Pro Asp
        755                 760                 765

Arg Val Arg Gln Arg Arg Ala Thr Gly Ile Trp Val Tyr Glu Arg Tyr
    770                 775                 780

Pro Ala Ala Asp Gly Ala Gln Pro Pro Tyr Thr Ile Asp Pro Asn Thr
785                 790                 795                 800

Gly Glu Val Thr Trp Lys Tyr Gln Gln Asp Asn Lys Pro Asp Asp Lys
                805                 810                 815

Pro Lys Leu Glu Val Ala Ser Trp Gln Glu Val Glu Gly Lys Gln
                820                 825                 830

Val Thr Arg Tyr Ala Phe Ile Asp Glu Ala Glu Tyr Thr Thr Glu Glu
    835                 840                 845

Ser Leu Glu Ala Ala Lys Ala Lys Ile Phe Glu Lys Phe Pro Gly Leu
    850                 855                 860

Gln Glu Cys Lys Asp Ser Thr Tyr His Tyr Glu Ile Asn Cys Leu Glu
865                 870                 875                 880

Arg Arg Pro Gly Thr Asp Val Pro Val Thr Gly Gly Met Tyr Val Pro
                885                 890                 895

Arg Tyr Thr Gln Leu Asn Leu Asp Ala Asp Thr Ala Lys Ala Met Val
                900                 905                 910

Gln Ala Ala Asp Leu Gly Thr Asn Ile Gln Arg Leu Tyr Gln His Glu
            915                 920                 925

Leu Tyr Phe Arg Thr Lys Gly Ser Lys Gly Arg Leu Asn Ser Val
930                 935                 940

Asp Leu Glu Arg Leu Tyr Gln Asn Met Ser Val Trp Leu Trp Asn Asp
945                 950                 955                 960

Thr Lys Tyr Arg Tyr Glu Glu Gly Lys Glu Asp Glu Leu Gly Phe Lys
                965                 970                 975

Thr Phe Thr Glu Phe Leu Asn Cys Tyr Ala Asn Asp Ala Tyr Ala Gly
            980                 985                 990

Gly Thr Lys Cys Ser Ala Asp Leu Lys Lys Ser Leu Val Asp Asn Asn
        995                 1000                1005

Met Ile Tyr Gly Asp Gly Ser Ser Lys Ala Gly Met Met Asn Pro Ser
    1010                1015                1020

Tyr Pro Leu Asn Tyr Met Glu Lys Pro Leu Thr Arg Leu Met Leu Gly
1025                1030                1035                1040

Arg Ser Trp Trp Asp Leu Asn Ile Lys Val Asp Val Glu Lys Tyr Pro
                1045                1050                1055

Gly Ser Val Ser Ala Lys Gly Glu Ser Val Thr Glu Asn Ile Ser Leu
                1060                1065                1070

Tyr Ser Asn Pro Thr Lys Trp Phe Ala Gly Asn Met Gln Ser Thr Gly
        1075                1080                1085

Leu Trp Ala Pro Ala Gln Gln Asp Val Thr Ile Lys Ser Ser Ala Ser
        1090                1095                1100

Val Pro Val Thr Val Thr Val Ala Leu Ala Asp Asp Leu Thr Gly Arg
1105                1110                1115                1120
```

```
Glu Lys His Glu Val Ala Leu Asn Arg Pro Pro Arg Val Thr Lys Thr
            1125                1130                1135

Tyr Thr Leu Glu Ala Asn Gly Glu Val Thr Phe Lys Val Pro Tyr Gly
            1140                1145                1150

Gly Leu Ile Tyr Ile Lys Gly Asp Ser Lys Asp Val Ser Ala Asn
            1155                1160                1165

Phe Thr Phe Thr Gly Val Val Lys Ala Pro Phe Tyr Lys Asp Gly Glu
            1170                1175                1180

Trp Lys Asn Asp Leu Asp Ser Pro Ala Pro Leu Gly Glu Leu Glu Ser
1185                1190                1195                1200

Ala Ser Phe Val Tyr Thr Thr Pro Lys Lys Asn Leu Glu Ala Ser Asn
            1205                1210                1215

Phe Thr Gly Gly Val Ala Glu Phe Ala Lys Asp Leu Asp Thr Phe Ala
            1220                1225                1230

Ser Ser Met Asn Asp Phe Tyr Gly Arg Asn Asp Glu Asp Gly Lys His
            1235                1240                1245

Arg Met Phe Glu Thr Pro Leu Asn Val Pro Gly Ala Thr Glu Val Ala
            1250                1255                1260

Asn Asn Val Leu Ala Leu Tyr Met Gln Asp Arg Tyr Leu Gly Lys Met
1265                1270                1275                1280

Asn Arg Val Ala Asp Asp Ile Thr Val Ala Pro Glu Tyr Leu Asp Glu
            1285                1290                1295

Ser Asn Gly Gln Ala Trp Ala Arg Gly Ala Gly Asp Arg Leu Leu
            1300                1305                1310

Met Tyr Ala Gln Leu Lys Glu Trp Ala Glu Glu Asn Phe Asp Ile Lys
            1315                1320                1325

Gln Trp Tyr Pro Asp Gly Glu Leu Pro Lys Phe Tyr Ser Asp Arg Lys
            1330                1335                1340

Gly Met Lys Gly Trp Asn Leu Phe Gln Leu Met His Arg Lys Ala Arg
1345                1350                1355                1360

Gly Asp Asp Val Gly Asn Ser Thr Phe Gly Gly Lys Asn Tyr Cys Ala
            1365                1370                1375

Glu Ser Asn Gly Asn Ala Ala Asp Thr Leu Met Leu Cys Ala Ser Trp
            1380                1385                1390

Val Ala Gln Ala Asp Leu Ser Glu Phe Phe Lys Lys Trp Asn Pro Gly
            1395                1400                1405

Ala Ser Ala Tyr Gln Leu Pro Gly Ala Thr Glu Met Ser Phe Gln Gly
            1410                1415                1420

Gly Val Ser Ser Ala Tyr Ser Thr Leu Ala Ser Leu Lys Leu Pro
1425                1430                1435                1440

Lys Pro Glu Lys Gly Pro Glu Thr Ile Asn Lys Val Thr Glu His Lys
            1445                1450                1455

Met Ser Ala Glu
            1460

<210> SEQ ID NO 40
<211> LENGTH: 1460
<212> TYPE: PRT
<213> ORGANISM: Escherichia coli

<400> SEQUENCE: 40

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Gly Ser Gly Ser Ser
            20                  25                  30
```

-continued

```
Ser Asp Thr Pro Ser Val Asp Ser Gly Ser Gly Thr Leu Pro Glu Val
         35                  40                  45

Lys Pro Asp Pro Thr Pro Thr Pro Glu Pro Thr Pro Glu Pro Thr Pro
 50                  55                  60

Asp Pro Glu Pro Thr Pro Asp Pro Thr Pro Asp Pro Asp Pro Glu Pro
 65                  70                  75                  80

Thr Pro Glu Pro Glu Pro Val Pro Thr Lys Thr Gly Tyr Leu
                 85                  90                  95

Thr Leu Gly Gly Ser Gln Arg Val Thr Gly Ala Thr Cys Asn Gly Glu
                100                 105                 110

Ser Ser Asp Gly Phe Thr Phe Thr Pro Gly Asn Thr Val Ser Cys Val
                115                 120                 125

Val Gly Ser Thr Thr Ile Ala Thr Phe Asn Thr Gln Ser Glu Ala Ala
                130                 135                 140

Arg Ser Leu Arg Ala Val Asp Lys Val Ser Phe Ser Leu Glu Asp Ala
145                 150                 155                 160

Gln Glu Leu Ala Asn Ser Glu Asn Lys Lys Thr Asn Ala Ile Ser Leu
                165                 170                 175

Val Thr Ser Ser Asp Ser Cys Pro Ala Asp Ala Glu Gln Leu Cys Leu
                180                 185                 190

Thr Phe Ser Ser Val Val Asp Arg Ala Arg Phe Glu Lys Leu Tyr Lys
                195                 200                 205

Gln Ile Asp Leu Ala Thr Asp Asn Phe Ser Lys Leu Val Asn Glu Glu
                210                 215                 220

Val Glu Asn Asn Ala Ala Thr Asp Lys Ala Pro Ser Thr His Thr Ser
225                 230                 235                 240

Thr Val Val Pro Val Thr Thr Glu Gly Thr Lys Pro Asp Leu Asn Ala
                245                 250                 255

Ser Phe Val Ser Ala Asn Ala Glu Gln Phe Tyr Gln Tyr Gln Pro Thr
                260                 265                 270

Glu Ile Ile Leu Ser Glu Gly Gln Leu Val Asp Ser Leu Gly Asn Gly
                275                 280                 285

Val Ala Gly Val Asp Tyr Tyr Thr Asn Ser Gly Arg Gly Val Thr Asp
                290                 295                 300

Glu Asn Gly Lys Phe Ser Phe Ser Trp Gly Glu Thr Ile Ser Phe Gly
305                 310                 315                 320

Ile Asp Thr Phe Glu Leu Gly Ser Val Arg Gly Asn Lys Ser Thr Ile
                325                 330                 335

Ala Leu Thr Glu Leu Gly Asp Glu Val Arg Gly Ala Asn Ile Asp Gln
                340                 345                 350

Leu Ile His Arg Tyr Ser Thr Thr Gly Gln Asn Asn Thr Arg Val Val
                355                 360                 365

Pro Asp Asp Val Arg Lys Val Phe Ala Glu Tyr Pro Asn Val Ile Asn
                370                 375                 380

Glu Ile Ile Asn Leu Ser Leu Ser Asn Gly Ala Thr Leu Asp Glu Gly
385                 390                 395                 400

Asp Gln Asn Val Val Leu Pro Asn Glu Phe Ile Glu Gln Phe Lys Thr
                405                 410                 415

Gly Gln Ala Lys Glu Ile Asp Thr Ala Ile Cys Ala Lys Thr Asn Gly
                420                 425                 430

Cys Asn Glu Ala Arg Trp Phe Ser Leu Thr Thr Arg Asn Val Asn Asp
                435                 440                 445
```

```
Gly Gln Ile Gln Gly Val Ile Asn Lys Leu Trp Gly Val Asp Thr Asn
450                 455                 460

Tyr Gln Ser Val Ser Lys Phe His Val Phe His Asp Ser Thr Asn Phe
465                 470                 475                 480

Tyr Gly Ser Thr Gly Asn Ala Arg Gly Gln Ala Val Val Asn Ile Ser
                485                 490                 495

Asn Ala Ala Phe Pro Ile Leu Met Ala Arg Asn Asp Lys Asn Tyr Trp
            500                 505                 510

Leu Ala Phe Gly Glu Lys Arg Ala Trp Asp Lys Asn Glu Leu Ala Tyr
        515                 520                 525

Ile Thr Glu Ala Pro Ser Ile Val Gln Pro Glu Asn Val Thr Arg Asp
530                 535                 540

Thr Ala Thr Phe Asn Leu Pro Phe Ile Ser Leu Gly Gln Val Gly Asp
545                 550                 555                 560

Gly Lys Leu Met Val Ile Gly Asn Pro His Tyr Asn Ser Ile Leu Arg
                565                 570                 575

Cys Pro Asn Gly Tyr Ser Trp Gly Gly Val Asn Ser Lys Gly Glu
            580                 585                 590

Cys Thr Leu Ser Gly Asp Ser Asp Met Lys His Phe Met Gln Asn
        595                 600                 605

Val Leu Arg Tyr Leu Ser Asn Asp Ile Trp Gln Pro Asn Thr Lys Ser
610                 615                 620

Ile Met Thr Val Gly Thr Asn Leu Glu Asn Val Tyr Phe Lys Lys Ala
625                 630                 635                 640

Gly Gln Val Leu Gly Asn Ser Ala Pro Phe Ala Phe His Glu Asp Phe
                645                 650                 655

Thr Gly Ile Thr Val Lys Gln Leu Thr Ser Tyr Gly Asp Leu Asn Pro
            660                 665                 670

Glu Glu Ile Pro Leu Leu Ile Leu Asn Gly Phe Glu Tyr Val Thr Gln
        675                 680                 685

Trp Ser Gly Asp Pro Tyr Ala Val Pro Leu Arg Ala Asp Thr Ser Lys
690                 695                 700

Pro Lys Leu Thr Gln Gln Asp Val Thr Asp Leu Ile Ala Tyr Leu Asn
705                 710                 715                 720

Lys Gly Gly Ser Val Leu Ile Met Glu Asn Val Met Ser Asn Leu Lys
                725                 730                 735

Glu Glu Ser Ala Ser Ser Phe Val Arg Leu Leu Asp Ala Ala Gly Leu
            740                 745                 750

Ser Met Ala Leu Asn Lys Ser Val Val Asn Asn Asp Pro Gln Gly Tyr
        755                 760                 765

Pro Asp Arg Val Arg Gln Gln Arg Glu Lys Gly Ile Trp Val Tyr Glu
770                 775                 780

Arg Tyr Pro Phe Val Asp Gly Lys Pro Pro Tyr Thr Ile Asp Glu Thr
785                 790                 795                 800

Thr Lys Glu Val Ile Trp Lys Tyr Gln Gln Asp Asn Lys Pro Asp Asp
                805                 810                 815

Lys Pro Lys Leu Glu Val Ala Ser Trp Leu Glu Asp Val Asp Gly Lys
            820                 825                 830

Gln Val Lys Arg Tyr Ala Phe Ile Asp Glu Ala Glu His Glu Thr Asn
        835                 840                 845

Glu Ser Leu Glu Ala Ala Lys Ala Lys Ile Ile Lys Ala Phe Pro Gly
850                 855                 860

Leu Glu Glu Cys Lys Asp Pro Thr Tyr His Tyr Glu Val Asn Cys Leu
```

```
                865                 870                 875                 880
        Glu Tyr Arg Pro Gly Thr Asn Val Pro Val Thr Gly Gly Met Tyr Val
                        885                 890                 895
        Pro Arg Tyr Thr Gln Leu Asn Leu Ser Ala Asp Thr Ala Lys Ala Met
                        900                 905                 910
        Val Gln Ala Ala Asp Leu Gly Thr Asn Ile Gln Arg Leu Tyr Gln His
                        915                 920                 925
        Glu Leu Tyr Phe Arg Thr Asn Gly Arg Lys Gly Glu Arg Leu Ser Ser
                        930                 935                 940
        Val Asp Leu Glu Arg Leu Tyr Gln Asn Met Ser Val Trp Leu Trp Asn
        945                 950                 955                 960
        Glu Ile Glu Tyr Ser Tyr Asp Ser Ser Lys Glu Asp Glu Leu Gly Phe
                        965                 970                 975
        Lys Thr Phe Thr Glu Phe Leu Asn Cys Tyr Ala Asn Asp Ala Tyr Thr
                        980                 985                 990
        Lys Gly Thr Leu Cys Ser Ala Glu Leu Lys Gln Ser Leu Ile Asp Asn
                        995                 1000                1005
        Lys Met Ile Tyr Gly Glu Gly Ser Lys Ala Gly Met Met Asn Pro Ser
                1010                1015                1020
        Tyr Pro Leu Asn Tyr Met Glu Lys Pro Leu Thr Arg Leu Met Leu Gly
        1025                1030                1035                1040
        Arg Ser Trp Trp Asp Leu Asn Ile Lys Val Asp Val Glu Lys Tyr Pro
                        1045                1050                1055
        Gly Ala Val Ser Val Gly Gly Glu Val Thr Glu Thr Ile Ser Leu
                        1060                1065                1070
        Tyr Ser Asn Pro Thr Lys Trp Phe Ala Gly Asn Met Gln Ser Thr Gly
                        1075                1080                1085
        Leu Trp Ala Pro Ala Gln Lys Glu Val Thr Ile Lys Ser Asn Ala Asn
                1090                1095                1100
        Val Pro Val Thr Val Thr Val Ala Leu Ala Asp Asp Leu Thr Gly Arg
        1105                1110                1115                1120
        Glu Lys His Glu Val Ala Leu Asn Arg Pro Pro Arg Val Thr Lys Thr
                        1125                1130                1135
        Tyr Ser Leu Asp Ala Ser Gly Thr Val Lys Phe Lys Val Pro Tyr Gly
                        1140                1145                1150
        Gly Leu Ile Tyr Ile Lys Gly Asn Ser Ser Thr Asn Glu Ser Ala Ser
                        1155                1160                1165
        Phe Thr Phe Thr Gly Val Val Lys Ala Pro Phe Tyr Lys Asp Gly Ala
                        1170                1175                1180
        Trp Lys Asn Asp Leu Asn Ser Pro Ala Pro Leu Gly Glu Leu Glu Ser
        1185                1190                1195                1200
        Ala Ser Phe Val Tyr Thr Thr Pro Lys Lys Asn Leu Asn Ala Ser Asn
                        1205                1210                1215
        Tyr Thr Gly Gly Leu Asp Gln Phe Ala Lys Asp Leu Asp Thr Phe Ala
                        1220                1225                1230
        Ser Ser Met Asn Asp Phe Tyr Gly Arg Asn Asp Glu Asp Gly Lys His
                        1235                1240                1245
        Arg Met Phe Glu Thr Pro Leu Asn Val Pro Gly Ala Thr Glu Val Ala
                        1250                1255                1260
        Asn Asn Val Leu Ala Leu Tyr Met Gln Asp Arg Tyr Leu Gly Lys Met
        1265                1270                1275                1280
        Asn Arg Val Ala Asp Asp Ile Thr Val Ala Pro Glu Tyr Leu Asp Glu
                        1285                1290                1295
```

```
Ser Asn Gly Gln Ala Trp Ala Arg Gly Gly Ala Gly Asp Arg Leu Leu
            1300                1305                1310

Met Tyr Ala Gln Leu Lys Glu Trp Ala Glu Lys Asn Phe Asp Ile Thr
        1315                1320                1325

Lys Trp Tyr Pro Asp Gly Lys Leu Pro Ala Phe Tyr Ser Glu Arg Glu
    1330                1335                1340

Gly Met Lys Gly Trp Asn Leu Phe Gln Leu Met His Arg Lys Ala Arg
1345                1350                1355                1360

Gly Asp Asp Val Gly Asn Ser Thr Phe Gly Gly Lys Asn Tyr Cys Ala
                1365                1370                1375

Glu Ser Asn Gly Asn Ala Ala Asp Thr Leu Met Leu Cys Ala Ser Trp
            1380                1385                1390

Val Ala Gln Thr Asp Leu Ser Glu Phe Phe Lys Lys Trp Asn Pro Gly
        1395                1400                1405

Ala Asn Ala Tyr Gln Leu Pro Gly Ala Ala Glu Met Ser Phe Glu Gly
    1410                1415                1420

Gly Val Ser Ser Ser Ala Tyr Ser Thr Leu Ala Ser Leu Asn Leu Pro
1425                1430                1435                1440

Lys Pro Glu Lys Gly Pro Glu Thr Ile Asn Lys Val Thr Glu His Lys
                1445                1450                1455

Met Ser Ala Glu
            1460

<210> SEQ ID NO 41
<211> LENGTH: 1242
<212> TYPE: DNA
<213> ORGANISM: Escherichia coli

<400> SEQUENCE: 41
```

| | | | | | |
|---|---|---|---|---|---|
| gttgctgatg | gtcagcaagc | ctacacgctg | acactgacag | cggtggactc | cgagggtaat | 60 |
| ccggtgacgg | gagaagccag | ccgcctgcga | cttgttccgc | aagacactaa | tggtgtaacc | 120 |
| gttggtgcca | tttcggaaat | aaaaccaggg | gtttacagcg | ccacggtttc | ttcgacccgt | 180 |
| gccggaaacg | ttgttgtgcg | tgccttcagc | gagcagtatc | agctgggcac | attacaacaa | 240 |
| acgctgaagt | ttgttgccgg | gccgcttgat | gcagcacatt | cgtccatcac | actgaatcct | 300 |
| gataaaccgg | tggttggcgg | tacagttacg | gcaatctgga | cggcaaaaga | tgctaatgac | 360 |
| aaccctgtaa | ctggcctcaa | tccggatgca | ccgtcattat | cgggcgcagc | tgctgctggt | 420 |
| tctacggcat | caggctggac | ggataatggc | gacgggacct | ggactgcgca | gatttctctc | 480 |
| ggcactacgg | cgggtgaatt | agacgttatg | ccgaagctca | atgggcagga | cgcggcagca | 540 |
| aatgcggcaa | agtaaccgt | ggtggctgat | gcattatctt | caaaccagtc | gaaagtctct | 600 |
| gtcgcagaag | atcacgtaaa | agccggtgaa | agcacaaccg | taacgctggt | ggcgaaagat | 660 |
| gcgcatggca | acgctatcag | tggtctttcg | ttgtcggcaa | gtttgacggg | gaccgcctct | 720 |
| gaaggggcga | ccgtttccag | ttggaccgaa | aaaggtgacg | gttcctatgt | tgctacgtta | 780 |
| actacaggcg | gaaagacggg | cgagcttcgt | gtcatgccgc | tcttcaacgg | ccagcctgca | 840 |
| gccaccgaag | ccgcgcagct | gactgttatt | gccggagaga | tgtcatcagc | gaactctacg | 900 |
| cttgttgcgg | acaataaaac | tccaacggtt | aaaacgacga | cggaactcac | cttcaccatg | 960 |
| aaggatgcgt | acgggaatcc | ggtcaccggg | ctgaagccag | atgcaccagt | gtttagtggt | 1020 |
| gccgccagca | cggggagtga | gcgtccttca | gcaggaaact | ggacagagaa | aggtaatggg | 1080 |
| gtctacgtgt | cgaccttaac | gctgggatct | gccgcgggtc | agttgtctgt | gatgccgcga | 1140 |

```
gtgaacggcc aaaatgccgt tgctcagcca ctggtgctga atgttgcagg tgacgcatct   1200
aaggctgaga ttcgtgatat gacagtgaag gttaataacc aa                      1242
```

<210> SEQ ID NO 42
<211> LENGTH: 414
<212> TYPE: PRT
<213> ORGANISM: Escherichia coli

<400> SEQUENCE: 42

```
Val Ala Asp Gly Gln Gln Ala Tyr Thr Leu Thr Leu Thr Ala Val Asp
 1               5                  10                  15

Ser Glu Gly Asn Pro Val Thr Gly Glu Ala Ser Arg Leu Arg Leu Val
             20                  25                  30

Pro Gln Asp Thr Asn Gly Val Thr Val Gly Ala Ile Ser Glu Ile Lys
         35                  40                  45

Pro Gly Val Tyr Ser Ala Thr Val Ser Ser Thr Arg Ala Gly Asn Val
     50                  55                  60

Val Val Arg Ala Phe Ser Glu Gln Tyr Gln Leu Gly Thr Leu Gln Gln
 65                  70                  75                  80

Thr Leu Lys Phe Val Ala Gly Pro Leu Asp Ala Ala His Ser Ser Ile
                 85                  90                  95

Thr Leu Asn Pro Asp Lys Pro Val Val Gly Thr Val Thr Ala Ile
            100                 105                 110

Trp Thr Ala Lys Asp Ala Asn Asp Asn Pro Val Thr Gly Leu Asn Pro
        115                 120                 125

Asp Ala Pro Ser Leu Ser Gly Ala Ala Ala Gly Ser Thr Ala Ser
    130                 135                 140

Gly Trp Thr Asp Asn Gly Asp Gly Thr Trp Thr Ala Gln Ile Ser Leu
145                 150                 155                 160

Gly Thr Thr Ala Gly Glu Leu Asp Val Met Pro Lys Leu Asn Gly Gln
                165                 170                 175

Asp Ala Ala Ala Asn Ala Ala Lys Val Thr Val Ala Asp Ala Leu
            180                 185                 190

Ser Ser Asn Gln Ser Lys Val Ser Val Ala Glu Asp His Val Lys Ala
        195                 200                 205

Gly Glu Ser Thr Thr Val Thr Leu Val Ala Lys Asp Ala His Gly Asn
    210                 215                 220

Ala Ile Ser Gly Leu Ser Leu Ser Ala Ser Leu Thr Gly Thr Ala Ser
225                 230                 235                 240

Glu Gly Ala Thr Val Ser Ser Trp Thr Glu Lys Gly Asp Gly Ser Tyr
                245                 250                 255

Val Ala Thr Leu Thr Thr Gly Val Lys Thr Gly Glu Leu Arg Val Met
            260                 265                 270

Pro Leu Phe Asn Gly Gln Pro Ala Ala Thr Glu Ala Ala Gln Leu Thr
        275                 280                 285

Val Ile Ala Gly Glu Met Ser Ser Ala Asn Ser Thr Leu Val Ala Asp
    290                 295                 300

Asn Lys Thr Pro Thr Val Lys Thr Thr Thr Glu Leu Thr Phe Thr Met
305                 310                 315                 320

Lys Asp Ala Tyr Gly Asn Pro Val Thr Gly Leu Lys Pro Asp Ala Pro
                325                 330                 335

Val Phe Ser Gly Ala Ala Ser Thr Gly Ser Glu Arg Pro Ser Ala Gly
            340                 345                 350
```

```
Asn Trp Thr Glu Lys Gly Asn Gly Val Tyr Val Ser Thr Leu Thr Leu
            355                 360                 365

Gly Ser Ala Ala Gly Gln Leu Ser Val Met Pro Arg Val Asn Gly Gln
    370                 375                 380

Asn Ala Val Ala Gln Pro Leu Val Leu Asn Val Ala Gly Asp Ala Ser
385                 390                 395                 400

Lys Ala Glu Ile Arg Asp Met Thr Val Lys Val Asn Asn Gln
                405                 410

<210> SEQ ID NO 43
<211> LENGTH: 1704
<212> TYPE: DNA
<213> ORGANISM: Escherichia coli

<400> SEQUENCE: 43
```

| | | | | | |
|---|---|---|---|---|---|
| gctgacacgg | ttgtacaggc | gggagaaacc | gtgaacggcg | aaacactgac | aaatcatgac | 60 |
| aaccagattg | tcctcggtac | ggccaacgga | atgaccatca | gtaccgggct | ggagtatggg | 120 |
| ccggataacg | aggccaatac | cggcgggcaa | tggatacaaa | atggcggtat | cgccaacaac | 180 |
| actactgtca | ccgtggtggg | tcttcagaga | gtgaatgccg | aggaagcgt | ttcagacacg | 240 |
| gttatcagtg | ccggaggcgg | acagagcctt | caggggcagg | cagtgaacac | cactctgaac | 300 |
| ggcggtgagc | agtgggtaca | tgaaggcggg | attgcaacgg | gtaccgtcat | taatgagaag | 360 |
| ggctggcagg | ccgtcaaatc | cggtgcaatg | caaccgaca | cggttgtgaa | taccggcgcg | 420 |
| gaaggaggac | cggatgcgga | aaatggtgat | accgggcaga | ccgtctacgg | agatgccgta | 480 |
| cgcaccacca | tcaataaaaa | tggtcgtcag | attgtggctg | ctgaaggaac | ggcaaatacc | 540 |
| actgtggttt | atgccggcgg | cgaccagact | gtacatggtc | acgcactgga | taccacgctg | 600 |
| aatggggggt | accagtatgt | gcacaacgga | ggtacagcat | ctgacactgt | tgttaacagt | 660 |
| gacggctggc | agattatcaa | ggaaggtggt | ctggcggatt | tcaccaccgt | taaccagaaa | 720 |
| ggtaaactgc | aggtgaacgc | cggtggtaca | gccacgaatg | tcaccctgac | gcagggcggc | 780 |
| gcactggtca | ccagtacggc | ggcaaccgtc | accggcagca | accgtctggg | caatttcact | 840 |
| gtggaaaacg | gtaatgctga | cggtgttgtt | ctggagtccg | gtggtcgcct | ggatgtactg | 900 |
| gagggccatt | cagcctggaa | aacactggtg | gatgacggcg | gtaccctggc | agtgtctgcc | 960 |
| ggtggtaagg | caacagatgt | caccatgaca | tccggtggtg | ccctgattgc | agacagtggg | 1020 |
| gccactgttg | aggggaccaa | tgccagcggt | aagttcagta | ttgatggcat | atccggtcag | 1080 |
| gccagcggcc | tgctgctgga | aaatggcggc | agctttacgg | ttaatgccgg | aggactggcc | 1140 |
| agcaacacca | ctgtcggaca | tcgtggaaca | ctgacgctgg | ccgccggggg | aagtctgagt | 1200 |
| ggcagaacac | agctcagtaa | aggcgccagt | atggtactga | atggtgatgt | ggtcagtacc | 1260 |
| ggcgatattg | ttaacgccgg | agagattcgc | tttgataatc | agacgacacc | ggatgccgca | 1320 |
| ctgagccgtg | ctgttgcaaa | aggcgactcc | ccggtaacgt | tccataaact | gaccaccagt | 1380 |
| aacctcaccg | gtcagggtgg | caccatcaat | atgcgtgttc | gccttgatgg | cagcaatgcc | 1440 |
| tctgaccagc | tggtgattaa | tggtggtcag | gcaaccggca | aaacctggct | tgcgtttaca | 1500 |
| aatgtcggaa | acagtaacct | cggggtggca | acctccggac | agggtatccg | ggttgtggat | 1560 |
| gcacagaatg | gtgccaccac | agaagaaggt | gcgtttgccc | tgagtcgccc | gcttcaggcc | 1620 |
| ggcgccttta | actacaccct | gaaccgtgac | agcgatgaag | actggtacct | gcgcagtgaa | 1680 |
| aatgcttatc | gtgctgaagt | cccc | | | | 1704 |

<210> SEQ ID NO 44
<211> LENGTH: 568
<212> TYPE: PRT
<213> ORGANISM: Escherichia coli

<400> SEQUENCE: 44

```
Ala Asp Thr Val Val Gln Ala Gly Glu Thr Val Asn Gly Gly Thr Leu
 1               5                  10                  15

Thr Asn His Asp Asn Gln Ile Val Leu Gly Thr Ala Asn Gly Met Thr
            20                  25                  30

Ile Ser Thr Gly Leu Glu Tyr Gly Pro Asp Asn Glu Ala Asn Thr Gly
        35                  40                  45

Gly Gln Trp Ile Gln Asn Gly Gly Ile Ala Asn Thr Thr Val Thr
    50                  55                  60

Gly Gly Gly Leu Gln Arg Val Asn Ala Gly Gly Ser Val Ser Asp Thr
65                  70                  75                  80

Val Ile Ser Ala Gly Gly Gln Ser Leu Gln Gly Gln Ala Val Asn
                85                  90                  95

Thr Thr Leu Asn Gly Gly Glu Gln Trp Val His Glu Gly Gly Ile Ala
            100                 105                 110

Thr Gly Thr Val Ile Asn Glu Lys Gly Trp Gln Ala Val Lys Ser Gly
        115                 120                 125

Ala Met Ala Thr Asp Thr Val Val Asn Thr Gly Ala Glu Gly Gly Pro
    130                 135                 140

Asp Ala Glu Asn Gly Asp Thr Gly Gln Thr Val Tyr Gly Asp Ala Val
145                 150                 155                 160

Arg Thr Thr Ile Asn Lys Asn Gly Arg Gln Ile Val Ala Ala Glu Gly
                165                 170                 175

Thr Ala Asn Thr Thr Val Val Tyr Ala Gly Gly Asp Gln Thr Val His
            180                 185                 190

Gly His Ala Leu Asp Thr Thr Leu Asn Gly Gly Tyr Gln Tyr Val His
        195                 200                 205

Asn Gly Gly Thr Ala Ser Asp Thr Val Val Asn Ser Asp Gly Trp Gln
    210                 215                 220

Ile Ile Lys Glu Gly Gly Leu Ala Asp Phe Thr Thr Val Asn Gln Lys
225                 230                 235                 240

Gly Lys Leu Gln Val Asn Ala Gly Gly Thr Ala Thr Asn Val Thr Leu
                245                 250                 255

Thr Gln Gly Gly Ala Leu Val Thr Ser Thr Ala Ala Thr Val Thr Gly
            260                 265                 270

Ser Asn Arg Leu Gly Asn Phe Thr Val Glu Asn Gly Asn Ala Asp Gly
        275                 280                 285

Val Val Leu Glu Ser Gly Gly Arg Leu Asp Val Leu Glu Gly His Ser
    290                 295                 300

Ala Trp Lys Thr Leu Val Asp Asp Gly Gly Thr Leu Ala Val Ser Ala
305                 310                 315                 320

Gly Gly Lys Ala Thr Asp Val Thr Met Thr Ser Gly Gly Ala Leu Ile
                325                 330                 335

Ala Asp Ser Gly Ala Thr Val Glu Gly Thr Asn Ala Ser Gly Lys Phe
            340                 345                 350

Ser Ile Asp Gly Ile Ser Gly Gln Ala Ser Gly Leu Leu Leu Glu Asn
        355                 360                 365

Gly Gly Ser Phe Thr Val Asn Ala Gly Gly Leu Ala Ser Asn Thr Thr
    370                 375                 380
```

```
Val Gly His Arg Gly Thr Leu Thr Leu Ala Ala Gly Gly Ser Leu Ser
385                 390                 395                 400

Gly Arg Thr Gln Leu Ser Lys Gly Ala Ser Met Val Leu Asn Gly Asp
            405                 410                 415

Val Val Ser Thr Gly Asp Ile Val Asn Ala Gly Glu Ile Arg Phe Asp
            420                 425                 430

Asn Gln Thr Thr Pro Asp Ala Ala Leu Ser Arg Ala Val Ala Lys Gly
            435                 440                 445

Asp Ser Pro Val Thr Phe His Lys Leu Thr Thr Ser Asn Leu Thr Gly
        450                 455                 460

Gln Gly Thr Ile Asn Met Arg Val Arg Leu Asp Gly Ser Asn Ala
465                 470                 475                 480

Ser Asp Gln Leu Val Ile Asn Gly Gly Gln Ala Thr Gly Lys Thr Trp
                485                 490                 495

Leu Ala Phe Thr Asn Val Gly Asn Ser Asn Leu Gly Val Ala Thr Ser
            500                 505                 510

Gly Gln Gly Ile Arg Val Val Asp Ala Gln Asn Gly Ala Thr Thr Glu
            515                 520                 525

Glu Gly Ala Phe Ala Leu Ser Arg Pro Leu Gln Ala Gly Ala Phe Asn
530                 535                 540

Tyr Thr Leu Asn Arg Asp Ser Asp Glu Asp Trp Tyr Leu Arg Ser Glu
545                 550                 555                 560

Asn Ala Tyr Arg Ala Glu Val Pro
                565

<210> SEQ ID NO 45
<211> LENGTH: 561
<212> TYPE: DNA
<213> ORGANISM: Escherichia coli

<400> SEQUENCE: 45
atgttaaaaa aaacattgtt atctatgttc gcaaccgcat tgttatcagg cgttgctttt      60
aacgctcttg ctgacgatgc taatcagggt tcaggtaaaa ttactttaa aggtgaagtt     120 atcgatgcac cttgttctat tgctcctggt gatgaagatc agacaataaa cctcggtgaa     180
gttgctgata ccgtattaaa aagcggtcag aaatcactgc ctgtagatgt caccattcat     240
ttgcaggatt gtattttatc tgacggcact aacactgttg ataaagtcaa atcacccttt     300
agttctgcca gtgttgacgc taccgactcc aacctgctta aaaacactct ggaaggtaac     360
atcggcggcg caactgatgt aggcgtacgt ctggtgaaat cagacaacac caacgtgact     420
cttggcactc caatcactat caacttcccg acgactaact cttaccagga gttgaacttt     480
aaagcccgta tggagtctct gggacgcacc gcgaccccgg gtaacgtgca ggcacaggct     540
aattacgtac tcgactacaa g                                              561

<210> SEQ ID NO 46
<211> LENGTH: 187
<212> TYPE: PRT
<213> ORGANISM: Escherichia coli

<400> SEQUENCE: 46

Met Leu Lys Lys Thr Leu Leu Ser Met Phe Ala Thr Ala Leu Leu Ser
1               5                   10                  15

Gly Val Ala Phe Asn Ala Leu Ala Asp Asp Ala Asn Gln Gly Ser Gly
                20                  25                  30

Lys Ile Thr Phe Lys Gly Glu Val Ile Asp Ala Pro Cys Ser Ile Ala
```

```
            35                  40                  45
Pro Gly Asp Glu Asp Gln Thr Ile Asn Leu Gly Glu Val Ala Asp Thr
 50                  55                  60

Val Leu Lys Ser Gly Gln Lys Ser Leu Pro Val Asp Val Thr Ile His
 65                  70                  75                  80

Leu Gln Asp Cys Ile Leu Ser Asp Gly Thr Asn Val Asp Lys Val
                 85                  90                  95

Lys Ile Thr Phe Ser Ser Ala Ser Val Asp Ala Thr Asp Ser Asn Leu
                100                 105                 110

Leu Lys Asn Thr Leu Glu Gly Asn Ile Gly Gly Ala Thr Asp Val Gly
                115                 120                 125

Val Arg Leu Val Lys Ser Asp Asn Thr Asn Val Thr Leu Gly Thr Pro
            130                 135                 140

Ile Thr Ile Asn Phe Pro Thr Thr Asn Ser Tyr Gln Glu Leu Asn Phe
145                 150                 155                 160

Lys Ala Arg Met Glu Ser Leu Gly Arg Thr Ala Thr Pro Gly Asn Val
                165                 170                 175

Gln Ala Gln Ala Asn Tyr Val Leu Asp Tyr Lys
                180                 185

<210> SEQ ID NO 47
<211> LENGTH: 1470
<212> TYPE: DNA
<213> ORGANISM: Escherichia coli

<400> SEQUENCE: 47
atgaaaaaat ctcttctggc tgtaatgctg acaggactgt tgctctcgt ttctcttccc      60 gctctgggaa atgtcaatct cgaacaatta aagcaaaaag ctgaaagtgg agaagctaaa    120
gcacagttgg agctgggata tcgctatttt cagggtaatg aaacgacaaa ggatctcacc    180
caggcgatgg actggtttcg ccgtgccgca gagcagggat acaccccggc agaatatgta    240
ctggggttac gctatatgaa cggtgaaggt gtgccgcaag attatgctca ggcagttatc    300
tggtacaaaa aagcggcact gaagggcctt ccgcaagcgc agcagaatct gggtgtaatg    360
taccatgaag gtaatggcgt gaaggttgat aaagccgaat ctgtgaaatg gtttcgcctg    420
gcagcagagc aaggtcgtga cagcggccag caaagtatgg gagacgcata ttttgaaggc    480
gatggtgtga cgcgggatta cgttatggca cgtgagtggt atagcaaagc agcggaacaa    540
ggtaacgtct ggtcctgtaa ccagcttggt tatatgtatt ccagagggtt aggcgttgaa    600
agaaacgatg ccatatcggc acaatggtat cgaaaatcag cgacatcagg cgacgagttg    660
gggcagcttc atttagccga tatgtactat ttcggtatcg tgttactca ggattacact    720 cagtcacggg tattattttc ccagtcggca gagcagggaa attctattgc gcagtttcgt    780
ctgggatata tattggagca aggtttagcg ggagcgaaag agccgttaaa agcactggag    840
tggtaccgta atcggcaga acagggaaat tccgatggtc agtattattt ggctcatctg    900
tatgataaag gcgcagaagg tgtagcaaaa atcgagaac aagccatctc ctggtacacg    960
aaatcggcag aacaggggga tgctaccgca caggctaatc tcggcgctat ttacttcaga    1020
cttggttcag aagaagaaca taaaaaggcg gtggaatggt tcgcaaggc cgccgcaaag    1080 ggtgagaaag cggcgcaatt taatttgggt aatgctttac tccagggaaa aggtgttaaa    1140
aaagatgagc aacaggccgc aatctggatg cgaaaagccg cagagcaagg attaagtgca    1200
gcgcaggtac aattaggtga aatctattat tatggcttgg gcgtagaacg tgattatgtg    1260
```

```
caggcctggg cgtggttcga taccgcatcg accaatgata tgaatctttt tggtacagaa    1320
aaccgcaaca ttacagagaa aaaactgaca gccaaacaac tgcaacaggc tgaattatta    1380
tcgcaacaat atatagaaaa atatgccccg gaagcctggg cgagaatgca aaagcttaaa    1440
gcgcaatcag cggtaaagac gggtaataaa                                     1470
```

<210> SEQ ID NO 48
<211> LENGTH: 490
<212> TYPE: PRT
<213> ORGANISM: Escherichia coli

<400> SEQUENCE: 48

```
Met Lys Lys Ser Leu Leu Ala Val Met Leu Thr Gly Leu Phe Ala Leu
 1               5                  10                  15

Val Ser Leu Pro Ala Leu Gly Asn Val Asn Leu Glu Gln Leu Lys Gln
            20                  25                  30

Lys Ala Glu Ser Gly Glu Ala Lys Ala Gln Leu Glu Leu Gly Tyr Arg
        35                  40                  45

Tyr Phe Gln Gly Asn Glu Thr Thr Lys Asp Leu Thr Gln Ala Met Asp
    50                  55                  60

Trp Phe Arg Arg Ala Ala Glu Gln Gly Tyr Thr Pro Ala Glu Tyr Val
65                  70                  75                  80

Leu Gly Leu Arg Tyr Met Asn Gly Glu Gly Val Pro Gln Asp Tyr Ala
                85                  90                  95

Gln Ala Val Ile Trp Tyr Lys Lys Ala Ala Leu Lys Gly Leu Pro Gln
           100                 105                 110

Ala Gln Gln Asn Leu Gly Val Met Tyr His Glu Gly Asn Gly Val Lys
        115                 120                 125

Val Asp Lys Ala Glu Ser Val Lys Trp Phe Arg Leu Ala Ala Glu Gln
    130                 135                 140

Gly Arg Asp Ser Gly Gln Gln Ser Met Gly Asp Ala Tyr Phe Glu Gly
145                 150                 155                 160

Asp Gly Val Thr Arg Asp Tyr Val Met Ala Arg Glu Trp Tyr Ser Lys
                165                 170                 175

Ala Ala Glu Gln Gly Asn Val Trp Ser Cys Asn Gln Leu Gly Tyr Met
            180                 185                 190

Tyr Ser Arg Gly Leu Gly Val Glu Arg Asn Asp Ala Ile Ser Ala Gln
        195                 200                 205

Trp Tyr Arg Lys Ser Ala Thr Ser Gly Asp Glu Leu Gly Gln Leu His
    210                 215                 220

Leu Ala Asp Met Tyr Tyr Phe Gly Ile Gly Val Thr Gln Asp Tyr Thr
225                 230                 235                 240

Gln Ser Arg Val Leu Phe Ser Gln Ser Ala Glu Gln Gly Asn Ser Ile
                245                 250                 255

Ala Gln Phe Arg Leu Gly Tyr Ile Leu Glu Gln Gly Leu Ala Gly Ala
            260                 265                 270

Lys Glu Pro Leu Lys Ala Leu Glu Trp Tyr Arg Lys Ser Ala Glu Gln
        275                 280                 285

Gly Asn Ser Asp Gly Gln Tyr Tyr Leu Ala His Leu Tyr Asp Lys Gly
    290                 295                 300

Ala Glu Gly Val Ala Lys Asn Arg Glu Gln Ala Ile Ser Trp Tyr Thr
305                 310                 315                 320

Lys Ser Ala Glu Gln Gly Asp Ala Thr Ala Gln Ala Asn Leu Gly Ala
                325                 330                 335
```

```
Ile Tyr Phe Arg Leu Gly Ser Glu Glu His Lys Lys Ala Val Glu
            340                 345                 350

Trp Phe Arg Lys Ala Ala Ala Lys Gly Glu Lys Ala Ala Gln Phe Asn
            355                 360                 365

Leu Gly Asn Ala Leu Leu Gln Gly Lys Gly Val Lys Lys Asp Glu Gln
        370                 375                 380

Gln Ala Ala Ile Trp Met Arg Lys Ala Ala Glu Gln Gly Leu Ser Ala
385                 390                 395                 400

Ala Gln Val Gln Leu Gly Glu Ile Tyr Tyr Gly Leu Gly Val Glu
            405                 410                 415

Arg Asp Tyr Val Gln Ala Trp Ala Trp Phe Asp Thr Ala Ser Thr Asn
            420                 425                 430

Asp Met Asn Leu Phe Gly Thr Glu Asn Arg Asn Ile Thr Glu Lys Lys
            435                 440                 445

Leu Thr Ala Lys Gln Leu Gln Gln Ala Glu Leu Leu Ser Gln Gln Tyr
        450                 455                 460

Ile Glu Lys Tyr Ala Pro Glu Ala Trp Ala Arg Met Gln Lys Leu Lys
465                 470                 475                 480

Ala Gln Ser Ala Val Lys Thr Gly Asn Lys
            485                 490

<210> SEQ ID NO 49
<211> LENGTH: 4556
<212> TYPE: DNA
<213> ORGANISM: Escherichia coli

<400> SEQUENCE: 49
atgaataaga aatttaaata taagaaatcg cttttagcgg ctattttaag cgcaaccctg      60
ttagccggtt gtgatggtgg tggttcagga tcgtcctccg atacgccgtc tgtagattct     120
ggatcaggga ctttgccgga agtgaaaccc gatccaacac caaccccgga gccgacacct     180
gagccgacgc cggacccaga acctacgccg atccaacac tgatcctga ccgacacca     240 gaaccggagc cagaacctgt tcctacgaaa acgggttatc tgaccctggg cggaagccag     300
cgggtaactg gtgctacctg taatggtgaa tccagcgatg ctttaccttt acgccaggc     360 aataccgtga gttgtgtggt gggcagtacg accattgcaa cattcaacac ccagtcagaa     420
gctgcgcgta gcctgcgtgc ggttgacaaa gtgtcgttta gcctggagga cgcgcaggag     480
ctggcgaatt ctgaaaataa gaaaaccaac gccatctctc tggtgacgtc cagcgacagt     540
tgccccgcag atgcagaaca gctttgtctt actttctcgt cagtggttga tcgcgcgcga     600
tttgaaaaac tgtataagca aattgatctg gcaacagaca atttcagcaa gctggtcaat     660
gaagaggtgg aaaacaatgc tgcgactgat aaagcgccgt ccacccatac ctcaacggta     720
gtgccagtca cgacagaggg aacaaaaccg gatctgaacg cgtccttcgt gtcggctaac     780
gcggaacagt tttatcagta tcaacccact gaaatcattc tttccgaagg ccaactggtg     840
gatagcctgg ggaacggtgt tgctggcgtt gactactaca ccaattcagg ccgtggcgta     900
actgacgaaa acgtaaaatt ttcctttagc tggggcgaaa ccatctcctt tggtatcgat     960
acctttgaac tgggctcagt acgtggcaat aagtcgacca ttgcgctgac tgaattgggt    1020
gatgaagttc gcggggcaaa tatcgatcag ctcattcatc gttattcgac gactggtcaa    1080
aataatactc gtgttgttcc ggacgatgta cgcaaggtct tgccgaata tcccaacgtg    1140 atcaacgaga taatcaatct ttcgttatcc aacggtgcga cgctggatga aggcgatcaa    1200
aacgttgtgc tgcctaacga atttatcgag cagtttaaga cgggtcaggc caaagagatc    1260
```

```
gataccgcga tttgtgcgaa aaccgacggt tgtaacgagg ctcgctggtt ctcgctgaca   1320
acgcgcaatg ttaatgacgg ccagattcag ggcgttatta acaagctgtg gggcgtggat   1380
acgaactatc agtctgtcag caagttccac gtcttccatg actctaccaa cttctatggc   1440
agcaccggta acgcgcgcgg tcaggcggtg gtaaatatct ccaactcggc attcccgatt   1500
ctgatggcgc gtaatgataa aaactactgg ctggcgtttg gcgaaaaacg cgcctgggat   1560
aaaaatgagc tggcgtacat tacggaagcg ccttccattg tgcagccaga gaacgttacg   1620
cgcgatactg cgactttcaa cctgccgttt atttcgctgg ggcaagtcgg tgaaggcaaa   1680
ctgatggtta tcggtaaccc gcactacaac agcatcctgc gttgcccgaa cggttacagt   1740
tggggcggtg gtgttaatag taaaggtgag tgtacgctca gcggtgattc tgatgacatg   1800
aagcacttta tgcagaacgt actgcgctac ttgtcaaatg acatctggca gccaaatacc   1860
aagagcatca tgactgtcgg caccaacctg gagaacgttt atttcaaaaa agcgggccag   1920
gtattgggaa atagtgcacc atttgctttc catgaggatt tcactggtat cacggttaaa   1980
cagttgacca gctatggcga tctgaatccg gaagagattc cgttgctgat cctcaacggc   2040
tttgaatatg tgactcagtg gtctggcgat ccctatgctg tgcctctgcg tgcagatacc   2100
agcaaaccga agctgactca gcaggatgtg accgatctga tcgcttatct gaacaaaggt   2160
ggctcggtgc tgatcatgga aaacgtgatg agcaatctta aggaagagag cgcgtccagt   2220
tttgtgcgtc tgctggatgc cgcgggtctg tcaatggctc tgaacaaatc ggtggtgaac   2280
aacgatccgc aagggtatcc ggatcgcgtt cgtcagcgtc gcgcgactgg catttgggtt   2340
tatgaacgtt atcctgctgc agacggcgcg caaccgccgt acaccatcga cccaaataca   2400
ggggaagtga cctggaaata ccagcaagac aacaagcctg atgacaagcc gaaactggaa   2460
gttgcgagct ggcaggagga agttgagggc aaacaggtaa cgcgttatgc ctttattgat   2520
gaagcggaat acacaacaga gaatctctg gaagcggcaa aggcaaaaat ctttgagaag   2580
tttcctgggt tacaggagtg taaggactcg acttaccatt acgagattaa ctgtttggag   2640
cgccgcccag gcacggatgt tccggtaaca ggtggcatgt atgttccgcg ctatacgcaa   2700
ctgaatcttg acgccgacac cgcgaaagcg atggtgcagg cggcggattt aggcaccaac   2760
attcagcgcc tgtatcagca tgagctttat ttccgtacca aaggcagtaa aggtgagcgt   2820
ctgaacagtg ttgatctgga acgtctgtac cagaacatgt cggtctggct gtggaacgat   2880
acgaaatatc gttacgaaga gggcaaggaa gatgagctgg gctttaaaac gttcaccgag   2940
ttcctgaact gctacgccaa tgatgcctat gcaggcggca ccaagtgctc cgcagatctg   3000
aaaaaatcgc tggtcgataa caacatgatc tacggtgacg gtagcagcaa agcgggcatg   3060
atgaacccaa gctatccgct caactatatg aaaaaccgc tgacgcgtct gatgctgggc   3120
cgttcctggt gggatctgaa cattaaggtt gatgtggaga agtacccagg atccgtatcg   3180
gcaaagggtg agagcgttac ggaaaacatc agcctgtact cgaatccgac caaatggttt   3240
gcgggtaaca tgcagtcaac cggcctgtgg gcaccggccc agcaggacgt caccattaag   3300
tcttcggcgt cagtcccagt gactgttacc gtggcgctgg ctgacgacct gactggacgt   3360
gagaagcatg aagttgcgct gaaccgtccg ccaagagtga ctaaaacgta tactctggag   3420
gctaacggtg aagtgacctt caaggtgcct tatggtggtc tgatttatat caagggcgac   3480
agtaaggatg atgtttctgc taacttcacc tttaccggtg tagtaaaagc gccgttctat   3540
aaagacggcg aatggaaaaa cgatctggac tcaccggcgc cgctgggcga gctggagtct   3600
```

-continued

```
gcgtcgttcg tctataccac gccgaagaag aaccttgagg ccagcaattt cactggtggt    3660
gtagcagaat tcgctaaaga tctggatacc tttgccagct cgatgaatga cttctacggt    3720
cgtaatgatg aagacggtaa gcaccggatg tttacctata aaaacttgac ggggcacaag    3780
catcgtttca ccaacgatgt gcagatctcc atcggtgatg cgcactcggg ttatccggta    3840
atgaacagca gcttctcgac gaacagcacc acgctgccga cgacgccgct gaacgactgg    3900
ctgatttggc acgaagtcgg tcataacgct gcagaaacac cgctgaacgt accgggtgca    3960
actgaagtgg cgaacaacgt gctggcgctg tacatgcagg atcgctatct cggtaagatg    4020
aaccgtgtcg ctgacgacat taccgtcgcg ccggaatatc tggacgagag caacggtcag    4080
gcctgggcgc gcggcggtgc gggtgaccgt ctgctgatgt acgcacagtt gaaggagtgg    4140
gcagaggaaa actttgatat caaacagtgg tatccagatg gtgagctgcc taagttctac    4200
agcgatcgta aagggatgaa gggctggaac ctgttccagt tgatgcaccg taaagcgcgc    4260
ggcgatgatg ttggtaacag cacctttggt ggcaagaatt actgtgctga atccaatggt    4320
aacgctgccg acacgctgat gctgtgtgca tcctgggtcg ctcaggcgga tctttcggaa    4380
ttctttaaga aatggaatcc gggtgcaagt gcttaccagt tgccgggagc aacggagatg    4440
agtttccagg gcggtgtgag ctcttcggct tacagcacgc tggcgtcact caagctgccg    4500
aaaccggaaa aagggccgga aaccattaac aaggttaccg agcataagat gtctgc        4556
```

<210> SEQ ID NO 50
<211> LENGTH: 1520
<212> TYPE: PRT
<213> ORGANISM: Escherichia coli

<400> SEQUENCE: 50

```
Met Asn Lys Lys Phe Lys Tyr Lys Lys Ser Leu Leu Ala Ala Ile Leu
  1               5                  10                  15

Ser Ala Thr Leu Leu Ala Gly Cys Asp Gly Gly Gly Ser Gly Ser Ser
             20                  25                  30

Ser Asp Thr Pro Ser Val Asp Ser Gly Ser Gly Thr Leu Pro Glu Val
         35                  40                  45

Lys Pro Asp Pro Thr Pro Thr Pro Glu Pro Thr Pro Glu Pro Thr Pro
     50                  55                  60

Asp Pro Glu Pro Thr Pro Asp Pro Thr Pro Asp Pro Glu Pro Thr Pro
 65                  70                  75                  80

Glu Pro Glu Pro Glu Pro Val Pro Thr Lys Thr Gly Tyr Leu Thr Leu
                 85                  90                  95

Gly Gly Ser Gln Arg Val Thr Gly Ala Thr Cys Asn Gly Glu Ser Ser
            100                 105                 110

Asp Gly Phe Thr Phe Thr Pro Gly Asn Thr Val Ser Cys Val Val Gly
        115                 120                 125

Ser Thr Thr Ile Ala Thr Phe Asn Thr Gln Ser Glu Ala Ala Arg Ser
    130                 135                 140

Leu Arg Ala Val Asp Lys Val Ser Phe Ser Leu Glu Asp Ala Gln Glu
145                 150                 155                 160

Leu Ala Asn Ser Glu Asn Lys Lys Thr Asn Ala Ile Ser Leu Val Thr
                165                 170                 175

Ser Ser Asp Ser Cys Pro Ala Asp Ala Glu Gln Leu Cys Leu Thr Phe
            180                 185                 190

Ser Ser Val Val Asp Arg Ala Arg Phe Glu Lys Leu Tyr Lys Gln Ile
        195                 200                 205
```

```
Asp Leu Ala Thr Asp Asn Phe Ser Lys Leu Val Asn Glu Glu Val Glu
210                 215                 220

Asn Asn Ala Ala Thr Asp Lys Ala Pro Ser Thr His Thr Ser Thr Val
225                 230                 235                 240

Val Pro Val Thr Thr Glu Gly Thr Lys Pro Asp Leu Asn Ala Ser Phe
                245                 250                 255

Val Ser Ala Asn Ala Glu Gln Phe Tyr Gln Tyr Gln Pro Thr Glu Ile
            260                 265                 270

Ile Leu Ser Glu Gly Gln Leu Val Asp Ser Leu Gly Asn Gly Val Ala
        275                 280                 285

Gly Val Asp Tyr Tyr Thr Asn Ser Gly Arg Gly Val Thr Asp Glu Asn
    290                 295                 300

Gly Lys Phe Ser Phe Ser Trp Gly Glu Thr Ile Ser Phe Gly Ile Asp
305                 310                 315                 320

Thr Phe Glu Leu Gly Ser Val Arg Gly Asn Lys Ser Thr Ile Ala Leu
                325                 330                 335

Thr Glu Leu Gly Asp Glu Val Arg Gly Ala Asn Ile Asp Gln Leu Ile
            340                 345                 350

His Arg Tyr Ser Thr Thr Gly Gln Asn Asn Thr Arg Val Val Pro Asp
        355                 360                 365

Asp Val Arg Lys Val Phe Ala Glu Tyr Pro Asn Val Ile Asn Glu Ile
    370                 375                 380

Ile Asn Leu Ser Leu Ser Asn Gly Ala Thr Leu Asp Glu Gly Asp Gln
385                 390                 395                 400

Asn Val Val Leu Pro Asn Glu Phe Ile Glu Gln Phe Lys Thr Gly Gln
                405                 410                 415

Ala Lys Glu Ile Asp Thr Ala Ile Cys Ala Lys Thr Asp Gly Cys Asn
            420                 425                 430

Glu Ala Arg Trp Phe Ser Leu Thr Thr Arg Asn Val Asn Asp Gly Gln
        435                 440                 445

Ile Gln Gly Val Ile Asn Lys Leu Trp Gly Val Asp Thr Asn Tyr Gln
    450                 455                 460

Ser Val Ser Lys Phe His Val Phe His Asp Ser Thr Asn Phe Tyr Gly
465                 470                 475                 480

Ser Thr Gly Asn Ala Arg Gly Gln Ala Val Val Asn Ile Ser Asn Ser
                485                 490                 495

Ala Phe Pro Ile Leu Met Ala Arg Asn Asp Lys Asn Tyr Trp Leu Ala
            500                 505                 510

Phe Gly Glu Lys Arg Ala Trp Asp Lys Asn Glu Leu Ala Tyr Ile Thr
        515                 520                 525

Glu Ala Pro Ser Ile Val Gln Pro Glu Asn Val Thr Arg Asp Thr Ala
    530                 535                 540

Thr Phe Asn Leu Pro Phe Ile Ser Leu Gly Gln Val Gly Glu Gly Lys
545                 550                 555                 560

Leu Met Val Ile Gly Asn Pro His Tyr Asn Ser Ile Leu Arg Cys Pro
                565                 570                 575

Asn Gly Tyr Ser Trp Gly Gly Val Asn Ser Lys Gly Glu Cys Thr
            580                 585                 590

Leu Ser Gly Asp Ser Asp Met Lys His Phe Met Gln Asn Val Leu
        595                 600                 605

Arg Tyr Leu Ser Asn Asp Ile Trp Gln Pro Asn Thr Lys Ser Ile Met
    610                 615                 620

Thr Val Gly Thr Asn Leu Glu Asn Val Tyr Phe Lys Lys Ala Gly Gln
```

-continued

```
            625                 630                 635                 640
Val Leu Gly Asn Ser Ala Pro Phe Ala Phe His Glu Asp Phe Thr Gly
                    645                 650                 655
Ile Thr Val Lys Gln Leu Thr Ser Tyr Gly Asp Leu Asn Pro Glu Glu
                660                 665                 670
Ile Pro Leu Leu Ile Leu Asn Gly Phe Glu Tyr Val Thr Gln Trp Ser
            675                 680                 685
Gly Asp Pro Tyr Ala Val Pro Leu Arg Ala Asp Thr Ser Lys Pro Lys
        690                 695                 700
Leu Thr Gln Gln Asp Val Thr Asp Leu Ile Ala Tyr Leu Asn Lys Gly
705                 710                 715                 720
Gly Ser Val Leu Ile Met Glu Asn Val Met Ser Asn Leu Lys Glu Glu
                    725                 730                 735
Ser Ala Ser Ser Phe Val Arg Leu Leu Asp Ala Ala Gly Leu Ser Met
                740                 745                 750
Ala Leu Asn Lys Ser Val Val Asn Asn Asp Pro Gln Gly Tyr Pro Asp
            755                 760                 765
Arg Val Arg Gln Arg Arg Ala Thr Gly Ile Trp Val Tyr Glu Arg Tyr
        770                 775                 780
Pro Ala Ala Asp Gly Ala Gln Pro Pro Tyr Thr Ile Asp Pro Asn Thr
785                 790                 795                 800
Gly Glu Val Thr Trp Lys Tyr Gln Gln Asp Asn Lys Pro Asp Asp Lys
                    805                 810                 815
Pro Lys Leu Glu Val Ala Ser Trp Gln Glu Glu Val Glu Gly Lys Gln
                820                 825                 830
Val Thr Arg Tyr Ala Phe Ile Asp Glu Ala Glu Tyr Thr Thr Glu Glu
            835                 840                 845
Ser Leu Glu Ala Ala Lys Ala Lys Ile Phe Glu Lys Phe Pro Gly Leu
        850                 855                 860
Gln Glu Cys Lys Asp Ser Thr Tyr His Tyr Glu Ile Asn Cys Leu Glu
865                 870                 875                 880
Arg Arg Pro Gly Thr Asp Val Pro Val Thr Gly Gly Met Tyr Val Pro
                    885                 890                 895
Arg Tyr Thr Gln Leu Asn Leu Asp Ala Asp Thr Ala Lys Ala Met Val
                900                 905                 910
Gln Ala Ala Asp Leu Gly Thr Asn Ile Gln Arg Leu Tyr Gln His Glu
            915                 920                 925
Leu Tyr Phe Arg Thr Lys Gly Ser Lys Gly Glu Arg Leu Asn Ser Val
        930                 935                 940
Asp Leu Glu Arg Leu Tyr Gln Asn Met Ser Val Trp Leu Trp Asn Asp
945                 950                 955                 960
Thr Lys Tyr Arg Tyr Glu Glu Gly Lys Glu Asp Glu Leu Gly Phe Lys
                    965                 970                 975
Thr Phe Thr Glu Phe Leu Asn Cys Tyr Ala Asn Asp Ala Tyr Ala Gly
                980                 985                 990
Gly Thr Lys Cys Ser Ala Asp Leu Lys Lys Ser Leu Val Asp Asn Asn
            995                 1000                1005
Met Ile Tyr Gly Asp Gly Ser Ser Lys Ala Gly Met Met Asn Pro Ser
        1010                1015                1020
Tyr Pro Leu Asn Tyr Met Glu Lys Pro Leu Thr Arg Leu Met Leu Gly
1025                1030                1035                1040
Arg Ser Trp Trp Asp Leu Asn Ile Lys Val Asp Val Glu Lys Tyr Pro
                    1045                1050                1055
```

```
Gly Ser Val Ser Ala Lys Gly Glu Ser Val Thr Glu Asn Ile Ser Leu
            1060                1065                1070

Tyr Ser Asn Pro Thr Lys Trp Phe Ala Gly Asn Met Gln Ser Thr Gly
        1075                1080                1085

Leu Trp Ala Pro Ala Gln Gln Asp Val Thr Ile Lys Ser Ser Ala Ser
1090                1095                1100

Val Pro Val Thr Val Thr Val Ala Leu Ala Asp Asp Leu Thr Gly Arg
1105                1110                1115                1120

Glu Lys His Glu Val Ala Leu Asn Arg Pro Pro Arg Val Thr Lys Thr
            1125                1130                1135

Tyr Thr Leu Glu Ala Asn Gly Glu Val Thr Phe Lys Val Pro Tyr Gly
        1140                1145                1150

Gly Leu Ile Tyr Ile Lys Gly Asp Ser Lys Asp Val Ser Ala Asn
            1155                1160                1165

Phe Thr Phe Thr Gly Val Val Lys Ala Pro Phe Tyr Lys Asp Gly Glu
    1170                1175                1180

Trp Lys Asn Asp Leu Asp Ser Pro Ala Pro Leu Gly Glu Leu Glu Ser
1185                1190                1195                1200

Ala Ser Phe Val Tyr Thr Thr Pro Lys Lys Asn Leu Glu Ala Ser Asn
            1205                1210                1215

Phe Thr Gly Gly Val Ala Glu Phe Ala Lys Asp Leu Asp Thr Phe Ala
        1220                1225                1230

Ser Ser Met Asn Asp Phe Tyr Gly Arg Asn Asp Glu Asp Gly Lys His
            1235                1240                1245

Arg Met Phe Thr Tyr Lys Asn Leu Thr Gly His Lys His Arg Phe Thr
1250                1255                1260

Asn Asp Val Gln Ile Ser Ile Gly Asp Ala His Ser Gly Tyr Pro Val
1265                1270                1275                1280

Met Asn Ser Ser Phe Ser Thr Asn Ser Thr Thr Leu Pro Thr Thr Pro
            1285                1290                1295

Leu Asn Asp Trp Leu Ile Trp His Glu Val Gly His Asn Ala Ala Glu
        1300                1305                1310

Thr Pro Leu Asn Val Pro Gly Ala Thr Glu Val Ala Asn Asn Val Leu
        1315                1320                1325

Ala Leu Tyr Met Gln Asp Arg Tyr Leu Gly Lys Met Asn Arg Val Ala
        1330                1335                1340

Asp Asp Ile Thr Val Ala Pro Glu Tyr Leu Asp Glu Ser Asn Gly Gln
1345                1350                1355                1360

Ala Trp Ala Arg Gly Gly Ala Gly Asp Arg Leu Leu Met Tyr Ala Gln
            1365                1370                1375

Leu Lys Glu Trp Ala Glu Glu Asn Phe Asp Ile Lys Gln Trp Tyr Pro
        1380                1385                1390

Asp Gly Glu Leu Pro Lys Phe Tyr Ser Asp Arg Lys Gly Met Lys Gly
            1395                1400                1405

Trp Asn Leu Phe Gln Leu Met His Arg Lys Ala Arg Gly Asp Asp Val
        1410                1415                1420

Gly Asn Ser Thr Phe Gly Gly Lys Asn Tyr Cys Ala Glu Ser Asn Gly
1425                1430                1435                1440

Asn Ala Ala Asp Thr Leu Met Leu Cys Ala Ser Trp Val Ala Gln Ala
            1445                1450                1455

Asp Leu Ser Glu Phe Phe Lys Lys Trp Asn Pro Gly Ala Ser Ala Tyr
            1460                1465                1470
```

```
Gln Leu Pro Gly Ala Thr Glu Met Ser Phe Gln Gly Val Ser Ser
         1475                1480                1485

Ser Ala Tyr Ser Thr Leu Ala Ser Leu Lys Leu Pro Lys Pro Glu Lys
         1490                1495                1500

Gly Pro Glu Thr Ile Asn Lys Val Thr Glu His Lys Met Ser Ala Glu
1505                1510                1515                1520

<210> SEQ ID NO 51
<211> LENGTH: 26
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(26)
<223> OTHER INFORMATION: n = Inosine

<400> SEQUENCE: 51 ncncncnc ncncncncnc ncncnc                                    26

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Lys Leu Lys Leu Leu Leu Leu Leu Lys Leu Lys
1               5                   10

<210> SEQ ID NO 53
<211> LENGTH: 1042
<212> TYPE: PRT
<213> ORGANISM: Artificial Sequence
<220> FEATURE:
<223> OTHER INFORMATION: Consensus Sequence
<221> NAME/KEY: VARIANT
<222> LOCATION: (1)...(1042)
<223> OTHER INFORMATION: Xaa = Any Amino Acid

<400> SEQUENCE: 53

Met Lys Arg His Leu Asn Thr Xaa Tyr Arg Leu Val Trp Asn His Xaa
1               5                   10                  15

Thr Gly Xaa Xaa Val Val Ala Ser Glu Leu Ala Arg Xaa Arg Gly Lys
            20                  25                  30

Xaa Xaa Gly Val Ala Xaa Ala Leu Ser Leu Ala Xaa Xaa Thr Xaa Xaa
        35                  40                  45

Pro Xaa Leu Xaa Ala Asp Xaa Val Val Xaa Xaa Gly Glu Thr Val Xaa
50                  55                  60

Xaa Gly Thr Leu Xaa Asn His Asp Xaa Gln Xaa Val Xaa Gly Thr Xaa
65                  70                  75                  80

Xaa Gly Xaa Thr Xaa Ser Xaa Gly Leu Glu Xaa Gly Xaa Asp Xaa Xaa
            85                  90                  95

Xaa Asn Thr Gly Gly Gln Xaa Xaa Xaa Xaa Gly Gly Xaa Xaa Xaa Xaa
            100                 105                 110

Thr Xaa Xaa Xaa Xaa Xaa Gly Xaa Gln Xaa Val Xaa Gly Gly Xaa
        115                 120                 125

Xaa Xaa Asp Thr Xaa Ile Xaa Xaa Gly Gly Gly Gln Xaa Leu Xaa Gly
        130                 135                 140

Xaa Ala Xaa Xaa Thr Xaa Leu Xaa Xaa Xaa Gly Xaa Gln Trp Xaa His
```

```
                145                 150                 155                 160
Xaa Gly Xaa Xaa Ala Xaa Xaa Thr Xaa Ile Asn Xaa Xaa Gly Xaa Gln
                    165                 170                 175
Xaa Xaa Lys Xaa Gly Xaa Xaa Xaa Thr Xaa Thr Xaa Xaa Asn Thr Gly
                    180                 185                 190
Ala Glu Gly Gly Pro Xaa Xaa Xaa Asn Xaa Xaa Xaa Gly Gln Xaa Val
            195                 200                 205
Xaa Gly Xaa Ala Xaa Xaa Thr Thr Ile Asn Xaa Asn Gly Arg Gln Xaa
        210                 215                 220
Xaa Xaa Xaa Xaa Gly Xaa Ala Xaa Xaa Thr Xaa Xaa Tyr Xaa Gly Gly
225                 230                 235                 240
Asp Gln Xaa Val His Gly Xaa Ala Xaa Xaa Thr Xaa Leu Xaa Gly Gly
                245                 250                 255
Xaa Gln Tyr Val His Xaa Xaa Gly Xaa Xaa Xaa Xaa Thr Xaa Xaa Asn
            260                 265                 270
Xaa Xaa Gly Trp Gln Xaa Xaa Lys Xaa Gly Gly Xaa Xaa Xaa Xaa Thr
        275                 280                 285
Xaa Xaa Asn Gln Xaa Gly Xaa Leu Xaa Val Xaa Ala Gly Gly Xaa Ala
        290                 295                 300
Xaa Xaa Val Thr Xaa Xaa Xaa Gly Gly Ala Leu Val Thr Ser Thr Ala
305                 310                 315                 320
Ala Thr Val Xaa Gly Xaa Asn Arg Leu Gly Xaa Phe Xaa Val Xaa Xaa
                325                 330                 335
Gly Xaa Ala Asp Xaa Val Val Leu Glu Xaa Gly Gly Arg Leu Asp Val
            340                 345                 350
Leu Xaa Xaa His Xaa Ala Xaa Xaa Thr Xaa Val Asp Asp Gly Gly Xaa
        355                 360                 365
Leu Xaa Xaa Xaa Xaa Gly Gly Xaa Ala Thr Xaa

```
Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Asn
        595                 600                 605

Leu Xaa Gly Gln Xaa Gly Thr Ile Xaa Xaa Arg Val Xaa Xaa Asp Xaa
    610                 615                 620

Xaa Xaa Asn Xaa Xaa Asp Xaa Leu Val Ile Xaa Gly Gly Xaa Ala Thr
625                 630                 635                 640

Gly Lys Thr Xaa Leu Xaa Xaa Xaa Asn Xaa Gly Asn Ser Xaa Xaa Gly
                645                 650                 655

Xaa Ala Thr Xaa Gly Xaa Gly Ile Xaa Val Val Xaa Ala Xaa Asn Gly
            660                 665                 670

Ala Thr Thr Glu Glu Xaa Xaa Phe Xaa Xaa Xaa Xaa Xaa Leu Xaa Ala
        675                 680                 685

Gly Ala Phe Asn Tyr Xaa Leu Asn Arg Asp Ser Asp Glu Xaa Trp Tyr
    690                 695                 700

Leu Arg Ser Glu Xaa Xaa Tyr Arg Ala Glu Val Pro Leu Tyr Xaa Ser
705                 710                 715                 720

Met Leu Thr Gln Ala Met Asp Tyr Asp Arg Ile Xaa Ala Gly Ser Arg
                725                 730                 735

Ser His Gln Gly Val Gly Glu Asn Asn Ser Xaa Arg Leu Ser Ile Gln
            740                 745                 750

Gly Gly His Leu Gly His Xaa Asn Asn Gly Gly Ile Ala Arg Gly Ala
        755                 760                 765

Thr Pro Glu Ser Xaa Gly Ser Tyr Gly Xaa Val Arg Leu Glu Xaa Asp
    770                 775                 780

Leu Xaa Arg Thr Xaa Val Ala Gly Met Ser Xaa Thr Xaa Gly Xaa Xaa
785                 790                 795                 800

Xaa Ala Ala Gly His Ser Ser Val Asp Val Lys Xaa Asp Asp Gly Ser
                805                 810                 815

Arg Ala Gly Thr Xaa Arg Asp Asp Ala Gly Xaa Leu Gly Gly Tyr Xaa
            820                 825                 830

Xaa Leu Xaa His Xaa Xaa Ser Gly Leu Trp Ala Asp Ile Xaa Ala Gln
        835                 840                 845

Gly Thr Xaa His Ser Met Lys Ala Ser Xaa Xaa Asn Asn Asp Phe Arg
    850                 855                 860

Xaa Arg Gly Xaa Gly Trp Leu Gly Ser Leu Glu Thr Gly Leu Pro Phe
865                 870                 875                 880

Ser Ile Thr Asp Asn Xaa Met Leu Glu Pro Xaa Leu Xaa Tyr Thr Trp
                885                 890                 895

Gln Gly Leu Ser Leu Asp Asp Gly Xaa Asp Asn Ala Xaa Tyr Val Lys
            900                 905                 910

Phe Gly His Gly Ser Xaa Gln His Xaa Arg Ala Gly Phe Arg Leu Gly
        915                 920                 925

Ser His Xaa Asp Met Xaa Phe Gly Xaa Gly Thr Ser Ser Arg Xaa Xaa
    930                 935                 940

Leu Xaa Xaa Ser Xaa Lys His Xaa Xaa Xaa Glu Leu Pro Val Asn Trp
945                 950                 955                 960

Trp Val Gln Pro Ser Val Ile Arg Thr Xaa Ser Ser Arg Gly Asp Met
                965                 970                 975

Xaa Xaa Gly Thr Xaa Xaa Ala Gly Ser Xaa Met Thr Phe Ser Pro Ser
            980                 985                 990

```
Xaa Asn Gly Thr Xaa Leu Asp Leu Gln Ala Gly Leu Glu Ala Arg Xaa
            995                 1000                1005

Arg Glu Asn Ile Thr Leu Gly Val Gln Ala Gly Tyr Xaa His Ser Xaa
    1010                1015                1020

Xaa Gly Xaa Ser Ala Glu Gly Tyr Asn Xaa Gln Ala Thr Leu Asn Xaa
1025                1030                1035                1040

Thr Phe

<210> SEQ ID NO 54
<211> LENGTH: 490
<212> TYPE: PRT
<213> ORGANISM: Artificial Sequence
<220> FEATURE:
<223> OTHER INFORMATION: Consensus Sequence
<221> NAME/KEY: VARIANT
<222> LOCATION: (1)...(490)
<223> OTHER INFORMATION: Xaa = Any Amino Acid

<400> SEQUENCE: 54

Met Lys Lys Ser Leu Leu Ala Xaa Xaa Leu Thr Gly Leu Phe Ala Leu
 1               5                  10                  15

Val Ser Leu Pro Ala Leu Gly Asn Val Asn Xaa Glu Gln Leu Lys Gln
             20                  25                  30

Lys Ala Glu Xaa Gly Glu Ala Lys Ala Gln Leu Glu Leu Gly Tyr Arg
         35                  40                  45

Tyr Phe Gln Gly Asn Glu Thr Thr Lys Asp Leu Thr Xaa Ala Xaa Asp
     50                  55                  60

Trp Phe Arg Arg Ala Ala Glu Gln Gly Tyr Thr Pro Ala Glu Xaa Val
 65                  70                  75                  80

Leu Gly Leu Arg Tyr Met Asn Gly Glu Gly Val Pro Xaa Asp Tyr Ala
                 85                  90                  95

Gln Ala Val Ile Trp Tyr Lys Lys Ala Ala Leu Lys Gly Leu Pro Gln
            100                 105                 110

Ala Gln Gln Asn Leu Gly Val Met Tyr His Xaa Gly Xaa Gly Val Lys
            115                 120                 125

Xaa Asp Lys Ala Glu Ser Val Lys Trp Phe Arg Leu Ala Ala Glu Gln
130                 135                 140

Gly Arg Asp Ser Gly Gln Gln Ser Met Gly Asp Ala Tyr Phe Glu Gly
145                 150                 155                 160

Asp Gly Val Thr Arg Asp Tyr Val Met Ala Arg Glu Trp Tyr Ser Lys
                165                 170                 175

Ala Ala Glu Gln Gly Asn Val Trp Ser Cys Asn Gln Leu Gly Tyr Xaa
            180                 185                 190

Tyr Ser Xaa Gly Leu Gly Val Glu Xaa Asn Asp Ala Ile Ser Ala Gln
        195                 200                 205

Trp Tyr Arg Lys Ser Ala Thr Ser Gly Asp Glu Leu Gly Gln Leu His
210                 215                 220

Leu Ala Asp Met Tyr Tyr Phe Gly Ile Gly Val Thr Gln Asp Tyr Thr
225                 230                 235                 240

Gln Ser Arg Xaa Leu Phe Xaa Gln Ser Ala Glu Gln Gly Asn Xaa Ile
                245                 250                 255

Ala Gln Xaa Arg Leu Gly Tyr Ile Leu Glu Xaa Gly Leu Ala Gly Ala
            260                 265                 270

Lys Glu Pro Leu Lys Ala Leu Glu Trp Tyr Arg Lys Ser Ala Glu Gln
            275                 280                 285

Gly Asn Xaa Xaa Gly Gln Tyr Tyr Leu Ala Xaa Xaa Tyr Xaa Xaa Xaa
```

```
                290                 295                 300
Ala Glu Gly Xaa Xaa Xaa Asn Arg Glu Gln Ala Ile Xaa Trp Tyr Thr
305                 310                 315                 320

Lys Ser Ala Glu Gln Gly Asp Xaa Xaa Ala Gln Xaa Asn Leu Gly Ala
                325                 330                 335

Xaa Xaa Xaa Arg Xaa Gly Ser Glu Glu Xaa Xaa Xaa Ala Val Xaa
                340                 345                 350

Trp Xaa Arg Lys Ala Ala Xaa Xaa Gly Xaa Xaa Xaa Ala Gln Phe Asn
                355                 360                 365

Leu Gly Asn Ala Leu Leu Gln Gly Lys Gly Val Lys Lys Asp Glu Gln
                370                 375                 380

Gln Ala Ala Ile Trp Met Arg Lys Ala Leu Glu Gln Gly Xaa Ser Xaa
385                 390                 395                 400

Ala Gln Val Gln Leu Gly Glu Ile Tyr Tyr Tyr Gly Leu Gly Val Glu
                405                 410                 415

Arg Asp Tyr Val Gln Ala Trp Ala Trp Phe Asp Thr Ala Ser Thr Asn
                420                 425                 430

Asp Met Asn Leu Phe Gly Thr Glu Asn Arg Asn Ile Thr Glu Lys Lys
                435                 440                 445

Leu Thr Xaa Lys Gln Leu Gln Gln Ala Glu Leu Leu Ser Gln Gln Tyr
                450                 455                 460

Ile Glu Lys Tyr Ala Xaa Glu Ala Trp Ala Arg Met Gln Lys Leu Xaa
465                 470                 475                 480

Ala Xaa Ser Xaa Val Xaa Thr Gly Asn Lys
                485                 490

<210> SEQ ID NO 55
<211> LENGTH: 1530
<212> TYPE: PRT
<213> ORGANISM: Artificial Sequence
<220> FEATURE:
<223> OTHER INFORMATION: Consensus Sequence
<221> NAME/KEY: VARIANT
<222> LOCATION: (1)...(1530)
<223> OTHER INFORMATION: Xaa = Any Amino Acid

<400> SEQUENCE: 55

Met Asn Lys Lys Phe Lys Tyr Lys Lys Ser Leu Leu Ala Ala Ile Leu
1               5                   10                  15

Ser Ala Thr Leu Leu Ala Gly Cys Asp Gly Gly Ser Gly Ser Ser
                20                  25                  30

Ser Asp Thr Pro Pro Val Asp Ser Gly Thr Gly Ser Leu Pro Glu Val
                35                  40                  45

Lys Pro Asp Pro Thr Pro Asn Pro Glu Pro Thr Pro Glu Pro Thr Pro
                50                  55                  60

Asp Pro Glu Pro Thr Pro Glu Pro Thr Pro Asp Pro Asp Pro Glu Pro
65                  70                  75                  80

Thr Pro Glu Pro Glu Pro Glu Pro Val Pro Thr Lys Thr Gly Tyr Leu
                85                  90                  95

Thr Leu Gly Gly Ser Gln Arg Val Thr Gly Asp Ala Thr Cys Asn Gly
                100                 105                 110

Glu Ser Ser Asp Gly Phe Thr Phe Thr Pro Gly Asp Lys Val Thr Cys
                115                 120                 125

Val Ala Gly Asn Asn Thr Thr Ile Ala Thr Phe Asp Thr Gln Ser Glu
                130                 135                 140

Ala Ala Arg Ser Leu Arg Ala Val Glu Lys Val Ser Phe Ser Leu Glu
```

```
                145                 150                 155                 160
Asp Ala Gln Glu Leu Ala Gly Ser Asp Asp Lys Lys Ser Asn Ala Val
                165                 170                 175

Ser Leu Val Thr Ser Ser Asn Ser Cys Pro Ala Asn Thr Glu Gln Val
                180                 185                 190

Cys Leu Thr Phe Ser Ser Val Ile Glu Ser Lys Arg Phe Asp Ser Leu
                195                 200                 205

Tyr Lys Gln Ile Asp Leu Ala Pro Glu Phe Lys Lys Leu Val Asn
        210                 215                 220

Glu Glu Val Glu Asn Asn Ala Ala Thr Asp Lys Ala Pro Ser Thr His
225                 230                 235                 240

Thr Ser Pro Val Val Pro Val Thr Thr Pro Gly Thr Lys Pro Asp Leu
                245                 250                 255

Asn Ala Ser Phe Val Ser Ala Asn Ala Glu Gln Phe Tyr Gln Tyr Gln
                260                 265                 270

Pro Thr Glu Ile Ile Leu Ser Glu Gly Arg Leu Val Asp Ser Gln Gly
                275                 280                 285

Tyr Gly Val Ala Gly Val Asn Tyr Tyr Thr Asn Ser Gly Arg Gly Val
                290                 295                 300

Thr Gly Glu Asn Gly Glu Phe Ser Phe Ser Trp Gly Glu Thr Ile Ser
305                 310                 315                 320

Phe Gly Ile Asp Thr Phe Glu Leu Gly Ser Val Arg Gly Asn Lys Ser
                325                 330                 335

Thr Ile Ala Leu Thr Glu Leu Gly Asp Glu Val Arg Gly Ala Asn Ile
                340                 345                 350

Asp Gln Leu Ile His Arg Tyr Ser Thr Thr Gly Gln Asn Asn Thr Arg
                355                 360                 365

Val Val Pro Asp Asp Val Arg Lys Val Phe Ala Glu Tyr Pro Asn Val
                370                 375                 380

Ile Asn Glu Ile Ile Asn Leu Ser Leu Ser Asn Gly Ala Thr Leu Gly
385                 390                 395                 400

Glu Gly Glu Gln Val Val Asn Leu Pro Asn Glu Phe Ile Glu Gln Phe
                405                 410                 415

Lys Thr Gly Gln Ala Lys Glu Ile Asp Thr Ala Ile Cys Ala Lys Thr
                420                 425                 430

Asp Gly Cys Asn Glu Ala Arg Trp Phe Ser Leu Thr Thr Arg Asn Val
                435                 440                 445

Asn Asp Gly Gln Ile Gln Gly Val Ile Asn Lys Leu Trp Gly Val Asp
        450                 455                 460

Thr Asn Tyr Lys Ser Val Ser Lys Phe His Val Phe His Asp Ser Thr
465                 470                 475                 480

Asn Phe Tyr Gly Ser Thr Gly Asn Ala Arg Gly Gln Ala Val Val Asn
                485                 490                 495

Ile Ser Asn Ala Ala Phe Pro Ile Leu Met Ala Arg Asn Asp Lys Asn
                500                 505                 510

Tyr Trp Leu Ala Phe Gly Glu Lys Arg Ala Trp Asp Lys Asn Glu Leu
                515                 520                 525

Ala Tyr Ile Thr Glu Ala Pro Ser Ile Val Glu Pro Glu Asn Val Thr
                530                 535                 540

Arg Asp Thr Ala Thr Phe Asn Leu Pro Phe Ile Ser Leu Gly Gln Val
545                 550                 555                 560

Gly Glu Gly Lys Leu Met Val Ile Gly Asn Pro His Tyr Asn Ser Ile
                565                 570                 575
```

```
Leu Arg Cys Pro Asn Gly Tyr Ser Trp Asn Gly Gly Val Asn Lys Asp
            580                 585                 590

Gly Gln Cys Thr Leu Asn Ser Asp Pro Asp Met Lys Asn Phe Met
        595                 600                 605

Glu Asn Val Leu Arg Tyr Leu Ser Asp Lys Trp Thr Pro Asp Ala
610                 615                 620

Lys Ala Ser Met Thr Val Gly Thr Asn Leu Asp Thr Val Tyr Phe Lys
625                 630                 635                 640

Arg His Gly Gln Val Thr Gly Asn Ser Ala Ala Phe Gly Phe His Pro
                645                 650                 655

Asp Phe Ala Gly Ile Ser Val Glu His Leu Ser Ser Tyr Gly Asp Leu
            660                 665                 670

Asp Pro Gln Glu Met Pro Leu Leu Ile Leu Asn Gly Phe Glu Tyr Val
        675                 680                 685

Thr Gln Val Gly Asn Asp Pro Tyr Ala Ile Pro Leu Arg Ala Asp Thr
    690                 695                 700

Ser Lys Pro Lys Leu Thr Gln Gln Asp Val Thr Asp Leu Ile Ala Tyr
705                 710                 715                 720

Leu Asn Lys Gly Gly Ser Val Leu Ile Met Glu Asn Val Met Ser Asn
                725                 730                 735

Leu Lys Glu Glu Ser Ala Ser Gly Phe Val Arg Leu Leu Asp Ala Ala
            740                 745                 750

Gly Leu Ser Met Ala Leu Asn Lys Ser Val Val Asn Asn Asp Pro Gln
        755                 760                 765

Gly Tyr Pro Asn Arg Val Arg Gln Gln Arg Ala Thr Gly Ile Trp Val
    770                 775                 780

Tyr Glu Arg Tyr Pro Ala Val Asp Gly Ala Leu Pro Pro Tyr Thr Ile
785                 790                 795                 800

Asp Ser Lys Thr Gly Glu Val Xaa Trp Lys Tyr Gln Gln Glu Asn Lys
                805                 810                 815

Pro Asp Asp Lys Pro Lys Leu Glu Val Ala Ser Trp Gln Glu Asp Val
            820                 825                 830

Asp Gly Lys Gln Val Thr Arg Tyr Ala Phe Ile Asp Glu Ala Asp His
        835                 840                 845

Lys Thr Glu Glu Ser Leu Lys Ala Ala Lys Ala Lys Ile Phe Xaa Ala
    850                 855                 860

Phe Pro Gly Leu Glu Glu Cys Lys Asp Ser Thr Tyr His Tyr Glu Val
865                 870                 875                 880

Asn Cys Leu Glu Tyr Arg Pro Gly Thr Gly Val Pro Val Thr Gly Gly
                885                 890                 895

Met Tyr Val Pro Gln Tyr Thr Gln Leu Ser Leu Asn Ala Asp Thr Ala
            900                 905                 910

Lys Ala Met Val Gln Ala Ala Asp Leu Gly Thr Asn Ile Gln Arg Leu
        915                 920                 925

Tyr Gln His Glu Leu Tyr Phe Arg Thr Asn Gly Arg Lys Gly Glu Arg
    930                 935                 940

Leu Ser Ser Val Asp Leu Glu Arg Leu Tyr Gln Asn Met Ser Val Trp
945                 950                 955                 960

Leu Trp Asn Xaa Thr Glu Tyr Arg Tyr Glu Glu Gly Lys Glu Asp Glu
                965                 970                 975

Leu Gly Phe Lys Thr Phe Thr Glu Phe Leu Asn Cys Tyr Ala Asn Asp
            980                 985                 990
```

-continued

```
Ala Tyr Ala Gly Gly Thr Gln Cys Ser Ala Glu Leu Lys Lys Ser Leu
            995                 1000                1005

Val Asp Asn Asn Met Ile Tyr Gly Glu Gly Ser Ser Asn Lys Ala Gly
1010                1015                1020

Met Met Asn Pro Ser Tyr Pro Leu Asn Tyr Met Glu Lys Pro Leu Thr
1025                1030                1035                1040

Arg Leu Met Leu Gly Arg Ser Trp Asp Leu Asn Ile Lys Val Asp
            1045                1050                1055

Val Glu Lys Tyr Pro Gly Ala Val Ser Xaa Glu Gly Glu Asn Val Thr
            1060                1065                1070

Glu Thr Ile Ser Leu Tyr Ser Asn Pro Thr Lys Trp Phe Ala Gly Asn
            1075                1080                1085

Met Gln Ser Thr Gly Leu Trp Ala Pro Ala Gln Lys Glu Val Thr Ile
            1090                1095                1100

Lys Ser Asn Ala Asn Val Pro Val Thr Val Thr Val Ala Leu Ala Asp
1105                1110                1115                1120

Asp Leu Thr Gly Arg Glu Lys His Glu Val Ala Leu Asn Arg Pro Pro
            1125                1130                1135

Arg Val Thr Lys Thr Tyr Ser Leu Asp Ala Ser Gly Thr Val Lys Phe
            1140                1145                1150

Lys Val Pro Tyr Gly Gly Leu Ile Tyr Ile Lys Gly Asn Ser Xaa Thr
            1155                1160                1165

Asn Asn Glu Ser Ala Ser Phe Thr Phe Thr Gly Val Val Lys Ala Pro
            1170                1175                1180

Phe Tyr Lys Asp Gly Ala Trp Lys Asn Asp Leu Asn Ser Pro Ala Pro
1185                1190                1195                1200

Leu Gly Glu Leu Glu Ser Asp Ala Phe Val Tyr Thr Thr Pro Lys Lys
            1205                1210                1215

Asn Leu Asn Ala Ser Asn Tyr Ser Asn Tyr Thr Gly Gly Leu Glu Gln
            1220                1225                1230

Phe Ala Asn Asp Leu Asp Thr Phe Ala Ser Ser Met Asn Asp Phe Tyr
            1235                1240                1245

Gly Arg Asp Ser Glu Asp Gly Lys His Arg Met Phe Thr Tyr Lys Asn
            1250                1255                1260

Leu Thr Gly His Lys His Arg Phe Thr Asn Asp Val Gln Ile Ser Ile
1265                1270                1275                1280

Gly Asp Ala His Ser Gly Tyr Pro Val Met Asn Ser Ser Phe Ser Pro
            1285                1290                1295

Asn Ser Thr Thr Leu Pro Thr Pro Leu Asn Asp Trp Leu Ile Trp
            1300                1305                1310

His Glu Val Gly His Asn Ala Ala Glu Thr Pro Leu Thr Val Pro Gly
            1315                1320                1325

Ala Thr Glu Val Ala Asn Asn Val Leu Ala Leu Tyr Met Gln Asp Arg
            1330                1335                1340

Tyr Leu Gly Lys Met Asn Arg Val Ala Asp Ile Thr Val Ala Pro
1345                1350                1355                1360

Glu Tyr Leu Glu Glu Ser Asn Gly Gln Ala Trp Ala Arg Gly Gly Ala
            1365                1370                1375

Gly Asp Arg Leu Leu Met Tyr Ala Gln Leu Lys Glu Trp Ala Glu Lys
            1380                1385                1390

Asn Phe Asp Ile Lys Lys Trp Tyr Pro Asp Gly Thr Pro Leu Pro Xaa
            1395                1400                1405

Phe Tyr Ser Glu Arg Glu Gly Met Lys Gly Trp Asn Leu Phe Gln Leu
```

-continued

```
            1410                1415                1420
Met His Arg Lys Ala Arg Gly Asp Glu Val Gly Asn Asp Lys Phe Gly
1425                1430                1435                1440

Gly Lys Asn Tyr Cys Ala Glu Ser Asn Gly Asn Ala Ala Asp Thr Leu
                1445                1450                1455

Met Leu Cys Ala Ser Trp Val Ala Gln Thr Asp Leu Ser Glu Phe Phe
                1460                1465                1470

Lys Lys Trp Asn Pro Gly Ala Asn Ala Tyr Gln Leu Pro Gly Ala Ser
            1475                1480                1485

Glu Met Ser Phe Glu Gly Gly Val Ser Gln Ser Ala Tyr Asn Thr Leu
        1490                1495                1500

Ala Ser Leu Asp Leu Pro Lys Pro Glu Gln Gly Pro Glu Thr Ile Asn
1505                1510                1515                1520

Lys Val Thr Glu His Lys Met Ser Ala Glu
                1525                1530
```